US007915411B2

(12) United States Patent
Betebenner et al.

(10) Patent No.: US 7,915,411 B2
(45) Date of Patent: Mar. 29, 2011

(54) ANTI-VIRAL COMPOUNDS

(75) Inventors: David A. Betebenner, Libertyville, IL (US); David A. DeGoey, Salem, WI (US); Clarence J. Maring, Palatine, IL (US); Allan C. Krueger, Gurnee, IL (US); Nobuhiko Iwasaki, Buffalo Grove, IL (US); Todd W. Rockway, Grayslake, IL (US); Curt S. Cooper, Vernon Hills, IL (US); David D. Anderson, Kenosha, WI (US); Pamela L. Donner, Mundelein, IL (US); Brian E. Green, Wonder Lake, IL (US); Dale J. Kempf, Libertyville, IL (US); Dachun Liu, Waukegan, IL (US); Keith F. McDaniel, Wauconda, IL (US); Darold L. Madigan, Elk Grove Village, IL (US); Christopher E. Motter, Oak Creek, WI (US); John K. Pratt, Kenosha, WI (US); Jason P. Shanley, Chicago, IL (US); Michael D. Tufano, Chicago, IL (US); Rolf Wagner, Antioch, IL (US); Rong Zhang, Niskayuna, NY (US); Akhteruzzaman Molla, Gurnee, IL (US); Hongmei Mo, Foster City, CA (US); Tami J. Pilot-Matias, Green Oaks, IL (US); Sherie V L. Masse, Kenosha, WI (US); Robert J. Carrick, Pleasant Prairie, WI (US); Wenping He, Libertyville, IL (US); Liangjun Lu, Kildeer, IL (US); David J. Grampovnik, Waukegan, IL (US)

(73) Assignee: Abbott Laboratories, Abbott Park, IL (US)

( * ) Notice: Subject to any disclaimer, the term of this patent is extended or adjusted under 35 U.S.C. 154(b) by 352 days.

(21) Appl. No.: 11/613,825

(22) Filed: Dec. 20, 2006

(65) Prior Publication Data
US 2007/0197558 A1    Aug. 23, 2007

Related U.S. Application Data

(60) Provisional application No. 60/752,473, filed on Dec. 21, 2005.

(51) Int. Cl.
*C07D 471/04* (2006.01)
*A61P 1/16* (2006.01)

(52) U.S. Cl. .................................................... 544/279
(58) Field of Classification Search .................. 544/279; 514/264.1, 264.11
See application file for complete search history.

(56) References Cited

U.S. PATENT DOCUMENTS

| 3,021,332 | A | 2/1962 | Hitchings et al. |
| 4,871,851 | A | 10/1989 | Beck |
| 5,034,393 | A | 7/1991 | Hackler et al. |
| 5,350,749 | A | 9/1994 | Hackler et al. |
| 5,464,781 | A | 11/1995 | Armitage et al. |
| 5,654,307 | A | 8/1997 | Bridges et al. |
| 5,925,644 | A | 7/1999 | Jakobi et al. |
| 5,965,563 | A | 10/1999 | Buzzetti et al. |
| 6,130,217 | A | 10/2000 | Arnold et al. |
| 6,169,091 | B1 | 1/2001 | Cockerill et al. |
| 6,174,889 | B1 | 1/2001 | Cockerill et al. |
| 6,184,226 | B1 | 2/2001 | Chakravarty et al. |
| 6,277,989 | B1 | 8/2001 | Chakravarty et al. |
| 6,284,764 | B1 | 9/2001 | Kath et al. |
| 6,323,180 | B1 | 11/2001 | Llinas-Brunet et al. |
| 6,348,587 | B1 | 2/2002 | Schinazi et al. |
| 6,395,733 | B1 | 5/2002 | Arnold et al. |
| 6,413,971 | B1 | 7/2002 | Arnold et al. |
| 6,476,031 | B1 | 11/2002 | Chakravarty et al. |
| 6,541,481 | B2 | 4/2003 | Kath et al. |
| 6,610,677 | B2 | 8/2003 | Davies et al. |
| 6,703,403 | B2 | 3/2004 | Norbeck et al. |
| 6,703,421 | B1 | 3/2004 | Nunokawa et al. |
| 6,723,726 | B1 | 4/2004 | Cockerill et al. |
| 6,784,174 | B1 | 8/2004 | Cumming |
| 6,809,097 | B1 | 10/2004 | Thomas et al. |
| 6,903,096 | B2 | 6/2005 | Chakravarty et al. |
| 7,037,913 | B2 | 5/2006 | Wang et al. |
| 7,183,302 | B2 | 2/2007 | Romine et al. |
| 2003/0125343 | A1 | 7/2003 | Gambacorti-Passerini et al. |
| 2004/0242604 | A1 | 12/2004 | Bhattacharya et al. |
| 2004/0265792 | A1 | 12/2004 | Glenn et al. |
| 2005/0075331 | A1 | 4/2005 | Pratt et al. |
| 2005/0090522 | A1 | 4/2005 | Wang et al. |
| 2005/0107364 | A1 | 5/2005 | Hutchinson et al. |
| 2005/0215575 | A1 | 9/2005 | Bakthavatchalam et al. |
| 2006/0035965 | A1 | 2/2006 | Dalton et al. |
| 2007/0232627 | A1 | 10/2007 | Betebenner et al. |
| 2007/1023264 |  | 10/2007 | Rockway et al. |

FOREIGN PATENT DOCUMENTS

| EP | 404355 | 12/1990 |
| EP | 0 414 386 | 2/1991 |
| EP | 0 912 570 | 5/1999 |

(Continued)

OTHER PUBLICATIONS

Barlin et al., "Potential Antimalarials. I 1,8-Naphthyridines, STN Accession No. 1984:530611, Document No. 101:130611 ," Abstract of Australian Journal of Chemistry, vol. 37 (5), pp. 1065-1173, 1984.

(Continued)

*Primary Examiner* — James O Wilson
*Assistant Examiner* — Cecilia M Jaisle
(74) *Attorney, Agent, or Firm* — Xu Zhang

(57) ABSTRACT

Compounds effective in inhibiting replication of Hepatitis C virus ("HCV") or other viruses are disclosed. This invention is also directed to compositions comprising such compounds, co-formulation or co-administration of such compounds with other anti-viral or therapeutic agents, processes and intermediates for the syntheses of such compounds, and methods of using such compounds for the treatment of HCV or other viral infections.

3 Claims, No Drawings

FOREIGN PATENT DOCUMENTS

| | | |
|---|---|---|
| EP | 1 162 196 | 12/2001 |
| ES | 2009217 | 9/1989 |
| GB | 774094 | 5/1957 |
| JP | 47025076 | 7/1972 |
| WO | 93/13097 | 7/1993 |
| WO | 95/00511 | 1/1995 |
| WO | 95/19774 | 7/1995 |
| WO | 96/09294 | 3/1996 |
| WO | 96/40142 | 12/1996 |
| WO | 97/13771 | 4/1997 |
| WO | 98/02428 | 1/1998 |
| WO | 98/02437 | 1/1998 |
| WO | 98/02438 | 1/1998 |
| WO | 98/05661 | 2/1998 |
| WO | 98/08846 | 3/1998 |
| WO | 98/13350 | 4/1998 |
| WO | 98/22444 | 5/1998 |
| WO | 98/23613 | 6/1998 |
| WO | 9846605 | 10/1998 |
| WO | 99/59587 | 11/1999 |
| WO | 00/12497 | 3/2000 |
| WO | 00/44728 | 8/2000 |
| WO | 00/56738 | 9/2000 |
| WO | 01/32153 | 5/2001 |
| WO | 01/32632 | 5/2001 |
| WO | 01/57040 | 8/2001 |
| WO | 01/60315 | 8/2001 |
| WO | 01/90121 | 11/2001 |
| WO | 02/04425 | 1/2002 |
| WO | 03051366 | 6/2003 |
| WO | 03059913 | 7/2003 |
| WO | 03062209 | 7/2003 |
| WO | 03097615 | 11/2003 |
| WO | 2004/055004 | 1/2004 |
| WO | 2004/014313 | 2/2004 |
| WO | 2004/014852 | 2/2004 |
| WO | 2004/024693 | 3/2004 |
| WO | 2004/047818 | 6/2004 |
| WO | 2004055003 | 7/2004 |
| WO | 2004055004 | 7/2004 |
| WO | 2004/065392 | 8/2004 |
| WO | 2004071460 | 8/2004 |
| WO | 2004/087056 | 10/2004 |
| WO | 2005/007652 | 1/2005 |
| WO | 2005003100 | 1/2005 |
| WO | 2005023807 | 3/2005 |
| WO | 2005032481 | 4/2005 |
| WO | 2005/047288 | 5/2005 |
| WO | 2005042498 | 5/2005 |
| WO | 2005049033 | 9/2005 |
| WO | 2005082865 | 9/2005 |
| WO | 2005087227 | 9/2005 |
| WO | 2005/105761 | 11/2005 |
| WO | 2006/012333 | 2/2006 |
| WO | 2006/035061 | 4/2006 |
| WO | 2006/038039 | 4/2006 |
| WO | 2006067614 | 6/2006 |
| WO | 2006071875 | 7/2006 |
| WO | 2006100310 | 9/2006 |
| WO | 2006105063 | 10/2006 |
| WO | 2006/120251 | 11/2006 |
| WO | 2006/120252 | 11/2006 |
| WO | 2006120252 | 11/2006 |
| WO | 2007/035010 | 3/2007 |
| WO | 2007060404 | 5/2007 |
| WO | WO-2007076035 A2 | 7/2007 |

OTHER PUBLICATIONS

Dorwald F.Z., "Side Reactions in Organic Synthesis—a Guid to Successful Synthesis Design," pp. 9-16, 2005.
International Search Report for application No. PCT/US07/088027, Mailed on Oct. 24, 2008, 1 page.
Livi et al., "Farmaco, STN Document No. 86:89704; Abstract of Edizione Scientifica," vol. 31 (11), pp. 797-808, 1976.
Martini C. et al., "Specific Inhibition of Benzodiazepine Receptor Binding by Some 1,2,3-Triazole Derivatives,STN Accession No. 1989:50722 Document No. 110:50722," Abstract of Journal of Pharmaceutical Sciences, vol. 77 (11), pp. 977-980, 1988.
US Office Action dated Mar. 20, 2008 from U.S. Appl. No. 11/613,810, filed Dec. 20, 2006.
US Office Action dated Apr. 23, 2008 from U.S. Appl. No. 11/613,836, filed Dec. 20, 2006.
US Office Action dated Nov. 4, 2008 from U.S. Appl. No. 11/613,836, filed Dec. 20, 2006.
US Office Action dated Dec. 5, 2008 from U.S. Appl. No. 11/613,810, filed Dec. 20, 2006.
US Office Action dated Jul. 7, 2009 from U.S. Appl. No. 11/613,836, filed Dec. 20, 2006.
US Office Action dated Sep. 4, 2009 from U.S. Appl. No. 11/613,810, filed Dec. 20, 2006.
USPQ, "Graham v. John Deere Co. of Kansas City", USPQ, 148:459-478 (1966).
Blight, K.J., et al., "Efficient Initiation of HCV RNA Replication in Cell Culture", Science, 290:1972-1974 (2000).
Bundgaard, H., "Design of prodrugs", pp. 7-9 & 21-24 (1985).
Cortese, F. & Bauman, L., "A Synthesis of Conjugatred Bile Acids. I. Glycochotic Acid", JACS, 57:1393-1395 (1935).
Cross, L.C. & Klyne, W., "Rules for the Nomenclature of Organic Chemistry—Section E: Stereochemistry", Pure Appl. Chem., 45:11-30 (1976).
Das, S., et al., "A Small yeast RNA Blocks Hepatitis C Virus Internal Ribosome Entry Site (HCV IRES)-Mediated Translation and Inhibits Replication of a Chimeric Poliovirus under Translational control of the HCV IRES Element", J of Virology, 72(7):5638-5647 (1998).
Deeb, A., et al., "Pyridazine Derivatives and Related Comp9unds Part 5. Pyrazolo[3,4-c]Pyridazine: Synthesis and Some Reactoins", Heterocycles, 32(5):895-900 (1991).
Gomtsyan, A., et al., "Design, Synthesis, and Structure-Activity Relationship of 6-Alkynylpyrimidines as Potent Adenosine Kinase Inhibitors", J. Med Chem., 45:3639-3648 (2002).
Greene & Wuts, Protective Groups in Organic Synthesis, $3^{rd}$ Ed.:Tbl of Cont., (1999).
Hoover, J.E., Remington's Pharmaceutical Sciences, Tbl of Cont., (1975).
Ikeda, M., et al., "Selectable Subgenomic and Genome-Length Dicistronic RNAs Derived from an Infectious Molecular Clone of the HCV-N Strain of Hepatitis C Virus Replicate Efficiently in Clutured Huh7 Cells", J. of Virology, 76(6):2997-3006 (2002).
Jacques, et al., Enantiomers, Racemates, and Resolutions, Tble of Cont., (1981).
Janout, V., et al., "Design and Synthesis of Molecular Umbrellas", J. Am. Chem. Soc., 119:640-647 (1997).
Lieberman, H.A. & Lachman, L., Pharmaceutical Dosage Forms, vol. 1:Tbl of Cont., (1980).
McKenzie, A. & Clough, G.W., "XLVIII—Experiments on the Ealden Inversion. Part VIII. α-Amino-a-phenylpropionic Acids", J. Chem. Soc., 101:390-397 (1912).
Miranda, E.I., et al., "Thiols, Unsymmetrical Sulfides and Thioacetals From the New Reagent: Trisopropysilanethiol", Tetrahedron Ltrs., 35(20):3221-3224 (1994).
Nakamura, S., "Studies on Growth Inhibition of hiochi-bacteria, Specific Saprophytes of Sake", Agr. Biol. Chem., 25(8):665-670 (1961).
Prakash, G.K.Su., et al., "Facile preparation of di- and monofluoromethyl ketones form trifluoromethyl ketones via fluorinated enol silyl ethers", J. of Fluorine Chem., 112:357-362 (2001).
Refai, M., et al., "New Synthesis of Some 1,8-Naphthoyridines of Possible Lantimicrobial Lactivity", Egypt. J. Pharm. Sci., 37(1-6):241-249 (1996).
Shuman, R.T., et al., "Structure-Activity Study of Tripeptide Thrombin Inhibitors Using α-Alkyl Amino Lacids and Other Conformationally Constrained Amino Acid Substitutions", J. Med. Chem.,38:4446-4453 (1995).
Yi, M., et al., "Subjenomic Hepatitis C Virus Replicaons Inducting Expression of a Secreted Enzymatic Reporter Protein", Virology, 304:197-210 (2002).
Elneairy, et al. Journal of Sulfur Chemistry (2005), 26(4-5), 381-391.
Monge, et al., Arzneimittel-Forschung (1990), 40(11), 1230-3.

Iwamura, et al., *Journal of Medicinal Chemistry* (1985), 28(5), 577-83.
Chen, et al., *Yaoxue Xuebao* (1982), 17(2), 112-17.
Soloducho, *Archiv der Pharmazie* (Weinheim, Germany), (1990), 323(8), 513-15.
Iwamura, et al., *Phytochemistry* (Elsevier) (1979), 18(8), 1265-8.
Hayashi, et al., *Yakugaku Zasshi* (1977), 97(9), 1022-33.
Nishikawa, et al., *Chem. & Pharm. Bulletin* (1976), 24(9), 2057-77.
Godefroy, et al., *Comptes Rendus des Seances de l'Academie des Sciences, Serie B: Sciences Physiques* (1973), 277(16), 703-6.
Godefroy, et al., *Journal of Heterocyclic Chemistry* (1973), 10(6), 1077-8.
Ahmed, et al., *Journal of Heterocyclic Chemistry* (2002), 39(2), 309-314.
Rewcastle, et al., *Journal of Medicinal Chemistry* (1996), 39(9), 1823-35.
Nishikawa, et al., *Bioscience, Biotech., and Biochem.* (1994), 58(9(, 1709-10).
International Search Report for PCT/US2006/049079 dated Aug. 17, 2007.
International Search Report for PCT/US2006/048685 dated Oct. 30, 2007.
International Search Report for PCT/uS2006/049080 dated Aug. 23, 2007.
U.S. Appl. No. 11/960,298, filed Dec. 19, 2007.

ANTI-VIRAL COMPOUNDS

This application claims the benefit and incorporates herein by references the entire content of U.S. Provisional Application No. 60/752,473, filed Dec. 21, 2005.

FIELD

The present invention relates to compounds effective in inhibiting replication of Hepatitis C virus ("HCV"). The present invention also relates to methods of making such compounds, compositions comprising such compounds, intermediates for the syntheses of such compounds, and methods of using such compounds/compositions for the treatment of HCV infection or conditions/symptoms associated therewith. In addition, the present invention relates to use of such compounds for the manufacture of medicaments for the treatment of HCV infection.

BACKGROUND

HCV, a human pathogen, is an RNA virus belonging to the *Hepacivirus* genus in the Flaviviridae family. As is characteristic with all other members of the Flaviviridae family, HCV has enveloped virions that contain a positive stranded RNA genome encoding all known virus-specific proteins in one single, uninterrupted, open reading frame. The open reading frame comprises approximately 9500 nucleotides encoding a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B. A cellular protease cleaves the viral protein at the NS2-NS3 junction allowing a viral protease (NS3 protease) to mediate subsequent cleavages. The NS3 protein also exhibits nucleoside triphosphatase and RNA helicase activities. NS2 and NS4A may, too, be involved in proteolytic activity. NS5A is a phosphoprotein involved in replication. NS5B is a RNA-dependent RNA polymerase. U.S. Patent Pub. No. 2004/0265792, published 30 Dec. 2004, mentions that inhibition of the aforementioned non-structural proteins may inhibit HCV replication.

HCV infection is associated with progressive liver pathology, including cirrhosis and hepatocellular carcinoma. HCV-associated end-stage liver disease is the most frequent indication for liver transplantation among adults. Chronic hepatitis C may be treated with a once-weekly injection of peginterferon-alpha in combination with daily ribavarin. Peginterferon-alpha is interferon-alpha attached to polyethylene glycol to slow elimination of the drug from the body. This results in enhanced compliance and clinically superior anti-viral activity when compared to treatments of interferon-alpha daily injections. Substantial limitations to efficacy and tolerability remain as many users suffer from side effects and viral elimination from the body is often inadequate.

Attempts have been made to design drugs that specifically inhibit functions of the hepatitis C virus. Boehringer Ingelheim U.S. Pat. No. 6,323,180 mentions tri-peptide compounds as HCV serine protease inhibitors proposed for treatment of HCV infection.

Another approach is ISIS-14803 (Isis Pharmaceuticals), an antisense inhibitor complementary to a conserved sequence of the hepatitis C virus RNA. This molecule binds to the viral RNA and inhibits the expression of proteins required for replication.

Inhibition of HCV translation, by a yeast RNA that binds to cellular polypeptides and prevents their interaction with the viral internal ribosome entry site (IRES), is described in Das et al, J. VIROLOGY, 72(7):5638-5647 (1998).

Fused-bicyclic heterocyclic compounds have been proposed for diverse life-science-related uses. Examples of such heterocyclic compounds include naphthyridine, pyridopyrimidine, pyrimidopyrimidine, pyrazolopyrimidine and thiazolo/thienopyrimidine compounds.

Naphthyridine-type fused-bicyclic compounds have been investigated for disease-treatment uses. For example, Boots WO 93/13097, published 8 Jul. 1993, mentions [1,8]naphthyridine compounds, such as ethyl 4-(4-methoxyanilino)-6-ethoxy-7-methyl-1,8-naphthyridine-3-carboxylate hydrochloride, proposed for use as anti-rheumatic agents. Boots WO 95/00511, published 5 Jan. 1995, mentions substituted ring-fused 4-aminopyridines, such as 3-ethoxy-5-(2-ethoxy-5-pyridylamino)-2-methyl-1,8-naphthyridine, proposed for use as anti-rheumatic agents. Zeneca WO 98/13350, published 2 Apr. 1998, mentions [1,8]naphthyridine compounds, such as 2-acetamido-5-(2-fluoro-5-hydroxy-4-methylanilino)-1,8-naphthyridine hydrochloride, proposed as anti-angiogenic agents. Neurogen WO 2004/055004, published 1 Jul. 2004, mentions naphthyridine compounds as capsaicin-receptor modulators, specific compounds being 5-(4-trifluoromethyl-phenylamino)-2-(3-trifluoromethyl-pyridin-2-yl)-[1,6]naphthyridine-7-carboxylic acid, and 2-methoxymethyl-4-(4-trifluoromethyl-phenylamino)-7-(3-trifluoromethyl-pyridin-2-yl)-[1,8]naphthyridine-3-carboxylic acid.

Pyridopyrimidine-type fused-bicyclic compounds have been investigated for various disease-treatment uses. For example, Pfizer WO 98/05661, published 12 Feb. 1998, mentions substituted pyridopyrimidine compounds, such as [8-(1-ethyl-propyl)-2-methyl-5,6,7,8-tetrahydro-pyrido(2,3-d)pyrimidin-4-yl]-(2,4,6-trimethyl-phenyl)-amine, as corticotrophin releasing factor (hormone) CRF (CRH) antagonists proposed for treatment of Alzheimer's Disease and obesity. Pfizer WO 98/23613, published 4 Jun. 1998, mentions fused-bicyclic pyrimidine compounds, including pyridopyrimidinyl-aminophenyl compounds, such as (3-ethynyl-phenyl)-pyrido[3,4-d]pyrimidin-4-yl-amine, proposed for treatment of hyperproliferative diseases such as cancer. Glaxo Wellcome U.S. Pat. No. 6,169,091, issued 2 Jan. 2001, mentions bicyclic heteroaromatic compounds, such as 4-(4-benzyloxyanilino)pyrido[2,3-d]-pyrimidine, as tyrosine kinase inhibitors proposed for treatment of fibrosis, inflammation, nervous system diseases and cancer. Eli Lilly WO 01/32632, published 10 May 2001, mentions 4-substituted pyrimidine compounds, including 2-trifluoromethyl-4-[2-(2-(2-chlorophenyl)ethylamino]pyrido-[2,3-d]pyrimidine hydrochloride, as mGluR1 antagonists proposed for treatment of neurological disorders associated with glutamate dysfunction such as convulsions, migraine, psychosis, anxiety and pain. Abbott Laboratories WO 01/57040 published 9 Aug. 2001, mentions 6, 7-disubstituted-4-aminopyrido[2,3-d]pyrimidine compounds, such as 4-amino-6-(4-methylphenyl)-7-(4-bromophenyl)pyrido[2,3-d]pyrimidine, as adenosine kinase inhibitors proposed for treatment of pain and inflammation. Neurogen WO 2004/055004, published 1 Jul. 2004, mentions pyridopyrmidinyl-aminophenyl compounds, such as 2-methyl-2-{4-[2-methyl-7-(3-methyl-pyridin-2-yl)-pyrido[2,3-d]pyrimidin-4-ylamino]-phenyl}-propionic acid, as capsaicin-receptor modulators. Pfizer U.S. Pat. No. 6,395,733, issued 28 May 2002, mentions heterocyclic ring-fused pyrimidine compounds, such as 3-chloro-phenyl-pyrido[2,3-d]pyrimidin-4-yl-amine, proposed for treatment of hyperproliferative disease, such as cancer.

Pyrimidopyrimidine-type fused bicyclic compounds have been investigated for both pest-control and disease-treatment uses. For example, Dow Elanco U.S. Pat. No. 5,350,749, issued 27 Sep. 1994, mentions 4-substituted-pyrimido[2,3-d]pyrimidine compounds proposed for use as fungicides, insecticides and miticides. Warner-Lambert WO 95/19774, published 27 Jul. 1995, mentions pyrimidopyrimidine compounds, such as 4-benzylamino-7-methylaminopyrimido[4,5-d]pyrimidine, as tyrosine kinase inhibitors proposed for treatment of cancer, vascular restenosis and psoriasis.

Thienopyrimidine-type fused-bicyclic compounds have been investigated for various disease-treatment uses. For example, Warner-Lambert WO 95/19774, published 27 Jul. 1995, mentions fused heterocyclic pyrimidine compounds, including 4-(3-bromoanilino)thieno[2,3-d]pyrimidine, as tyrosine kinase inhibitors proposed for treatment of cancer, vascular restenosis and psoriasis. Glaxo Wellcome U.S. Pat. No. 6,169,091, issued 2 Jan. 2001, mentions bicyclic heteroaromatic compounds, such as 5-methyl-4-(4-phenoxyanilino)thieno[2,3-d]pyrimidine hydrochloride as tyrosine kinase inhibitors, proposed for treatment of fibrosis, inflammation, nervous system diseases and cancer. Eli Lilly WO 01/32632, published 10 May 2001, mentions 4-substituted-pyrimidine compounds, such as 6-methyl-4-[2,6-dichlorobenzylthio)ethylamino]thieno[2,3-d]pyrimidine hydrochloride, as mGluR1 antagonists proposed for treatment of neurological disorders associated with glutamate dysfunction such as convulsions, migraine, psychosis, anxiety and pain.

Bristol-Myers Squibb WO 2004/014852, published 19 Feb. 2004, mentions iminothiazolidinones, including fused-bicyclic derivatives of 2-(4-aminophenyl)-5H-thiazolo[2,3-6]quinazolin-3-one, as NS5A-protein-inhibitors proposed to prevent HCV replication.

Bristol-Myers Squibb WO 2004/014313, published 19 Feb. 2004, mentions combination therapies for treatment of viral diseases, including iminothiazolidinone NS5A-protein-inhibiting anti-HCV compounds in combination with other agents capable of interfering with HCV function.

SUMMARY

The present invention features compounds having I, II, III, IV, V, VI, VII or VIII, tautomers of these compounds, and pharmaceutically acceptable salts of these compounds or tautomers. These compounds, tautomers or salts can be used, either individually or in combination with other drugs or agents, to inhibit the replication of HCV or other viruses. These compounds, tautomers or salts can also be used, either individually or in combination with other drugs or agents, to disrupt functions of HCV or other viruses.

The present invention also features compositions that comprise the compounds, tautomers or salts of the present invention. A composition of the present invention can include one or more compounds, tautomers or salts of the present invention. A composition of the present invention can also include one or more other antiviral or therapeutic agents.

In addition, the present invention features methods of using the compounds, tautomers or salts of the present invention, or compositions comprising the same, to inhibit the replication of HCV or other viruses. These methods comprise contacting HCV or another virus, or cells infected with HCV or said another virus, with an effective amount of a compound, tautomer or salt of the present invention, thereby inhibiting the replication of HCV or said another virus.

The present invention further features methods of using the compounds, tautomers or salts of the present invention, or compositions comprising the same, to inhibit the proliferation or transmission of HCV or other viruses. These methods comprise contacting HCV or another virus, or contacting cells infected with HCV or another virus, with an effective amount of a compound, tautomer or salt of the present invention, thereby inhibiting the proliferation or transmission of HCV or said another virus.

Moreover, the present invention features methods of using the compounds, tautomers or salts of the present invention, or compositions comprising the same, to treat HCV or other viral infections. These methods comprise administering to a patient in need of such treatment an effective amount of a compound, tautomer or salt of the present invention, thereby reducing the blood or tissue level of HCV or other viruses in the patient.

The present invention also features use of the compounds, tautomers or salts of the present invention for the manufacture of medicaments for the treatment of HCV or other viral infections.

Furthermore, the present invention features processes of making the compounds, tautomers or salts of the present invention, and intermediates employed in these processes.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The following description is exemplary in nature and is not intended to limit the present disclosure, application, or uses.

Compounds

The present invention features compounds having Formula I, tautomers thereof, and pharmaceutically acceptable salts of the compounds or tautomers,

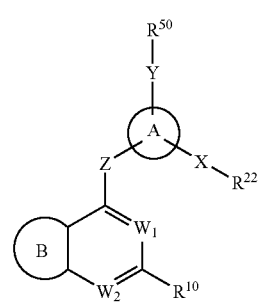

wherein:
A and B are each independently selected from carbocyclyl or heterocyclyl, and are each independently optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, carbocyclyl, heterocyclyl, $-L_S-O-R_S$, $-L_S-S-R_S$, $-L_S-C(O)R_S$, $-L_S-OC(O)R_S$, $-L_S-C(O)OR_S$, $-L_S-N(R_SR_{S'})$, $-L_S-C(=NR_S)R_{S'}$, $-L_S-S(O)R_S$, $-L_S-SO_2R_S$, $-L_S-C(O)N(R_SR_{S'})$, $-L_S-N(R_S)C(O)R_{S'}$, -$L_S$-C(=$NR_S$)N($R_{S'}R_{S''}$), -$L_S$-N($R_{S'}$)C(=$NR_S$)$R_{S''}$, -$L_S$-N($R_S$)C(O)N($R_{S'}R_{S''}$), -$L_S$-N($R_S$)SO$_2$$R_{S'}$, -$L_S$-SO$_2$N($R_S$$R_{S'}$), and -$L_S$-N($R_S$)SO$_2$N($R_{S'}R_{S''}$);

$W_1$ and $W_2$ are each independently selected from N or C($R^{33}$);

Z is a bond, —C$R^{41}R^{41'}$— or —N$R^{41}$—, wherein $R^{41}$ and $R^{41'}$ are each independently selected from the group consisting of hydrogen, alkyl, alkenyl and alkynyl;

$R^{10}$ and $R^{33}$ are each independently selected at each occurrence from the group consisting of hydrogen, halogen, oxo, thioxo, hydroxy, mercapto, nitro, cyano, amino, carboxy, formyl, phosphate, azido, alkyl, alkenyl, alkynyl, carbocyclyl, heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=$NR_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=$NR_S$)N($R_{S'}R_{S''}$), -$L_S$-N($R_{S'}$)C(=$NR_S$)$R_{S''}$, -$L_S$-N($R_S$)C(O)N($R_{S'}R_{S''}$), -$L_S$-N($R_S$)SO$_2$$R_{S'}$, -$L_S$-SO$_2$N($R_S$$R_{S'}$), -$L_S$-N($R_S$)SO$_2$N($R_{S'}R_{S''}$), -$L_E$-Q-$L_{E'}$-($C_3$-$C_{18}$carbocyclyl) and -$L_E$-Q-$L_{E'}$-($M_3$-$M_{18}$heterocyclyl);

X is selected from the group consisting of a bond, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=$NR_S$)N($R_{S'}$)—, -$L_S$-N($R_{S'}$)C(=$NR_S$)—, -$L_S$-S(O)—, -$L_S$-SO$_2$—, -$L_S$-C(O)O— and -$L_S$-OC(O)—;

$R^{22}$ is carbocyclyl or heterocyclyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=$NR_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=$NR_S$)N($R_{S'}R_{S''}$), -$L_S$-N($R_{S'}$)C(=$NR_S$)$R_{S''}$, -$L_S$-N($R_S$)C(O)N($R_{S'}R_{S''}$), -$L_S$-N=C(N$R_S$$R_{S'}$)(N$R_S$$R_{S'}$), -$L_S$-N($R_S$)SO$_2$$R_{S'}$, -$L_S$-SO$_2$N($R_S$$R_{S'}$), -$L_S$-N($R_S$)SO$_2$N($R_{S'}R_{S''}$), -$L_E$-Q-$L_{E'}$-($C_3$-$C_{18}$carbocyclyl) and -$L_E$-Q-$L_{E'}$-($M_3$-$M_{18}$heterocyclyl); or $R^{22}$ is alkyl, alkenyl or alkynyl, and is optionally substituted with one or more $R^{26}$; or $R^{22}$ is hydrogen;

Y is selected from the group consisting of a bond, -$L_S$-O—, -$L_S$-C(O)—, -$L_S$-S(O)$_2$—, -$L_S$-S(O)—, -$L_S$-OS(O)$_2$—, -$L_S$-OS(O)—, -$L_S$-C(O)O—, -$L_S$-OC(O)—, -$L_S$-OC(O)O—, -$L_S$-C(O)N($R^{15}$)—, -$L_S$-N($R^{15}$)C(O)—, -$L_S$-C(O)N($R^{15}$)O—, -$L_S$-N($R^{15}$)C(O)O—, -$L_S$-C(O)N($R^{15}$)N($R^{15'}$)-, -$L_S$-S—, -$L_S$-C(S)—, -$L_S$-C(S)O—, -$L_S$-OC(S)—, -$L_S$-N($R^{15}$)—, -$L_S$-C(S)N($R^{15}$)—, -$L_S$-N($R^{15}$)C(S)—, -$L_S$-N($R^{15}$)S(O)—, -$L_S$-N($R^{15}$)S(O)$_2$—, -$L_S$-S(O)$_2$N($R^{15}$)—, -$L_S$-S(O)N($R^{15}$)—, -$L_S$-C(S)N($R^{15}$)O—, and -$L_S$-C(S)N($R^{15}$)N($R^{15'}$)—, wherein $R^{15}$ and $R^{15'}$ are each independently selected at each occurrence from the group consisting of hydrogen, alkyl, alkenyl and alkynyl;

$R^{50}$ is -$L^1$-$A^1$, wherein $A^1$ is selected from the group consisting of carbocyclyl, heterocyclyl, alkyl, alkenyl and alkynyl, and $L^1$ is selected from the group consisting of a bond, alkylene, alkenylene and alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=$NR_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=$NR_S$)N($R_S$$R_{S''}$), -$L_S$-N($R_{S'}$)C(=$NR_S$)$R_{S''}$, -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), -$L_S$-N($R_S$)SO$_2$N($R_S$$R_{S''}$), -$L_E$-Q-$L_{E'}$-($C_3$-$C_{18}$carbocyclyl) and -$L_E$-Q-$L_{E'}$-($M_3$-$M_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, alkoxy, thioalkoxy, alkylcarbonyl, alkoxycarbonyl, alkylcarbonyloxy, alkylamino, alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S$$R_{S'}$), -$L_S$-C(=$NR_S$)$R_{S'}$, -$L_S$-S(O)$R_S$, -$L_S$-SO$_2$$R_S$, -$L_S$-C(O)N($R_S$$R_{S'}$), -$L_S$-N($R_S$)C(O)$R_{S'}$, -$L_S$-C(=$NR_S$)N($R_S$$R_{S''}$), -$L_S$-N($R_{S'}$)C(=$NR_S$)$R_{S''}$, -$L_S$-N($R_S$)C(O)N($R_S$$R_{S''}$), -$L_S$-N($R_S$)SO$_2$$R_{S'}$, -$L_S$-SO$_2$N($R_S$$R_{S'}$), -$L_S$-N($R_S$)SO$_2$N($R_S$$R_{S''}$), carbocyclyl, heterocyclyl, carbocyclylalkyl, heterocyclylalkyl, -$L_E$-Q-$L_{E'}$-($C_3$-$C_{18}$carbocyclyl) and -$L_E$-Q-$L_{E'}$-($M_3$-$M_{18}$heterocyclyl);

$L_S$ is independently selected at each occurrence from the group consisting of a bond, alkylene, alkenylene and alkynylene;

$R_S$, $R_{S'}$ and $R_{S''}$ are each independently selected at each occurrence from the group consisting of hydrogen, alkyl, alkenyl, alkynyl, alkoxy, thioalkoxy, alkoxyalkyl, alkoxyalkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl;

$L_E$ and $L_{E'}$ are each independently selected at each occurrence from the group consisting of a bond, alkylene, alkenylene and alkynylene;

Q is independently selected at each occurrence from the group consisting of a bond, alkylene, alkenylene, alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=$NR_S$)N($R_{S'}$)—, —N($R_{S'}$)C(=$NR_S$)—, —S(O)—, —SO$_2$—, —O—SO$_2$—, —SO$_2$—O—, —O—S(O)—, —S(O)—O—, —C(O)O— and —OC(O)—;

$R^{10}$, $R^{15}$, $R^{15'}$, $R^{18}$, $R^{26}$, $R^{30}$, $R^{33}$, $R^{38}$, $R^{41}$, and $R^{41'}$ are each independently optionally substituted at each occurrence with at least one substituent selected from the group consisting of halogen, oxo, thioxo, hydroxy, mercapto, nitro, cyano, amino, carboxy, formyl, phosphate and azido; and each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-$M_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, alkyl, alkenyl, alkynyl, alkoxy, thioalkoxy, alkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl.

In one embodiment, the present invention features compounds having Formula I, tautomers thereof, and pharmaceutically acceptable salts of the compounds or tautomers, wherein:

A and B are each independently selected from $C_4$-$C_{11}$carbocyclyl or $M_4$-$M_{11}$heterocyclyl, and are each independently optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$carbocyclyl, $M_3$-$M_6$heterocyclyl, -$L_S$-O—$R_S$, -$L_S$-S—$R_S$, -$L_S$-C(O) $R_S$, -$L_S$-OC(O)$R_S$, -$L_S$-C(O)O$R_S$, -$L_S$-N($R_S R_{S'}$), -$L_S$-C (=N$R_S$)$R_{S'}$, -$L_S$-S(O)$R_S$, -$L_S$-SO$_2 R_S$, -$L_S$-C(O)N ($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), and -$L_S$-N($R_S$) SO$_2$N($R_S R_{S''}$);

$W_1$ and $W_2$ are each independently selected from N or C($R^{33}$);

Z is a bond, —C$R^{41}R^{41'}$— or —N$R^{41}$—, wherein $R^{41}$ and $R^{41'}$ are each independently selected from the group consisting of hydrogen, $C_1$-$C_6$alkyl, $C_2$-$C_6$alkenyl and $C_2$-$C_6$alkynyl;

$R^{10}$ and $R^{33}$ are each independently selected at each occurrence from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$carbocyclyl, $M_3$-$M_6$heterocyclyl, -$L_S$-O—$R_S$, -$L_S$-S—$R_S$, -$L_S$-C(O) $R_S$, -$L_S$-OC(O)$R_S$, -$L_S$-C(O)O$R_S$, -$L_S$-N($R_S R_{S'}$), -$L_S$-C (=N$R_S$)$R_{S'}$, -$L_S$-S(O)$R_S$, -$L_S$-SO$_2 R_S$, -$L_S$-C(O)N ($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N ($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl);

X is selected from the group consisting of a bond, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N ($R_S$)—, -$L_S$-N($R_S$)C(O)N($R_{S'}$)—, -$L_S$-C(=N$R_S$)N ($R_{S'}$)—, -$L_S$-N($R_{S'}$)C(=N$R_S$)—, -$L_S$-S(O)—, -$L_S$-SO$_2$—, -$L_S$-C(O)O— and -$L_S$-OC(O)—;

$R^{22}$ is $C_4$-$C_{11}$carbocyclyl or $M_4$-$M_{11}$heterocyclyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S (O)$R_S$, -$L_S$-SO$_2 R_S$, -$L_S$-C(O)N($R_S R_{S'}$), -$L_S$-N($R_S$)C(O) $R_{S'}$, -$L_S$-C(=N$R_S$)N($R_{S'} R_{S''}$), -$L_S$-N($R_{S'}$)C(=N$R_S$)$R_{S''}$, -$L_S$-N=C(N$R_S R_{S'}$)(N$R_S R_{S'}$), -$L_S$-N($R_S$)C(O)N ($R_{S'} R_{S''}$), -$L_S$-N($R_S$)SO$_2 R_{S'}$, -$L_S$-SO$_2$N($R_S R_{S'}$), -$L_S$-N ($R_S$)SO$_2$N($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl); or $R^{22}$ is $C_1$-$C_6$alkyl, $C_1$-$C_6$alkenyl or $C_1$-$C_6$alkynyl, and is optionally substituted with one or more $R^{26}$; or $R^{22}$ is hydrogen;

Y is selected from the group consisting of a bond, -$L_S$-O—, -$L_S$-C(O)—, -$L_S$-S(O)$_2$—, -$L_S$-S(O)—, -$L_S$-OS(O)$_2$—, -$L_S$-OS(O)—, -$L_S$-C(O)O—, -$L_S$-OC(O)—, -$L_S$-OC(O) O—, -$L_S$-C(O)N($R^{15}$)—, -$L_S$-N($R^{15}$)C(O)—, -$L_S$-C(O) N($R^{15}$)O—, -$L_S$-N($R^{15}$)C(O)O—, -$L_S$-C(O)N($R^{15}$)N ($R^{15}$)—, -$L_S$-S—, -$L_S$-C(S)—, -$L_S$-C(S)O—, -$L_S$-OC (S)—, -$L_S$-N($R^{15}$)—, -$L_S$-C(S)N($R^{15}$)—, -$L_S$-N($R^{15}$)C (S)—, -$L_S$-N($R^{15}$)S(O)—, -$L_S$-N($R^{15}$)S(O)$_2$—, -$L_S$-S (O)$_2$N($R^{15}$)—, -$L_S$-S(O)N($R^{15}$)—, -$L_S$-C(S)N($R^{15}$) O—, and -$L_S$-C(S)N($R^{15}$)N($R^{15}$)—, wherein $R^{15}$ and $R^{15'}$ are each independently selected at each occurrence from the group consisting of hydrogen, $C_1$-$C_6$alkyl, $C_2$-$C_6$alkenyl and $C_2$-$C_6$alkynyl;

$R^{50}$ is -$L^1$-$A^1$, wherein $A^1$ is selected from the group consisting of $C_4$-$C_{11}$carbocyclyl, $M_4$-$M_{11}$heterocyclyl, $C_1$-$C_6$alkyl, $C_2$-$C_6$alkenyl and $C_2$-$C_6$alkynyl, and $L^1$ is selected from the group consisting of a bond, $C_1$-$C_6$alkylene, $C_2$-$C_6$alkenylene and $C_2$-$C_6$alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C (=N$R_S$)$R_{S'}$, -$L_S$-S(O)$R_S$, -$L_S$-SO$_2 R_S$, -$L_S$-C(O)N ($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N ($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C (O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N ($R_S R_{S'}$), -$L_S$-N($R_S$)SO$_2$N($R_{S'} R_{S''}$), carbocyclyl, heterocyclyl, carbocyclyl$C_1$-$C_6$alkyl, heterocyclylcl-$C_1$-$C_6$alkyl, -$L_E$-Q-$L_{E'}$-($C_3$-$C_{18}$carbocyclyl) and -$L_E$-Q-$L_{E'}$-($M_3$-$M_{18}$heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkylene, $C_2$-$C_6$alkenylene and $C_2$-$C_6$alkynylene;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N ($R_S$)—, —N($R_S$)C(O)O—, —C(O)N($R_S$)—, —N($R_S$)C (O)N($R_{S'}$)—, —C(=N$R_S$)N($R_{S'}$)—, —N($R_{S'}$)C (=N$R_S$)—, —S(O)—, —SO$_2$—, —O—SO$_2$—, —SO$_2$—(O)—, —O—S(O)—, —S(O)—(O)—, —C(O)O— and —OC(O)—;

$R^{10}$, $R^{15}$, $R^{15'}$, $R^{18}$, $R^{26}$, $R^{30}$, $R^{33}$, $R^{48}$, $R^{41}$, and $R^{41'}$ are each independently optionally substituted at each occurrence with at least one substituent selected from the group consisting of halogen, oxo, thioxo, hydroxy, mercapto, nitro, cyano, amino, carboxy, formyl, phosphate, and azido; and each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-

$M_{18}$heterocyclyl) is independently optionally substituted at each occurrence with at least one substituent selected from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl.

In one example of this embodiment, Y is -$L_S$-O—, -$L_S$-S— or -$L_S$-N($R^{15}$)—, and $R^{50}$ is -$L^1$-$A^1$, wherein $L^1$ is a bond, $C_1$-$C_6$alkylene, $C_2$-$C_6$alkenylene or $C_2$-$C_6$alkynylene and is optionally substituted with one or more $R^{38}$, and $A^1$ is $C_4$-$C_{11}$carbocyclyl or $M_4$-$M_{11}$heterocyclyl and is optionally substituted with one or more $R^{30}$.

In another example of this embodiment, Y is a bond, and $R^{50}$ is -$L^1$-$A^1$, wherein $L^1$ is a bond, $C_1$-$C_6$alkylene, $C_2$-$C_6$alkenylene or $C_2$-$C_6$alkynylene and is optionally substituted with one or more $R^{38}$, and $A^1$ is $C_4$-$C_{11}$carbocyclyl or $M_4$-$M_{11}$heterocyclyl and is optionally substituted with one or more $R^{30}$.

In still another example of this embodiment, Y is a bond, and $R^{50}$ is -$L^1$-$A^1$, wherein $L^1$ is selected from the group consisting of a bond, $C_1$-$C_6$alkylene, $C_2$-$C_6$alkenylene and $C_2$-$C_6$alkynylene and is optionally substituted with one or more $R^{38}$, and $A^1$ is hydrogen or $R^{18}$.

In yet another example of this embodiment, Y is selected from the group consisting of -$L_S$-S(O)$_2$N($R^{15}$)—, -$L_S$-OS(O)$_2$—, -$L_S$-OC(O)—, -$L_S$-C(O)O—, -$L_S$-C(O)— and —N($R^{15}$)C(O)O—.

In still yet another example of this embodiment, A and B are each independently selected from $C_5$-$C_6$carbocyclyl or $M_5$-$M_6$heterocyclyl and are each independently optionally substituted with one or more $R^{18}$.

In still another example of this embodiment, $W_1$ and $W_2$ are N, and Z is —$NR^{41}$—.

In yet another example of this embodiment, X is —O— or —S—, and $R^{22}$ is $C_5$-$C_6$carbocyclyl or $M_5$-$M_6$heterocyclyl and is optionally substituted with one or more $R^{26}$.

In yet another example of this embodiment, the moiety

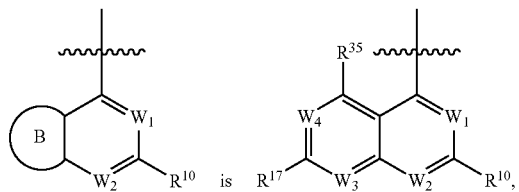

wherein:
$W_1$, $W_2$, $W_3$ and $W_4$ are each independently selected from N or C($R^{33}$); and
$R^{10}$, $R^{17}$, $R^{33}$ and $R^{35}$ are each independently selected at each occurrence from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$carbocyclyl, $M_3$-$M_6$heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2$$R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2$$R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl).

In yet another example of this embodiment, the moiety

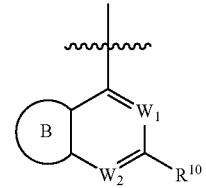

is selected from the group consisting of

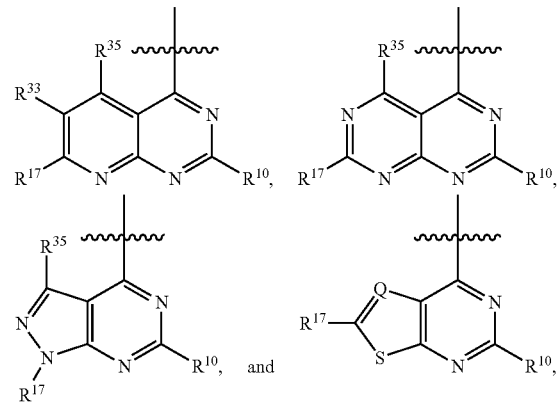

wherein:
Q is N or C($R^{33}$); and
$R^{10}$, $R^{17}$, $R^{33}$ and $R^{35}$ are each independently selected at each occurrence from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$carbocyclyl, $M_3$-$M_6$heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2$$R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2$$R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl).

In a further example of this embodiment, A and B are each independently selected from $C_5$-$C_6$carbocyclyl or $M_5$-$M_6$heterocyclyl and are each independently optionally substituted with one or more $R^{18}$, wherein:
$W_1$ and $W_2$ are N;
Z is —$NR^{41}$—;
X is —O— or —S—;
$R^{22}$ is $C_5$-$C_6$carbocyclyl or $M_5$-$M_6$heterocyclyl and is optionally substituted with one or more $R^{26}$
Y is a bond, -$L_S$-O—, -$L_S$-S— or -$L_S$-N($R^{15}$)—; and
$A^1$ is $C_5$-$C_{10}$carbocyclyl or $M_5$-$M_{10}$heterocyclyl and is optionally substituted with one or more $R^{30}$.

In another example of this embodiment, A and B are each independently selected from $C_5$-$C_6$carbocyclyl or $M_5$-$M_6$heterocyclyl and are each independently optionally substituted with one or more $R^{18}$, wherein:
  $W_1$ and $W_2$ are N;
  Z is —$NR^{41}$—;
  X is —O— or —S—;
  $R^{22}$ is

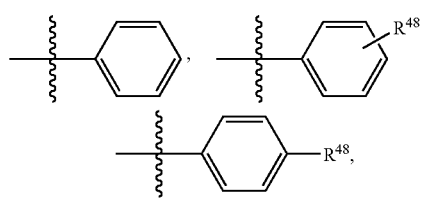

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ (e.g., $R^{48}$ or the phenyl ring in $R^{22}$) is optionally substituted with one or more $R^{26}$;
  Y is a bond, -$L_S$-O—, -$L_S$-S— or -$L_S$-N($R^{15}$)—; and
  $A^1$ is $C_5$-$C_{10}$carbocyclyl or $M_5$-$M_{10}$heterocyclyl and is optionally substituted with one or more $R^{30}$.

In still another example of this embodiment, the moiety

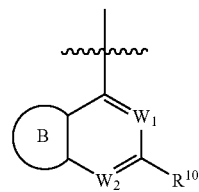

is selected from the group consisting of

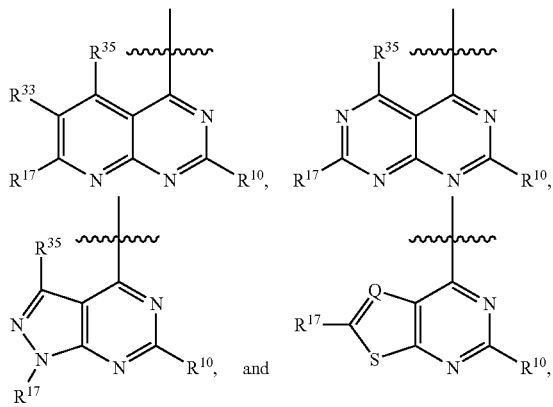

wherein:
  Q is N or C($R^{33}$);
  $R^{10}$, $R^{17}$, $R^{33}$ and $R^{35}$ are each independently selected at each occurrence from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$carbocyclyl, $M_3$-$M_6$heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl);

A is $C_5$-$C_6$carbocyclyl or $M_5$-$M_6$heterocyclyl and is optionally substituted with one or more $R^{18}$,
  Z is —$NR^{41}$—;
  X is —O— or —S—;
  $R^{22}$ is

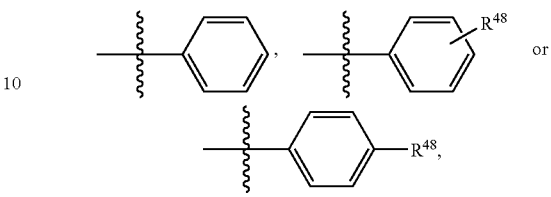

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ (e.g., $R^{48}$ or the phenyl ring in $R^{22}$) is optionally substituted with one or more $R^{26}$;
  Y is a bond, -$L_S$-O—, -$L_S$-S— or -$L_S$-N($R^{15}$)—; and
  $A^1$ is $C_5$-$C_{10}$carbocyclyl or $M_5$-$M_{10}$heterocyclyl and is optionally substituted with one or more $R^{30}$.

In another embodiment, the present invention features a family of pyridopyrimidinyl-aminophenyl ether compounds, tautomers of the compounds, or pharmaceutically acceptable salts of the compounds or tautomers, wherein the compounds of this family correspond in structure to Formula II:

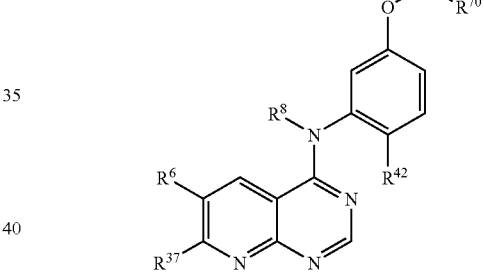

II wherein:
  $R^6$ is selected from the group consisting of hydrogen and cyano;
  $R^8$ is selected from the group consisting of hydrogen and arylalkyl;
  $R^{25}$ is selected from the group consisting of hydrogen and alkyl;
  $R^{37}$ is selected from the group consisting of hydrogen, alkyl, hydroxyalkyl, and cycloalkyl;
  $R^{42}$ is selected from the group consisting of arylsulfanyl, heteroarylsulfanyl, and aryloxy; wherein $R^{42}$ is optionally substituted with one or more substituents independently selected from $R^{46}$;
  $R^{46}$ is one or more substituents selected from the group consisting of hydrogen, hydroxy, amino, halogen, dialkylamino, and alkoxycarbonylamino;
  $R^{70}$ is selected from the group consisting of aryl, and heterocyclo; wherein $R^{70}$ is optionally substituted with $R^{75}$;
  $R^{75}$ is one or more substituents independently selected from the group consisting of hydrogen, halogen, alkoxy, cyano, alkyl, haloalkyl, and aryl.

In a subset family of this embodiment within Formula II, $R^6$ is selected from the group consisting of hydrogen and cyano;
  $R^8$ is selected from the group consisting of hydrogen and phenylmethyl;

$R^{25}$ is selected from the group consisting of hydrogen and methyl;

$R^{37}$ is selected from the group consisting of hydrogen, methyl, ethyl, t-butyl, isopropyl, hydroxymethylethyl, and cyclohexyl;

$R^{42}$ is selected from the group consisting of phenylsulfanyl, phenoxy, and pyrimidinylsulfanyl;

$R^{46}$ is selected from the group consisting of hydrogen, hydroxy, amino, N,N-dimethylamino, and t-butoxycarbonylamino;

$R^{70}$ is selected from the group consisting of phenyl, thiazolyl, pyridinyl, tetrahydrofuranyl, naphthyl, quinolinyl, and thienyl;

$R^{75}$ is one or more substituents selected from the group consisting of hydrogen, methyl, butyl, hydroxy, methoxy, bromo, chloro, fluoro, cyano, trifluoromethyl, and phenyl.

In still another embodiment, the present invention features a family of pyridopyrimidinyl-aminophenyl alkyl ether compounds, tautomers of the compounds, or pharmaceutically acceptable salts of the compounds or tautomers, wherein the compounds of this family correspond in structure to Formula III:

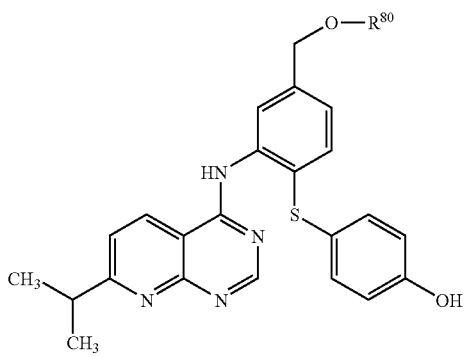

III wherein $R^{80}$ is selected from the group consisting of hydrogen, alkylcarbonyl, and haloaryl.

In a subset family of this embodiment within Formula III, $R^{80}$ is selected from the group consisting of hydrogen, methylcarbonyl, and bromophenyl.

In yet another embodiment, the present invention features a family of thiazolopyrimidinyl-aminophenyl and thienopyrimidinyl-aminophenyl compounds, tautomers of the compounds, or pharmaceutically acceptable salts of the compounds or tautomers, wherein the compounds of this family correspond in structure to Formula IV:

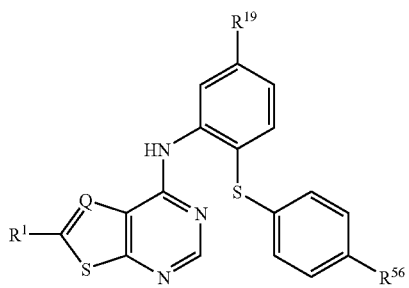

IV wherein:

Q is selected from the group consisting of N and CH;

$R^1$ is selected from the group consisting of alkylsulfanyl, cyanoalkylsulfanyl, and alkyl;

$R^{19}$ is selected from the group consisting of alkyl and haloarylalkoxy;

$R^{56}$ is selected from the group consisting of hydrogen, hydroxy, alkyl, and alkylcarbonylamino.

In a subset family of this embodiment within Formula IV, $R^1$ is selected from the group consisting of methylsulfanyl, cyanomethylsulfanyl, propyl, and butyl;

$R^{19}$ is selected from the group consisting of methyl and bromophenylmethoxy;

$R^{56}$ is selected from the group consisting of hydrogen, hydroxy, methyl, and methylcarbonylamino.

In a further embodiment, the present invention features a family of pyrimidopyrimidinyl-aminophenyl compounds, tautomers of the compounds, or pharmaceutically acceptable salts of the compounds or tautomers, wherein the compounds of this family correspond in structure to Formula V:

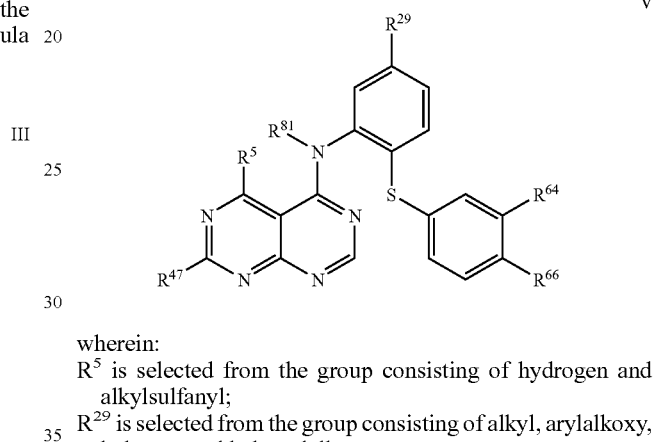

V wherein:

$R^5$ is selected from the group consisting of hydrogen and alkylsulfanyl;

$R^{29}$ is selected from the group consisting of alkyl, arylalkoxy, halogen, and haloarylalkoxy;

$R^{47}$ is selected from the group consisting of alkyl, haloalkyl, alkylsulfanyl, arylalkylsulfanyl, and heterocyclo;

$R^{64}$ is selected from the group consisting of hydrogen, alkoxy, and alkyl;

$R^{66}$ is selected from the group consisting of hydrogen, hydroxy, aryloxy, alkylsulfonyloxy, alkylcarbonylaminoarylsulfonoyloxy, haloarylsulfonyloxy, cyano, arylalkoxy, alkylcarbonylamino, halogen, and alkyl;

$R^{81}$ is selected from the group consisting of hydrogen, alkoxy, and carbonyl.

In a subset family of this embodiment within Formula V, $R^5$ is selected from the group consisting of hydrogen and methylsulfanyl;

$R^{29}$ is selected from the group consisting of methyl, ethyl, fluoro, phenylmethoxy, and bromophenylmethoxy;

$R^{47}$ is selected from the group consisting of hydrogen, propyl, isopropyl, ethylsulfanyl, piperidinyl, morpholinyl, heptafluororpropyl, and phenylmethylsulfanyl;

$R^{64}$ is selected from the group consisting of hydrogen, methoxy, hydroxy, and methoxy;

$R^{66}$ is selected from the group consisting of hydrogen, methyl, hydroxy, methoxy, phenoxy, phenylmethoxy, phenylsulfanyloxy, isopropylsulfonyloxy, methylcarbonylaminophenylsulfonyloxy, bromophenylsulfanyloxy, cyano, methylcarbonylamino, and fluoro;

$R^{81}$ is selected from the group consisting of hydrogen, t-butoxy, and carbonyl.

In another embodiment, the present invention features a family of pyrazolopyrimidinyl-aminophenyl compounds, tautomers of the compounds, or pharmaceutically acceptable salts of the compounds or tautomers, wherein the compounds of this family correspond in structure to Formula VI:

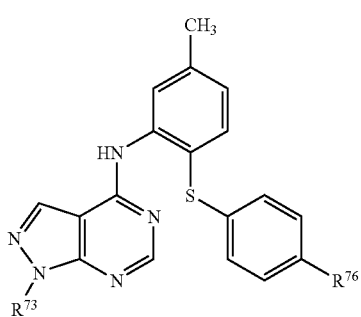

wherein:

$R^{73}$ is alkyl;

$R^{76}$ is selected from the group consisting of hydroxy, alkylaminocarbonyl, and alkylcarbonylamino.

In a subset family of this embodiment within Formula VI, $R^{73}$ is selected from the group consisting of methyl and butyl; $R^{76}$ is selected from the group consisting of hydroxy, methylaminocarbonyl, and methylcarbonylamino.

In still yet another embodiment, the present invention features a family of pyridopyrimidinyl-aminophenyl compounds, tautomers of the compounds, or pharmaceutically acceptable salts of the compounds or tautomers, wherein the compounds of this family correspond in structure to Formula VII:

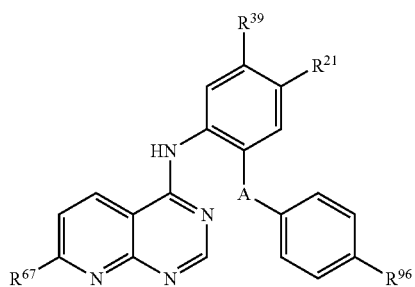

wherein:

A is selected from the group consisting of O and S;

$R^{21}$ is selected from the group consisting of hydrogen and hydroxy;

or $R^{21}$ taken together with $R^{39}$ form a 5-12 membered heterocycle containing at least two heteroatoms selected from the group consisting of O, N, and S; wherein the heterocycle is optionally substituted aryl or halogen; or $R^{39}$ is selected from the group consisting of hydrogen, alkyl, arylalkenyl, dialkylamino, heteroaryl, haloheteroaryl, haloarylaminosulfonyl, arylsulfonyloxy, alkylcarbonyloxy, cycloalkylaminocarbonyl, arylalkoxycarbonylamino, haloheteroaryl, alkoxycarbonyl, and NH—$R^{99}$;

$R^{99}$ is selected from the group consisting of hydrogen, arylalkyl, cycloalkylalkyl, aryl, heteroaryl, haloarylalkylamino, arylalkylamino, and alkylheteroaryl;

$R^{67}$ is selected from the group consisting of hydrogen, alkyl, cycloalkyl, and alkylcycloalkyl;

$R^{96}$ is selected from the group consisting of hydrogen, hydroxy, amino, alkoxy, arylsulfonyloxy, alkylcarbonylamino, alkoxy, halogen, alkoxycarbonyloxy, haloalkoxycarbonylamino, and arylalkoxy.

In a subset family of this embodiment within Formula VII, $R^{21}$ is selected from the group consisting of hydrogen and hydroxy, or when taken together with $R^{39}$ form benzooxazolyl optionally substituted with phenyl or bromo; or $R^{39}$ is selected from the group consisting of hydrogen, methyl, phenylethenyl, N,N-dipropylamino, pyrrolyl, bromophenylaminosulfonyl, phenylsulfonyloxy, t-butylcarbonyloxy, N-cyclohexylaminocarbonyl, N-cyclopentylaminocarbonyl, phenylmethoxycarbonylamino, methoxycarbonylamino, methoxycarbonyl and bromobenzimidazolyl;

$R^{67}$ is selected from the group consisting of hydrogen, methyl, ethyl, isopropyl, t-butyl, sec-butyl, cyclopropyl, cyclobutyl, and methylcyclopropyl;

$R^{96}$ is selected from the group consisting of hydrogen, hydroxy, amino, phenylsulfonyloxy, methylcarbonylamino, methoxy, fluoro, t-butoxycarbonylamino, trichloroethoxycarbonylamino, and phenylmethoxy;

$R^{99}$ is selected from the group consisting of hydrogen, phenylmethyl, phenylethyl, cyclopentylmethyl, furanyl, thienyl, naphthayl, bromophenylmethylamino, phenylmethylamino, and methylpyrido[2,3-d]pyrimidinyl.

In yet another embodiment, the present invention features a family of pyridopyrimidinyl-aminophenyl compounds, tautomers of the compounds, or pharmaceutically acceptable salts of the compounds or tautomers, wherein the compounds of this family correspond in structure to Formula VIII:

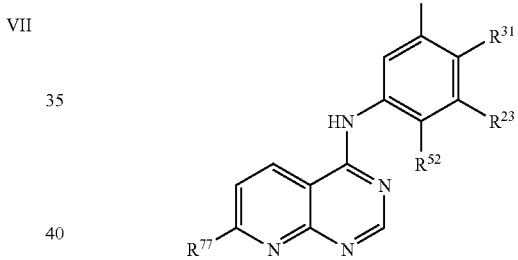

wherein:

$R^{23}$ is selected from the group consisting of hydrogen, alkoxyaryl, alkoxyarylsulfanyl, hydroxyarylsulfanyl, haloarylalkoxy, cyanoarylalkoxy, and arylalkoxy;

$R^{31}$ is selected from the group consisting of hydrogen and halogen;

$R^{49}$ is selected from the group consisting of hydrogen, arylalkoxy, haloarylcarbonylamino, alkoxyarylcarbonylamino, arylalkenyl, arylalkyl, halogen, cyano, haloaryloxyalkyl, alkyl, alkoxyarylsulfanyl, haloheteroaryl, and alkoxycarbonyl;

$R^{52}$ is selected from the group consisting of hydrogen, halogen, alkyl, hydroxyaryloxy, aryloxy, hydroxyalkylaryloxy, alkoxyarylalkyl, alkoxyaryloxy, alkylarylalkoxyarylamino, arylalkyl, heteroaryl, and aminoaryloxy;

$R^{77}$ is selected from the group consisting of hydrogen, alkyl, and cycloalkyl.

In a subset family of this embodiment within Formula VIII, $R^{23}$ is selected from the group consisting of hydrogen, methoxyphenyl, methoxyphenylsulfanyl, hydroxyphenylsulfanyl, fluorophenylmethoxy, difluorophenylmethoxy, cyanophenylmethoxy, phenylmethoxy, bromophenylmethoxy, and methoxyphenylmethoxy;

$R^{31}$ is selected from the group consisting of hydrogen, chloro, and fluoro;

$R^{49}$ is selected from the group consisting of hydrogen, methyl, phenylmethoxy, bromophenylcarbonylamino, chlorophenylcarbonylamino, methoxyphenylcarbonylamino, fluorophenylcarbonylamino, phenylethenyl, phenylethyl, chloro, fluoro, bromo, cyano, bromophenoxymethyl, and hydroxyphenylsulfanyl.

$R^{52}$ is selected from the group consisting of hydrogen, fluoro, bromo, methyl, phenoxy, hydroxyphenoxy, hydroxyethylphenoxy, methoxyphenylethyl, methoxyphenoxy, N-methyl-N-4-phenylmethoxyjphenylamino, phenylmethyl, and thiazolylbenzimidazolyl;

$R^{77}$ is selected from the group consisting of hydrogen, methyl, and isopropyl.

Salts of the Compounds of this Invention

The compounds of the present invention, or tautomers thereof, can be used in the form of salts. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient, the salt preferably is pharmaceutically acceptable. Pharmaceutically acceptable salts include, but are not limited to, salts commonly used to form alkali metal salts and/or to form addition salts of free acids or free bases. In general, these salts typically may be prepared by conventional means with a compound of this invention by reacting, for example, the appropriate acid or base with the compound.

Pharmaceutically acceptable acid addition salts of the compounds of this invention may be prepared from an inorganic or organic acid. Examples of suitable inorganic acids include hydrochloric, hydrobromic acid, hydroionic, nitric, carbonic, sulfuric, and phosphoric acid. Suitable organic acids generally include, for example, aliphatic, cycloaliphatic, aromatic, araliphatic, heterocyclyl, carboxyic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically acceptable base addition salts of the compounds of this invention include, for example, metallic salts and organic salts. Preferred metallic salts include, but are not limited to, alkali metal (group Ia) salts, alkaline earth metal (group IIa) salts, and other physiological acceptable metal salts. Such salts may be made from aluminum, calcium, lithium, magnesium, potassium, sodium, and zinc. Non-limiting examples of preferred organic salts can be made from tertiary amines and quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), aralkyl halides (e.g., benzyl and phenethyl bromides), and others.

Solvates, Prodrugs, and Isomers

The compounds of the present invention, tautomers thereof, and their salts, may also exist in the form of solvates with water, for example hydrates, or with organic solvents such as methanol, ethanol or acetonitrile to form, respectively, a methanolate, ethanolate or acetonitrilate. The compounds of the present invention may exist in each form of solvate or mixtures thereof.

In one aspect, the compounds, tautomers or salts of the present invention may be in the form of prodrugs. Some are aliphatic or aromatic esters derived from acidic groups on compounds of this invention. Others are aliphatic or aromatic esters of hydroxyl or amino groups on compounds of this invention. The present invention also features phosphate prodrugs of hydroxyl groups on the compounds of this invention.

The compounds of the invention may comprise asymmetrically substituted carbon atoms known as chiral centers. These chiral centers are designated as "R" or "S" depending on the configuration of substituents around the chiral carbon atom. The terms "R" and "S" used herein are configurations as defined in Nomenclature of Organic Chemistry, Section E: Stereochemistry, Recommendations 1974, PURE APPL. CHEM., 45:11-30 (1976). The compounds of this invention may exist, without limitation, as single stereoisomers (e.g., single enantiomers or single diastereomer), mixtures of stereoisomers (e.g. any mixture of enantiomers or diastereomers), or racemic mixtures. All such single stereoisomers, mixtures and racemates are encompassed within the scope of the invention. Compounds identified herein as single stereoisomers are meant to describe compounds that are present in a form that is substantially free from other stereoisomers (e.g., other enantiomers or diastereomers). By "substantially free," it means that at least 80% of the compound in a composition is the desired stereoisomer; preferably, at least 90% of the compound in a composition is the desired stereoisomer; and more preferably, at least 95%, 96%, 97%, 98% or 99% of the compound in a composition is the desired stereoisomer. Where the stereochemistry of the chiral carbon(s) present in a chemical structure is not specified, the chemical structure is intended to encompass compounds containing either stereoisomer of each chiral center present in the chemical structure.

Individual stereoisomers of the compounds of this invention can be prepared using many methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished on chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The compounds of the invention includes each conformational isomer of these compounds and mixtures thereof.

Certain compounds of the invention may also exist in zwitterionic form and the invention includes each zwitterionic form of these compounds and mixtures thereof.

DEFINITIONS

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers.

Where a recited compound exists in various tautomeric forms, the compound is intended to encompass all tautomeric forms. Certain compounds are described herein using general formulas that include variables (e.g., $R^{10}$, $W_1$, A, $L^1$, X, or Y). Unless otherwise specified, each variable within such a formula is defined independently of any other variable, and any variable that occurs more than one time in a formula is defined independently at each occurrence. If substituents are described as being "independently selected" from a group, each substituent is selected independently from the other. Each substituent therefore can be identical to or different from the other substituent(s).

The number of carbon atoms in a hydrocarbyl substituent can be indicated by the prefix "$C_x$-$C_y$," where x is the minimum and y is the maximum number of carbon atoms in the substituent. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms. A prefix attached to a multiple-component substituent only applies to the first component that immediately follows the prefix. To illustrate, the term "alkylaryl" contains two components: alkyl and aryl. Thus, for example, $C_1$-$C_6$alkylaryl refers to a $C_1$-$C_6$alkyl appended to the parent molecular moiety through an aryl group. Likewise, alkyl$C_6$-$C_{10}$aryl refers to an alkyl group appended to the parent molecular moiety through a $C_6$-$C_{10}$aryl group. Similarly, the prefix "halo" on haloalkoxyalkyl indicates that the alkoxy component is substituted with one or more halogen radicals, while the prefix "halo" on alkoxyhaloalkyl indicates that the alkyl component is substituted with one or more halogen radicals.

When words are used to describe a linking element between two other elements of a depicted chemical structure, the leftmost-described component of the linking element is the component that is bound to the left element in the depicted structure. To illustrate, if the chemical structure is X-L-Y and L is described as methylarylethyl, then the chemical would be X-methyl-aryl-ethyl-Y.

If a linking element in a depicted structure is a bond, then the left element in the depicted structure is bound directly to the right element in the depicted structure. For example, if a chemical structure is depicted as X-L-Y and L is selected as a bond, then the chemical structure would be X—Y. For another example, if a chemical moiety is depicted as -L-X and L is selected as a bond, then the chemical moiety would be —X. For yet another example, if a chemical structure is depicted as X-$L_1$-$L_2$-Y, X-$L_1$-$L_2$-$L_3$-Y or X-$L_1$-$L_2$-...-$L_N$-Y, and $L_1$, $L_2$, $L_3$, ... $L_N$ are selected as bonds, then the chemical structure would be X—Y.

When a chemical formula is used to describe a substituent, the dash on the right (or left) side of the formula indicates the portion of the substituent that has the free valence(s).

If a substituent is described as being "substituted," a non-hydrogen radical is in the place of one or more hydrogen radials on a carbon, nitrogen or oxygen of the substituent. Thus, for example, a substituted alkyl substituent is an alkyl substituent wherein at least one non-hydrogen radical is in the place of a hydrogen radical(s) on the alkyl substituent. To illustrate, monofluoroalkyl is alkyl substituted with one fluoro radical, and difluoroalkyl is alkyl substituted with two fluoro radicals. It should be recognized that if there are two or more substitutions on a substituent, each of the non-hydrogen radicals may be identical or different unless otherwise stated.

A substituent is "substitutable" if it comprises at least one carbon, nitrogen or oxygen atom that is bonded to one or more hydrogen atoms.

If a substituent is described as being "optionally substituted", the substituent may be either substituted or not substituted. If a substituent is described as being optionally substituted with up to a particular number of non-hydrogen radicals, that substituent may be either not substituted, or substituted by up to that particular number of non-hydrogen radicals or by up to the maximum number of substitutable positions on the substituent, whichever is less. Thus, for example, if a substituent is described as a heteroaryl optionally substituted with up to three non-hydrogen radicals, then any heteroaryl with less than three substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

The term "alkenyl" (alone or in combination with another term(s)) means a straight- or branched-chain hydrocarbyl substituent containing one or more double bonds and typically from 2 to 20 carbon atoms, more typically from 2 to 8 carbon atoms, and even more typically from 2 to 6 carbon atoms. Each carbon-carbon double bond may have either cis or trans geometry within the alkenyl moiety, relative to groups substituted on the double bond carbons. Non-limiting examples of such substituents include ethenyl (vinyl), 2-propenyl, 3-propenyl, 1,4-pentadienyl, 1,4-butadienyl, 1-butenyl, 2-butenyl, and 3-butenyl.

The term "alkenylene" (alone or in combination with another term(s)) refers to a divalent unsaturated hydrocarbyl group which may be linear or branched and which has at least one carbon-carbon double bond. An alkenylene group typically contains 2 to 20 carbon atoms, more typically from 2 to 8 carbon atoms, and even more typically from 2 to 6 carbon atoms. Non-limiting examples of alkenylene groups include —C(H)=C(H)—, —C(H)=C(H)—CH$_2$—, —C(H)=C(H)—CH$_2$—CH$_2$—, —CH$_2$—C(H)=C(H)—CH$_2$—, —C(H)=C(H)—CH(CH$_3$)—, and —CH$_2$—C(H)=C(H)—CH(CH$_2$CH$_3$)—.

The term "alkoxy" (alone or in combination with another term(s)) refers to an alkyl group appended to the parent molecular moiety through an oxy moiety (i.e., —O-alkyl). Non-limiting examples of such a substituent include methoxy (—O—CH$_3$), ethoxy, n-propoxy, isopropoxy, n-butoxy, isobutoxy, sec-butoxy, and tert-butoxy.

The term "alkoxyalkyl" (alone or in combination with another term(s)) refers to an alkoxy group appended to the parent molecular moiety through an alkylene group. Non-limiting examples of alkoxyalkyl include tert-butoxymethyl, 2-ethoxyethyl, 2-methoxyethyl, and methoxymethyl.

The term "alkoxycarbonyl" (alone or in combination with another term(s)) refers to an alkoxy group appended to the parent molecular moiety through a carbonyl group (i.e., —C(O)—O-alkyl). Representative examples of alkoxycarbonyl include, but are not limited to, methoxycarbonyl, ethoxycarbonyl

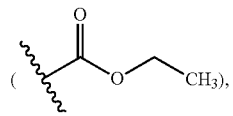

and tert-butoxycarbonyl.

The term "alkoxycarbonylamino" (alone or in combination with another term(s)) refers to N(R$_A$R$_B$)—, where R$_A$ is alkyl-O—C(O)—, and R$_B$ is alkyl-O—C(O)— or hydrogen. R$_A$ and R$_B$ may be identical or different.

The term "alkoxycarbonylaminoalkyl" (alone or in combination with another term(s)) refers to N(R$_A$R$_B$)-alkylene-, where R$_A$ is alkyl-O—C(O)—, and R$_B$ is alkyl-O—C(O)— or hydrogen. R$_A$ and R$_B$ may be identical or different.

The term "alkoxycarbonylalkyl" (alone or in combination with another term(s)) refers to an alkoxycarbonyl group appended to the parent molecular moiety through an alkylene group. Representative examples of alkoxycarbonylalkyl include, but are not limited to, 2-methoxy-2-oxoethyl, 2-ethoxy-2-oxoethyl, 3-methoxy-3-oxopropyl, 3-ethoxy-3-oxopropyl, 4-ethoxy-2-(ethoxycarbonyl)-4-oxobutyl, 5-methoxy-5-oxopentyl, and 6-methoxy-6-oxohexyl.

The term "alkyl" (alone or in combination with another term(s)) means a straight- or branched-chain saturated hydrocarbyl substituent typically containing from 1 to 20 carbon atoms, more typically from 1 to 8 carbon atoms, and even more typically from 1 to 6 carbon atoms. Non-limiting examples of such substituents include methyl, ethyl, n-propyl, isopropyl, n-butyl, isobutyl, sec-butyl, t-butyl, pentyl, iso-amyl, hexyl, and octyl.

The term "alkylamino" (alone or in combination with another term(s)) refers to —NR$_A$R$_B$, wherein R$_A$ is alkyl, and R$_B$ is hydrogen or alkyl. R$_A$ and R$_B$ may be identical or different. For instance, C$_1$-C$_6$alkylamino refers to —NR$_A$R$_B$, wherein R$_A$ is C$_1$-C$_6$alkyl, and R$_B$ is hydrogen or C$_1$-C$_6$alkyl.

The term "alkylaminoalkyl" (alone or in combination with another term(s)) refers to N(R$_A$R$_B$)-alkylene-, wherein R$_A$ is alkyl, and R$_B$ is hydrogen or alkyl. R$_A$ and R$_B$ may be identical or different. Thus, C$_1$-C$_6$alkylaminoC$_1$-C$_6$alky refers to N(R$_A$R$_B$)—C$_1$-C$_6$alkylene-, wherein R$_A$ is C$_1$-C$_6$alkyl, and R$_B$ is hydrogen or C$_1$-C$_6$alkyl.

The term "alkylcarbonyl" (alone or in combination with another term(s)) refers to an alkyl group appended to the parent molecular moiety through a carbonyl group (i.e., —C(O)-alkyl). Representative examples of alkylcarbonyl include, but are not limited to, acetyl, ethylcarbonyl

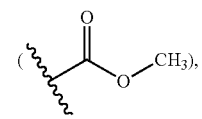

1-oxopropyl, 2,2-dimethyl-1-oxopropyl, 1-oxobutyl, and 1-oxopentyl.

The term "alkylcarbonylalkyl" (alone or in combination with another term(s)) refers to an alkylcarbonyl group appended to the parent molecular moiety through an alkylene group. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" (alone or in combination with another term(s)) refers to an alkylcarbonyl group appended to the parent molecular moiety through an oxy moiety. Representative examples of alkylcarbonyloxy include, but are not limited to, acetyloxy, ethylcarbonyloxy, and tert-butylcarbonyloxy.

The term "alkylcarbonyloxyalkyl" (alone or in combination with another term(s)) refers to an alkylcarbonyloxy group appended to the parent molecular moiety through an alkylene moiety. Representative examples of alkylcarbonyloxyalkyl include, but are not limited to, 2-(acetyloxy)ethyl, 3-(acetyloxy)propyl, and 3-(propionyloxy)propyl.

The terms "alkylene" or "alkylenyl" (alone or in combination with another term(s)) denote a divalent group derived from a straight or branched saturated hydrocarbyl chain typically containing from 1 to 20 carbon atoms, more typically from 1 to 8 carbon atoms, and even more typically from 1 to 6 carbon atoms. Representative examples of alkylene include, but are not limited to, —CH₂—, —CH₂CH₂—, —CH₂CH₂CH₂—, —CH₂CH₂CH₂CH₂—, and —CH₂CH (CH₃)CH₂—.

The term "alkynyl" (alone or in combination with another term(s)) means a straight- or branched-chain hydrocarbyl substituent containing one or more triple bonds and typically from 2 to 20 carbon atoms, more typically from 2 to 8 carbon atoms, and even more typically from 2 to 6 carbon atoms. Non-limiting examples of such substituents include ethynyl, 1-propynyl, 2-propynyl, 3-propynyl, decynyl, 1-butynyl, 2-butynyl, and 3-butynyl.

The terms "alkynylene" (alone or in combination with another term(s)) refers to a divalent unsaturated hydrocarbon group which may be linear or branched and which has at least one carbon-carbon triple bonds. Representative alkynylene groups include, by way of example, —C≡C—, —C≡C—CH₂—, —C≡C—CH₂—CH₂—, —CH₂—C≡C—CH₂—, —C≡C—CH(CH₃)—, and —CH₂—C≡C—CH (CH₂CH₃)—.

The term "amino" (alone or in combination with another term(s)) means —NH₂. The term "monosubstituted amino" (alone or in combination with another term(s)) means an amino substituent wherein one of the hydrogen radicals is replaced by a non-hydrogen substituent. The term "disubstituted amino" (alone or in combination with another term(s)) means an amino substituent wherein both of the hydrogen atoms are replaced by non-hydrogen substituents, which may be identical or different.

The term "aminocarbonyl" (alone or in combination with another term(s)) means —C(O)—NH₂, which also may be depicted as:

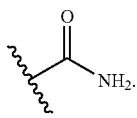

The term "aminoalkyl" (alone or in combination with another term(s)) means -alkylene-NH₂.

The term "aminoalkylcarbonyl" (alone or in combination with another term(s)) means —C(O)-alkylene-NH₂. For example, "aminomethylcarbonyl" may be depicted as:

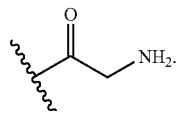

The term "aminosulfonyl" (alone or in combination with another term(s)) means —S(O)₂—NH₂, which also may be depicted as:

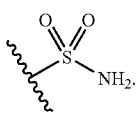

The term "aryl" (alone or in combination with another term(s)) refers to an aromatic carbocyclyl containing from 6 to 14 carbon ring atoms. Non-limiting examples of aryls include phenyl, naphthalenyl, anthracenyl, and indenyl. An aryl group can be connected to the parent molecular moiety through any substitutable carbon atom of the group.

The term "arylalkyl" (alone or in combination with another term(s)) refers to an aryl group appended to the parent molecular moiety through an alkylene group. Representative examples of substituted/unsubstituted arylalkyl include, but are not limited to, benzyl, 4-(benzyloxy)benzyl, 4-methoxybenzyl, 4-hydroxybenzyl, 3-(1,3-benzodioxol-5-yl)-2-methylpropyl, 3-(phenoxy)benzyl, 3-(1,3-benzodioxol-5-yl)propyl, 2-phenylethyl, 3-phenylpropyl, 2-naphthylmethyl, 3,5-ditert-butyl-2-hydroxybenzyl, 3-methoxybenzyl, 3,4-dimethoxybenzyl, 4-(dimethylamino)benzyl, 4-[3-(dimethylamino)propoxy]benzyl, (6-methoxy-2-naphthyl)methyl, and 2-naphth-2-ylethyl.

The term "arylalkylcarbonyl" (alone or in combination with another term(s)) refers to an arylalkyl group appended to the parent molecular moiety through a carbonyl group (i.e., arylalkyl-C(O)—). Representative examples of arylalkylcarbonyl include, but are not limited to, 2-naphthylacetyl and phenylacetyl.

The term "arylalkoxy" (alone or in combination with another term(s)) refers to an arylalkyl group appended to the parent molecular moiety through an oxy moiety (i.e., arylalkyl-O—). Representative examples of arylalkoxy include, but are not limited to, 2-phenylethoxy, 3-naphth-2-ylpropoxy, and 5-phenylpentyloxy.

The term "arylalkoxyalkyl" (alone or in combination with another term(s)) refers to an arylalkoxy group appended to the parent molecular moiety through an alkylene group. Representative examples of arylalkoxyalkyl include, but are not limited to, benzyloxymethyl, 2-(benzyloxy)ethyl, and (2-phenylethoxy)methyl.

The term "arylalkoxycarbonyl" (alone or in combination with another term(s)) refers to an arylalkoxy group appended to the parent molecular moiety through a carbonyl group. Representative examples of arylalkoxycarbonyl include, but are not limited to, benzyloxycarbonyl, and naphth-2-ylmethoxycarbonyl.

The term "arylcarbonyl" (alone or in combination with another term(s)) refers to an aryl group appended to the parent molecular moiety through a carbonyl group. Representative examples of arylcarbonyl include, but are not limited to, benzoyl and naphthoyl.

The term "aryloxy" (alone or in combination with another term(s)) refers to an aryl group appended to the parent molecular moiety through an oxy moiety. Representative examples of substituted/unsubstituted aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" (alone or in combination with another term(s)) refers to an aryloxy group appended to the parent molecular moiety through an alkylene group. Representative examples of aryloxyalkyl include, but are not limited to, 2-phenoxyethyl, 3-naphth-2-yloxypropyl, and phenoxymethyl.

The term "aryloxycarbonyl" (alone or in combination with another term(s)) refers to an aryloxy group appended to the parent molecular moiety through a carbonyl group.

The term "arylthio" (alone or in combination with another term(s)) refers to an aryl group appended to the parent molecular moiety through a sulfur atom (i.e., aryl-S—). Representative examples of arylthio include, but are not limited to, phenylthio, naphthalen-1-ylthio, and naphthalen-2-ylthio.

The term "arylthioalkyl" (alone or in combination with another term(s)) refers to aryl-S-alkylene-. Representative examples of arylthioalkyl include, but are not limited to, (phenylthio)methyl, 2-(phenylthio)ethyl, and 3-(phenylthio) propyl.

The term "arylthioalkoxy" (alone or in combination with another term(s)) refers to an arylthioalkyl group appended to the parent molecular moiety through an oxy group.

The term "arylthioalkoxyalkyl" (alone or in combination with another term(s)) refers to an arylthioalkoxy group appended to the parent molecular moiety through an alkylene group.

The terms "carbocycle" or "carbocyclic" or "carbocyclyl" (alone or in combination with another term(s)) refer to a saturated (e.g., "cycloalkyl"), partially saturated (e.g., "cycloalkenyl" or "cycloalkynyl") or completely unsaturated (e.g., "aryl") ring system containing zero heteroatom ring atom and typically from 3 to 18 carbon ring atoms. "Ring atoms" or "ring members" are the atoms bound together to form the ring or rings of a cyclic substituent. A carbocyclyl may be, without limitation, a single ring, or two or more fused rings, or bridged or spiro rings. A carbocyclyl may contain from 3 to 14 ring members (i.e., $C_3$-$C_{14}$carbocyclyl, such as $C_3$-$C_{14}$cycloalkyl), from 3 to 10 ring members (i.e., $C_3$-$C_{10}$carbocyclyl, such as $C_3$-$C_{10}$cycloalkyl), from 3 to 8 ring members (i.e., $C_3$-$C_8$carbocyclyl, such as $C_3$-$C_8$cycloalkyl), from 3 to 6 ring members (i.e., $C_3$-$C_6$carbocyclyl, such as $C_3$-$C_6$cycloalkyl), from 4 to 10 ring members (i.e., $C_4$-$C_{10}$carbocyclyl, such as $C_4$-$C_{10}$cycloalkyl and $C_4$-$C_{10}$cycloalkenyl), from 4 to 8 ring members (i.e., $C_4$-$C_8$carbocyclyl, such as $C_4$-$C_8$cycloalkyl and $C_4$-$C_8$cycloalkenyl), or from 5 to 7 ring members (i.e., $C_5$-$C_7$carbocyclyl, such as $C_5$-$C_7$cycloalkyl, $C_5$-$C_7$cycloalkenyl and phenyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydroindenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl. A carbocyclyl group can be attached to the parent molecular moiety through any substitutable carbon atom of the group.

The term "carbocyclylalkyl" (alone or in combination with another term(s)) refers to a carbocyclyl group appended to the parent molecular moiety through an alkylene group. For instance, $C_3$-$C_{10}$carbocyclyl$C_1$-$C_6$alkyl refers to a $C_3$-$C_{10}$carbocyclyl group appended to the parent molecular moiety through $C_1$-$C_6$alkylene. Likewise, $C_5$-$C_7$carbocyclyl$C_1$-$C_6$alkyl refers to a $C_5$-$C_7$carbocyclyl group appended to the parent molecular moiety through $C_1$-$C_6$alkylene.

The term "carbocyclylalkoxy" (alone or in combination with another term(s)) refers to a carbocyclylalkyl group appended to the parent molecular moiety through an oxy group (i.e., carbocyclyl-alkylene-O—). For instance, $C_3$-$C_{10}$carbocyclyl$C_1$-$C_6$alkoxy refers to a $C_3$-$C_{10}$carbocyclyl$C_1$-$C_6$alkyl group appended to the parent molecular moiety through an oxy group. Likewise, a $C_5$-$C_7$carbocyclyl$C_1$-$C_6$alkoxy group refers to a $C_5$-$C_7$carbocyclyl$C_1$-$C_6$alkyl group appended to the parent molecular moiety through an oxy group.

The term "carbocyclylalkoxyalkyl" (alone or in combination with another term(s)) refers to a carbocyclylalkoxy group appended to the parent molecular moiety through an alkylene group (i.e., carbocyclyl-alkylene-O-alkylene-). For instance, $C_3$-$C_{10}$carbocyclyl$C_1$-$C_6$alkoxy$C_1$-$C_6$alkyl refers to a $C_3$-$C_{10}$carbocyclyl$C_1$-$C_6$alkoxy group appended to the parent molecular moiety through a $C_1$-$C_6$alkylene group.

The term "carbocyclylalkoxycarbonyl" (alone or in combination with another term(s)) refers to a carbocyclylalkoxy group appended to the parent molecular moiety through a carbonyl group (i.e., —C(O)—O-alkylene-carbocyclyl). For instance, $C_3$-$C_{10}$carbocyclyl$C_1$-$C_6$alkoxycarbonyl refers to a $C_3$-$C_{10}$carbocyclyl$C_1$-$C_6$alkoxy group appended to the parent molecular moiety through a carbonyl group. As a non-limiting example, "phenylethoxycarbonyl" may be depicted as:

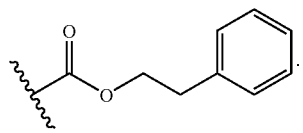

The term "carbocyclylalkylcarbonyl" (alone or in combination with another term(s)) refers to a carbocyclylalkyl group appended to the parent molecular moiety through a carbonyl group (i.e., —C(O)-alkylene-carbocyclyl). For example, "phenylethylcarbonyl" may be depicted as:

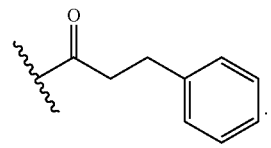

The term "carbocyclylcarbonyl" (alone or in combination with another term(s)) refers to a carbocyclyl group appended to the parent molecular moiety through a carbonyl group (i.e., carbocyclyl-C(O)—). For example, "phenylcarbonyl" may be depicted as:

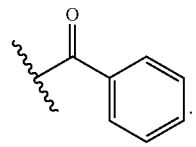

The term "carbocyclyloxy" (alone or in combination with another term(s)) refers to a carbocyclyl group appended to the parent molecular moiety through an oxy moiety (i.e., carbocyclyl-O—).

The term "carbocyclyloxyalkyl" (alone or in combination with another term(s)) refers to a carbocyclyloxy group appended to the parent molecular moiety through an alkylene group (i.e., carbocyclyl-O-alkylene-).

The term "carbocyclyloxycarbonyl" (alone or in combination with another term(s)) refers to a carbocyclyloxy group appended to the parent molecular moiety through a carbonyl group (i.e., —C(O)—O-carbocyclyl). For example, "phenyloxycarbonyl" may be depicted as:

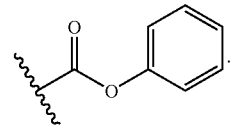

The term "carbocyclylthio" (alone or in combination with another term(s)) refers to a carbocyclyl group appended to the parent molecular moiety through a sulfur atom (i.e., carbocyclyl-S—).

The term "carbocyclylthioalkoxy" (alone or in combination with another term(s)) refers to carbocyclyl-alkylene-S—.

The term "carbocyclylthioalkoxyalkyl" (alone or in combination with another term(s)) refers to carbocyclyl-alkylene-S-alkylene-.

The term "carbocyclylthioalkyl" (alone or in combination with another term(s)) refers to a carbocyclylthio group appended to the parent molecular moiety through an alkylene group (i.e., carbocyclyl-S-alkylene-).

The term "carbocyclylcarbocyclyl" (alone or in combination with another term(s)) refers to a carbocyclyl group appended to the parent molecular moiety through another carbocyclyl group (i.e., carbocyclyl-carbocyclyl-). For instance, $C_3$-$C_{10}$carbocyclyl$C_5$-$C_7$carbocyclyl refers to a $C_3$-$C_{10}$carbocyclyl group appended to the parent molecular moiety through a $C_5$-$C_7$carbocyclyl group (i.e., $C_3$-$C_{10}$carbocyclyl-$C_5$-$C_7$carbocyclyl-).

The term "carbocyclylcarbocyclylalkyl" (alone or in combination with another term(s)) refers to a carbocyclylcarbocyclyl group appended to the parent molecular moiety through an alkylene group.

The term "carbocyclylalkoxycarbocyclylalkyl" (alone or in combination with another term(s)) refers to carbocyclyl-alkylene-O-carbocyclyl-alkylene-. For instance, $C_3$-$C_{10}$carbocyclyl$C_1$-$C_6$alkoxy$C_5$-$C_7$carbocyclyl$c_3$-$C_4$alkyl refers to $C_3$-$C_{10}$carbocyclyl-$C_1$-$C_6$alkylene-O—$C_5$-$C_7$carbocyclyl-$C_3$-$C_4$alkylene-.

The term "(carbocyclylalkyl)carbocyclylalkyl" (alone or in combination with another term(s)) refers to carbocyclyl-alkylene-carbocyclyl-alkylene-. For instance, $C_3$-$C_{10}$carbocyclyl$C_1$-$C_6$alkyl$C_5$-$C_7$carbocyclyl$C_3$-$C_4$alkyl refers to $C_3$-$C_{10}$carbocyclyl-$C_1$-$C_6$alkylene-$C_5$-$C_7$carbocyclyl-$C_3$-$C_4$alkylene-.

The term "carbocyclylalkoxyheterocycloalkyl" (alone or in combination with another term(s)) refers to carbocyclyl-alkylene-O-heterocyclyl-alkylene-.

The term "carbocyclylcarbonylheterocycloalkyl" (alone or in combination with another term(s)) refers to carbocyclyl-C(O)-heterocyclyl-alkylene-.

The term "carbocyclylheterocycloalkyl" (alone or in combination with another term(s)) refers to carbocyclyl-heterocyclyl-alkylene-.

The term "carbocyclylcarbonylcarbocyclylalkyl" (alone or in combination with another term(s)) refers to carbocyclyl-C(O)-carbocyclyl-alkylene-. For instance, $C_3$-$C_{10}$carbocyclylcarbonyl$C_4$-$C_8$carbocyclyl$C_1$-$C_6$alkyl refers to $C_3$-$C_{10}$carbocyclyl-C(O)—$C_4$-$C_8$carbocyclyl-$C_1$-$C_6$alkylene-.

The term "(carbocyclylalkyl)heterocycloalkyl" (alone or in combination with another term(s)) refers to carbocyclyl-alkylene-heterocyclyl-alkylene.

The term "carbonyl" (alone or in combination with another term(s)) refers to —C(O)—, which also may be depicted as:

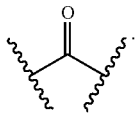

The term "carboxy" (alone or in combination with another term(s)) means —C(O)—OH, which also may be depicted as:

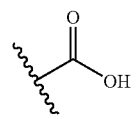

The term "carboxyalkyl" (alone or in combination with another term(s)) refers to a carboxy group appended to the parent molecular moiety through an alkylene group. Representative examples of carboxyalkyl include, but are not limited to, carboxymethyl, 2-carboxyethyl, and 3-carboxypropyl.

The term "cyclic amino" (alone or in combination with another term(s)) means a heterocyclyl moiety comprising at least one nitrogen ring atom, with the remaining ring atoms being carbon and optionally nitrogen or sulfur. Non-limiting examples of such moieties include piperidinyl, piperazinyl, and thiazine groups.

The term "cycloalkenyl" (alone or in combination with another term(s)) refers to a non-aromatic, partially unsaturated carbocyclyl substituent having zero heteroatom ring member and typically from 4 to 18 carbon ring members. Representative examples of cycloalkenyl groups include, but are not limited to, cyclobutenyl, cyclopentenyl, cyclohexenyl, and octahydronaphthalenyl.

The term "cycloalkyl" (alone or in combination with another term(s)) refers to a saturated carbocyclyl group containing zero heteroatom ring member and typically from 3 to 18 carbon ring members. Non-limiting examples of cycloalkyls include cyclopropyl, cyclobutyl, cyclopentyl, cyclohexyl, cycloheptyl, cyclooctyl, decalinyl and norpinanyl.

The term "cycloalkylcarbonyl" (alone or in combination with another term(s)) refers to a cycloalkyl group appended to the parent molecular moiety through a carbonyl group.

The term "cyano" (alone or in combination with another term(s)) means —CN, which also may be depicted as

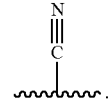

The term "dialkylamino" (alone or in combination with another term(s)) refers to —$NR_AR_B$, wherein $R_A$ and $R_B$ are independently selected from alkyl groups.

The term "dialkylaminocarbonyl" (alone or in combination with another term(s)) refers to a dialkylamino group appended to the parent molecular moiety through a carbonyl group (i.e., N($R_AR_B$)—C(O)—, wherein $R_A$ and $R_B$ are independently selected from alkyl groups).

The term "formyl" (alone or in combination with another term(s)) refers to a —C(O)H group.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

The prefix "halo" indicates that the substituent to which the prefix is attached is substituted with one or more independently selected halogen radicals. For example, "haloalkyl" (alone or in combination with another term(s)) means an alkyl substituent wherein at least one hydrogen radical is replaced with a halogen radical. Non-limiting examples of haloalkyls include chloromethyl, 1-bromoethyl, fluoromethyl, difluoromethyl, trifluoromethyl, and 1,1,1-trifluoroethyl. Illustrating further, "haloalkoxy" (alone or in combination with another term(s)) means an alkoxy substituent wherein at least one hydrogen radical is replaced by a halogen radical. Non-limiting examples of haloalkoxy substituents include chloromethoxy, 1-bromoethoxy, fluoromethoxy, difluoromethoxy, trifluoromethoxy (also known as "perfluoromethyloxy"), and 1,1,1,-trifluoroethoxy. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical. Non-limiting examples of perfluoroalkyl substituents include trifluoromethyl (—$CF_3$), perfluoroisopropyl, perfluorobutyl, perfluorodecyl, and perfluorododecyl. To illustrate further, the term "perfluoroalkoxy" means an alkoxy substituent wherein each hydrogen radical is replaced with a fluorine radical. Non-limiting examples of perfluoroalkoxy substituents include trifluoromethoxy (—O—$CF_3$), perfluoroisopropoxy, perfluorobutoxy, perfluorodecoxy, and perfluorododecoxy.

The terms "heterocycle" or "heterocyclo" or "heterocyclyl" (alone or in combination with another term(s)) refer to a saturated (e.g., "heterocycloalkyl"), partially unsaturated (e.g., "heterocycloalkenyl" or "heterocycloalkynyl") or completely unsaturated (e.g., "heteroaryl") ring system typically containing from 3 to 18 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results.

A heterocyclyl may be, without limitation, a single ring, which typically contains from 3 to 14 ring atoms (i.e., $M_3$-$M_{14}$heterocyclyl), from 3 to 8 ring atoms (i.e., $M_3$-$M_8$heterocyclyl), from 3 to 6 ring atoms (i.e., $M_3$-$M_6$heterocyclyl), or from 5 to 6 ring atoms (i.e., $M_5$-$M_6$heterocyclyl). Non-limiting examples of single-ring heterocyclyls include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2, 3-triazinyl, oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5, 2-oxadiazinyl), morpholinyl, azepinyl, oxepinyl, thiepinyl, and diazepinyl.

A heterocyclyl may also include, without limitation, two or more rings fused together, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocyclyls include benzo-fused heterocyclyls, such as indolyl, isoindolyl, indoleninyl (also known as "pseudoindolyl"), isoindazolyl (also known as "benzpyrazolyl"), benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1, 4-benzoxazinyl), benzisoxazinyl (including 1,2-benzisoxazinyl and 1,4-benzisoxazinyl), tetrahydroisoquinolinyl, carbazolyl, xanthenyl, and acridinyl.

The term "two-fused-ring" heterocyclyl (alone or in combination with another term(s)) means a saturated, partially saturated, or aromatic heterocyclyl containing two fused rings. Non-limiting examples of two-fused-ring heterocyclyls include naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzoimidazolyl, benzotriazolyl, benzoxazinyl, benzoisoxazinyl, and tetrahydroisoquinolinyl.

A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

As used herein, the number of ring atoms in a heterocyclyl moiety can be identified by the prefix "$M_x$-$M_y$," where x is the minimum and y is the maximum number of ring atoms in the heterocyclyl moiety.

The term "heterocycloalkoxy" (alone or in combination with another term(s)) refers to a heterocycloalkyl group appended to the parent molecular moiety through an oxy group.

The term "heterocycloalkoxyalkyl" (alone or in combination with another term(s)) refers to a heterocycloalkoxy group appended to the parent molecular moiety through an alkylene group (i.e., heterocyclyl-alkylene-O-alkylene-).

The term "heterocycloalkoxycarbonyl" (alone or in combination with another term(s)) refers to a heterocycloalkoxy group appended to the parent molecular moiety through a carbonyl group (i.e., heterocyclyl-alkylene-O—C(O)—).

The term "heterocycloalkyl" (alone or in combination with another term(s)) refers to a heterocyclyl appended to the parent molecular moiety through an alkylene group (e.g., heterocyclo$C_1$-$C_6$alkyl).

The term "heterocycloalkylcarbonyl" (alone or in combination with another term(s)) refers to a heterocycloalkyl group appended to the parent molecular moiety through a carbonyl group (i.e., —C(O)-alkylene-heterocyclyl).

The term "heterocyclocarbonyl" (alone or in combination with another term(s)) refers to a heterocyclyl appended to the parent molecular moiety through a carbonyl group (i.e., —C(O)-heterocyclyl).

The terms "heterocyclyloxy" or "(heterocyclo)oxy" (alone or in combination with another term(s)) refers to a heterocyclyl group appended to the parent molecular moiety through an oxy moiety.

The term "(heterocyclyo)oxyalkyl" (alone or in combination with another term(s)) refers to a heterocyclyloxy group appended to the parent molecular moiety through an alkylene group (i.e., heterocyclyl-O-alkylene-).

The term "(heterocyclo)oxycarbonyl" (alone or in combination with another term(s)) refers to a (heterocyclo)oxy group appended to the parent molecular moiety through a carbonyl group (i.e., heterocyclyl-O—C(O)—).

The term "heterocyclothio" (alone or in combination with another term(s)) refers to a heterocyclyl appended to the parent molecular moiety through —S—.

The term "heterocyclothioalkoxy" (alone or in combination with another term(s)) refers to heterocyclyl-alkylene-S—.

The term "heterocyclothioalkoxyalkyl" (alone or in combination with another term(s)) refers to heterocyclyl-alkylene-S-alkylene-.

The term "heterocyclothioalkyl" (alone or in combination with another term(s)) refers to a heterocyclothio group appended to the parent molecular moiety through an alkylene group (i.e., heterocyclyl-S-alkylene-).

The term "heterocyclocarbocyclyl" (alone or in combination with another term(s)) refers to a heterocyclyl appended to the parent molecular moiety through a carbocyclyl group (i.e., heterocyclo-carbocyclyl-).

The term "heterocyclocarbocyclylalkyl" (alone or in combination with another term(s)) refers to a heterocyclocarbocyclyl group appended to the parent molecular moiety through an alkylene group (i.e., heterocyclyl-carbocyclyl-alkylene-).

The term "(heterocyclo)alkoxycarbocyclylalkyl" (alone or in combination with another term(s)) refers to heterocycloalkylene-O-carbocyclyl-alkylene-.

The term "(heterocyclo)carbonylcarbocyclylalkyl" (alone or in combination with another term(s)) refers to heterocyclo-C(O)-carbocyclyl-alkylene-.

The term "(heterocyclo)heterocycloalkyl" (alone or in combination with another term(s)) refers to heterocyclo-heterocyclo-alkylene-.

The term "(heterocyclo)alkoxyheterocycloalkyl" (alone or in combination with another term(s)) refers to heterocycloalkylene-O-heterocyclo-alkylene-.

The term "(heterocyclo)carbonylheterocycloalkyl" (alone or in combination with another term(s)) refers to heterocyclo-C(O)-heterocyclo-alkylene-.

The term "(heterocycloalkyl)carbocyclylalkyl" (alone or in combination with another term(s)) refers to heterocycloalkylene-carbocyclyl-alkylene-.

The term "(heterocycloalkyl)heterocycloalkyl" (alone or in combination with another term(s)) refers to heterocycloalkylene-heterocyclo-alkylene-. Thus, for example, ($M_3$-$M_{10}$heterocyclo$C_1$-$C_6$alkyl)$M_5$-$M_6$heterocyclo$C_1$-$C_3$alkyl means $M_3$-$M_{10}$heterocyclo-$C_1$-$C_6$alkylene-$M_5$-$M_6$heterocyclo-$C_1$-$C_3$alkylene-.

The term "heteroaryl" (alone or in combination with another term(s)) means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heteroarylalkoxy" (alone or in combination with another term(s)) refers to a heteroarylalkyl appended to the parent molecular moiety through an oxy group (i.e., heteroaryl-alkylene-O—). Representative examples of heteroarylalkoxy include, but are not limited to, 2-pyridin-3-ylethoxy, 1,3-thiazol-5-ylmethoxy, 3-quinolin-3-ylpropoxy, and 5-pyridin-4-ylpentyloxy.

The term "heteroarylalkoxyalkyl" (alone or in combination with another term(s)) refers to a heteroarylalkoxy group appended to the parent molecular moiety through an alkylene group (i.e., heteroaryl-alkylene-O-alkylene-). Representative examples of heteroarylalkoxyalkyl include, but are not limited to, (2-pyridin-3-ylethoxy)methyl, (3-quinolin-3-ylpropoxy)methyl, (1,3-thiazol-5-ylmethoxy)methyl, and 2-(5-pyridin-4-ylpentyloxy)ethyl.

The term "heteroarylalkoxycarbonyl" (alone or in combination with another term(s)) refers to a heteroarylalkoxy group appended to the parent molecular moiety through a carbonyl group (i.e., heteroaryl-alkylene-O—C(O)—). Representative examples of heteroarylalkoxycarbonyl include, but are not limited to, (2-pyridin-3-ylethoxy)carbonyl, (3-quinolin-3-ylpropoxy)carbonyl, 2-(1,3-thiazol-5-ylmethoxy)carbonyl, and (5-pyridin-4-ylpentyloxy)carbonyl.

The term "heteroarylalkyl" (alone or in combination with another term(s)) refers to a heteroaryl group appended to the parent molecular moiety through an alkylene group. Representative examples of heteroarylalkyl include, but are not limited to, 3-quinolinylmethyl, 3-pyridinylmethyl, 4-pyridinylmethyl, 1H-imidazol-4-ylmethyl, 1H-pyrrol-2-ylmethyl, pyridin-3-ylmethyl, and 2-pyrimidin-2-ylpropyl.

The term "heteroarylalkylcarbonyl" (alone or in combination with another term(s)) refers to a heteroarylalkyl group appended to the parent molecular moiety through a carbonyl group (i.e., heteroaryl-alkylene-C(O)—).

The term "heteroarylcarbonyl" (alone or in combination with another term(s)) refers to a heteroaryl group appended to the parent molecular moiety through a carbonyl group. Representative examples of heteroarylcarbonyl include, but are not limited to, pyridin-3-ylcarbonyl, (1,3-thiazol-5-yl)carbonyl, and quinolin-3-ylcarbonyl.

The term "heteroaryloxy" (alone or in combination with another term(s)) refers to a heteroaryl group appended to the parent molecular moiety through an oxy moiety. Representative examples of heteroaryloxy include, but are not limited to, pyridin-3-yloxy, and quinolin-3-yloxy.

The term "heteroaryloxyalkyl" (alone or in combination with another term(s)) refers to a heteroaryloxy group appended to the parent molecular moiety through an alkylene group (i.e., heteroaryl-O-alkylene-).

The term "heteroaryloxycarbonyl" (alone or in combination with another term(s)) refers to a heteroaryloxy group appended to the parent molecular moiety through a carbonyl group (i.e., heteroaryl-O—C(O)—).

The term "heteroarylthio" (alone or in combination with another term(s)) refers to a heteroaryl group appended to the parent molecular moiety through —S—.

The term "heteroarylthioalkoxy" (alone or in combination with another term(s)) refers to heteroaryl-alkylene-S—.

The term "heteroarylthioalkoxyalkyl" (alone or in combination with another term(s)) refers to heteroaryl-alkylene-S-alkylene-.

The term "heteroarylthioalkyl" (alone or in combination with another term(s)) refers to a heteroarylthio group appended to the parent molecular moiety through an alkylene group (i.e., heteroaryl-S-alkylene-).

The term "hydrogen" (alone or in combination with another term(s)) refers to a hydrogen radical, and may be depicted as —H.

The term "hydroxy" (alone or in combination with another term(s)) refers to —OH.

The term "hydroxyalkyl" (alone or in combination with another term(s)) refers to an alkyl substituent wherein one or more hydrogen radicals are replaced with —OH. Representative examples of hydroxyalkyl include, but are not limited to, hydroxymethyl, 2-hydroxyethyl, 3-hydroxypropyl, and 2-ethyl-4-hydroxyheptyl.

The term "keto" (alone or in combination with another term(s)) means an oxo radical, and may be depicted as =O.

The term "iminoalkyl" (alone or in combination with another term(s)) refers to a radical of the formula

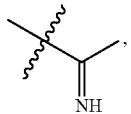

wherein the H may be optionally substituted with alkyl or hydroxy, in which case the substituent would be alkyliminoalkyl or hydroxyiminoalkyl respectively.

The term "nitro" (alone or in combination with another term(s)) means —NO₂.

The term "oxo" (alone or in combination with another term(s)) refers to a =O moiety (i.e.,

The term "oxy" (alone or in combination with another term(s)) means —O—.

The term "propargyl" (alone or in combination with another term(s)) means the monovalent radical depicted as: —CH₂—CH≡CH.

The term "sulfonyl" (alone or in combination with another term(s)) means —S(O)₂—, which also may be depicted as:

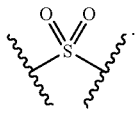

The term "sulfinyl" (alone or in combination with another term(s)) means —S(O)—, which also may be depicted as:

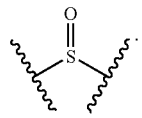

The term "thio" or "thia" (alone or in combination with another term(s)) means —S—.

The term "thiol," "mercapto" or "sulfhydryl" (alone or in combination with another term(s)) means a sulfhydryl substituent, (i.e., —SH). Thus, for example, thiolalkyl means an alkyl substituent wherein one or more hydrogen radicals are replaced with —SH, while alkylthio means alkyl-S—.

The term "thioalkoxy" (alone or in combination with another term(s)) refers to an alkyl group appended to the parent molecular moiety through —S—. Representative examples of thioalkoxy include, but are not limited to, methylthio, ethylthio, and butylthio.

The term "thioalkoxyalkyl" (alone or in combination with another term(s)) refers to a thioalkoxy group appended to the parent molecular moiety through an alkylene group (i.e., alkyl-S-alkylene-).

The term "thiocarbonyl" (alone or in combination with another term(s)) means a carbonyl wherein the oxygen atom has been replaced with a sulfur. Such a substituent may be depicted as —C(S)—, and also may be depicted as:

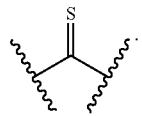

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). The prodrug derivative form often offers advantages of solubility, tissue compatibility, or delayed release in a mammalian organism (see, Bungard, H., Design of Prodrugs, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The term "chiral" refers to molecules that do not have a plane of symmetry and are therefore not superimposable on their mirror image. A chiral molecule may exists in two forms, one right-handed and one left-handed.

The term "stereoisomer" refers to isomers that have their atoms connected in the same order but have different three-dimensional arrangements. The term stereoisomer includes, for example, enantiomers and diastereomers.

The term "cis-trans isomer" refers to stereoisomers that differ in their stereochemistry about a double bond or ring. Cis-trans isomers are also called geometric isomers.

The term "enantiomer" refers to stereoisomers of a chiral substance that have a mirror-image relationship.

The term "diastereomer" refers to stereoisomers that are not enantiomers, or mirror images of each other.

The term "racemic mixture" refers to a mixture consisting of equal parts (+) and (−) enantiomers of a chiral substance. Even though the individual molecules are chiral, racemic mixtures are optically inactive.

The term "tautomer" refers to isomers that are interconvertable. For example, enols and ketones are tautomers because they are interconverted by treatment with either acid or base.

The term "position isomer" refers to any of two or more constitutional isomers that differ in the position of a particular substituent or group. Functional groups can be attached at structurally nonequivalent positions on a carbon skeleton. For example, [1,3]imidazole, depicted as

and [1,4]imidazole, depicted as

are position isomers.

The term "N-protecting group" or "N-protected" refers to those groups capable of protecting an amino group against undesirable reactions. Commonly used N-protecting groups are described in Greene and Wuts, PROTECTING GROUPS IN CHEMICAL SYNTHESIS (3$^{rd}$ ed., John Wiley & Sons, NY (1999), which is incorporate herein by reference in its entirety. Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The following abbreviations are used in the General Synthetic Methods and Examples described below:
AcOH=acetic acid
atm=atmospheres
Boc=N-t-butoxycarbonyl (protecting group)
CDI=1,1'-carbonyldiimidazole
$CH_2Cl_2$=methylene chloride (dichloromethane)
CuI=cuprous iodide [copper (I) iodide]
DCE=1,2-dichloroethane
DEAD=diethyl azodicarboxylate
DMA=N—N-dimethylacetamide
DMAP=4-dimethylaminopyridine
DMF=N,N-dimethylformamide
DMSO=dimethylsulfoxide
EDCI=(N-ethyl-N'-(3-dimethylaminopropyl)carbodiimide hydrochloride
EMME=2-ethoxymethylene-malonic acid diethyl ester
$Et_3N$=triethylamine
Ether=diethyl ether
EtI=ethyl iodide
EtOAc=ethyl acetate
EtOH=ethanol
Fe=iron
Fe(AcAc)3=Iron(III)-acetylacetonate
Fmoc chloride=9-fluorenylmethyl chloroformate
HOBt=N-Hydroxybenzotriazole
Hunig's base=N,N-diisopropylethylamine
IPA=isopropyl alcohol
$K_2CO_3$=potassium carbonate
KOH=potassium hydroxide
LDA=lithium diisopropylamine
MeOH=methanol
MsCl=methanesulfonyl chloride
NaH=sodium hydride
$NH_2OH.HCl$=hydroxylamine hydrochloride
NMP=1-methyl-2-pyrrolidinone
$Mg_2SO_4$=magnesium sulfate
$Na_2SO_4$=sodium sulfate
$NH_3$=ammonia
$NH_4Cl$=ammonium chloride
$NH_4OH$=ammonium hydroxide
PG=protecting group such as Boc- or Troc-
$POCl_3$=phosphorous oxy chloride
R—MgCl=Grignard reagent
R—I=alkyl iodide or substituted alkyl iodide
SnCl2=Stannous chloride (Tin (II) chloride)
TFA=trifluoroacetic acid
THF=tetrahydrofuran
TLC=thin layer chromatography
Triflic Anhydride=trifluoromethanesulfonic anhydride
Troc=2,2,2-trichloroethoxycarbonyl- (protecting group)

General Synthetic Methods and Examples

The following synthetic methods and schemes illustrate the general methods by which the compounds of the present invention can be prepared. Starting materials can be obtained from commercial sources or prepared using methods well known to those of ordinary skill in the art. By way of example, synthetic routes similar to those shown hereinbelow may be used, together with synthetic methods known in the art of synthetic organic chemistry, or variations thereon, as appreciated by those skilled in the art.

The present invention is intended to encompass compounds prepared by either synthetic processes or metabolic processes. Metabolic processes include those occurring in the human or animal body (in vivo), or those occurring in vitro.

If a substituent described herein is not compatible with the synthetic methods of this invention, the substituent may be protected with a suitable protecting group that is stable to the reaction conditions used in these methods. The protecting group may be removed at a suitable point in the reaction sequence to provide a desired intermediate or target compound. Suitable protecting groups and methods for protecting or deprotecting substituents are well know in the art, examples of which can be found in Greene and Wuts, supra.

Preparation of Compounds of Formulae I-VIII

Compounds of Formula I can be synthesized by reacting

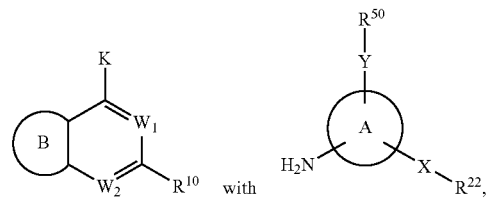

wherein $W_1$, $W_2$, A, B, X, Y, $R^{10}$, $R^{22}$, and $R^{50}$ have the meanings as set forth in the above embodiments or examples, and K is Cl or another halogen. Likewise, compounds of Formulae II-VIII can be prepared by reacting

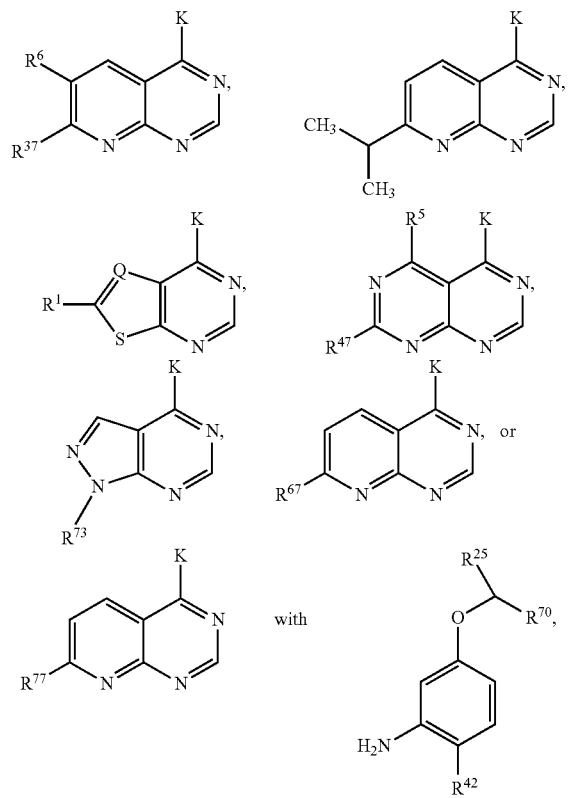

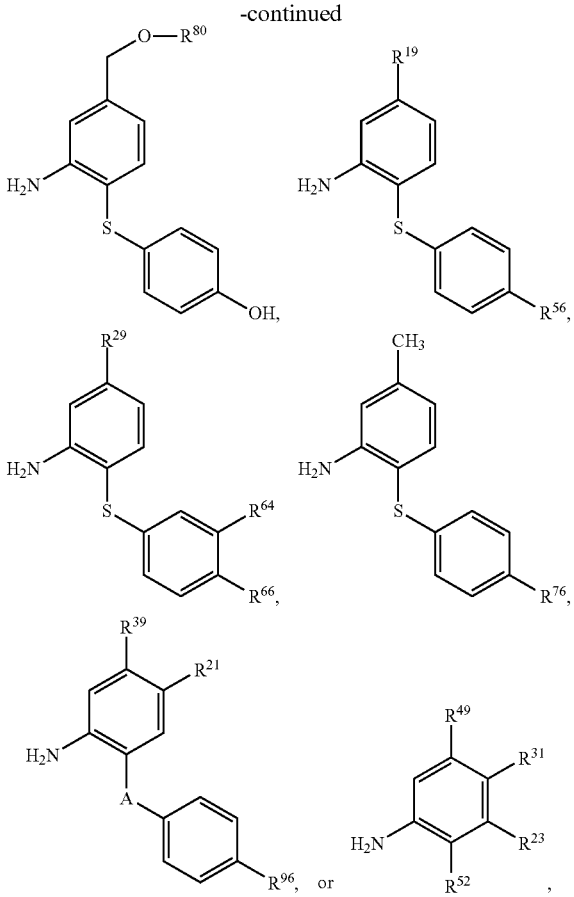

respectively.

The synthesis of compounds of Formulae I-VIII is exemplified in Schemes 1-8. Representative compounds of Formula I, wherein

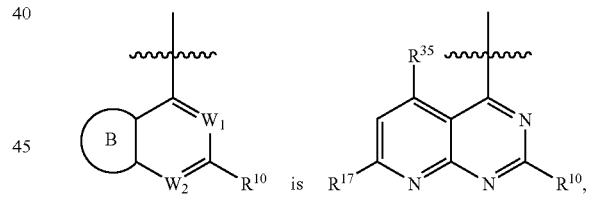

$R^{10}$, $R^{17}$ and $R^{35}$ are as defined hereinabove, and Z is $NR^{41}$, can be prepared using the procedure as outlined in Scheme 1.

Scheme 1

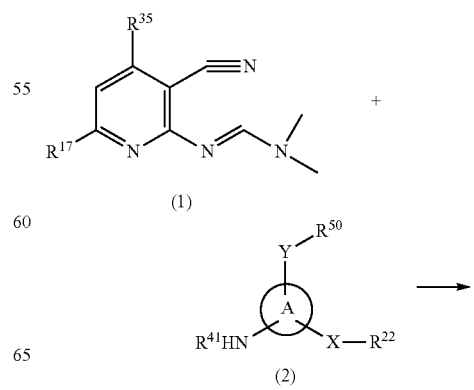

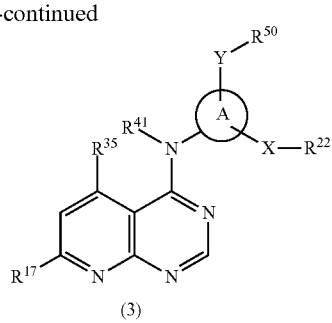

(3)

Amines of formula (2) wherein $R^{41}$ is hydrogen can be treated with N,N-dimethylformamidine compounds of formula (1) in the presence of an acid such as, but not limited to, acetic acid, at elevated temperature (for example, from about 80° C. to about 150° C.), thereby producing compounds of formula (3). The acetic acid can function as a solvent. Other suitable solvents can also be used in the reaction.

N alkylation of compounds of formula (2) wherein $R^{41}$ is hydrogen provides formula (2) or (3) wherein $R^{41}$ is alkyl. This process can be facilitated with an alkylating reagent of formula $R^{41}X^1$, wherein $X^1$ is halogen, tosylate, triflate or mesylate, in the presence of a base such as, but not limited to, an organic base such as triethylamine or diisopropylamine, or an inorganic base such as sodium, cesium or potassium carbonate, in a suitable solvent, and at a temperature ranging from about room temperature to about 100° C.

Scheme 2

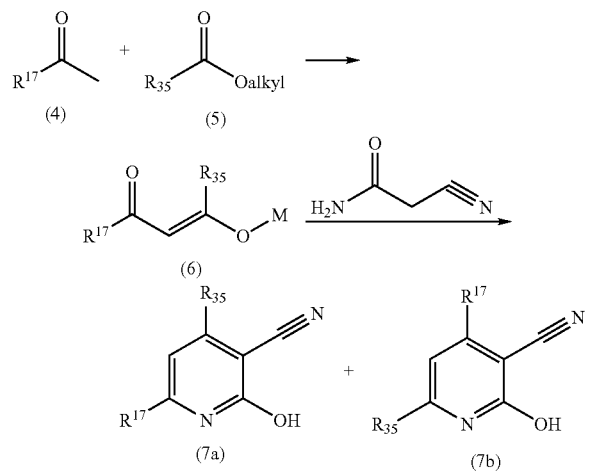

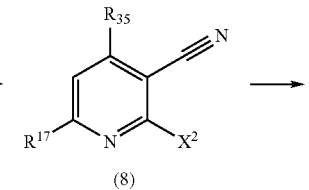

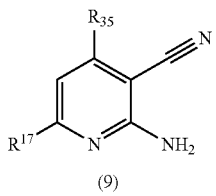

Preparation of the N,N-dimethylformamidine compounds of formula (1) can be accomplished as described in Scheme 2. Ketones of formula (4) and esters of formula (5), in the presence of a base such as, but not limited to, sodium or potassium hydride (or sodium metal) at about 0° C. in a suitable solvent such as, but not limited to, diethyl ether, provide a salt of formula (6) wherein M is potassium or sodium. Treatment of formula (6) with 2-cyanoacetamide in the presence of piperidine acetate, at about reflux gives nitriles of formula (7a) and (7b). The regioisomers (7a) and (7b) can be separated at this point or later in the synthetic route, using purification techniques known to those skilled in the art. Compounds of formula (7a) can either be converted to compounds of formula (8) wherein $X^2$ is Cl by treatment with phosphorous oxychloride or to compounds of formula (8) wherein $X^2$ is Br by treatment with tetrabutylammonium bromide and phosphorous pentoxide in a suitable solvent, at reflux. A solution of compounds of formula (8) wherein $X^2$ is Cl or Br and liquid ammonia are reacted in a sealed high pressure vessel at elevated temperature, for example, at about 130° C. to provide compounds of formula (9). Compounds of formula (9) and N,N-dimethylformamide dimethyl acetal in a solvent such as, but not limited to, toluene, at reflux yield the N,N-dimethylformamidine compounds of formula (1).

Scheme 3

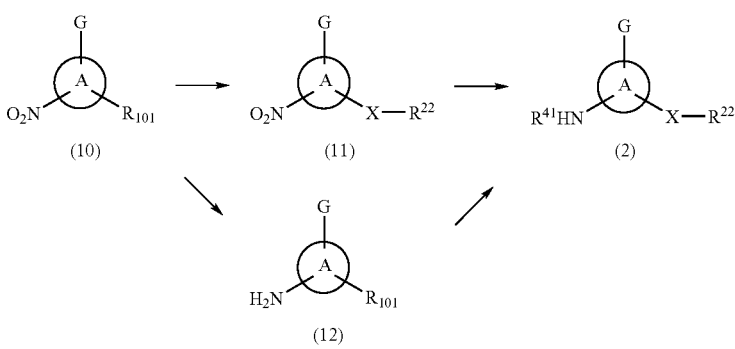

Compounds of formula (2) wherein $R^{41}$ is hydrogen and X is O or S, can be prepared from compounds of formula (10) according to Scheme 3, wherein $R_{101}$ is a leaving group such as, but not limited to, halogen, triflate or mesylate (the latter two can be prepared from the corresponding alcohol using methodologies known to one skilled in the art), via a two-step synthesis, namely, reduction of the nitro group followed by displacement of $R_{101}$, or displacement of $R_{101}$ followed by reduction of the nitro group.

Displacement of $R_{101}$ with $R^{22}XH$ wherein X is O or S can be facilitated in the presence of a suitable base such as, but not limited to, potassium, cesium or sodium carbonate or bicarbonate, or sodium or potassium hydride, and optionally in the presence of 18-crown-6, at elevated temperature. The reaction can generally be performed in a solvent such as, but not limited to, N,N-dimethylformamide or dimethylsulfoxide, at a temperature from about room temperature to about 180° C. The reaction can generally be performed in a solvent such as, but not limited to, N,N-dimethylformamide or dimethylsulfoxide, at a temperature from about room temperature to about 180° C. The reaction can also be conducted in a microwave oven. It is appreciated compounds of formula (10) can also be obtained from the reaction of formula (10) wherein $R_{101}$ is —X—H with compounds of formula $R^{22}X^3$ wherein $X^3$ is a leaving group such as, but not limited to, halogen, triflate or mesylate, using the aforementioned reaction conditions. The displacement reactions can also be effected in the presence of a metal catalyst such as, but not limited to, copper metal, CuI, or palladium acetate, optionally in the presence of a ligand such as, but not limited to, 2,2'-bis(diphenylphosphino)-1,1'-binaphthyl or tri-tert-butylphosphine, and optionally in the presence of a base such as, but not limited to, pyridine, triethylamine, sodium tert-butoxide, cesium carbonate, or sodium hydride. The reaction is generally performed at a temperature from about room temperature to about 180° C., in a solvent such as, but not limited to, toluene or N,N-dimethylformamide.

Reduction of the nitro group can be accomplished by treatment of nitro compound with a reducing agent such as, but not limited to, iron powder/ammonium chloride or tin(II) chloride, in a suitable solvent.

It is also appreciated that compounds of formula (10) can also be converted to compounds of formula (2) by first reducing the nitro functionality, followed by the displacement reaction, using reaction conditions as described hereinabove.

Preparation of Aminophenyl Coupling Agents (10, 11 and 12)

A wide variety of aminophenyl coupling agents are possible. The agents in Scheme 4 are exemplary of this variety.

In a typical preparation, a substituted 2-chloro-nitrobenzene compound in dimethylformamide (DMF) is treated with a sodium thiophenolate at about 50° C. for about 2 hours, is cooled and diluted with methylene chloride, washed with water, dried over sodium sulfate, filtered and concentrated under vacuum to give the substituted-2-phenylsulfanyl-nitrobenzene compound. This nitrobenzene compound is then reduced with stannous chloride ($SnCl_2$) or iron (Fe) in ethanol. The reaction mixture is adjusted to pH 12 with 1 N sodium hydroxide, extracted with ethyl acetate, dried over sodium sulfate, filtered and concentrated under vacuum giving the substituted-2-phenylsulfanyl-aminobenzene compound 10.

Similarly, the corresponding substituted-2-hydroxy-nitrobenzene compound is dissolved in dimethylformamide reacted with a sodium phenoxide solution, stirred and heated to 100° C. for about 5 days. The reaction mixture is cooled and diluted with methylene chloride, washed with water, dried over sodium sulfate, filtered and concentrated under vacuum to give the substituted-2-phenoxy-nitrobenzene compound. This nitrobenzene compound is then reduced with stannous chloride ($SnCl_2$) and iron (Fe) in ethanol. The reaction mixture is adjusted to pH 12 with 1 N sodium hydroxide, extracted with ethyl acetate, dried over sodium sulfate, filtered and concentrated under vacuum giving the substituted-2-phenoxy-aminobenzene compound 12.

Similarly, either compound 10 where $R^9$ is hydroxy—or protected hydroxyl—can be further modified by alkylating the hydroxy-group using a substituted benzyl bromide to give the corresponding 5-substituted-phenoxy-2-substituted-phenylsulfanyl-aminobenzene compound 11.

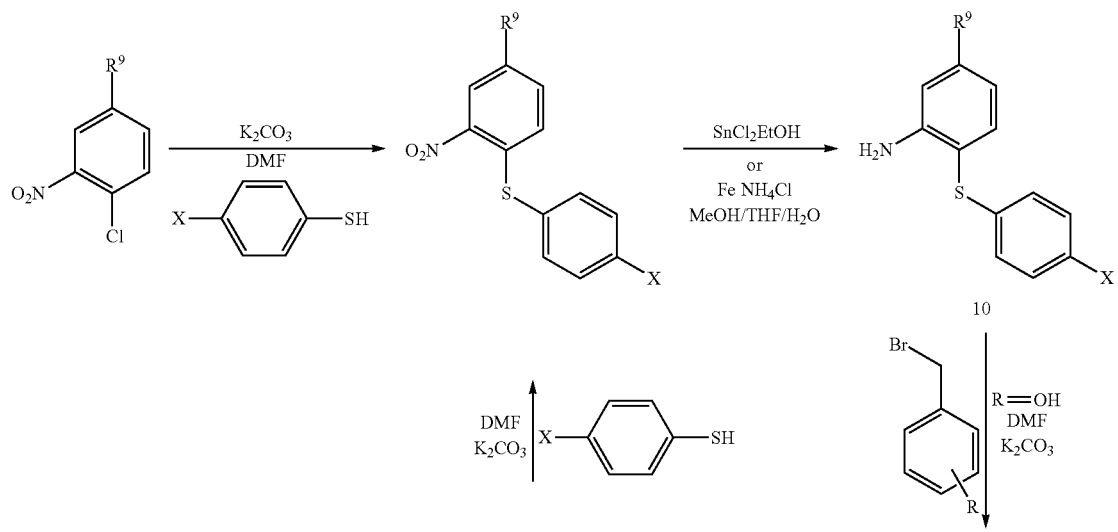

Scheme 4

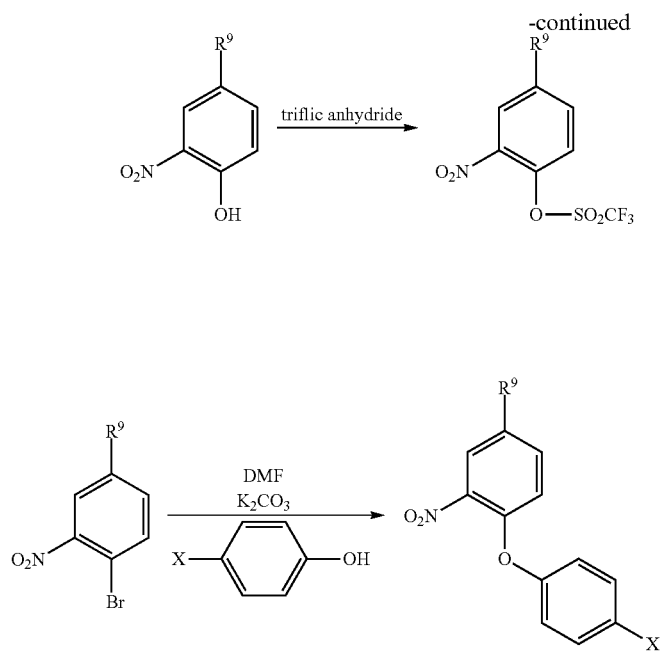
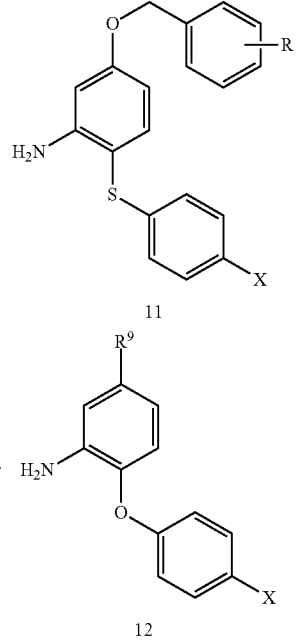

$R^9$ is defined above;
X is OH, NH₂, NHR, halo, alkyl, or alkoxy
R is alkyl, alkoxy, bromo, fluoro, chloro, or cyano Preparation of 7-Substituted-4-Aminophenyl-substituted-pyrido[2,3-d]pyrimidine Compounds A typical preparation of 7-substituted-4-aminophenyl-substituted-pyrido[2,3-d]pyrimidine compounds (Scheme 6) involves the coupling reaction of a substituted aminophenyl coupling agent (described in Scheme 4) with a 6-substituted-2-amidino-3-cyanopyridine compound 9 (Scheme 5).

As described in Scheme 4, a wide variety of aminophenyl coupling agents are possible.

Preparation of the 7-substituted-4-aminophenyl-substituted-pyrido[2,3-d]pyrimidines can be accomplished by coupling a N,N-dimethylformamidino compound 9 with a variety of coupling agents some of which are described in Scheme 4.

Preparation of the N,N-dimethylformamidine compounds 9 can be accomplished as described in Scheme 5. A substituted alkyl methyl ketone and ethyl formate are added to a diethyl ether solution of sodium hydride (or sodium metal) at about 0° C. for about 2 hours. After the addition the reaction is allowed to stir at room temperature overnight. Additional diethyl ether is added and the precipitate is quickly isolated by vacuum filtration died in a vacuum desiccator. This material was dissolved in water with 2-cyanoacetamide. A piperidine acetate solution is added and the resulting solution is heated at reflux for about 2 hours. The mixture is cooled to room temperature and adjusted to pH 4 with glacial acetic acid. The resulting solid is isolated by vacuum filtration rinsed with water and dried and identified as the 6-substituted-2-oxo-1, 2-dihydropyridine-3-carbonitrile 24. Compound 24 can either be converted to the 2-chloro-pyridine with phosphorous oxychloride (as shown in Scheme 5) or the 2-bromopyridine. The 2-bromoyridine is prepared by taking a toluene solution of compound 24 and reacting with tetrabutylammonium bromide and phosphorous pentoxide at reflux for about 5 hours. The reaction mixture is cooled, water added and the mixture stirred for about 2 hours at room temperature. The reaction mixture was diluted with toluene, the organic layer separated, washed with brine and dried over magnesium sulfate, filtered and concentrated under vacuum to give the 2-bromopyridine. An ethanol solution of either the 2-chloropyridine or the 2-bromopyridine and liquid ammonia are reacted in a sealed high pressure vessel at about 130° C. for about 20 hours. The reaction mixture is concentrated under vacuum and the residue washed with water and dried to give the 6-substituted-2-amino-nicotinonitrile 25. Compound 25 and N,N-dimethylformamide dimethyl acetal is dissolved in toluene and heated to reflux for about 3 hours. The resulting solution is cooled to room temperature and concentrated under vacuum to give the 6-substituted-3-cyano-pyridin-2-yl-N,N-dimethylformamidine 9.

Scheme 5

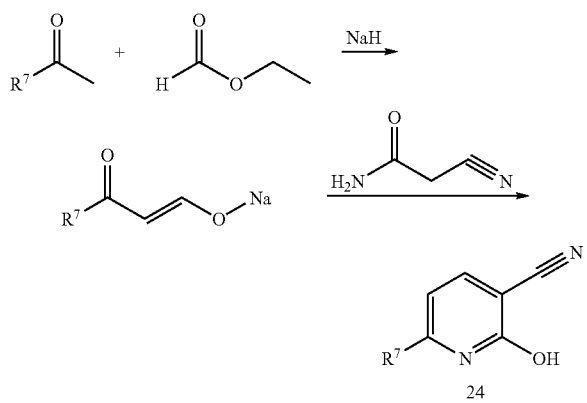

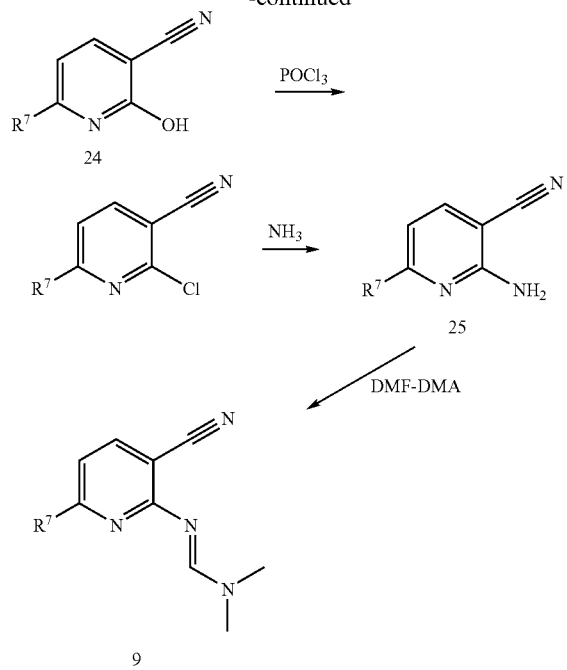

9

R[7] is selected from the group consisting of hydrogen, alkyl, haloalkyl, alkoxy, cycloalkyl, alkoxycarbonylalkyl, alkoxycarbonylalkylamino, cyanoalkoxycarbonylalkyl, cyanoalkyl, hydroxyalkyl, morpholino, hydrazino, alkylaminoalkoxy, alkoxyalkylamino, and aryl As described above, the preparation of 7-substituted-4-aminophenyl-substituted-pyrido[2,3-d]pyrimidines can be accomplished by coupling the substituted 6-substituted-3-cyano-pyridin-2-yl-N,N-dimethylformamidine 9 as shown in Scheme 5 with a variety of coupling agents some of which are described in Scheme 4. This coupling reaction is described in Scheme 6.

In a typical preparation, compound 9 and an aminophenyl coupling agent similar to those described in Scheme 4 are dissolved in acetic acid and stirred at about 130° C. for about 15 minutes. The mixture is cooled to room temperature, the acetic acid removed under vacuum and the resulting residue purified by reverse phase chromatography. At this point any functional protecting group such as the Boc, Troc or other group can be removed by known methods to give the final products.

Scheme 6

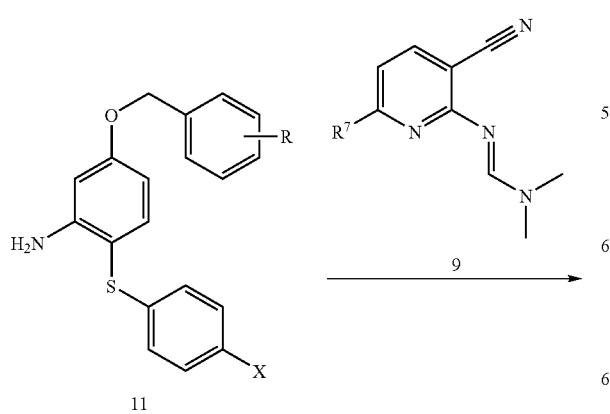

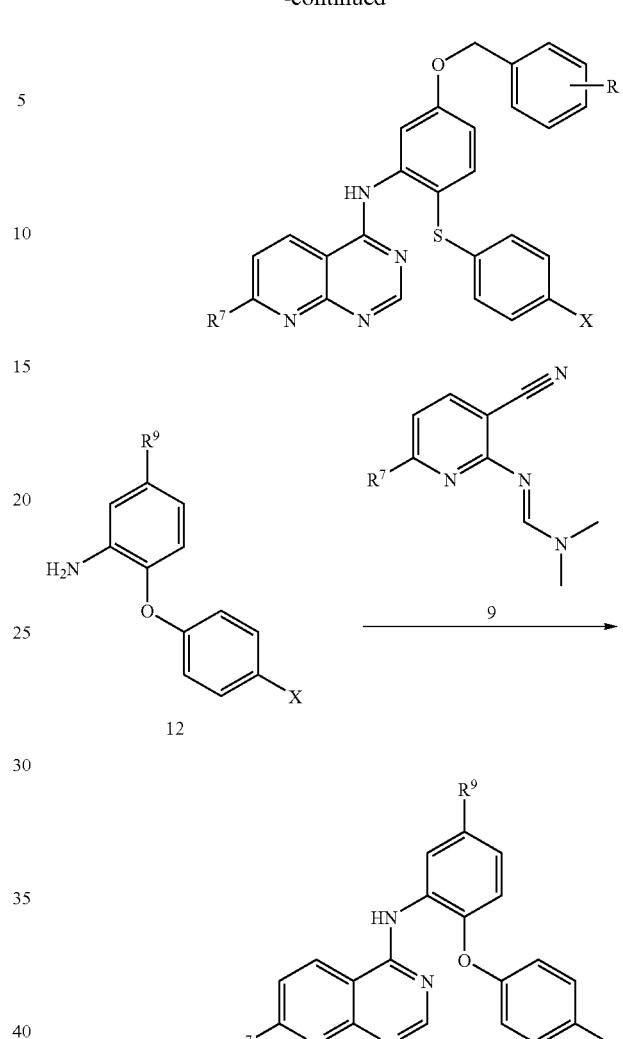

R[7], R[9], X and R are as defined above

Representative compounds of Formula I, wherein the ring B of

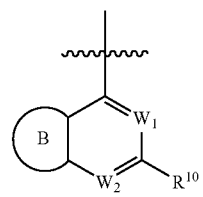

is a five-membered ring heterocycle and $W_1$ is CH, $R^{10}$, $R^{17}$ and $R^{35}$ are as defined hereinabove, and Z is $NR^{41}$, can be prepared using the procedure as outlined in Scheme 7 and consists of reacting an alkylamino-substituted heterocycles such as 13 with Meldrum's acid and triethylorthoformate and heating to about 100° C. The reaction mixture is concentrated and purified by chromatography to give the aminomethylene malonic acid ester 14. Compound 14 is then dissolved in diphenylether and the resulting solution heated to 250° C. for about 30 minutes, giving 15. A mixture of compound 15 is mixed with phosphorous oxychloride (POCl₃) and heated to about 50° C. with stirring for 6 hours, cooled quenched by pouring unto ice. It is cooled then adjusted to pH 10 with concentrated ammonium hydroxide and extracted with methylene chloride, dried over anhydrous sodium sulfate, filtered and concentrated under vacuum giving 16. In a typical preparation, compounds 16 and an aminophenyl coupling agent similar to those described in Scheme 4 are coupled with 2,8,9-triisobutyl-2,5,8,9-tetraaza-1-phospha-bicyclo[3.3.3]undecane tris(dibenzylideneacetone)-dipalladium, and sodium tert-butoxide in a solvent typically toluene and the like to provide 21.

Representative compounds of Formula I, wherein the ring B of

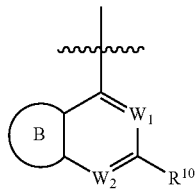

is a five-membered ring heterocycle and $W_1$ is N, $R^{10}$, $R^{17}$ and $R^{35}$ are as defined hereinabove, and Z is $NR^{41}$, can be prepared using the procedure as outlined in Scheme 8 and consists of reacting an alkylamino-substituted heterocycles such as 17 with formamide at reflux. The pyrimidine product 18 is then reacted with phosphorous oxychloride (POCl₃) to give the coupling partner 19. In a typical preparation, compounds 19 and an aminophenyl coupling agent similar to those described in Scheme 4 are dissolved in ethanol and heated to reflux for 12 hours to provide 20.

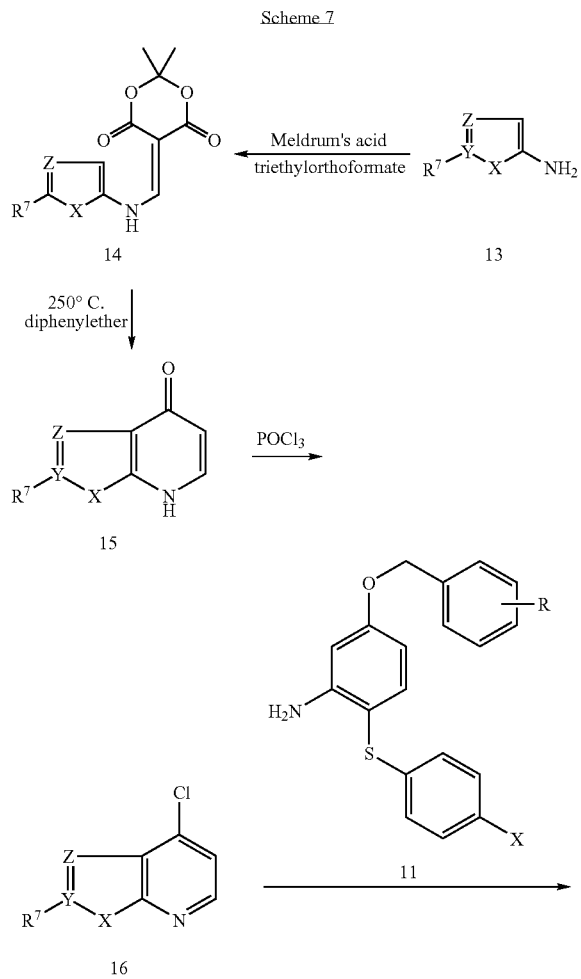

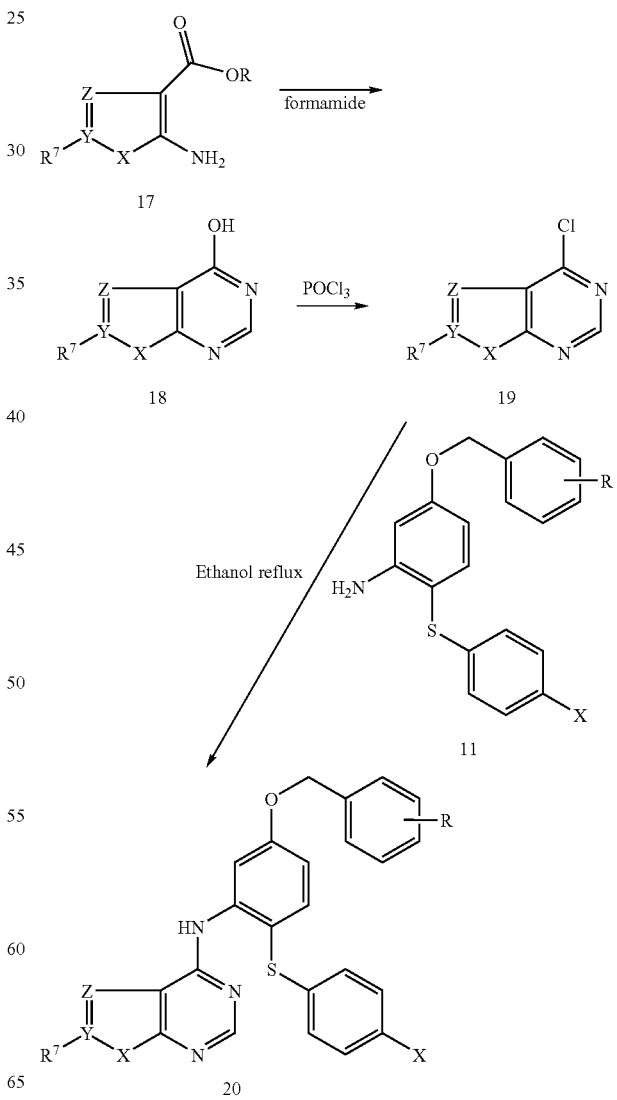

Representative compounds of Formula I, wherein the ring B of

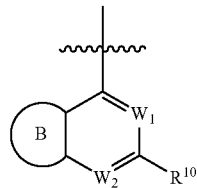

is a five-membered ring heterocycle and W1 is N or CH, R10, R17 and R35 are as defined hereinabove, and Z is NR41, can be prepared Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Reactions may be worked up in the convention manner, e.g. by eliminating the solvent from the residue and further purified according to methodologies generally known in the art such as, but not limited to, crystallization, distillation, extraction, trituration and chromatography.

It should be understood that the above-described embodiments and schemes and the following examples are given by way of illustration, not limitation. Various changes and modifications within the scope of the present invention will become apparent to those skilled in the art from the present description.

Example 1

4-Amino-N-[2-(4-hydroxy-phenylsulfanyl)-5-methyl-phenyl]-2-(2-methoxy-ethylamino)-pyrimidine-5-carboxamidine The product from Example 156 (42 mg, 0.1 mmol) in 2-methoxy-ethylamine (1 mL) was heated at 180° C. for 2 hours in a microwave reactor. The solvent was evaporated and the residue was purified by HPLC with TFA method to give the title compound as a trifluoroacetic acid salt (15 mg, 28%). $^1$H NMR (300 MHz, DMSO-$d_6$) δ ppm: 2.31 (s, 3H) 3.28 (s, 3H) 3.49 (m, 4H) 6.86 (m, 3H) 7.28 (m, 4H) 8.17 (s, br, 3H) 8.73 (s, br, 1H) 9.75 (s, br, 2H) 11.33 (s, br, 1H); MS (ESI+) m/z 425 (M+H)+.

Example 2

4-Amino-2-butylamino-N-[2-(4-hydroxy-phenylsulfanyl)-5-methyl-phenyl]-pyrimidine-5-carboxamidine The product from Example 156 (42 mg, 0.1 mmol) in butylamine (1 ml) was heated at 180° C. for 2 hours in a microwave reactor. The solvent was evaporated and the residue was purified HPLC with TFA method to give the title compound as the trifluoroacetic acid salt (13 mg, 24%). $^1$H NMR (300 MHz, DMSO-$d_6$) δ ppm: 0.90 (t, J=7.35 Hz, 3H) 1.29 (m, 2H) 1.51 (m, 2H) 2.30 (s, 3H) 3.32 (m, 2H) 6.85 (m, 3H) 7.27 (m, 4H) 8.15 (s, 3H) 8.71 (s, br, 1H) 9.55 (s, br, 1H) 9.92 (s, br, 1H) 11.23 (s, br, 1H); MS (ESI+) m/z 423 (M+H)+.

Example 3

N-{4-[4-Methyl-2-(6-propyl-thieno[2,3-d]pyrimidin-4-ylamino)-phenylsulfanyl]-phenyl}-acetamide

Example 3a ethyl 2-amino-5-propylthiophene-3-carboxylate

A solution of equimolar amounts of ethyl cyanoacetate and sulfur in dimethylformamide at ambient temperature was treated with triethylamine (0.5 equivalent) then upon warming to 50° C., valeraldehyde (1 equivalent) was added dropwise. After 3 hours the reaction was quenched with water and extracted with ethyl acetate. The organic layer was concentrated to provide the title compound.

Example 3b 6-propylthieno[2,3-d]pyrimidin-4-ol

The product of example 3a was reacted with excess formamide at reflux for 3 hours. The reaction mixture was quenched with water and the resulting precipitate was collected by filtration and washed with water and dried under vacuum to provide the title compound.

Example 3c 4-chloro-6-propylthieno[2,3-d]pyrimidine

The product of Example 3b was reacted with excess POCl$_3$ at reflux for 3 h then at room temperature for 16 h. The reaction was poured over ice and partitioned between water and ethyl acetate. The organic layer was concentrated to provide the title compound.

Example 3d

N-{4-[4-Methyl-2-(6-propyl-thieno[2,3-d]pyrimidin-4-ylamino)-phenylsulfanyl]-phenyl}-acetamide The product of Example 3c was reacted with the product of Example 7b were reacted in ethanol at reflux for 16 hours. The reaction was concentrated to produce the title compound.

Example 4

(6-Butyl-thieno[2,3-d]pyrimidin-4-yl)-(5-methyl-2-phenylsulfanyl-phenyl)-amine

The title compound was prepared according to the procedures of Example 3 substituting hexanal for valeraldehyde in Example 3a.

Example 5

(5-Methyl-2-phenylsulfanyl-phenyl)-(2-propyl-thiazolo[5,4-b]pyridin-7-yl)-amine

Example 5A

Butyrylamino-acetic acid methyl ester

A suspension of glycine hydrochloride (1.00 g, 7.964 mmol) in methylene chloride (40 mL), cooled to 0° under a nitrogen atmosphere, was treated with triethylamine (4.44 mL, 31.86 mmol) and butyryl chloride (0.93 mL, 8.76 mmol), and the mixture stirred at room temperature for 2.5 hours. The reaction was washed with saturated aqueous sodium bicarbonate (50 mL), water (50 mL) and brine. The organic phase was dried over anhydrous sodium sulfate, filtered and concentrated under vacuum giving the title compound. Purification by silica gel flash chromatography with 25% ethyl acetate/methylene chloride afforded the title compound as a colorless oil (0.776 g, 4.88 mmol, 61%).

Example 5B

Thiobutyrylamino-acetic acid methyl ester

A solution of the product of Example 5A (0.774 g, 4.862 mmol) in anhydrous THF (50 mL) was treated with Lawesson reagent (1.338 g, 3.209 mmol), then heated at reflux under a nitrogen atmosphere for 30 minutes. The reaction was cooled to 0° and a saturated aqueous sodium bicarbonate solution (40 mL) was slowly added dropwise. The mixture was stirred at room temperature for 15 minutes, and then extracted with ethyl acetate (100 mL), and the organic extract washed with saturated aqueous sodium bicarbonate (50 mL), water (2×25 mL), and brine. Dried the organic phase over anhydrous sodium sulfate, filtered, and concentrated under vacuum giving the title compound. Purification by silica gel flash chromatography with 1% ethyl acetate/methylene chloride afforded the title compound as a colorless oil (0.790 g, 4.508 mmol, 93%).

Example 5C

2-Thiobutyrylamino-acetamide

A solution of the product of Example 5B (0.788 g, 4.496 mmol) in methanol (30 mL) was saturated with ammonia gas and the reaction was stirred in a stoppered flask at room temperature for 17 hours. The solvent was concentrated under vacuum giving the title compound and the solid purified by silica gel flash chromatography with 10% methanol/methylene chloride to give the title compound as a white solid (500 mg, 3.12 mmol, 69%).

Example 5D

2-Propyl-thiazol-5-ylamine

A solution of the product of Example 5C (395 mg, 2.465 mmol) in anhydrous ethyl acetate (12 mL) was treated with phosphorous tribromide (0.189 mL, 1.972 mmol) under a nitrogen atmosphere and stirred at room temperature for 20 minutes. Added additional phosphorous tribromide (0.050 mL) and let stir for 5 minutes. The reaction mixture was diluted with ethyl acetate (50 mL) and washed with saturated aqueous sodium bicarbonate (25 mL). The aqueous wash was extracted with ethyl acetate (2×50 mL), and the organic extracts were combined and washed with brine, dried over anhydrous sodium sulfate, filtered and concentrated under vacuum giving the title compound. Purification by silica gel flash chromatography with 3% methanol/methylene afforded the title product (175 mg, 1.23 mmol, 50%).

Example 5E 2,2-Dimethyl-5-[(2-propyl-thiazol-5-ylamino)-methylene]-[1,3]dioxane-4,6-dione A solution of the product of Example 5D (212.7 mg, 1.496 mmol) in anhydrous ethanol (5 mL) was treated with Meldrum's acid (237 mg, 1.645 mmol) and triethylorthoformate (0.25 mL, 1.496 mmol) at room temperature, and the reaction was heated in a preheated 100° oil bath. After 15 minutes, the reaction was cooled to room temperature and the solvent removed by rotary evaporation under vacuum. Purification by silica gel flash chromatography with a gradient of 10% to 20% ethyl acetate/methylene chloride afforded the title compound as an off-white solid (240 mg, 0.8099 mmol, 54%).

Example 5F

2-Propyl-4H-thiazolo[5,4-b]pyridin-7-one

The product of Example 5E (230 mg, 0.7781 mmol) was added to refluxing diphenyl ether (5 mL) under a nitrogen atmosphere. After refluxing for 5 minutes, the solution was cooled in an ice bath and diluted with hexanes (50 mL). The resulting golden solid was collected by vacuum filtration and thoroughly washed with hexanes to give the title compound (125 mg, 0.644 mmol, 83%).

Example 5G

7-Chloro-2-propyl-thiazolo[5,4-b]pyridine

The product of Example 5F (123 mg, 0.6332 mmol) and phosphorous oxychloride (2 mL) were refluxed for 1 hour under a nitrogen atmosphere. The solution was cooled in an ice bath, treated with ice, and the pH adjusted to 7 with 6N aqueous sodium hydroxide. Extracted with methylene chloride (3×50 mL) and dried the combined organic extracts over anhydrous sodium sulfate, filtered and concentrated under vacuum giving the title compound as a brown oil (120 mg, 0.564 mmol, 89%).

Example 5H

4-Methyl-2-nitro-1-phenylsulfanyl-benzene

A solution of sodium thiophenolate (3.96 g, 30 mmol) in 60 mL of DMF was heated at 50° C. with 4-chloro-3-nitrotoluene (2.65 mL, 20 mmol) with stirring for 2 days. Cooled to room temperature and diluted with $CH_2Cl_2$. Washed with water and dried the organic layer over $Na_2SO_4$. Filtered and concentrated under vacuum giving the title compound (4.29 g, 87%) $^1H$ NMR (300 MHz, $CDCl_3$) δ ppm: 2.36 (s, 3H) 6.76 (d, J=8.09 Hz, 1H) 7.16 (d, J=8.46 Hz, 1H) 7.45 (m, 3H) 7.58 (m, 2H) 8.03 (s, 1H).

Example 5I

5-Methyl-2-phenylsulfanyl-phenylamine

A solution of the product from Example 5H (1.17 g, 7.0 mmol) in 25 mL of absolute EtOH and $SnCl_2$ (3.58 g, 29.8 mmol) was stirred at room temperature for 16 h. Adjusted to pH 12 with 1N NaOH and extracted with EtOAc. Dried over $Na_2SO_4$, filtered and concentrated under vacuum giving the title compound (835 mg, 82%) $^1H$ NMR (300 MHz, $CDCl_3$) δ ppm: 2.30 (2, 3H) 6.62 (d, J=8.83 Hz, 1H) 6.69 (s, 1H) 7.10 (m, 3H) 7.21 (m, 2H) 7.54 (d, J=7.72 Hz, 2H).

Example 5J (5-Methyl-2-phenylsulfanyl-phenyl)-(2-propyl-thiazolo[5,4-b]pyridin-7-yl)-amine A dry nitrogen-purged flask was charged with 2,8,9-triisobutyl-2,5,8,9-tetraaza-1-phospha-bicyclo[3.3.3]undecane (38 mg, 0.111 mmol), tris(dibenzylideneacetone)-dipalladium (25.4 mg, 0.0277 mmol), and sodium tert-butoxide (82.4 mg, 0.8322 mmol). A solution of the product of Example 5G (118 mg, 0.5548 mmol) in anhydrous toluene (2 mL) and a solution of the product from Example 5I (107.5 mg, 0.4993 mmol) in toluene (3 mL) were added via syringe. The reaction was heated at reflux in a preheated 120° oil bath for 18 hours, cooled to room temperature, treated with additional tris(dibenzylideneacetone)dipalladium (25.4 mg), and heated at reflux for an additional 2.5 hours. The reaction was cooled to room temperature and the solvent removed by rotary evaporation in vacuo. Purification by silica gel flash chromatography with a gradient of 1% to 3% ethyl acetate/methylene chloride afforded the title compound (29 mg, 0.074 mmol, 15%). $^1$H NMR (300 MHz, DMSO-D6) δ ppm: 1.00 (t, J=7.35 Hz, 3H) 1.71-1.90 (m, 2H) 2.38 (s, 3H) 3.05 (t, J=7.35 Hz, 2H) 6.87 (d, J=5.52 Hz, 1H) 7.07 (dd, J=7.91, 1.29 Hz, 1H) 7.12-7.31 (m, 5H) 7.37-7.46 (m, 2H) 8.15 (d, J=5.52 Hz, 1H) 8.52 (s, 1H); MS (DCI/NH$_3$) m/z 392 (M+H)$^+$.

Example 6

4-[4-Methyl-2-(2-propyl-thiazolo[5,4-b]pyridin-7-ylamino)-phenylsulfanyl]-phenol

Example 6a

Trifluoro-methanesulfonic acid 4-methyl-2-nitro-phenyl ester

A solution of the 4-methyl-2-nitro phenol (6.0 g, 39.1 mmol) and Et$_3$N (16.38 mL, 117.5 mmol) in 100 mL of CH$_2$Cl$_2$ under a N$_2$ atmosphere was treated with trifluoromethanesulfonic anhydride (7.25 mL, 43.1 mmol) at 0° C. for 30 min. Quenched by addition of MeOH. Washed sequentially with 10% citric acid, 0.5 m KOH and water. Dried over MgSO$_4$, filtered and concentrated under vacuum giving the title compound which was purified by silica gel column chromatography eluting with CH$_2$Cl$_2$ giving an amber oil (11.22 g, 100%).

Example 6b 4-(4-Methyl-2-nitro-phenylsulfanyl)-phenol

The product from Example 6a (11.22 g, 39.3 mmol) and 4-mercaptophenol (4.96 g, 39.3 mmol) in 100 mL of EtOH was treated with Na$_2$CO$_3$ and heated overnight under efflux. Cooled to room temperature and quenched with water. Extracted with EtOAc. Dried over MgSO$_4$, filtered and concentrated under vacuum giving the title compound, which was purified by silica gel column chromatography eluting with 25% EtOAc/hexane giving a red oil (8.65 g, 85%).

Example 6c 4-(2-Amino-4-methyl-phenylsulfanyl)-phenol

The product from Example 6b (8.65 g, 31.3 mmol) was reduced with SnCl$_2$ following the procedure from Example 5I giving the title compound as a white solid (8.51 g, 100%).

Example 6d 4-(4-methyl-2-(2-propylthiazolo[5,4-b]pyridin-7-ylamino)phenylthio)phenol A dry nitrogen-purged flask was charged with 2,8,9-triisobutyl-2,5,8,9-tetraaza-1-phospha-bicyclo[3.3.3]undecane (40.4 mg, 0.118 mmol), tris(dibenzylideneacetone)-dipalladium (27 mg, 0.0295 mmol), and sodium tert-butoxide (87.7 mg, 0.885 mmol). A solution of the product of Example 5G (125.5 mg, 0.590 mmol) in anhydrous toluene (5 mL) was added via syringe, followed by the product from Example 6c (136 mg, 0.590 mmol). The reaction was heated at reflux in a preheated 110° oil bath for 14 hours, cooled to room temperature, treated with additional 2,8,9-triisobutyl-2,5,8,9-tetraaza-1-phospha-bicyclo[3.3.3]undecane (40.4 mg) and tris (dibenzylideneacetone)dipalladium (27 mg), and heated at reflux for an additional 7 hours. The reaction was cooled to room temperature and the solvent removed by rotary evaporation in vacuo. Purification by silica gel flash chromatography with a gradient of 15% to 30% ethyl acetate/methylene chloride gave impure material. Purification by silica gel flash chromatography with a gradient of 1% to 2% methanol/methylene chloride afforded the desired title compound as a light yellow solid (20 mg, 0.049 mmol, 8%). $^1$H NMR (300 MHz, DMSO-D6) δ ppm: 1.03 (t, J=7.35 Hz, 3H) 1.76-1.94 (m, 2H) 2.31 (s, 3H) 3.10 (t, J=7.35 Hz, 2H) 5.76 (s, 1H) 6.67-6.73 (m, 2H) 6.96-7.04 (m, 1H) 7.08-7.14 (m, 1H) 7.20 (d, J=8.46 Hz, 2H) 7.29 (s, 1H) 8.14 (d, J=5.52 Hz, 1H) 8.55 (s, 1H) 9.73 (s, 1H); MS (DCI/NH$_3$) m/z 408 (M+H)$^+$.

Example 7

N-{4-[4-Methyl-2-(2-propyl-thiazolo[5,4-b]pyridin-7-ylamino)-phenylsulfanyl]-phenyl}-acetamide

Example 7a

N-[4-(4-Methyl-2-nitro-phenylsulfanyl)-phenyl]-acetamide

The product from Example 6a (1 g, 3.51 mmol) was reacted with N-(4-mercapto-phenyl)-acetamide (0.65 g, 351 mmol) for 18 h following the procedure from Example 6b giving the title compound (1.04 g, 98%).

Example 7b

N-[4-(2-Amino-4-methyl-phenylsulfanyl)-phenyl]-acetamide

The product from Example 7a (0.30 gm, 1 mmol) was reacted with SnCl$_2$ as described in Example 5I to give the title compound (0.27 gm, 100%) as an amber oil which was used without further purification.

Example 7c

N-(4-(4-methyl-2-(2-propylthiazolo[5,4-b]pyridin-7-ylamino)phenylthio)phenyl)acetamide A dry nitrogen-purged flask was charged with 2,8,9-triisobutyl-2,5,8,9-tetraaza-1-phospha-bicyclo[3.3.3]undecane (38.6 mg, 0.1128 mmol), tris(dibenzylideneacetone)-dipalladium (25.8 mg, 0.0282 mmol), and sodium tert-butoxide (83.8 mg, 0.8463 mmol). A solution of the product of Example 5G (120 mg, 0.5642 mmol) in anhydrous toluene (5 mL) was added via syringe, followed by the product from Example 7b (130 mg, 0.4773 mmol). The reaction was heated in a preheated 100° C. oil bath for 2.5 hours, cooled to room temperature, treated with additional 2,8,9-triisobutyl-2,5,8,9-tetraaza-1-phospha-bicyclo[3.3.3]undecane (38.6 mg), tris (dibenzylideneacetone)dipalladium (25.8 mg) and starting aniline (130 mg), and heated at 100° C. for an additional 18 hours. The reaction was cooled to room temperature and the solvent removed by rotary evaporation in vacuo. Purification by silica gel flash chromatography with a gradient of 40% to 60% ethyl acetate/methylene chloride gave the desired title compound as a tan foam (26 mg, 10%). $^1$H NMR (300 MHz, DMSO-$d_6$) δ ppm: 1.01 (t, J=7.35 Hz, 3H) 1.73-1.91 (m, 2H) 2.01 (s, 3H) 2.34 (s, 3H) 3.07 (t, J=7.54 Hz, 2H) 6.78 (d, J=5.52 Hz, 1H) 6.97-7.09 (m, 1H) 7.16-7.30 (m, 3H) 7.36 (s, 1H) 7.51 (d, J=8.82 Hz, 2H) 8.15 (d, J=5.52 Hz, 1H) 8.53 (s, 1H) 9.99 (s, 1H); MS (DCI/NH$_3$) m/z 449 (M+H)$^+$.

Example 8

N-{4-[4-Methyl-2-(2-methyl-2H-pyrazolo[3,4-b]pyridin-4-ylamino)-phenylsulfanyl]-phenyl}-acetamide

Example 8a 2,2-Dimethyl-5-[(1-methyl-1H-pyrazol-3-ylamino)-methylene]-[1,3]dioxane-4,6-dione A mixture of 1-methyl-1H-pyrazol-3-ylamine (1.05 g, 10.8 mmol), 2,2-dimethyl-[1,3]dioxane-4,6-dione (1.71 g, 11.9 mmol), and triethylorthoformate (1.60 g, 10.8 mmol,) in a 25 mL round bottomed flask was heated in a 100° C. oil bath for 15 min. The mixture was cooled to room temperature and EtOH (10 mL) was added. The reaction mixture was heated to dissolve all solids and then cooled back to room temperature. The solid that was formed was isolated by filtration, rinsed with ethanol, and dried to provide the title compound (1.81 g, 66% yield).

Example 8b

2-Methyl-2,7-dihydro-pyrazolo[3,4-b]pyridin-4-one

A mixture of the product of Example 8a (1.50 g, 5.97 mmol) and diphenyl ether (25 mL) was heated under reflux for 1 h, with removal of the resultant acetone by distillation. The solvent was then decanted, and the remaining solid residue was dissolved in dichloromethane (5 mL) and purified by chromatography on silica gel, eluting with a 0-10% MeOH/CH$_2$Cl$_2$ gradient, to provide the title compound (0.360 g, 40% yield).

Example 8c

4-Chloro-2-methyl-2H-pyrazolo[3,4-b]pyridine

A mixture of the product of Example 8b (0.177 g, 1.19 mmol) and phosphorus oxychloride (3 mL) was heated under reflux for 30 min and then cooled to room temperature. The reaction mixture was poured over ice, taken to pH 8 by the addition of 1N aqueous sodium hydroxide solution, and extracted with dichloromethane (3×30 mL). The combined organic phase was dried over anhydrous magnesium sulfate, filtered, and evaporated under reduced pressure to provide the title compound (0.170 g, 88% yield).

Example 8d

N-{4-[4-Methyl-2-(2-methyl-2H-pyrazolo[3,4-b]pyridin-4-ylamino)-phenylsulfanyl]-phenyl}-acetamide A mixture of the product of Example 8c (47.3 mg, 0.282 mmol), the product of Example 7b (84.6 mg, 0.310 mmol), Pd$_2$(dba)$_3$ (12.9 mg, 0.0141 mmol), sodium t-butoxide (67.8 mg, 0.706 mmol), and 2,8,9-triisobutyl-2,5,8,9-tetraaza-1-phosphabicycl[3,3,3]undecane (19.3 mg, 0.0564 mmol) in toluene (4 mL) was degassed, left under a positive pressure of nitrogen, and heated under reflux for 2 h. Additional amounts of Pd$_2$(dba)$_3$ (4.0 mg, 0.0044 mmol) and PN3 (4.5 mg, 0.013 mmol) were added the reaction mixture was heated under reflux for an addition 2 h. The mixture was then cooled to room temperature and partitioned between ethyl acetate (30 mL) and water (30 mL). The aqueous phase was extracted with ethyl acetate and the combined organic phase was dried over anhydrous magnesium sulfate, filtered, and evaporated under reduced pressure. The residue was purified by chromatography on silica gel, eluting with 5% MeOH/CH$_2$Cl$_2$, to provide the title compound (0.0195 g, 17% yield). $^1$H NMR (300 MHz, DMSO-$d_6$) δ ppm: 2.03 (s, 3H), 2.29 (s, 3H), 4.11 (s, 3H), 5.97 (d, J=5.15 Hz, 1H), 6.94-7.00 (m, 1H), 7.05 (dd, J=8.09, 1.47 Hz, 1H), 7.19 (s, 1H), 7.26 (d, J=8.82 Hz, 2H), 7.56 (d, J=8.82 Hz, 2H), 8.09 (d, J=5.15 Hz, 1H), 8.20 (s, 1H), 8.80 (s, 1H), 10.04 (s, 1H); MS (ESI$^+$) m/z 404.1 (M+H)$^+$.

Example 9

4-[4-Methyl-2-(2-methyl-2H-pyrazolo[3,4-b]pyridin-4-ylamino)-phenylsulfanyl]-phenol A mixture of the product of Example 8c (62.1 mg, 0.371 mmol), the product of Example 6c (85.7 mg, 0.371 mmol), Pd$_2$(dba)$_3$ (16.9 mg, 0.0185 mmol), sodium t-butoxide (89.0 mg, 0.926 mmol), and 2,8,9-triisobutyl-2,5,8,9-tetraaza-1-phosphabicycl[3,3,3]undecane (25.4 mg, 0.0741 mmol) in toluene (3 mL) was degassed, left under a positive pressure of nitrogen, and heated under reflux for 2 h. Additional amounts of Pd$_2$(dba)$_3$ (7.0 mg, 0.0076 mmol) and 2,8,9-triisobutyl-2,5,8,9-tetraaza-1-phosphabicycl[3,3,3]undecane (15 mg, 0.044 mmol) were added the reaction mixture was heated under reflux for an addition 2 h. The mixture was then cooled to room temperature and partitioned between ethyl acetate (30 mL) and water (30 mL). The aqueous phase was extracted with ethyl acetate and the combined organic phase was washed with brine, dried over anhydrous magnesium sulfate, filtered, and evaporated under reduced pressure. The residue was purified by chromatography on silica gel, eluting with a 2-5% MeOH/CH$_2$Cl$_2$, gradient to provide the title compound (0.0279 g, 21% yield). $^1$H NMR (300 MHz, DMSO-$d_6$) δ ppm: 2.27 (s, 3H), 4.11 (s, 3H), 5.92 (d, J=5.15 Hz, 1H), 6.75-6.85 (m, 3H), 7.02 (dd, J=8.27, 0.92 Hz, 1H), 7.14 (s, 1H), 7.18-7.27 (m, 2H), 8.09 (d, J=5.15 Hz, 1H), 8.20 (s, 1H), 8.77 (s, 1H), 9.82 (s, 1H); MS (ESI$^+$) m/z 363.0 (M+H)$^+$ (ESI$^-$) m/z 360.9 (M−H)$^-$.

Example 10

4-[4-(4-Methoxy-benzyloxy)-2-(7-methyl-pyrido[2,3-d]pyrimidin-4-ylamino)-phenylsulfanyl]-phenol

Example 10A

2-Amino-6-methyl-nicotinonitrile

2-Chloro-6-methyl-nicotinonitrile (25 g, 0.164 mol) and liquid ammonia (250 mL) in 500 mL of ethanol were reacted in a sealed high-pressure vessel at 130° C. for 20 hours. The reaction mixture was concentrated under vacuum and the residue washed with water (2×50 mL) then dried in a vacuum oven for 24 hours to provide the title compound as a light yellow solid (18 g, 82%). $^1$H NMR (300 MHz, DMSO-d$_6$) δ ppm: 2.30 (s, 3H), 6.52 (d, J=7.7 Hz, 1H), 6.78 (s, 2H), 7.73 (d, J=7.7 Hz, 1H).

Example 10B

N'-(3-Cyano-6-methyl-pyridin-2-yl)-N,N-dimethyl-formamidine

A solution of the product of Example 10A (10 g, 75.19 mmol) and N,N-Dimethylformamide dimethyl acetal (11 mL, 82.71 mmol) in toluene (100 mL) was heated at reflux for 6 hours. After cooling to room temperature, the solution was concentrated under vacuum to provide the title compound as a yellow solid (13.78 g, 98%). $^1$H NMR (300 MHz, DMSO-d$_6$) δ ppm: 2.41 (s, 3H), 3.06 (s, 3H), 3.14 (s, 3H), 6.87 (d, J=7.7 Hz, 1H), 7.89 (d, J=8.1 Hz, 1H), 8.59 (s, 1H).

Example 10C

1-Chloro-4-(4-methoxy-benzyloxy)-2-nitro-benzene

A solution of 4-chloro-3-nitro-phenol (0.5 g, 2.88 mmol), 1-chloromethyl-4-methoxy-benzene (0.496 g, 3.17 mmol), potassium carbonate (1.19 g, 8.64 mmol) and tetrabutylammonium iodide (0.005 g, 0.0135 mmol) in N,N-dimethylformamide (5 ml) was stirred at room temperature for 16 hours. Afterwards ice water (10 mL) was added to the solution and the resultant solid was collected by filtration and dried in a vacuum oven to provide the title compound (0.812 g, 96%).

Example 10D

4-[4-(4-Methoxy-benzyloxy)-2-nitro-phenylsulfanyl]-phenol

A solution of the product of Example 10C (0.812 g, 2.76 mmol), 4-hydroxythiophenol (0.419, 3.32 mmol) and cesium carbonate (2.16 g, 6.64 mmol) in N,N-dimethylformamide (5 mL) was heated to 100° C. for 16 hours. After cooling to room temperature the mixture was poured into ice water (20 mL) and the resultant solution acidified with 1N aqueous hydrochloric acid. The solution was then extracted with ethyl acetate (3×10 mL), the combined extracts dried over magnesium sulfate, filtered and concentrated under vacuum to provide the title compound (1.06 g, 100%).

Example 10E

4-[2-Amino-4-(4-methoxy-benzyloxy)-phenylsulfanyl]-phenol

A solution of the product of Example 10D (1.06 g, 2.76 mmol), iron powder (0.63 g, 11.04 mmol) and ammonium chloride (0.18 g, 3.31 mmol) in a methanol (18 mL), tetrahydrofuran (18 mL), and water (6 mL) solution was heated to reflux for 3 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were dried over magnesium sulfate, filtered and concentrated under vacuum to provide the title compound (0.99 g, 100%).

Example 10F

4-[4-(4-Methoxy-benzyloxy)-2-(7-methyl-pyrido[2,3-d]pyrimidin-4-ylamino)-phenylsulfanyl]-phenol A solution of the product of Example 10B (28.4 mg, 0.151 mmol), and the product of Example 10E (53.3 mg, 0.151 mmol) in acetic acid (1 mL) was stirred in an oil bath preheated to 130° C. for 20 minutes. The mixture was then cooled to room temperature, the acetic acid removed under vacuum, and the resultant residue triturated with methanol to provide the title compound as a tan solid (26.5 mg, 35%). $^1$H NMR (300 MHz, DMSO-d$_6$) δ ppm: 9.92 (s, 1H), 9.63 (s, 1H), 8.70 (d, J=8.09 Hz, 1H), 8.55 (s, 1H), 7.52 (d, J=8.46 Hz, 1H), 7.38 (d, J=8.82 Hz, 2H), 7.27 (s, 1H), 7.06-7.18 (m, 3H), 6.94 (d, J=8.46 Hz, 3H), 6.61-6.72 (m, 2H), 5.02 (s, 2H), 3.75 (s, 3H), 2.66 (s, 3H); MS (ESI+) m/z 497.2 (M+H)+, (ESI−) m/z 495.3 (M−H)−.

Example 11

3-[4-(4-Hydroxy-phenylsulfanyl)-3-(7-methyl-pyrido[2,3-d]pyrimidin-4-ylamino)-phenoxymethyl]-benzonitrile Example 11A 3-[3-Amino-4-(4-hydroxy-phenylsulfanyl)-phenoxymethyl]-benzonitrile A solution of 4-chloro-3-nitro-phenol was reacted with 3-bromomethyl-benzonitrile using the conditions described in Example 10C to provide 3-(4-chloro-3-nitro-phenoxymethyl)-benzonitrile which was treated sequentially using the procedures from Examples 10D and 10E to provide the title product.

Example 11B

3-[4-(4-Hydroxy-phenylsulfanyl)-3-(7-methyl-pyrido[2,3-d]pyrimidin-4-ylamino)-phenoxymethyl]-benzonitrile The product of Example 11A was reacted with the product of Example 10B using the procedure of Example 10F substituting the product of Example 11A for the product of Example 10E to provide the crude title compound which was purified by reverse phase preparative HPLC on a Waters Symmetry C8 column (25 mm×100 mm, 7 μm particle size) using a gradient of 10% to 100% acetonitrile/0.1% trifluoroacetic acid in water over 8 minutes (10 minutes run time) at a flow rate of 40 mL/min to provide the title compound as a trifluoroacetic acid salt (20 mg, 23%). 1H NMR (300 MHz, DMSO-d$_6$) δ ppm: 11.39 (s, 1H), 9.70 (s, 1H), 8.89 (d, J=8.46 Hz, 1H), 8.77 (s, 1H), 7.92 (s, 1H), 7.75-7.86 (m, 3H), 7.62 (t, J=7.72 Hz, 1H), 7.18-7.29 (m, 2H), 7.03-7.14 (m, 3H), 6.55-6.69 (m, 2H), 5.18 (s, 2H), 2.74 (s, 3H); MS (ESI+) m/z 492.1 (M+H)+ (ESI−) m/z 490.2 (M−H)−.

Example 12

4-[2-(7-Methyl-pyrido[2,3-d]pyrimidin-4-ylamino)-4-(pyridin-2-ylmethoxy)-phenysulfanyl]-phenol Example 12A 4-[2-Amino-4-(pyridin-2-ylmethoxy)-phenylsulfanyl]-phenol A solution of 4-chloro-3-nitro-phenol was reacted with 2-Bromomethyl-pyridine hydrobromide salt using the conditions described in Example 10C to provide 2-(4-Chloro-3-nitro-phenoxymethyl)-pyridine which was treated sequentially using the procedures from Examples 10D and 10E to provide the title product.

Example 12B

4-[2-(7-Methyl-pyrido[2,3-d]pyrimidin-4-ylamino)-4-(pyridin-2-ylmethoxy)-phenysulfanyl]-phenol The product of Example 12A was reacted with the product of Example 10B using the procedure of Example 10F substituting the product of Example 12A for the product of Example 10E to provide the crude title compound which was purified by HPLC with TFA to provide the title compound as a trifluoroacetic acid salt (15 mg, 17%). 1H NMR (300 MHz, DMSO-D6) δ ppm 2.76 (s, 3H) 5.19 (s, 2H) 6.63 (d, J=8.82 Hz, 2H) 6.98-7.17 (m, 3H) 7.20 (d, J=2.57 Hz, 1H) 7.22-7.30 (m, 1H) 7.38 (dd, J=6.43, 4.96 Hz, 1H) 7.53 (d, J=7.72 Hz, 1H) 7.71-7.94 (m, 2H) 8.58 (d, J=4.04 Hz, 1H) 8.82 (s, 1H) 8.93 (d, J=7.72 Hz, 1H) 9.71 (br s, 1H) 11.66 (br s, 1H); MS (ESI+) m/z 468 (M+H)+.

Example 13

4-[4-(4-tert-Butyl-benzyloxy)-2-(7-methyl-pyrido[2,3-d]pyrimidin-4-ylamino)-phenylsulfanyl]-phenol Example 13A 4-[2-Amino-4-(4-tert-butyl-benzyloxy)-phenylsulfanyl]-phenol A solution of 4-chloro-3-nitro-phenol was reacted with 1-Bromomethyl-4-tert-butyl-benzene using the conditions described in Example 10C to provide 4-(4-tert-Butyl-benzyloxy)-1-chloro-2-nitro-benzene which was treated sequentially using the procedures from Examples 10D and 10E to provide the title product.

Example 13B

4-[4-(4-tert-Butyl-benzyloxy)-2-(7-methyl-pyrido[2,3-d]pyrimidin-4-ylamino)-phenylsulfanyl]-phenol The product of Example 13A was reacted with the product of Example 10B using the procedure of Example 10F substituting the product of Example 13A for the product of Example 10E to provide the crude title compound which was purified by HPLC with TFA to provide the title compound as a trifluoroacetic acid salt (52 mg, 36%). 1H NMR (300 MHz, DMSO-D6) δ ppm: 1.28 (s, 9H) 2.74 (s, 3H) 5.06 (s, 2H) 6.63 (d, J=8.46 Hz, 2H) 7.00-7.12 (m, 3H) 7.15-7.27 (m, 2H) 7.30-7.47 (m, 5H) 7.79 (d, J=8.46 Hz, 1H) 8.77 (s, 1H) 8.89 (d, J=8.46 Hz, 1H) 9.69 (s, 1H); MS (ESI+) m/z 523 (M+H)+.

Example 14

4-[4-(2-Bromo-benzyloxy)-2-(7-methyl-pyrido[2,3-d]pyrimidin-4-ylamino)-phenylsulfanyl]-phenol Example 14A 4-[2-Amino-4-(2-bromo-benzyloxy)-phenylsulfanyl]-phenol A solution of 4-chloro-3-nitro-phenol was reacted with 1-Bromo-2-bromomethyl-benzene using the conditions described in Example 10C to provide 4-(2-Bromo-benzyloxy)-1-chloro-2-nitro-benzene which was treated sequentially using the procedures from Examples 10D and 10E to provide the title product.

Example 14B

4-[4-(2-Bromo-benzyloxy)-2-(7-methyl-pyrido[2,3-d]pyrimidin-4-ylamino)-phenylsulfanyl]-phenol The product of Example 14A was reacted with the product of Example 10B using the procedure of Example 10F substituting the product of Example 14A for the product of Example 10E to provide the crude title compound which was purified by HPLC with TFA to provide the title compound as a trifluoroacetic acid salt (42 mg, 39%). 1H NMR (300 MHz, DMSO-D6) δ ppm: 2.68 (s, 3H) 5.13 (s, 2H) 6.67 (m, 2H) 6.96 (d, J=7.68 Hz, 1H) 7.14 (m, 3H) 7.30 (m, 2H) 7.44 (m, 1H) 7.59 (m, 2H) 7.68 (d, J=7.68 Hz, 1H) 8.59 (s, 1H) 8.73 (d, J=8.09 Hz, 1H) 9.66 (s, 1H) 10.27 (s, 1H); MS (ESI+) m/z 545, 547 (M+H)+.

Example 15

4-[4-(3-Bromo-benzyloxy)-2-(7-methyl-pyrido[2,3-d]pyrimidin-4-ylamino)-phenylsulfanyl]-phenol Example 15A 4-[2-Amino-4-(3-bromo-benzyloxy)-phenylsulfanyl]-phenol A solution of 4-chloro-3-nitro-phenol was reacted with 1-Bromo-3-bromomethyl-benzene using the conditions described in Example 10C to provide 4-(3-Bromo-benzyloxy)-1-chloro-2-nitro-benzene which was treated sequentially using the procedures from Examples 10D and 10E to provide the title product.

Example 15B

4-[4-(3-Bromo-benzyloxy)-2-(7-methyl-pyrido[2,3-d]pyrimidin-4-ylamino)-phenylsulfanyl]-phenol The product of Example 15A was reacted with the product of Example 10B using the procedure of Example 10F substituting the product of Example 15A for the product of Example 10E to provide the crude title compound which was purified by HPLC with TFA to provide the title compound as a trifluoroacetic acid salt (25 mg, 23%). 1H NMR (300 MHz, DMSO-D6) δ ppm: 2.72 (s, 3H) 5.13 (s, 2H) 6.65 (m, 2H) 7.11 (m, 5H) 7.40 (m, 2H) 7.54 (d, J=7.72 Hz, 1H) 7.66 (s, 1H) 7.72 (d, J=8.82 Hz, 1H) 8.71 (s, 1H) 8.84 (d, J=8.09 Hz, 1H) 9.68 (s, 1H), 11.04 (m, 1H); MS (ESI+) m/z 545, 547 (M+H)+.

Example 16

4-[4-(4-Bromo-benzyloxy)-2-(7-methyl-pyrido[2,3-d]pyrimidin-4-ylamino)-phenylsulfanyl]-phenol Example 16A 4-[2-Amino-4-(4-bromo-benzyloxy)-phenylsulfanyl]-phenol A solution of 4-chloro-3-nitro-phenol was reacted with 1-Bromo-4-bromomethyl-benzene using the conditions described in Example 10C to provide 4-(4-Bromo-benzyloxy)-1-chloro-2-nitro-benzene which was treated sequentially using the procedures from Examples 10D and 10E to provide the title product.

Example 16B

4-[4-(4-Bromo-benzyloxy)-2-(7-methyl-pyrido[2,3-d]pyrimidin-4-ylamino)-phenylsulfanyl]-phenol The product of Example 16A was reacted with the product of Example 10B using the procedure of Example 10F substituting the product of Example 16A for the product of Example 10E to provide the crude title compound which was purified by HPLC with TFA to provide the title compound as a trifluoroacetic acid salt (19 mg, 17%). 1H NMR (300 MHz, DMSO-D6) δ ppm: 2.72 (s, 3H) 5.13 (s, 2H) 6.63 (m, 2H) 7.03 (dd, J=8.82, 2.57 Hz, 1H) 7.10 (m, 2H) 7.21 (d, J=8.46 Hz, 2H) 7.40 (m, 2H) 7.54 (d, J=8.09 Hz, 1H) 7.66 (s, 1H) 7.73 (d, J=8.46 Hz, 1H) 8.72 (s, 1H) 8.84 (d, J=8.46 Hz, 1H) 9.69 (s, 1H) 11.08 (m, 1H); MS (ESI+) m/z 545, 547 (M+H)+.

Example 17

4-[4-(2-Methyl-benzyloxy)-2-(7-methyl-pyrido[2,3-d]pyrimidin-4-ylamino)-phenylsulfanyl]-phenol Example 17A 4-[2-Amino-4-(2-methyl-benzyloxy)-phenylsulfanyl]-phenol A solution of 4-chloro-3-nitro-phenol was reacted with 1-Bromomethyl-2-methyl-benzene using the conditions described in Example 10C to provide 1-Chloro-4-(2-methyl-benzyloxy)-2-nitro-benzene which was treated sequentially using the procedures from Examples 10D and 10E to provide the title product.

Example 17B

4-[4-(2-Methyl-benzyloxy)-2-(7-methyl-pyrido[2,3-d]pyrimidin-4-ylamino)-phenylsulfanyl]-phenol The product of Example 17A was reacted with the product of Example 10B using the procedure of Example 10F substituting the product of Example 17A for the product of Example 10E to provide the crude title compound which was purified by HPLC with TFA to provide the title compound as a trifluoroacetic acid salt (35 mg, 36%). 1H NMR (300 MHz, DMSO-D6) δ ppm: 2.32 (s, 3H) 2.71 (s, 3H) 5.09 (s, 2H) 6.65 (m, 2H) 7.03 (dd, J=8.82, 2.57 Hz, 1H) 7.11 (m, 2H) 7.24 (m, 5H) 7.41 (d, J=6.99 Hz, 1H) 7.69 (d, J=8.46 Hz, 1H) 8.69 (s, 1H) 8.82 (d, J=8.82 Hz, 1H) 9.67 (s, 1H) 10.84 (s, 1H); MS (ESI+) m/z 481 (M+H)+.

Example 18

4-[4-(3-Methyl-benzyloxy)-2-(7-methyl-pyrido[2,3-d]pyrimidin-4-ylamino)-phenylsulfanyl]-phenol Example 18A 4-[2-Amino-4-(3-methyl-benzyloxy)-phenylsulfanyl]-phenol A solution of 4-chloro-3-nitro-phenol was reacted with 1-Bromomethyl-3-methyl-benzene using the conditions described in Example 10C to provide 1-Chloro-4-(3-methyl-benzyloxy)-2-nitro-benzene which was treated sequentially using the procedures from Examples 10D and 10E to provide the title product.

Example 18B

4-[4-(3-Methyl-benzyloxy)-2-(7-methyl-pyrido[2,3-d]pyrimidin-4-ylamino)-phenylsulfanyl]-phenol The product of Example 18A was reacted with the product of Example 10B using the procedure of Example 10F substituting the product of Example 18A for the product of Example 10E to provide the crude title compound which was purified by HPLC with TFA to provide the title compound as a trifluoroacetic acid salt (37 mg, 39%). 1H NMR (300 MHz, DMSO-D6) δ ppm: 2.31 (s, 3H) 2.73 (s, 3H) 5.07 (s, 2H) 6.64 (m, 2H) 7.16 (m, 9H) 7.75 (d, J=8.46 Hz, 1H) 8.73 (s, 1H) 8.86 (d, J=8.46 Hz, 1H) 9.69 (s, 1H) 11.16 (s, 1H); MS (ESI+) m/z 481 (M+H)+.

Example 19

4-[4-(4-Methyl-benzyloxy)-2-(7-methyl-pyrido[2,3-d]pyrimidin-4-ylamino)-phenylsulfanyl]-phenol Example 19A 4-[2-Amino-4-(4-methyl-benzyloxy)-phenylsulfanyl]-phenol A solution of 4-chloro-3-nitro-phenol was reacted with 1-Bromomethyl-4-methyl-benzene using the conditions described in Example 10C to provide 1-Chloro-4-(4-methyl-benzyloxy)-2-nitro-benzene which was treated sequentially using the procedures from Examples 10D and 10E to provide the title product.

Example 19B

4-[4-(4-Methyl-benzyloxy)-2-(7-methyl-pyrido[2,3-d]pyrimidin-4-ylamino)-phenylsulfanyl]-phenol The product of Example 19A was reacted with the product of Example 10B using the procedure of Example 10F substituting the product of Example 19A for the product of Example 10E to provide the crude title compound which was purified by HPLC with TFA to provide the title compound as a trifluoroacetic acid salt (29 mg, 30%). 1H NMR (300 MHz, DMSO-D6) δ ppm: 2.30 (s, 3H) 2.67 (s, 3H) 5.05 (s, 2H) 6.64 (m, 2H) 6.94 (d, J=7.38 Hz, 1H) 7.17 (m, 6H) 7.33 (d, J=8.09 Hz, 2H) 7.56 (d, J=8.46 Hz, 1H) 8.57 (s, 1H) 8.72 (d, J=8.09 Hz, 1H) 9.63 (s, 1H) 10.12 (s, 1H); MS (ESI+) m/z 481 (M+H)+.

Example 20

2-[4-(4-Hydroxy-phenylsulfanyl)-3-(7-methyl-pyrido[2,3-d]pyrimidin-4-ylamino)-phenoxymethyl]-benzonitrile Example 20A 2-[3-Amino-4-(4-hydroxy-phenylsulfanyl)-phenoxymethyl]-benzonitrile A solution of 4-chloro-3-nitro-phenol was reacted with 2-Bromomethyl-benzonitrile using the conditions described in Example 10C to provide 2-(4-Chloro-3-nitro-phenoxymethyl)-benzonitrile which was treated sequentially using the procedures from Examples 10D and 10E to provide the title product.

Example 20B

2-[4-(4-Hydroxy-phenylsulfanyl)-3-(7-methyl-pyrido[2,3-d]pyrimidin-4-ylamino)-phenoxymethyl]-benzonitrile The product of Example 20A was reacted with the product of Example 10B using the procedure of Example 10F substituting the product of Example 20A for the product of Example 10E to provide the crude title compound which was purified by HPLC with TFA to provide the title compound as a trifluoroacetic acid salt (21 mg, 16%). 1H NMR (300 MHz, DMSO-D6) δ ppm: 9.93 (s, 1H), 9.63 (s, 1H), 8.75 (d, J=8.46 Hz, 1H), 8.57 (s, 1H), 7.60 (d, J=8.09 Hz, 1H), 7.38 (d, J=8.46 Hz, 2H), 7.27 (s, 1H), 7.05-7.19 (m, 3H), 6.85-7.00 (m, 3H), 6.67 (d, J=8.82 Hz, 2H), 5.02 (s, 2H), 3.75 (s, 3H), 3.14-3.28 (m, 1H), 1.32 (d, J=6.62 Hz, 6H); MS (ESI+) m/z 492.2 (M+H)+ (ESI−) m/z 490.2 (M−H)−.

Example 21

4-[4-(4-Hydroxy-phenylsulfanyl)-3-(7-methyl-pyrido[2,3-d]pyrimidin-4-ylamino)-phenoxymethyl]-benzonitrile

Example 21A

4-[3-Amino-4-(4-hydroxy-phenylsulfanyl)-phenoxymethyl]-benzonitrile

A solution of 4-chloro-3-nitro-phenol was reacted with 4-Bromomethyl-benzonitrile using the conditions described in Example 10C to provide 4-(4-Chloro-3-nitro-phenoxymethyl)-benzonitrile which was treated sequentially using the procedures from Examples 10D and 10E to provide the title product.

Example 21B

4-[4-(4-Hydroxy-phenylsulfanyl)-3-(7-methyl-pyrido[2,3-d]pyrimidin-4-ylamino)-phenoxymethyl]-benzonitrile The product of Example 21A was reacted with the product of Example 10B using the procedure of Example 10F substituting the product of Example 21A for the product of Example 10E to provide the crude title compound which was purified by HPLC with TFA to provide the title compound as a trifluoroacetic acid salt (15 mg, 14%). 1H NMR (300 MHz, DMSO-D6) δ ppm: 11.69 (s, 1H), 9.72 (s, 1H), 8.94 (d, J=8.46 Hz, 1H), 8.83 (s, 1H), 7.78-7.96 (m, 3H), 7.63 (d, J=8.46 Hz, 2H), 7.22-7.27 (m, 1H), 7.18 (d, J=2.57 Hz, 1H), 7.06-7.13 (m, 3H), 6.59-6.66 (m, 2H), 5.23 (s, 2H), 2.76 (s, 3H); MS (ESI+) m/z 492.1 (M+H)+ (ESI−) m/z 490.1 (M−H)−.

Example 22

4-[4-[1-(4-Bromo-phenyl)-ethoxy]-2-(7-methyl-pyrido[2,3-d]pyrimidin-4-ylamino)-phenylsulfanyl]-phenol

Example 22A

1-Bromo-4-(1-bromo-ethyl)-benzene

A solution of 1-(4-bromo-phenyl)-ethanol (4.21 g, 20.9 mmol) in 15 mL of CH$_2$Cl$_2$ was reacted with 15 mL of 1.0M PBr$_3$ in CH$_2$Cl$_2$ at room temperature for 4 h. Quenched by pouring into ice and adjusted to pH 9 with 5% aqueous NaHCO$_3$. Extracted with CH$_2$Cl$_2$ and dried over Na$_2$SO$_4$, filtered and concentrated under vacuum giving the title compound (4.1 g, 75%).

Example 22B

4-[1-(4-Bromo-phenyl)-ethoxy]-1-chloro-2-nitro-benzene

The product from Example 22A (995 mg, 3.77 mmol) was reacted with 4-chloro-3-nitro-phenol (650 mg, 3.77 mmol) in 15 mL of DMF with K$_2$CO$_3$ (10.4 g, 3.77 mmol) at 80° C. for 3 h. Cooled to room temperature and diluted with water. Extracted with CH$_2$Cl$_2$, washed four times with water. Dried over Na$_2$SO$_4$, filtered and concentrated under vacuum giving the title compound (1.24 g, 92%).

Example 22C

4-{4-[1-(4-Bromo-phenyl)-ethoxy]-2-nitro-phenylsulfanyl}-phenol

The product from Example 22B (1.15 g, 3.22 mmol) was reacted with 4-mercapto-phenol (403 mg, 3.22 mmol) and K$_2$CO$_3$ (890 mg, 6.44 mmol) in 25 mL of DMF at 80° C. for 18 h. Cooled to room temperature and poured into water. Extracted with CH$_2$Cl$_2$ and washed several times with water. Dried over Na$_2$SO$_4$, filtered and concentrated under vacuum giving the title compound (980 mg, 68%).

Example 22D

4-[2-Amino-4-(1-phenyl-ethoxy)-phenylsulfanyl]-phenol

The product from Example 22C (560 mg, 1.25 mmol) was reacted with Fe (279 mg, 5.0 mmol) and NH$_4$Cl (76 mg, 1.40 mmol) in 5 mL MeOH/5 mL THF/2.5 mL water following the procedure from Example 10E giving the title compound as a solid (439 mg, 84%).

Example 22E

4-[4-[1-(4-Bromo-phenyl)-ethoxy]-2-(7-methyl-pyrido[2,3-d]pyrimidin-4-ylamino)-phenylsulfanyl]-phenol The product from Example 22D (204 mg, 0.49 mmol) was reacted with the product from Example 10B (93 mg, 0.49 mmol) following the procedure from Example 10F to provide the crude title compound which was purified by HPLC with TFA to provide the title compound as a trifluoroacetic acid salt (38 mg, 12%). $^1$H NMR (300 MHz, DMSO-d$_6$) δ ppm:

11.24 (br s, 1H) 9.70 (s, 1H) 8.83 (d, J=8.09 Hz, 1H) 8.74 (s, 1H) 7.76 (d, J=8.45 Hz, 1H) 7.55 (d, J=8.46 Hz, 2H) 7.37 (d, J=8.46 Hz, 2H) 7.09 (m, 4H) 6.93 (dd, J=6.62 Hz, J=2.20 Hz, 1H) 6.63 (d, J=8.82 Hz, 2H) 5.51 (q, J=6.25 Hz, 2H) 2.73 (s, 3H), 1.53 (d, J=6.25 Hz, 3H); MS (ESI+) m/z, 559, 561 (M+H−TFA)+; (ESI−) m/z, 557, 559 (M−H−TFA)−.

Example 23

4-[4-[1-(4-Fluoro-phenyl)-ethoxy]-2-(7-methyl-pyrido[2,3-d]pyrimidin-4-ylamino)-phenylsulfanyl]-phenol Example 23A 4-{2-Amino-4-[1-(4-fluoro-phenyl)-ethoxy]-phenylsulfanyl}-phenol A solution of 1-(4-fluoro-phenyl)-ethanol was converted to 1-(1-Bromo-ethyl)-4-fluoro-benzene using the conditions described in Example 22A which was treated sequentially using the procedures from Examples 22B-22D to provide the title product.

Example 23B

4-[4-[1-(4-Fluoro-phenyl)-ethoxy]-2-(7-methyl-pyrido[2,3-d]pyrimidin-4-ylamino)-phenylsulfanyl]-phenol The product from Example 23A (207 mg, 0.584 mmol) was reacted with the product from Example 10B (110 mg, 0.584 mmol) following the procedure from Example 10F to provide the crude title compound which was purified by HPLC with TFA to provide the title compound as a trifluoroacetic acid salt (30 mg, 35%). 1H NMR (300 MHz, DMSO-$d_6$) δ ppm: 1.54 (d, J=6.25 Hz, 3H) 2.73 (s, 3H) 5.53 (q, J=6.13 Hz, 1H) 6.63 (d, J=8.82 Hz, 2H) 6.93 (dd, J=8.82, 2.57 Hz, 1H) 7.05-7.14 (m, 4H) 7.18 (t, J=9.01 Hz, 2H) 7.41-7.49 (m, 2H) 7.76 (d, J=8.46 Hz, 1H) 8.73 (s, 1H) 8.84 (d, J=8.46 Hz, 1H) 9.71 (s, 1H); MS (ESI+) m/z 497 (MH)−.

Example 24

4-[4-[1-(3-Fluoro-phenyl)-ethoxy]-2-(7-methyl-pyrido[2,3-d]pyrimidin-4-ylamino)-phenylsulfanyl]-phenol Example 24A 4-{2-Amino-4-[1-(3-fluoro-phenyl)-ethoxy]-phenylsulfanyl}-phenol A solution of 1-(3-fluoro-phenyl)-ethanol was converted to 1-(1-Bromo-ethyl)-3-fluoro-benzene using the conditions described in Example 22A which was treated sequentially using the procedures from Examples 22B-22D to provide the title product.

Example 24B

4-[4-[1-(3-Fluoro-phenyl)-ethoxy]-2-(7-methyl-pyrido[2,3-d]pyrimidin-4-ylamino)-phenylsulfanyl]-phenol The product from Example 24A (226 mg, 0.637 mmol) was reacted with the product from Example 10B (120 mg, 0.637 mmol) following the procedure from Example 10F to provide the crude title compound which was purified by HPLC with TFA to provide the title compound as a trifluoroacetic acid salt (87 mg, 22%). 1H NMR (300 MHz, DMSO-D6) δ ppm: 1.55 (d, J=6.62 Hz, 3H) 2.72 (s, 3H) 5.54 (q, J=6.13 Hz, 1H) 6.64 (d, J=8.46 Hz, 2H) 6.91 (dd, J=8.82, 2.57 Hz, 1H) 7.06-7.15 (m, 5H) 7.20-7.28 (m, 2H) 7.35-7.44 (m, 1H) 7.70 (d, J=8.46 Hz, 1H) 8.68 (s, 1H) 8.81 (d, J=8.46 Hz, 1H) 9.73 (s, 1H); MS (ESI+) m/z 499 (M+H)+.

Example 25

4-[4-(2-Chloro-thiazol-5-ylmethoxy)-2-(7-methyl-pyrido[2,3-d]pyrimidin-4-ylamino)-phenylsulfanyl]-phenol Example 25A 4-[2-Amino-4-(2-chloro-thiazol-5-ylmethoxy)-phenylsulfanyl]-phenol A solution of 4-chloro-3-nitro-phenol was reacted with 5-Bromomethyl-2-chloro-thiazole (prepared according to the method of Kim, H.-J., Liu, S., Keum, Y.-S., Qing, X. *J. Agric. Food Chem.* 2003, 51, 1823-1830) using the conditions described in Example 10C to provide 2-Chloro-5-(4-chloro-3-nitro-phenoxymethyl)-thiazole which was treated sequentially using the procedures from Examples 10D and 10E to provide the title product.

Example 25B

4-[4-(2-Chloro-thiazol-5-ylmethoxy)-2-(7-methyl-pyrido[2,3-d]pyrimidin-4-ylamino)-phenylsulfanyl]-phenol The product of Example 25A was reacted with the product of Example 10B using the procedure of Example 10F substituting the product of Example 25A for the product of Example 10E to provide the crude title compound which was purified by HPLC with TFA to provide the title compound as a trifluoroacetic acid salt. 1H NMR (300 MHz, DMSO-D6) δ ppm: 2.71 (s, 3H) 5.34 (s, 2H) 6.66 (d, J=8.46 Hz, 2H) 7.01 (dd, J=8.64, 2.02 Hz, 1H) 7.06-7.28 (m, 4H) 7.68 (d, J=8.46 Hz, 1H) 7.80 (s, 1H) 8.67 (s, 1H) 8.82 (d, J=8.46 Hz, 1H) 9.70 (s, 1H), 10.81 (bs, 1H); MS (ESI+) m/z 508 (M+H)+.

Example 26

4-[2-(7-Methyl-pyrido[2,3-d]pyrimidin-4-ylamino)-4-(3-trifluoromethyl-benzyloxy)-phenylsulfanyl]-phenol Example 26A 4-[2-Amino-4-(3-trifluoromethyl-benzyloxy)-phenylsulfanyl]-phenol A solution of 4-chloro-3-nitro-phenol was reacted with 1-Chloromethyl-3-trifluoromethyl-benzene using the conditions described in Example 10C to provide 1-Chloro-2-nitro-4-(3-trifluoromethyl-benzyloxy)-benzene which was treated sequentially using the procedures from Examples 10D and 10E to provide the title product.

Example 26B

4-[2-(7-Methyl-pyrido[2,3-d]pyrimidin-4-ylamino)-4-(3-trifluoromethyl-benzyloxy)-phenylsulfanyl]-phenol The product of Example 26A was reacted with the product of Example 10B using the procedure of Example 10F substituting the product of Example 26A for the product of Example 10E to provide the crude title compound which was purified by HPLC with TFA to provide the title compound as a trifluoroacetic acid salt (9.9 mg, 9%). 1H NMR (300 MHz, DMSO-D6) δ ppm: 2.74 (s, 3H), 5.22 (s, 2H), 6.64 (d, J=8.46 Hz, 2H), 7.10 (d, J=8.82 Hz, 3H), 7.19-7.30 (m, 2H), 7.62-7.72 (m, J=7.35 Hz, 2H), 7.72-7.84 (m, 4H), 8.75 (s, 1H), 8.88 (d, J=7.35 Hz, 1H), 9.69 (s, 1H); MS ESI+ m/z 535 (M+H)+, ESI– m/z 533 (M–H)–.

Example 27

4-[4-Benzyloxy-2-(7-methyl-pyrido[2,3-d]pyrimidin-4-ylamino)-phenylsulfanyl]-phenol Example 27A 4-(2-Amino-4-benzyloxy-phenylsulfanyl)-phenol A solution of 4-chloro-3-nitro-phenol was reacted with Bromomethyl-benzene using the conditions described in Example 10C to provide 4-Benzyloxy-1-chloro-2-nitro-benzene which was treated sequentially using the procedures from Examples 10D and 10E to provide the title product.

Example 27B

4-[4-Benzyloxy-2-(7-methyl-pyrido[2,3-d]pyrimidin-4-ylamino)-phenylsulfanyl]-phenol The product of Example 27A was reacted with the product of Example 10B using the procedure of Example 10F substituting the product of Example 27A for the product of Example 10E to provide the crude title compound which was purified by HPLC with TFA to provide the title compound as a trifluoroacetic acid salt (73 mg, 25%). 1H NMR (300 MHz, DMSO-D6) δ ppm: 2.70 (s, 3H) 5.11 (s, 2H) 6.65 (d, J=8.46 Hz, 2H) 6.98 (d, J=7.72 Hz, 1H) 7.10 (d, J=8.46 Hz, 2H) 7.18 (d, J=8.46 Hz, 1H) 7.24 (s, 1H) 7.28-7.51 (m, 5H) 7.63 (d, J=8.82 Hz, 1H) 8.64 (s, 1H) 8.78 (d, J=8.82 Hz, 1H) 9.65 (s, 1H) 10.56 (br s, 1H); MS (ESI+) m/z 467 (M+H)+.

Example 28

4-[4-(3-Fluoro-benzyloxy)-2-(7-methyl-pyrido[2,3-d]pyrimidin-4-ylamino)-phenylsulfanyl]-phenol Example 28A 4-[2-Amino-4-(3-fluoro-benzyloxy)-phenylsulfanyl]-phenol A solution of 4-chloro-3-nitro-phenol was reacted with 1-Bromomethyl-3-fluoro-benzene using the conditions described in Example 10C to provide 1-Chloro-4-(3-fluoro-benzyloxy)-2-nitro-benzene which was treated sequentially using the procedures from Examples 10D and 10E to provide the title product.

Example 28B

4-[4-(3-Fluoro-benzyloxy)-2-(7-methyl-pyrido[2,3-d]pyrimidin-4-ylamino)-phenylsulfanyl]-phenol The product of Example 28A was reacted with the product of Example 10B using the procedure of Example 10F substituting the product of Example 28A for the product of Example 10E to provide the crude title compound which was purified by HPLC with TFA to provide the title compound as a trifluoroacetic acid salt (41 mg, 42%). 1H NMR (300 MHz, DMSO-D6) δ ppm: 2.72 (s, 3H) 5.14 (s, 2H) 6.65 (m, 2H) 7.02 (dd, J=8.64, 2.76 Hz, 1H) 7.10 (m, 2H) 7.23 (m, 5H) 7.44 (m, 1H) 7.71 (d, J=8.46 Hz, 1H) 8.69 (s, 1H) 8.83 (d, J=8.46 Hz, 1H) 9.69 (s, 1H) 10.96 (s, 1H); MS (ESI+) m/z 485 (M+H)+.

Example 29

4-[2-(7-Methyl-pyrido[2,3-d]pyrimidin-4-ylamino)-4-(tetrahydro-furan-2-ylmethoxy)-phenylsulfanyl]-phenol Example 29A 4-[2-Amino-4-(tetrahydro-furan-2-ylmethoxy)-phenylsulfanyl]-phenol A solution of 4-chloro-3-nitro-phenol was reacted with 2-Bromomethyl-tetrahydro-furan using the conditions described in Example 10C to provide 2-(4-Chloro-3-nitro-phenoxymethyl)-tetrahydro-furan which was treated sequentially using the procedures from Examples 10D and 10E to provide the title product.

Example 29B

4-[2-(7-Methyl-pyrido[2,3-d]pyrimidin-4-ylamino)-4-(tetrahydro-furan-2-ylmethoxy)-phenylsulfanyl]-phenol The product of Example 29A was reacted with the product of Example 10B using the procedure of Example 10F substituting the product of Example 29A for the product of Example 10E to provide the crude title compound which was purified by HPLC with TFA to provide the title compound as a trifluoroacetic acid salt (29 mg, 17%). 1H NMR (300 MHz, DMSO-D6) δ ppm: 1.55-1.84 (m, 1H) 1.84-2.07 (m, 1H) 2.67 (s, 3H) 3.59-3.71 (m, 2H) 3.73-3.83 (m, 1H) 3.85-4.02 (m, 2H) 4.15 (dd, J=6.43, 4.23 Hz, 2H) 6.66 (d, J=8.46 Hz, 2H) 6.87 (dd, J=8.64, 2.76 Hz, 1H) 7.02-7.15 (m, 2H) 7.12-7.24 (m, 2H) 7.53 (d, J=8.46 Hz, 1H) 8.56 (s, 1H) 8.71 (d, J=8.46 Hz, 1H) 9.62 (s, 1H) 9.92 (s, 1H); MS (ESI+) m/z 461 (M+H)+.

Example 30

4-[2-(7-Methyl-pyrido[2,3-d]pyrimidin-4-ylamino)-4-(naphthalen-1-ylmethoxy)-phenylsulfanyl]-phenol Example 30A 4-[2-Amino-4-(naphthalen-1-ylmethoxy)-phenylsulfanyl]-phenol A solution of 4-chloro-3-nitro-phenol was reacted with 1-Chloromethyl-naphthalene using the conditions described in Example 10C to provide 1-(4-Chloro-3-nitro-phenoxymethyl)-naphthalene which was treated sequentially using the procedures from Examples 10D and 10E to provide the title product.

Example 30B

4-[2-(7-Methyl-pyrido[2,3-d]pyrimidin-4-ylamino)-4-(naphthalen-1-ylmethoxy)-phenylsulfanyl]-phenol The product of Example 30A was reacted with the product of Example 10B using the procedure of Example 10F substituting the product of Example 30A for the product of Example 10E to provide the crude title compound which was purified by HPLC with TFA to provide the title compound as a trifluoroacetic acid salt (31 mg, 25%). 1H NMR (300 MHz, DMSO-D6) δ ppm: 2.68 (s, 3H) 5.56 (s, 2H) 6.67 (d, J=8.82 Hz, 2H) 7.01-7.16 (m, 3H) 7.16-7.24 (m, 1H) 7.35 (s, 1H) 7.45-7.64 (m, 4H) 7.69 (d, J=6.62 Hz, 1H) 7.87-8.02 (m, 2H) 8.05-8.14 (m, 1H) 8.59 (s, 1H) 8.74 (d, J=8.46 Hz, 1H) 9.65 (s, 1H) 10.23 (s, 1H); MS (ESI+) 517 (M+H)+.

Example 31

4-[4-(3-Methoxy-benzyloxy)-2-(7-methyl-pyrido[2,3-d]pyrimidin-4-ylamino)-phenylsulfanyl]-phenol

Example 31A

4-[2-Amino-4-(3-methoxy-benzyloxy)-phenylsulfanyl]-phenol

A solution of 4-chloro-3-nitro-phenol was reacted with 1-Chloromethyl-3-methoxy-benzene using the conditions described in Example 10C to provide 1-Chloro-4-(3-methoxy-benzyloxy)-2-nitro-benzene which was treated sequentially using the procedures from Examples 10D and 10E to provide the title product.

Example 31B

4-[4-(3-Methoxy-benzyloxy)-2-(7-methyl-pyrido[2,3-d]pyrimidin-4-ylamino)-phenylsulfanyl]-phenol The product of Example 31A was reacted with the product of Example 10B using the procedure of Example 10F substituting the product of Example 31A for the product of Example 10E to provide a solid which was triturated with methanol to provide the title compound (24 mg, 26%). $^1$H NMR (300 MHz, DMSO-D6) δ ppm 9.93 (s, 1H), 9.63 (s, 1H), 8.71 (d, J=8.09 Hz, 1H), 8.55 (s, 1H), 7.53 (d, J=8.09 Hz, 1H), 7.26-7.35 (m, 2H), 7.15 (d, J=8.46 Hz, 1H), 7.07-7.13 (m, 2H), 6.98-7.04 (m, J=5.15 Hz, 2H), 6.96 (s, 1H), 6.90 (dd, J=8.09, 2.57 Hz, 1H), 6.62-6.71 (m, 2H), 5.08 (s, 2H), 3.75 (s, 3H), 2.67 (s, 3H); MS (ESI+) m/z 497.2 (M+H)+ (ESI−) m/z 495.2 (M−H)−.

Example 32

4-[2-(7-Methyl-pyrido[2,3-d]pyrimidin-4-ylamino)-4-(quinolin-2-ylmethoxy)-phenylsulfanyl]-phenol

Example 32A

4-[2-Amino-4-(quinolin-2-ylmethoxy)-phenylsulfanyl]-phenol

A solution of 4-chloro-3-nitro-phenol was reacted with 2-Chloromethyl-quinoline hydrochloride salt using the conditions described in Example 10C to provide 2-(4-Chloro-3-nitro-phenoxymethyl)-quinoline which was treated sequentially using the procedures from Examples 10D and 10E to provide the title product.

Example 32B

4-[2-(7-Methyl-pyrido[2,3-d]pyrimidin-4-ylamino)-4-(quinolin-2-ylmethoxy)-phenylsulfanyl]-phenol The product of Example 32A was reacted with the product of Example 10B using the procedure of Example 10F substituting the product of Example 32A for the product of Example 10E to provide the crude title compound which was purified by HPLC with TFA to provide the title compound as a trifluoroacetic acid salt (13 mg, 27%). 1H NMR (500 MHz, DMSO-D6) δ ppm: 2.75 (s, 3H) 5.39 (s, 2H) 6.62 (d, J=8.54 Hz, 2H) 7.09 (d, J=8.54 Hz, 2H) 7.14 (dd, J=8.54, 2.44 Hz, 1H) 7.22-7.28 (m, 2H) 7.63 (t, J=7.93 Hz, 1H) 7.68 (d, J=8.54 Hz, 1H) 7.74-7.81 (m, 1H) 7.83 (d, J=8.54 Hz, 1H) 8.00 (t, J=7.93 Hz, 2H) 8.44 (d, J=8.54 Hz, 1H) 8.76 (s, 1H) 8.92 (d, J=8.54 Hz, 1H) 9.68 (s, 1H) 11.64 (br s, 1H); MS (ESI+) 518 (M+H)+.

Example 33

4-[4-(Biphenyl-4-ylmethoxy)-2-(7-methyl-pyrido[2,3-d]pyrimidin-4-ylamino)-phenylsulfanyl]-phenol The product of Example 16B (free salt form, 0.055 g, 0.1 mmol), phenylboronic acid (0.017 g, 0.14 mmol), cesium carbonate (0.05 g, 0.15 mmol) and dichlorobis(triphenylphosphine)palladium(II) (0.007 g, 0.01 mmol) were combined in N,N-dimethylformamide (1 mL) and heated to 100° C. for 24 hours. After cooling to room temperature the mixture was poured into ice water (20 mL) and the resultant solution acidified with 1N aqueous hydrochloric acid. The solution was then extracted with ethyl acetate (3×10 mL), the combined extracts dried over sodium sulfate, filtered and concentrated under vacuum. The crude product was purified by HPLC with TFA to provide the title compound as a trifluoroacetic acid salt (10 mg, 15%). 1H NMR (300 MHz, DMSO-D6) δ ppm: 2.67 (s, 3H), 5.16 (s, 2H), 6.60-6.72 (m, 2H), 6.98 (d, J=8.09 Hz, 1H), 7.06-7.22 (m, 3H), 7.27-7.41 (m, 2H), 7.47 (t, J=7.54 Hz, 2H), 7.54 (d, J=8.46 Hz, 3H), 7.60-7.73 (m, 4H), 8.58 (s, 1H), 8.72 (d, J=8.09 Hz, 1H), 9.64 (s, 1H), 10.08 (s, 1H); MS (ESI+) m/z 543 (M+H+)+.

Example 34

4-[4-(5-Chloro-thiophen-2-ylmethoxy)-2-(7-methyl-pyrido[2,3-d]pyrimidin-4-ylamino)-phenylsulfanyl]-phenol

Example 34A

4-[2-Amino-4-(5-chloro-thiophen-2-ylmethoxy)-phenylsulfanyl]-phenol

A solution of 4-chloro-3-nitro-phenol was reacted with 2-Chloro-5-chloromethyl-thiophene using the conditions described in Example 10C to provide 2-Chloro-5-(4-chloro-3-nitro-phenoxymethyl)-thiophene which was treated sequentially using the procedures from Examples 10D and 10E to provide the title product.

Example 34B

4-[4-(5-Chloro-thiophen-2-ylmethoxy)-2-(7-methyl-pyrido[2,3-d]pyrimidin-4-ylamino)-phenylsulfanyl]-phenolphenylsulfanyl]-phenol The product of Example 34A was reacted with the product of Example 10B using the procedure of Example 10F substituting the product of Example 34A for the product of Example 10E to provide the crude title compound which was purified by HPLC with TFA to provide the title compound as a trifluoroacetic acid salt (6.6 mg, 10%). 1H NMR (300 MHz, DMSO-D6) δ ppm: 2.72 (s, 3H) 5.25 (s, 2H) 6.65 (d, J=8.46 Hz, 2H) 6.97-7.14 (m, 4H) 7.19 (d, J=8.46 Hz, 2H) 7.72 (d, J=8.09 Hz, 1H) 8.71 (s, 1H) 8.84 (d, J=8.46 Hz, 1H) 9.69 (s, 1H) 11.01 (br s, 1H); MS (ESI+) m/z 543 (M+H)+.

Example 35

4-[4-(4-Fluoro-benzyloxy)-2-(7-methyl-pyrido[2,3-d]pyrimidin-4-ylamino)-phenylsulfanyl]-phenol

Example 35A

4-[2-Amino-4-(4-fluoro-benzyloxy)-phenylsulfanyl]-phenol

A solution of 4-chloro-3-nitro-phenol was reacted with 1-Bromomethyl-4-fluoro-benzene using the conditions described in Example 10C to provide 1-Chloro-4-(4-fluoro-benzyloxy)-2-nitro-benzene which was treated sequentially using the procedures from Examples 10D and 10E to provide the title product.

Example 35B

4-[4-(4-Fluoro-benzyloxy)-2-(7-methyl-pyrido[2,3-d]pyrimidin-4-ylamino)-phenylsulfanyl]-phenol The product of Example 35A was reacted with the product of Example 10B using the procedure of Example 10F substituting the product of Example 35A for the product of Example 10E to provide the crude title compound which was purified by HPLC with TFA to provide the title compound as a trifluoroacetic acid salt (40 mg, 41%). 1H NMR (300 MHz, DMSO-D6) δ ppm: 2.69 (s, 3H) 5.09 (s, 2H) 6.65 (m, 2H) 6.97 (dd, J=8.64, 2.39 Hz, 1H) 7.09 (m, 2H) 7.21 (m, 4H) 7.50 (m, 2H) 7.61 (d, J=8.46 Hz, 1H) 8.61 (s, 1H) 8.75 (d, J=8.46 Hz, 1H) 9.65 (s, 1H) 10.41 (s, 1H); MS (ESI+) m/z 485 (M+H)+.

Example 36

3-[4-(4-Hydroxy-phenylsulfanyl)-3-(7-isopropyl-pyrido[2,3-d]pyrimidin-4-ylamino)-phenoxymethyl]-benzonitrile

Example 36A

4-Methyl-3-oxo-pentanal, sodium salt

A flame-dried 100-mL flask equipped with a 25-mL addition funnel was purged with nitrogen gas and charged with anhydrous diethyl ether (40 mL) followed by the addition of sodium slivers (1.65 g, 0.0725 mol). The reaction mixture was cooled to ice/water bath temperature and a solution of methyl isopropyl ketone (6.244 g, 0.0725 mol) and ethyl formate (5.481 g, 0.0725 mol) in anhydrous diethyl ether (5 mL) was added slowly dropwise over 1.5 hours, at 0° C. After the addition was complete the cooling bath was removed and the reaction mixture stirred at room temperature overnight. Additional ether (10 mL) was then added to break up the resulting precipitate, and the solid was isolated quickly by vacuum filtration. The solid was rinsed with small amounts of ether and then dried in a vacuum desiccator for one hour to provide the title product as an off-white solid (5.35 g, 54% yield). This material was used in the next step without further purification.

Example 36B

6-Isopropyl-2-oxo 1,2-dihydro-pyridine-3-carbonitrile

To a solution of the product of Example 36A (5.35 g, 0.0393 mol) and 2-cyanoacetamide (3.47 g, 0.0413 mol) in water (35 mL) was stirred at room temperature for 10 minutes. To this mixture was added 2.5 mL of a stock piperidine acetate solution (prepared from 9.8 mL of piperidine, 6 mL of acetic acid and 10 mL of water), and the solution was heated under reflux for 2 hours. The mixture was then cooled to room temperature and taken to pH 4 by the addition of glacial acetic acid. The resulting light yellow solid was isolated by vacuum filtration, rinsed with water (2×30 mL), and dried under vacuum to provide the title product (4.36 g, 68%).

Example 36C

2-Bromo-6-isopropyl-nicotinonitrile

To a solution of the product of Example 36B (4.35 g, 0.0269 mol), tertrabutylammonium bromide (10.4 g, 0.0323 mol) and phosphorous pentoxide (8.01 g, 1.05 mol) in toluene (80 mL) was heated under reflux for 5 hours. The reaction mixture was then cooled to room temperature, water (80 mL) was added, and the mixture was stirred for 2 h at room temperature. The reaction mixture was diluted with toluene (20 mL) and the organic layer separated. The aqueous layer was washed with toluene (50 mL) and the combined organic layers were washed with brine (50 mL), dried over anhydrous magnesium sulfate, filtered, and concentrated under vacuum to provide the title product as a yellow oil (5.64 g, 93%).

Example 36D

2-Amino-6-isopropyl-nicotinonitrile

To a solution of the product of Example 36C (21 g, 0.093 mol) and liquid ammonia (250 mL) in 500 mL of ethanol were reacted in a sealed high-pressure vessel at 130° C. for 20 hours. The reaction mixture was concentrated under vacuum and the residue ground to a fine powder then washed with water (2×50 mL) and dried in a vacuum oven for 24 hours to provide the title compound as a beige solid (14 g, 93%).

Example 36E

N'-(3-Cyano-6-isopropyl-pyridin-2-yl)-N-N-dimethyl-formamidine

To a solution of the product of Example 36D (7.1 g, 0.044 mol) and N,N-Dimethylformamide dimethyl acetal (6.44 mL, 0.0484 mol) in toluene (100 mL) was heated at reflux for 3 hours. The resulting solution was cooled to room temperature and concentrated under vacuum to provide the title compound (9.5 g, 100%) as a thick brown oil that solidified upon standing. Although this material appears to be pure by NMR, it contains small amounts of highly colored impurities. It can be chromatographed on silica gel (ethyl acetate/hexane gradient) to provide a slightly yellow oil that solidifies upon standing (about 70% recovery from chromatography).

Example 36F 3-(4-Chloro-3-nitro-phenoxymethyl)-benzonitrile

The title compound was prepared according to the procedure of Example 10C substituting 3-bromomethyl-benzonitrile for 1-chloromethyl-4-methoxy-benzene (0.813 g, 98%).

Example 36G

3-[4-(4-Hydroxy-phenylsulfanyl)-3-nitro-phenoxymethyl]-benzonitrile

The title compound was prepared according to the procedure of Example 10D substituting 3-(4-Chloro-3-nitro-phenoxymethyl)-benzonitrile for 1-Chloro-4-(4-methoxy-benzyloxy)-2-nitro-benzene (1.07 g, 100%).

Example 36H

3-[3-Amino-4-(4-hydroxy-phenylsulfanyl)-phenoxymethyl]-benzonitrile

The title compound was prepared according to the procedure of Example 10E substituting 3-[4-(4-Hydroxy-phenylsulfanyl)-3-nitro-phenoxymethyl]-benzonitrile for 4-[4-(4-Methoxy-benzyloxy)-2-nitro-phenylsulfanyl]-phenol (0.97 g, 98%).

Example 36I

3-[4-(4-Hydroxy-phenylsulfanyl)-3-(7-isopropyl-pyrido[2,3-d]pyrimidin-4-ylamino)-phenoxymethyl]-benzonitrile A solution of the product of Example 36E (47.4 mg, 0.219 mmol), and the product of Example 36H (76.3 mg, 0.219 mmol) in acetic acid (1 mL) was stirred in an oil bath preheated to 130° C. for 15 minutes. The mixture was then cooled to room temperature, the acetic acid removed under vacuum, and the resultant residue purified by reverse phase preparative HPLC on a Waters Symmetry C8 column (25 mm×100 mm, 7 μm particle size) using a gradient of 10% to 100% acetonitrile/0.1% trifluoroacetic acid in water over 8 minutes (10 minutes run time) at a flow rate of 40 mL/min to provide the title compound as a trifluoroacetic acid salt (14 mg, 10%). $^1$H NMR (300 MHz, DMSO-d$_6$) δ ppm: 10.94 (s, 1H), 9.69 (s, 1H), 8.88 (d, J=8.46 Hz, 1H), 8.70 (s, 1H), 7.92 (s, 1H), 7.72-7.87 (m, 3H), 7.62 (t, J=7.72 Hz, 1H), 7.15-7.28 (m, J=8.82 Hz, 2H), 7.08-7.15 (m, 2H), 6.99-7.06 (m, 1H), 6.61-6.72 (m, 2H), 5.18 (s, 2H), 3.19-3.30 (m, 1H), 1.34 (d, J=6.99 Hz, 6H); MS (ESI) m/z 520.3 (M+H)+, (ESI–) m/z 518.3 (M–H)–.

Example 37

4-[2-(7-Isopropyl-pyrido[2,3-d]pyrimidin-4-ylamino)-4-(2-methoxy-benzyloxy)-phenylsulfanyl]-phenol

Example 37A

4-[2-Amino-4-(2-methoxy-benzyloxy)-phenylsulfanyl]-phenol

A solution of 4-chloro-3-nitro-phenol was reacted with 1-Bromomethyl-2-methyl-benzene using the conditions described in Example 10C to provide 1-Chloro-4-(2-methyl-benzyloxy)-2-nitro-benzene which was treated sequentially using the procedures from Examples 10D and 10E to provide the title product.

Example 37B

4-[2-(7-Isopropyl-pyrido[2,3-d]pyrimidin-4-ylamino)-4-(2-methoxy-benzyloxy)-phenylsulfanyl]-phenol The product of Example 37A was reacted with the product of Example 36E using the procedure of Example 36I substituting the product of Example 37A for the product of Example 36H to provide a solid which was triturated with methanol to provide the title compound (31 mg, 31%). 1H NMR (500 MHz, DMSO-D6) δ ppm: 9.88 (s, 1H), 9.57 (s, 1H), 8.73 (d, J=5.49 Hz, 1H), 8.56 (s, 1H), 7.58 (d, J=7.32 Hz, 1H), 7.40 (dd, J=7.63, 1.53 Hz, 1H), 7.31-7.37 (m, 1H), 7.30 (s, 1H), 7.18 (d, J=6.10 Hz, 1H), 7.11 (d, J=8.54 Hz, 2H), 7.05 (d, J=7.93 Hz, 1H), 6.97 (t, J=7.32 Hz, 1H), 6.93 (s, 1H), 6.67 (d, J=8.54 Hz, 2H), 5.06 (s, 2H), 3.80 (s, 3H), 3.16-3.25 (m, 1H), 1.33 (d, J=6.71 Hz, 6H); MS (ESI+) m/z 525.2 (M+H)+ (ESI–) m/z 523.2 (M–H)–.

Example 38

4-[2-(7-Isopropyl-pyrido[2,3-d]pyrimidin-4-ylamino)-4-(4-methoxy-benzyloxy)-phenylsulfanyl]-phenol The product from Example 10E was reacted with the product of Example 36E following the procedure of Example 36I substituting the product of Example 10E for the product of Example 36H to provide a solid which was triturated with methanol to provide the title compound (43 mg, 49%). 1H NMR (300 MHz, DMSO-D6) δ ppm: 9.93 (s, 1H), 9.63 (s, 1H), 8.75 (d, J=8.46 Hz, 1H), 8.57 (s, 1H), 7.60 (d, J=8.09 Hz, 1H), 7.38 (d, J=8.46 Hz, 2H), 7.27 (s, 1H), 7.05-7.19 (m, 3H), 6.85-7.00 (m, 3H), 6.67 (d, J=8.82 Hz, 2H), 5.02 (s, 2H), 3.75 (s, 3H), 3.14-3.28 (m, 1H), 1.32 (d, J=6.62 Hz, 6H); MS (ESI+) m/z 525.3 (M+H)+ (ESI–) m/z 523.3 (M–H)–.

Example 39

4-[2-(7-Isopropyl-pyrido[2,3-d]pyrimidin-4-ylamino)-4-(1-phenyl-ethoxy)-phenylsulfanyl]-phenol

Example 39A

4-[2-Amino-4-(1-phenyl-ethoxy)-phenylsulfanyl]-phenol

A solution of 1-(3-fluoro-phenyl)-ethanol was converted to 1-(1-Bromo-ethyl)-3-fluoro-benzene using the conditions described in Example 22A which was treated sequentially using the procedures from Examples 22B-22D to provide the title product.

Example 39B

4-[2-(7-Isopropyl-pyrido[2,3-d]pyrimidin-4-ylamino)-4-(1-phenyl-ethoxy)-phenylsulfanyl]-phenol The product from Example 39A was reacted with the product from Example 36E following the procedure from Example 36I substituting the product of Example 39A for the product of Example 36H to provide the crude title compound which was purified by HPLC with TFA to provide the title compound as a trifluoroacetic acid salt. 1H NMR (300 MHz, DMSO-D6) δ ppm: 1.34 (d, J=6.99 Hz, 6H) 1.55 (d, J=6.25 Hz, 3H) 3.14-3.29 (m, 1H) 5.49 (q, J=6.37 Hz, 1H) 6.63 (d, J=8.82 Hz, 2H) 6.89 (dd, J=8.82, 2.57 Hz, 1H) 7.09 (dd, J=9.01, 2.76 Hz, 3H) 7.19-7.48 (m, 6H) 7.75 (d, J=8.82 Hz, 1H) 8.67 (s, 1H) 8.83 (d, J=8.46 Hz, 1H) 9.67 (s, 1H) 10.85 (s, 1H); MS ESI+ (m/z) 509, ESI− (m/z) 507.

Example 40

4-[4-[1-(4-Bromo-phenyl)-ethoxy]-2-(7-isopropyl-pyrido[2,3-d]pyrimidin-4-ylamino)-phenylsulfanyl]-phenol The product from Example 22D (211 mg, 0.506 mmol) was reacted with the product from Example 36E (109 mg, 0.506 mmol) following the procedure from Example 36I substituting the product of Example 22D for the product of Example 36H to provide the crude title compound which was purified by HPLC with TFA to provide the title compound as a trifluoroacetic acid salt (150 mg, 42%). 1H NMR (300 MHz, DMSO d6) δ ppm: 10.87 (br s, 1H) 9.68 (s, 1H) 8.83 (d, J=8.45 Hz, 1H) 8.67 (s, 1H) 7.75 (d, J=7.72 Hz, 1H) 7.55d, J=8.46 Hz, 2H) 7.37 (d, J=8.46 Hz, 2H) 7.09 (m, 4H) 6.89 (dd, J=8.46 Hz, J=2.20 Hz, 1H) 6.66 (d, J=8.82 Hz, 2H) 5.50 (q, J=6.25 Hz, 2H) 3.25 (sept, J=6.99 Hz, 1H) 1.53 (d, J=6.25 Hz, 3H) 1.34 (d, J=6.99 Hz, 6H). MS (ESI+) m/z 587, 589 (M+H−TFA)+; (ESI−) m/z 585, 587 (M−H−TFA)−.

Example 41

4-[4-[1-(3-Fluoro-phenyl)-ethoxy]-2-(7-isopropyl-pyrido[2,3-d]pyrimidin-4-ylamino)-phenylsulfanyl]-phenol The product from Example 24A (197 mg, 0.555 mmol) was reacted with the product from Example 36E (120 mg, 0.555 mmol) following the procedure from Example 36I substituting the product of Example 24A for the product of Example 36H to provide the crude title compound which was purified by HPLC with TFA to provide the title compound as a trifluoroacetic acid salt (100 mg, 28%). 1H NMR (300 MHz, DMSO-D6) δ ppm: 1.34 (d, J=6.99 Hz, 6H) 1.55 (d, J=6.62 Hz, 3H) 3.19-3.32 (m, J=13.70, 6.94, 6.94 Hz, 1H) 5.53 (q, J=6.62 Hz, 1H) 6.64 (d, J=8.46 Hz, 2H) 6.91 (dd, J=8.82, 2.57 Hz, 1H) 7.09 (d, J=8.46 Hz, 5H) 7.19-7.29 (m, 2H) 7.39 (d, J=8.09, 5.88 Hz, 1H) 7.78 (d, J=8.46 Hz, 1H) 8.68 (s, 1H) 8.85 (d, J=8.46 Hz, 1H) 9.70 (s, 1H); MS (ESI+) m/z 527 (M+H)+.

Example 42

4-[2-(7-Isopropyl-pyrido[2,3-d]pyrimidin-4-ylamino)-4-(3-trifluoromethyl-benzyloxy)-phenyl-sulfanyl]-phenol The product from Example 26A was reacted with the product from Example 36E following the procedure from Example 36I substituting the product of Example 26A for the product of Example 36H to provide the crude title compound which was purified by HPLC with TFA to provide the title compound as a trifluoroacetic acid salt (22 mg, 21%). 1H NMR (300 MHz, DMSO-D6) δ ppm: 1.34 (d, J=6.99 Hz, 6H), 5.22 (s, 2H), 6.65 (d, J=8.46 Hz, 2H), 7.01-7.13 (m, 3H), 7.20 (d, J=8.82 Hz, 2H), 7.66 (d, J=7.35 Hz, 1H), 7.70-7.82 (m, 4H), 8.68 (s, 1H), 8.87 (d, J=8.46 Hz, 1H), 9.68 (s, 1H); MS ESI+ m/z 563 (M+H)+, ESI− m/z 561 (M−H)−.

Example 43

4-[4-(3-Fluoro-benzyloxy)-2-(7-isopropyl-pyrido[2,3-d]pyrimidin-4-ylamino)-phenylsulfanyl]-phenol The product from Example 57D was reacted with the product from Example 36E following the procedure of Example 36I substituting the product of Example 57D for the product of Example 36H to provide the crude title compound which was purified by HPLC with TFA to provide the title compound as a trifluoroacetic acid salt (26 mg, 51%). 1H NMR (300 MHz, DMSO-D6) δ ppm: 1.35 (d, J=6.99 Hz, 6H) 3.28 (m, 1H) 5.14 (s, 2H) 6.65 (m, 2H) 7.16 (m, 8H) 7.44 (m, 1H) 7.81 (d, J=8.46 Hz, 1H) 8.73 (s, 1H) 8.90 (d, J=8.46 Hz, 1H) 9.69 (s, 1H) 11.08 (s, 1H); MS (ESI+) m/z 513 (M+H)+.

Example 44

4-[4-(4-Fluoro-benzyloxy)-2-(7-isopropyl-pyrido[2,3-d]pyrimidin-4-ylamino)-phenylsulfanyl]-phenol The product of Example 35A was reacted with the product of Example 36E using the procedure of Example 36I substituting the product of Example 35A for the product of Example 36H to provide the crude title compound which was purified by HPLC with TFA to provide the title compound as a trifluoroacetic acid salt (23 mg, 45%). 1H NMR (300 MHz, DMSO-D6) δ ppm: 1.35 (d, J=6.99 Hz, 6H) 3.26 (m, 1H) 5.09 (s, 2H) 6.62 (m, 2H) 7.14 (m, 7H) 7.48 (m, 2H) 7.81 (d, J=8.46 Hz, 1H) 8.73 (s, 1H) 8.90 (d, J=8.46 Hz, 1H) 9.68 (s, 1H) 11.12 (s, 1H); MS (ESI+) m/z 513 (M+H)+.

Example 45

4-[4-[1-(4-Fluoro-phenyl)-ethoxy]-2-(7-isopropyl-pyrido[2,3-d]pyrimidin-4-ylamino)-phenylsulfanyl]-phenol The product from Example 23A (180 mg, 0.510 mmol) was reacted with the product from Example 36E (110 mg, 0.510 mmol) following the procedure from Example 36I substituting the product of Example 23A for the product of Example 36H to provide the crude title compound which was purified by HPLC with TFA to provide the title compound as a trifluoroacetic acid salt (35 mg, 12%). 1H NMR (300 MHz, DMSO-D6) δ ppm: 1.35 (d, J=6.99 Hz, 6H) 1.54 (d, J=6.62 Hz, 3H) 3.23-3.34 (m, 1H) 5.52 (q, J=5.88 Hz, 1H) 6.63 (d, J=8.82 Hz, 2H) 6.94 (dd, J=8.82, 2.57 Hz, 1H) 7.08 (m, J=8.82 Hz, 4H) 7.14 (d, J=4.78 Hz, 1H) 7.17-7.21 (m, 1H)

7.41-7.49 (m, 2H) 7.86 (d, J=8.82 Hz, 1H) 8.76 (s, 1H) 8.91 (d, J=8.46 Hz, 1H); MS (ESI+) m/z 527 (M+H)+.

Example 46

4-[2-(7-Isopropyl-pyrido[2,3-d]pyrimidin-4-ylamino)-4-(3-methoxy-benzyloxy)-phenylsulfanyl]-phenol The product of Example 31A was reacted with the product of Example 36E using the procedure of Example 36I substituting the product of Example 31A for the product of Example 36H to provide the crude title compound which was purified by HPLC with TFA to provide the title compound as a trifluoroacetic acid salt (23 mg, 45%). 1H NMR (300 MHz, DMSO-D6) δ ppm: 10.98 (s, 1H), 9.67 (s, 1H), 8.88 (d, J=8.09 Hz, 1H), 8.70 (s, 1H), 7.78 (d, J=8.09 Hz, 1H), 7.31 (t, J=8.09 Hz, 1H), 7.15-7.24 (m, J=8.82 Hz, 2H), 7.06-7.15 (m, 2H), 6.95-7.05 (m, J=6.62 Hz, 3H), 6.90 (dd, J=7.72, 2.21 Hz, 1H), 6.54-6.73 (m, 2H), 5.09 (s, 2H), 3.75 (s, 3H), 3.19-3.28 (m, 1H), 1.34 (d, J=6.99 Hz, 6H); MS (ESI+) m/z 525.2 (M+H)+ (ESI−) m/z 523.2 (M−H)−.

Example 47

4-[4-(3-Bromo-benzyloxy)-2-(7-isopropyl-pyrido[2,3-d]pyrimidin-4-ylamino)-phenylsulfanyl]-phenol The product of Example 15A was reacted with the product of Example 36E using the procedure of Example 36I substituting the product of Example 15A for the product of Example 36H to provide the crude title compound which was purified by HPLC with TFA to provide the title compound as a trifluoroacetic acid salt (16 mg, 28%). 1H NMR (300 MHz, DMSO-D6) δ ppm: 1.33 (d, J=6.62 Hz, 6H) 3.21 (m, 1H) 5.13 (s, 2H) 6.68 (d, J=8.82 Hz, 2H) 6.95 (dd, J=8.64, 2.76 Hz, 1H) 7.12 (m, 3H) 7.34 (m, 2H) 7.50 (m, 2H) 7.60 (d, J=8.82 Hz, 1H) (s, 1H) 8.57 (s, 1H) 8.76 (d, J=8.46 Hz, 1H) 9.65 (s, 1H) 9.95 (s, 1H); MS (ESI+) m/z 573, 575 (M+H)+.

Example 48

4-[4-(4-Bromo-benzyloxy)-2-(7-isopropyl-pyrido[2,3-d]pyrimidin-4-ylamino)-phenylsulfanyl]-phenol The product of Example 16A was reacted with the product of Example 36E using the procedure of Example 36I substituting the product of Example 16A for the product of Example 36H to provide the crude title compound which was purified by HPLC with TFA to provide the title compound as a trifluoroacetic acid salt (28 mg, 49%). 1H NMR (300 MHz, DMSO-D6) δ ppm: 1.32 (d, J=6.99 Hz, 6H) 3.22 (m, 1H) 5.10 (s, 2H) 6.67 (d, J=8.46 Hz, 2H) 6.94 (dd, J=8.82, 2.57 Hz, 1H) 7.12 (m, 3H) 7.28 (d, J=2.57 Hz, 1H) 7.41 (d, J=8.46 Hz, 2H) 7.59 (m, 3H) 8.56 (s, 1H) 8.75 (d, J=8.46 Hz, 1H) 9.65 (s, 1H) 9.94 (s, 1H); MS (ESI+) m/z 573, 575 (M+H)+.

Example 49

4-[4-(4-Hydroxy-phenylsulfanyl)-3-(7-isopropyl-pyrido[2,3-d]pyrimidin-4-ylamino)-phenoxymethyl]-benzonitrile The product of Example 21A was reacted with the product of Example 36E using the procedure of Example 36I substituting the product of Example 21A for the product of Example 36H to provide the crude title compound which was purified by HPLC with TFA to provide the title compound as a trifluoroacetic acid salt (32 mg, 26%). 1H NMR (300 MHz, DMSO-D6) δ ppm: 10.91 (s, 1H), 9.69 (s, 1H), 8.87 (d, J=9.19 Hz, 1H), 8.69 (s, 1H), 7.88 (d, J=8.09 Hz, 2H), 7.77 (d, J=8.46 Hz, 1H), 7.64 (d, J=8.46 Hz, 2H), 7.15-7.26 (m, J=8.82 Hz, 2H), 7.08-7.15 (m, 2H), 7.01 (d, J=8.82 Hz, 1H), 6.58-6.72 (m, 2H), 5.23 (s, 2H), 3.20-3.31 (m, 1H), 1.34 (d, J=6.99 Hz, 6H); MS (ESI+) m/z 520.2 (M+H)+ (ESI−) m/z 518.2 (M−H)−.

Example 50

2-[4-(4-Hydroxy-phenylsulfanyl)-3-(7-isopropyl-pyrido[2,3-d]pyrimidin-4-ylamino)-phenoxymethyl]-benzonitrile The product of Example 20A was reacted with the product of Example 36E using the procedure of Example 36I substituting the product of Example 20A for the product of Example 36H to provide the crude title compound which was purified by HPLC with TFA to provide the title compound as a trifluoroacetic acid salt (11 mg, 9%). 1H NMR (300 MHz, DMSO-D6) δ ppm: 11.30 (s, 1H), 9.71 (s, 1H), 8.93 (d, J=8.82 Hz, 1H), 8.76 (s, 1H), 7.92 (d, J=7.35 Hz, 1H), 7.84 (d, J=8.82 Hz, 1H), 7.72-7.80 (m, 2H), 7.59 (ddd, J=7.72, 6.25, 2.58 Hz, 1H), 7.19-7.28 (m, 2H), 7.06-7.17 (m, 3H), 6.64-6.69 (m, 2H), 5.25 (s, 2H), 3.22-3.33 (m, 1H), 1.35 (d, J=6.99 Hz, 6H); MS (ESI+) m/z 520.2 (M+H)+ (ESI−) m/z 518.2 (M−H)−.

Example 51

4-[4-Benzyloxy-2-(7-isopropyl-pyrido[2,3-d]pyrimidin-4-ylamino)-phenylsulfanyl]-phenol The product of Example 27A was reacted with the product of Example 36E using the procedure of Example 36I substituting the product of Example 27A for the product of Example 36H to provide a solid which was triturated with methanol to provide the title compound. 1H NMR (300 MHz, DMSO-D6) δ ppm: 1.32 (d, J=6.62 Hz, 6H) 3.10-3.30 (m, 1H) 5.11 (s, 2H) 6.67 (d, J=8.82 Hz, 2H) 6.90-6.99 (m, 1H) 7.07-7.19 (m, 1H) 7.11 (d, J=8.82 Hz, 2H) 7.23-7.52 (m, 6H) 7.59 (d, J=8.09 Hz, 1H) 8.56 (s, 1H) 8.75 (d, J=8.09 Hz, 1H) 9.64 (s, 1H) 9.95 (s, 1H); MS (DCI/NH3) m/z 495 (M+H)+.

Example 52

3-[3-[7-(1-Hydroxy-1-methyl-ethyl)-pyrido[2,3-d]pyrimidin-4-ylamino]-4-(4-hydroxy-phenylsulfanyl)-phenoxymethyl]-benzonitrile The product from Example 36E (45.9 mg, 0.212 mmol) and the product from Example 36H (73.5 mg, 0.212 mmol) in acetic acid (1 mL) was gradually heated form room temperature to 130° C. in an oil bath over a 15 minute time period, followed by heating at 130° C. for an additional 1.5 hours. The mixture was then cooled to room temperature, concentrated under vacuum to provide the crude title compound which was purified by reverse phase preparative HPLC on a Waters Symmetry C8 column (25 mm×100 mm, 7 μm particle size) using a gradient of 10% to 100% acetonitrile/0.1% trifluoroacetic acid in water over 8 minutes (10 minutes run time) at a flow rate of 40 mL/min to provide the title compound as the trifluoroacetic acid salt (22 mg, 20%). 1H NMR (300 MHz, DMSO-$d_6$) δ ppm: 11.76 (s, 1H), 9.72 (s, 1H), 9.06 (d, J=8.09 Hz, 1H), 8.83 (s, 1H), 8.20 (d, J=8.46 Hz, 1H), 7.92 (s, 1H), 7.75-7.88 (m, 2H), 7.63 (t, J=7.72 Hz, 1H), 7.21-7.26 (m, 1H), 7.19 (d, J=2.57 Hz, 1H), 7.07-7.15 (m, 3H), 6.64 (d, J=8.46 Hz, 2H), 5.18 (s, 2H), 1.56 (s, 6H); MS (ESI) m/z 536.2 (M+H)+, (ESI−) m/z 534.2 (M−H)−.

Example 53

2-[3-[7-(1-Hydroxy-1-methyl-ethyl)-pyrido[2,3-d]pyrimidin-4-ylamino]-4-(4-hydroxy-phenylsulfanyl)-phenoxymethyl]-benzonitrile The product of Example 20A was reacted with the product of Example 36E using the procedure of Example 52 substituting the product of Example 20A for the product of Example 36H to provide the crude title compound which was purified by HPLC with TFA to provide the title compound as a trifluoroacetic acid salt (11 mg, 11%). 1H NMR (300 MHz, DMSO-D6) δ ppm: 11.73 (s, 1H), 9.75 (s, 1H), 9.05 (d, J=8.46 Hz, 1H), 8.84 (s, 1H), 8.20 (d, J=8.82 Hz, 1H), 7.92 (d, J=7.35 Hz, 1H), 7.69-7.84 (m, 2H), 7.54-7.64 (m, 1H), 7.23-7.27 (m, 1H), 7.21 (d, J=2.57 Hz, 1H), 7.10-7.17 (m, 3H), 6.64-6.69 (m, 2H), 5.25 (s, 2H), 1.56 (s, 6H); MS (ESI+) m/z 536.2 (M+H)+ (ESI−) m/z 534.3 (M−H).

Example 54

4-[3-[7-(1-Hydroxy-1-methyl-ethyl)-pyrido[2,3-d]pyrimidin-4-ylamino]-4-(4-hydroxy-phenylsulfanyl)-phenoxymethyl]-benzonitrile The product of Example 21A was reacted with the product of Example 36E using the procedure of Example 52 substituting the product of Example 21A for the product of Example 36H to provide the crude title compound which was purified by HPLC with TFA to provide the title compound as a trifluoroacetic acid salt (10 mg, 10%). 1H NMR (300 MHz, DMSO-D6) δ ppm: 11.64 (s, 1H), 9.73 (s, 1H), 9.05 (s, 1H), 8.82 (s, 1H), 8.19 (d, J=8.82 Hz, 1H), 7.88 (d, J=8.09 Hz, 2H), 7.64 (d, J=8.46 Hz, 2H), 7.23 (d, J=8.82 Hz, 1H), 7.18 (d, J=2.57 Hz, 1H), 7.04-7.15 (m, 3H), 6.62-6.69 (m, 2H), 5.23 (s, 2H), 2.54 (s, 1H), 1.56 (s, 6H); MS (ESI+) m/z 536.2 (M+H)+ (ESI−) m/z 534.2 (M−H)−.

Example 55

4-[2-[7-(1-Hydroxy-1-methyl-ethyl)-pyrido[2,3-d]pyrimidin-4-ylamino]-4-(2-methoxy-benzyloxy)-phenylsulfanyl]-phenol The product of Example 37A was reacted with the product of Example 36E using the procedure of Example 52 substituting the product of Example 37A for the product of Example 36H to provide a solid which was triturated with methanol to provide the title compound (8 mg, 8%). 1H NMR (300 MHz, DMSO-D6) δ ppm: 11.81 (s, 1H), 9.40-9.95 (m, 1H), 9.06 (d, J=8.46 Hz, 1H), 8.85 (s, 1H), 8.21 (d, J=8.46 Hz, 1H), 7.31-7.44 (m, 2H), 7.25 (d, J=8.46 Hz, 1H), 7.15 (d, J=2.57 Hz, 1H), 7.02-7.14 (m, 4H), 6.97 (t, J=7.54 Hz, 1H), 6.61-6.67 (m, 2H), 5.05 (s, 2H), 3.80 (s, 3H), 2.54 (s, 1H), 1.56 (s, 6H); MS (ESI+) m/z 541.2 (M+H)+ (ESI−) m/z 539.2 (M−H)−.

Example 56

4-{4-(4-Bromo-benzyloxy)-2-[7-(1-hydroxy-1-methyl-ethyl)-pyrido[2,3-d]pyrimidin-4-ylamino]-phenylsulfanyl}-phenol The product of Example 16A was reacted with the product of Example 36E using the procedure of Example 52 substituting the product of Example 16A for the product of Example 36H to provide the crude title compound which was purified by HPLC with TFA to provide the title compound as a trifluoroacetic acid salt (8 mg, 13%). 1H NMR (300 MHz, DMSO-D6) δ ppm: 1.55 (s, 6H) 2.08 (s, 1H) 5.10 (s, 2H) 6.65 (d, J=8.46 Hz, 2H) 7.13 (m, 5H) 7.41 (d, J=8.46 Hz, 2H) 7.60 (d, J=8.09 Hz, 2H) 8.15 (d, J=8.46 Hz, 1H) 8.77 (s, 1H) 9.00 (d, J=8.46 Hz, 1H) 9.70 (s, 1H) 11.43 (s, 1H); MS (ESI+) m/z 589, 591 (M+H)+.

Example 57

4-[4-(3-Fluoro-benzyloxy)-2-(pyrido[2,3-d]pyrimidin-4-ylamino)-phenylsulfanyl]-phenol

Example 57A

N'-(3-Cyano-pyridin-2-yl)-N,N-dimethyl-formamidine

A solution of 2-Amino-nicotinonitrile (5 g, 42 mmol) and N,N-Dimethylformamide dimethyl acetal (6.13 mL, 46.2 mmol) in toluene (20 mL) was heated at reflux for 3 hours. After cooling to room temperature, the solution was concentrated under vacuum to provide the title compound (7.3 g, 100%).

Example 57B

1-Chloro-4-(3-fluoro-benzyloxy)-2-nitro-benzene

The title compound was prepared according to the procedure of Example 10C substituting 1-Bromomethyl-3-fluoro-benzene for 1-chloromethyl-4-methoxy-benzene (0.56 g, 100%).

Example 57C

4-[4-(3-Fluoro-benzyloxy)-2-nitro-phenylsulfanyl]-phenol

The title compound was prepared according to the procedure of Example 10D substituting 1-Chloro-4-(3-fluoro-benzyloxy)-2-nitro-benzene for 1-Chloro-4-(4-methoxy-benzyloxy)-2-nitro-benzene (0.57 g, 77%).

Example 57D

4-[2-Amino-4-(3-fluoro-benzyloxy)-phenylsulfanyl]-phenol

The title compound was prepared according to the procedure of Example 10E substituting 4-[4-(3-Fluoro-benzyloxy)-2-nitro-phenylsulfanyl]-phenol for 4-[4-(4-Methoxy-benzyloxy)-2-nitro-phenylsulfanyl]-phenol (0.501 g, 96%).

Example 57E

4-[4-(3-Fluoro-benzyloxy)-2-(pyrido[2,3-d]pyrimidin-4-ylamino)-phenylsulfanyl]-phenol A solution of the product from Example 57A (35 mg, 0.2 mmol) and the product from Example 57D (68 mg, 0.2 mmol) in acetic acid (1 mL) was gradually heated form room temperature to 130° C. in an oil bath over a 15 minute time period, followed by heating at 130° C. for an additional 1.5 hours. The mixture was then cooled to room temperature, concentrated under vacuum to provide the crude title compound which was purified by reverse phase preparative HPLC on a Waters Symmetry C8 column (25 mm×100 mm, 7 µm particle size) using a gradient of 10% to 100% acetonitrile/0.1% trifluoroacetic acid in water over 8 minutes (10 minutes run time) at a flow rate of 40 mL/min to provide the title compound as the trifluoroacetic acid salt (28 mg, 30%). $^1$H NMR (300 MHz, DMSO-$d_6$) δ ppm: 5.14 (s, 2H) 6.65 (m, 2H) 7.14 (m, 8H) 7.49 (m, 1H) 7.66 (m, 1H) 8.61 (s, 1H) 8.88 (d, J=7.47 Hz, 1H) 9.07 (s, 1H) 9.65 (s, 1H) 10.34 (s, 1H); MS (ESI) m/z 471 (M+H)+.

Example 58

4-[4-(2-Methyl-benzyloxy)-2-(pyrido[2,3-d]pyrimidin-4-ylamino)-phenylsulfanyl]-phenol The product of Example 17A was reacted with the product of Example 57A using the procedure of Example 57E substituting the product of Example 17A for the product of Example 57D to provide the crude title compound which was purified by HPLC with TFA to provide the title compound as a trifluoroacetic acid salt (50 mg, 54%). 1H NMR (300 MHz, DMSO-D6) δ ppm: 2.31 (s, 3H) 5.09 (s, 2H) 6.66 (m, 2H) 7.01 (m, 1H) 7.19 (m, 7H) 7.42 (d, J=6.99 Hz, 1H) 7.71 (dd, J=7.91, 4.23 Hz, 1H) 8.63 (s, 1H) 8.89 (d, J=7.35 Hz, 1H) 9.09 (s, 1H) 9.66 (s, 1H) 10.50 (s, 1H); MS (ESI+) m/z 467 (M+H)+.

Example 59

4-[4-(4-Methyl-benzyloxy)-2-(pyrido[2,3-d]pyrimidin-4-ylamino)-phenylsulfanyl]-phenol The product of Example 19A was reacted with the product of Example 57A using the procedure of Example 57E substituting the product of Example 19A for the product of Example 57D to provide the crude title compound which was purified by HPLC with TFA to provide the title compound as a trifluoroacetic acid salt (45 mg, 48%). 1H NMR (300 MHz, DMSO-D6) δ ppm: 2.30 (s, 3H) 5.05 (s, 2H) 6.65 (m, 2H) 7.10 (m, 7H) 7.33 (d, J=8.07 Hz, 2H) 7.69 (dd, J=8.27, 4.23 Hz, 1H) 8.62 (s, 1H) 8.87 (d, J=7.72 Hz, 1H) 9.07 (s, 1H) 9.64 (s, 1H) 10.42 (s, 1H); MS (ESI+) m/z 467 (M+H)+.

Example 60

4-[4-(2-Bromo-benzyloxy)-2-(pyrido[2,3-d]pyrimidin-4-ylamino)-phenylsulfanyl]-phenol The product of Example 14A was reacted with the product of Example 57A using the procedure of Example 57E substituting the product of Example 14A for the product of Example 57D to provide the crude title compound which was purified by HPLC with TFA to provide the title compound as a trifluoroacetic acid salt (40 mg, 38%). 1H NMR (300 MHz, DMSO-D6) δ ppm: 5.13 (s, 2H) 6.66 (m, 2H) 6.99 (d, J=8.43 Hz, 1H) 7.15 (m, 3H) 7.35 (m, 3H) 7.64 (m, 3H) 8.60 (s, 1H) 8.85 (d, J=7.32 Hz, 1H) 9.07 (s, 1H) 9.66 (s, 1H) 10.28 (s, 1H); MS (ESI+) m/z 531, 533 (M+H)+.

Example 61

3-[4-(4-Hydroxy-phenylsulfanyl)-3-(pyrido[2,3-d]pyrimidin-4-ylamino)-phenoxymethyl]-benzonitrile The product from Example 36H and the product from Example 57A were reacted according to the procedure in Example 57E substituting the product of Example 36H for the product of Example 57D to provide a solid which was triturated with methanol to provide the title compound (44 mg, 44%). 1H NMR (300 MHz, DMSO-D6) δ ppm: 10.08 (s, 1H), 9.65 (s, 1H), 9.06 (s, 1H), 8.86 (s, 1H), 8.58 (s, 1H), 7.92 (s, 1H), 7.77-7.86 (m, 2H), 7.54-7.70 (m, J=7.72, 7.72 Hz, 2H), 7.28 (s, 1H), 7.07-7.19 (m, 3H), 6.97 (s, 1H), 6.63-6.72 (m, 2H), 5.18 (s, 2H); MS (ESI+) m/z 478.2 (M+H)+, (ESI−) m/z 476.1 (M−H)−.

Example 62

4-[4-(3-Methyl-benzyloxy)-2-(pyrido[2,3-d]pyrimidin-4-ylamino)-phenylsulfanyl]-phenol The product of Example 18A was reacted with the product of Example 57A using the procedure of Example 57E substituting the product of Example 18A for the product of Example 57D to provide the crude title compound which was purified by HPLC with TFA to provide the title compound as a trifluoroacetic acid salt (50 mg, 54%). 1H NMR (300 MHz, DMSO-D6) δ ppm: 2.31 (s, 3H) 5.07 (s, 2H) 6.65 (m, 2H) 7.12 (m, 9H) 7.78 (dd, J=8.10 Hz, 4.77 Hz, 1H) 8.72 (s, 1H) 8.94 (d, J=7.47 Hz, 1H) 9.12 (d, J=3.15 Hz, 1H) 9.67 (s, 1H) 11.03 (s, 1H); MS (ESI+) m/z 467 (M+H)+.

Example 63

4-[4-(4-Methoxy-benzyloxy)-2-(pyrido[2,3-d]pyrimidin-4-ylamino)-phenylsulfanyl]-phenol The product from Example 10E and the product from Example 57A were reacted according to the procedure in Example 57E substituting the product of Example 10E for the product of Example 57D to provide a solid which was triturated with methanol to provide the title compound (49 mg, 55%). 1H NMR (300 MHz, DMSO-D6) δ ppm: 10.07 (s, 1H), 9.63 (s, 1H), 9.05 (s, 1H), 8.83 (s, 1H), 8.58 (s, 1H), 7.64 (s, 1H), 7.38 (d, J=8.46 Hz, 2H), 7.20-7.29 (m, 1H), 7.12-7.18 (m, 1H), 7.06-7.12 (m, 2H), 6.90-6.99 (m, 3H), 6.62-6.69 (m, 2H), 5.02 (s, 2H), 3.75 (s, 3H); MS (ESI+) m/z 483.2 (M+H)+, (ESI−) m/z 481.2 (M−H)−.

Example 64

4-[4-(2-Methoxy-benzyloxy)-2-(pyrido[2,3-d]pyrimidin-4-ylamino)-phenylsulfanyl]-phenol The product of Example 37A was reacted with the product of Example 57A using the procedure of Example 57E substituting the product of Example 37A for the product of Example 57D to provide a solid which was triturated with methanol to provide the title compound (47 mg, 56%). 1H NMR (300 MHz, DMSO-D6) δ ppm: 10.08 (s, 1H), 9.63 (s, 1H), 9.07 (s, 1H), 8.85 (d, J=6.62 Hz, 1H), 8.59 (s, 1H), 7.64 (s, 1H), 7.41 (dd, J=7.35, 1.47 Hz, 1H), 7.30-7.38 (m, 1H), 7.24 (s, 1H), 7.16 (d, J=8.46 Hz, 1H), 7.08-7.14 (m, 2H), 7.05 (d, J=8.09 Hz, 1H), 6.89-7.01 (m, J=7.54, 7.54 Hz, 2H), 6.61-6.71 (m, 2H), 5.05 (s, 2H), 3.80 (s, 3H); MS (ESI+) m/z 483.2 (M+H)+, (ESI−) m/z 481.2 (M−H)−.

Example 65

4-[4-(4-Hydroxy-phenylsulfanyl)-3-(pyrido[2,3-d]pyrimidin-4-ylamino)-phenoxymethyl]-benzonitrile The product of Example 21A was reacted with the product of Example 57A using the procedure of Example 57E substituting the product of Example 21A for the product of Example 57D to provide the crude title compound which was purified by HPLC with TFA to provide the title compound as a trifluoroacetic acid salt (6 mg, 6%). 1H NMR (300 MHz, DMSO-D6) δ ppm: 11.17 (s, 1H), 9.69 (s, 1H), 9.09-9.20 (m, J=3.68 Hz, 1H), 8.97 (d, J=8.82 Hz, 1H), 8.74 (s, 1H), 7.78-7.96 (m, 3H), 7.64 (d, J=8.46 Hz, 2H), 7.20 (d, J=8.46 Hz, 2H), 7.07-7.16 (m, 2H), 7.03 (d, J=6.25 Hz, 1H), 6.57-6.70 (m, 2H), 5.23 (s, 2H); MS (ESI+) m/z 478.2 (M+H)+, (ESI−) m/z 476.2 (M−H)−.

Example 66

4-[4-(3-Methoxy-benzyloxy)-2-(pyrido[2,3-d]pyrimidin-4-ylamino)-phenylsulfanyl]-phenol The product from Example 31A and the product from Example 57A were reacted according to the procedure in Example 57E substituting the product of Example 31A for the product of Example 57D to provide a solid which was triturated with methanol to provide the title compound (38 mg, 45%). 1H NMR (300 MHz, DMSO-D6) δ ppm: 10.07 (s, 1H), 9.63 (s, 1H), 9.07 (s, 1H), 8.86 (d, J=7.72 Hz, 1H), 8.59 (s, 1H), 7.64 (s, 1H), 7.23-7.36 (m, 2H), 7.16 (dd, J=8.64, 1.65 Hz, 1H), 7.07-7.13 (m, 2H), 6.93-7.05 (m, 3H), 6.89 (dd, J=8.27, 2.02 Hz, 1H), 6.61-6.71 (m, 2H), 5.08 (s, 2H), 3.75 (s, 3H); MS (ESI+) m/z 483.2 (M+H)+, (ESI−) m/z 481.2 (M−H)−.

Example 67

4-[4-(4-Bromo-benzyloxy)-2-(pyrido[2,3-d]pyrimidin-4-ylamino)-phenylsulfanyl]-phenol The product from Example 16A and the product from Example 57A were reacted according to the procedure in Example 57E substituting the product of Example 16A for the product of Example 57D to provide the crude title compound which was purified by HPLC with TFA to provide the title compound as a trifluoroacetic acid salt (11 mg, 16%). 1H NMR (300 MHz, DMSO-D6) δ ppm: 5.09 (s, 2H), 6.66 (d, J=8.46 Hz, 2H), 6.94 (s, 1H), 7.11 (d, J=8.46 Hz, 3H), 7.25 (s, 1H), 7.41 (d, J=8.09 Hz, 2H), 7.57-7.69 (m, 3H), 8.59 (s, 1H), 8.84 (s, 1H), 9.06 (s, 1H), 9.64 (s, 1H), 10.07 (s, 1H); MS ESI+ m/z 531 (M+H)+, ESI− m/z 529 (M−H)−.

Example 68

4-[4-(3-Bromo-benzyloxy)-2-(pyrido[2,3-d]pyrimidin-4-ylamino)-phenylsulfanyl]-phenol The product from Example 15A and the product from Example 57A were reacted according to the procedure in Example 57E substituting the product of Example 15A for the product of Example 57D to provide the crude title compound which was purified by HPLC with TFA to provide the title compound as a trifluoroacetic acid salt (40 mg, 16%). 1H NMR (300 MHz, DMSO-D6) δ ppm: 5.12 (s, 2H), 6.67 (d, J=8.46 Hz, 2H), 6.94 (s, 1H), 7.12 (d, J=8.46 Hz, 3H), 7.26 (s, 1H), 7.36 (t, J=7.72 Hz, 1H), 7.45 (s, 1H), 7.54 (d, J=6.62 Hz, 1H), 7.66 (s, 2H), 8.57 (s, 1H), 8.83 (s, 1H), 9.04 (s, 1H), 9.64 (s, 1H), 10.08 (s, 1H); MS ESI+ m/z 531 (M+H)+, ESI− m/z 529 (M−H)−.

Example 69

4-[4-Benzyloxy-2-(pyrido[2,3-d]pyrimidin-4-ylamino)-phenylsulfanyl]-phenol

The product from Example 27A and the product from Example 57A were reacted according to the procedure in Example 57E substituting the product of Example 27A for the product of Example 57D to provide the title compound which was isolated as the acetic acid salt (79 mg, 48%). 1H NMR (300 MHz, DMSO-D6) δ ppm: 5.10 (s, 3H), 6.61-6.72 (m, 2H), 6.93 (d, J=9.56 Hz, 1H), 7.11 (d, J=8.46 Hz, 4H), 7.24 (s, 1H), 7.32-7.47 (m, 5H), 7.59-7.68 (m, 1H), 8.54 (s, 1H), 8.83 (d, J=9.56 Hz, 1H), 9.04 (s, 1H); ESI+ m/z 453 (M+H)+, ESI− m/z 451 (M−H)−.

Example 70

4-[4-[1-(4-Bromo-phenyl)-ethoxy]-2-(pyrido[2,3-d]pyrimidin-4-ylamino)-phenylsulfanyl]-phenol The product from Example 22D (153 mg, 0.367 mmol) was reacted with the product from Example 57A (63 mg, 0.367 mmol) following the procedure from Example 57E to provide the crude title compound which was purified by HPLC with TFA to provide the title compound as a trifluoroacetic acid salt (97 mg, 40%). 1H NMR (300 MHz, DMSO-d6) δ ppm: 10.60 (br s, 1H) 9.67 (s, 1H) 9.09 (s, 1H) 8.88 (d, J=8.46 Hz, 1H) 8.64 (s, 1H) 7.73 (m, J=3.31 Hz, 1H) 7.54 (d, J=8.46 Hz, 2H) 7.36 (d, J=8.46 Hz, 2H) 7.11 (m, 4H) 6.86 (d, J=9.19 Hz, 1H) 6.64 (d, J=8.46 Hz, 2H) 5.51 (q, J=6.62 Hz, 1H) 1.53 (d, J=6.62Ha, 3H); MS (ESI+) m/z, 545, 547 (M+H−TFA)+; (ESI−) m/z, 543, 545 (M−H−TFA)−.

Example 71

4-[4-[1-(4-Fluoro-phenyl)-ethoxy]-2-(pyrido[2,3-d]pyrimidin-4-ylamino)-phenylsulfanyl]-phenol The product from Example 23A (180 mg, 0.803 mmol) was reacted with the product from Example 57A (140 mg, 0.803 mmol) following the procedure from Example 57E to provide the crude title compound which was purified by HPLC with TFA to provide the title compound as a trifluoroacetic acid salt (60 mg, 12%). 1H NMR (500 MHz, DMSO-D6) δ ppm: 1.53 (d, J=6.35 Hz, 3H) 5.51 (q, 1H) 6.61 (d, J=8.79 Hz, 2H) 6.74-6.82 (m, 1H) 6.93 (dd, J=8.79, 2.44 Hz, 1H) 7.06-7.09 (m, 3H) 7.11-7.19 (m, 2H) 7.44 (dd, J=8.54, 5.62 Hz, 2H) 7.83-7.86 (m, J=8.54, 5.13 Hz, 1H) 8.75 (s, 1H) 8.96 (d, J=7.32 Hz, 1H) 9.14 (d, J=2.93 Hz, 1H); MS (ESI+) m/z 485.

Example 72

4-[4-[1-(3-Fluoro-phenyl)-ethoxy]-2-(pyrido[2,3-d]pyrimidin-4-ylamino)-phenylsulfanyl]-phenol The product from Example 24A (285 mg, 0.80 mmol) was reacted with the product from Example 57A (140 mg, 0.803 mmol) following the procedure from Example 57E to provide the crude title compound which was purified by HPLC with TFA to provide the title compound as a trifluoroacetic acid salt (150 mg, 31%). 1H NMR (300 MHz, DMSO-D6) δ ppm: 1.55 (d, J=6.25 Hz, 3H) 5.53 (q, J=6.13 Hz, 1H) 6.65 (d, J=8.46 Hz, 2H) 6.85 (d, J=6.99 Hz, 1H) 7.03-7.18 (m, 4H) 7.21-7.29 (m, 2H) 7.37-7.45 (m, 1H) 7.67 (dd, J=8.09, 4.41 Hz, 1H) 8.57 (s, 1H) 8.81 (s, 1H) 9.06 (s, 1H) 9.66 (s, 1H); MS (ESI+) m/z 485 (M+H)+.

Example 73

(5-Benzyloxy-4-chloro-2-fluoro-phenyl)-(7-methyl-pyrido[2,3-d]pyrimidin-4-yl)-amine

Example 73A

Carbonic acid 2-chloro-4-fluoro-phenyl ester ethyl ester

To a solution of 2-chloro-4-fluoro-phenol (0.8 mL, 7.64 mmol) and triethylamine (1.3 mL, 9.16 mmol) in dichloromethane (10 mL) at 0° C. was added ethyl chloroformate (0.9 mL, 9.16 mmol) dropwise. The ice bath was removed and the solution was allowed to warm to room temperature and stirred for an additional 16 hours. Afterwards dichloromethane (20 mL) was added to the mixture, the organic solution was washed with brine (50 mL), dried over anhydrous magnesium sulfate, filtered, and concentrated under vacuum to provide the title product as an oil (1.65 g, 100%).

Example 73B

Carbonic acid 2-chloro-4-fluoro-5-nitro-phenyl ester ethyl ester

A solution of the product from Example 73A (0.88 g, 4.03 mmol) in concentrated sulfuric acid (2 mL) cooled in an ice bath was added fuming nitric acid (0.27 mL, 6.45 mmol) slowly to maintain the temperature at 0° C. The mixture was stirred for an additional 2 hours, then ice water (10 mL) was added to the solution and the resultant solid was collected by filtration washed with water and dried in a vacuum oven to provide the title compound (0.87 g, 82%).

Example 73C

2-Chloro-4-fluoro-5-nitro-phenol

To a solution of the product from Example 73B (0.87 g, 3.30 mmol) in methanol (20 mL) and water (1 mL) was added sodium bicarbonate (2.22 g, 26.4 mmol) and the mixture stirred at room temperature for 16 hours. The methanol was then removed under vacuum, dichloromethane (20 mL) was added to the mixture, the organic solution was washed with brine (50 mL), dried over anhydrous magnesium sulfate, filtered, and concentrated under vacuum to provide the title product (0.62 g, 98%).

Example 73D

1-Benzyloxy-2-chloro-4-fluoro-5-nitro-benzene

The title compound was prepared according to the procedure of Example 10C substituting benzyl bromide and the product from Example 73C for 1-chloromethyl-4-methoxy-benzene and 4-chloro-3-nitro-phenol (0.72 g, 79%).

Example 73E

5-Benzyloxy-4-chloro-2-fluoro-phenylamine

The title compound was prepared according to the procedure of Example 10D substituting the product from Example 73D for 1-Chloro-4-(4-methoxy-benzyloxy)-2-nitro-benzene (77 mg, 100%).

Example 73F (5-Benzyloxy-4-chloro-2-fluoro-phenyl)-(7-methyl-pyrido[2,3-d]pyrimidin-4-yl)-amine A solution of the product of Example 10B (17 mg, 0.0927 mmol), and the product of Example 73E (28 mg, 0.111 mmol) in acetic acid (1 mL) was stirred in an oil bath preheated to 130° C. for 15 minutes. The mixture was then cooled to room temperature, the acetic acid removed under vacuum, and the resultant residue was purified by HPLC with TFA to provide the title compound as a trifluoroacetic acid salt (8.1 mg, 17%). $^1$H NMR (300 MHz, DMSO-$d_6$) δ ppm: 2.72 (s, 3H), 5.19 (s, 2H), 7.28-7.53 (m, 6H), 7.66 (d, J=9.56 Hz, 1H), 7.70 (d, J=8.82 Hz, 1H), 8.73 (s, 1H), 8.84 (d, J=8.09 Hz, 1H), 10.85 (s, 1H); MS (ESI) m/z 395 (M+H)+.

Example 74

(5-Benzyloxy-4-chloro-2-fluoro-phenyl)-pyrido[2,3-d]pyrimidin-4-yl-amine

The title compound was prepared according to the procedure of Example 73F substituting the product from Example 57A for the product from Example 10B (7.9 mg, 19%). $^1$H NMR (300 MHz, DMSO-$d_6$) δ ppm: 5.19 (s, 2H), 7.20-7.54 (m, 6H), 7.65 (d, J=9.56 Hz, 1H), 7.78 (dd, J=8.27, 4.60 Hz, 1H), 8.73 (s, 1H), 8.95 (d, J=8.09 Hz, 1H), 9.12 (d, J=3.31 Hz, 1H), 10.82 (s, 1H); MS (ESI+) m/z 381 (M+H)+.

Example 75

(5-Benzyloxy-2,4-difluoro-phenyl)-(7-methyl-pyrido[2,3-d]pyrimidin-4-yl)-amine

Example 75A

Carbonic acid 2,4-difluoro-phenyl ester ethyl ester

The title compound was prepared according to the procedure of Example 73A substituting 2,4-Difluoro-phenol for 2-chloro-4-fluoro-phenol (1.48 g, 96%).

Example 75B

Carbonic acid 2,4-difluoro-5-nitro-phenyl ester ethyl ester

The title compound was prepared according to the procedure of Example 73B.

Example 75C 2,4-Difluoro-5-nitro-phenol

The title compound was prepared according to the procedure of Example 73C substituting the product from Example 73B for the product of 313B (0.59 g, 89%).

Example 75D

1-Benzyloxy-2,4-difluoro-5-nitro-benzene

The title compound was prepared according to the procedure of Example 73D substituting the product from Example 75C for the product of 313C (0.56 g, 63%).

Example 75E

5-Benzyloxy-2,4-difluoro-phenylamine

The title compound was prepared according to the procedure of Example 73E substituting the product from Example 75D for the product of 313D (89 mg, 100%).

Example 75F

(5-Benzyloxy-2,4-difluoro-phenyl)-(7-methyl-pyrido[2,3-d]pyrimidin-4-yl)-amine The title compound was prepared according to the procedure of Example 73F substituting the product from Example 75E for the product of Example 73E. The resultant residue was purified by HPLC with TFA to provide the title compound as a trifluoroacetic acid salt (7.4 mg, 16%). $^1$H NMR (300 MHz, DMSO-d$_6$) δ ppm: 2.72 (s, 3H), 5.17 (s, 2H), 7.19-7.60 (m, 7H), 7.71 (d, J=8.46 Hz, 1H), 8.75 (s, 1H), 8.85 (d, J=8.46 Hz, 1H), 10.84 (s, 1H); MS (ESI) m/z 379 (M+H)+.

Example 76

(5-Benzyloxy-2,4-difluoro-phenyl)-pyrido[2,3-d]pyrimidin-4-yl-amine

A solution of the product of Example 57A (17 mg, 0.099 mmol), and the product of Example 73E (28 mg, 0.119 mmol) in acetic acid (1 mL) was stirred in an oil bath preheated to 130° C. for 15 minutes. The mixture was then cooled to room temperature, the acetic acid removed under vacuum, and the resultant residue was purified by HPLC with TFA to provide the title compound as a trifluoroacetic acid salt (21.4 mg, 45%). 1H NMR (300 MHz, DMSO-D6) δ ppm: 5.17 (s, 2H) 7.19-7.61 (m, 7H) 7.80 (dd, J=8.09, 4.41 Hz, 1H) 8.77 (s, 1H) 8.97 (d, J=7.35 Hz, 1H) 9.14 (d, J=2.94 Hz, 1H) 10.88 (s, 1H); MS (ESI+) m/z 365 (M+H)+.

Example 77

4-{2-[Benzyl-(7-methyl-pyrido[2,3-d]pyrimidin-4-yl)-amino]-4-benzyloxy-phenylsulfanyl}-phenol To a solution of the product of Example 27 (26.3 mg, 0.062 mmol), benzyl bromide (0.0075 mL, 0.062 mmol) and potassium carbonate (8.6 mg, 0.062 mmol) in N,N-dimethylformamide (0.5 mL) was stirred at room temperature for 16 hours. Afterwards, the mixture was poured into ice water (10 mL) and the resultant solution acidified with 1N aqueous hydrochloric acid. The solution was then extracted with ethyl acetate (3×10 mL), the combined extracts dried over magnesium sulfate, filtered and concentrated under vacuum to provide the crude title compound which was purified by HPLC with TFA to provide the title compound as a trifluoroacetic acid salt (6.7 mg, 18%). 1H NMR (300 MHz, DMSO-D6) δ ppm: 2.74 (s, 3H) 5.10 (s, 2H) 5.69 (s, 1H) 6.65 (d, J=8.82 Hz, 2H) 7.02-7.18 (m, 2H) 7.14-7.26 (m, 1H) 7.26-7.58 (m, 12H) 7.86 (s, 1H) 8.93 (s, 1H) 9.23 (s, 1H) 9.73 (s, 1H) 12.09 (s, 1H); MS (ESI+) m/z 557 (M+H)+.

Example 78

(5-Benzyloxy-2-bromo-phenyl)-(7-methyl-pyrido[2,3-d]pyrimidin-4-yl)-amine

Example 78A

5-Benzyloxy-2-bromo-phenylamine

The title compound was made according to the method of: Boger, D. L., Wysocki, R. J., Ishizaki, T. J. Am. Chem. Soc. 112, 1990, p. 5230-5240. The amount obtained was 4.58 g, 48%.

Example 78B

(5-Benzyloxy-2-bromo-phenyl)-(7-methyl-pyrido[2,3-d]pyrimidin-4-yl)-amine

The product from Example 78A (2.0 g, 7.19 mmol) and the product from Example 10B (1.35 g, 7.19 mmol) in acetic acid (15 mL) was gradually heated form room temperature to 130° C. in an oil bath over a 15 minute time period, followed by heating at 130° C. for an additional 1.5 hours. The mixture was then cooled to room temperature, concentrated under vacuum to provide the crude title compound (3.4 g of a sticky red syrup, 100%) a portion of which was purified by HPLC with TFA to provide the title compound as the trifluoroacetic acid salt (81 mg). $^1$H NMR (300 MHz, DMSO-d$_6$) δ ppm: 2.74 (s, 3H), 5.14 (s, 2H), 7.06 (dd, J=8.8, 2.9 Hz, 1H), 7.23 (m, 1H), 7.41 (m, 5H), 7.70 (d, J=8.8 Hz, 1H), 7.78 (d, J=8.5 Hz, 1H), 8.79 (s, 1H), 8.91 (d, J=8.8 Hz, 1H), 11.40 (bs, 1H); MS (ESI+) m/z 421/423 (M+H)+.

Example 79

2-Chloro-N-[3-(pyrido[2,3-d]pyrimidin-4-ylamino)-phenyl]-benzamide

Example 79A

N-(3-Amino-phenyl)-2-chloro-benzamide

The title compound was prepared according to the procedure of Example 254A substituting 2-chloro-benzoyl chloride for 4-bromo-benzoyl chloride followed by reduction of the nitro group using the procedure from Example 255B to provide the title product.

Example 79B

2-Chloro-N-[3-(pyrido[2,3-d]pyrimidin-4-ylamino)-phenyl]-benzamide

The product from Example 79A was reacted with the product from Example 57A using the procedure from Example 254C substituting the product from Example 79A for the product from Example 254B to provide the crude product which was purified by HPLC with TFA to provide the title compound as a trifluoroacetic acid salt (18 mg, 22%). 1H NMR (300 MHz, DMSO-D6) δ ppm: 7.45-7.54 (m, 4H), 7.56-7.62 (m, 3H), 7.83-7.90 (m, 1H), 8.25-8.29 (m, 1H), 8.93 (s, 1H), 9.12-9.18 (m, 2H), 10.70 (s, 1H), 11.23 (s, 1H); MS ESI+ m/z 376 (M+H)+, ESI– m/z 374 (M–H)–.

Example 80

2-Bromo-N-[3-(pyrido[2,3-d]pyrimidin-4-ylamino)-phenyl]-benzamide

Example 80A

N-(3-Amino-phenyl)-2-bromo-benzamide

The title compound was prepared according to the procedure of Example 254A substituting 2-bromo-benzoyl chloride for 4-bromo-benzoyl chloride followed by reduction of the nitro group using the procedure from Example 255B to provide the title product.

Example 80B

2-Bromo-N-[3-(pyrido[2,3-d]pyrimidin-4-ylamino)-phenyl]-benzamide

The product from Example 80A was reacted with the product from Example 57A using the procedure from Example 254C substituting the product from Example 80A for the product from Example 254B to provide the crude product which was purified by HPLC with TFA to provide the title compound as a trifluoroacetic acid salt (18 mg, 22%). 1H NMR (300 MHz, DMSO-D6) δ ppm: 7.44-7.54 (m, 4H), 7.56-7.60 (m, 2H), 7.74 (dd, J=7.91, 0.92 Hz, 1H), 7.82-7.89 (m, 1H), 8.27 (s, 1H), 8.92 (s, 1H), 9.11-9.19 (m, 2H), 10.68 (s, 1H), 11.20 (s, 1H); MS ESI+ m/z 420 (M+H)+, ESI– m/z 418 (M–H)–.

Example 81

2-Methoxy-N-[3-(pyrido[2,3-d]pyrimidin-4-ylamino)-phenyl]-benzamide

Example 81A

N-(3-Amino-phenyl)-2-methoxy-benzamide

The title compound was prepared according to the procedure of Example 254A substituting 2-methoxy-benzoyl chloride for 4-bromo-benzoyl chloride followed by reduction of the nitro group using the procedure from Example 255B to provide the title product.

Example 81B

2-Methoxy-N-[3-(pyrido[2,3-d]pyrimidin-4-ylamino)-phenyl]-benzamide

The product from Example 81A was reacted with the product from Example 57A using the procedure from Example 254C substituting the product from Example 81A for the product from Example 254B to provide the crude product which was purified by HPLC with TFA to provide the title compound as a trifluoroacetic acid salt (26 mg, 33%). 1H NMR (300 MHz, DMSO-D6) δ ppm: 3.90 (s, 3H), 7.08 (t, J=6.99 Hz, 1H), 7.20 (d, J=8.46 Hz, 1H), 7.41-7.56 (m, 4H), 7.62 (dd, J=7.54, 1.65 Hz, 1H), 7.88 (dt, 1H), 8.28 (s, 1H), 8.94 (s, 1H), 9.12-9.19 (m, 2H), 10.30 (s, 1H), 11.30 (s, 1H); MS ESI+ m/z 372 (M+H)+, ESI– m/z 370 (M–H)–.

Example 82

3-Methoxy-N-[3-(pyrido[2,3-d]pyrimidin-4-ylamino)-phenyl]-benzamide

Example 82A

N-(3-Amino-phenyl)-3-methoxy-benzamide

The title compound was prepared according to the procedure of Example 254A substituting 3-methoxy-benzoyl chloride for 4-bromo-benzoyl chloride followed by reduction of the nitro group using the procedure from Example 255B to provide the title product.

Example 82B

3-Methoxy-N-[3-(pyrido[2,3-d]pyrimidin-4-ylamino)-phenyl]-benzamide

The product from Example 82A was reacted with the product from Example 57A using the procedure from Example 254C substituting the product from Example 82A for the product from Example 254B to provide the crude product which was purified by HPLC with TFA to provide the title compound as a trifluoroacetic acid salt (35 mg, 45%). 1H NMR (300 MHz, DMSO-D6) δ ppm: 3.85 (s, 3H), 7.18 (dd, J=7.54, 2.02 Hz, 1H), 7.42-7.51 (m, 3H), 7.53-7.61 (m, 3H), 7.82 (dd, J=7.72, 5.15 Hz, 1H), 8.32 (t, J=1.84 Hz, 1H), 8.89 (s, 1H), 9.09-9.17 (m, 2H), 10.38 (s, 1H), 10.99 (s, 1H); MS ESI+ m/z 372 (M+H)+, ESI– m/z 370 (M+H)–.

Example 83

3-Fluoro-N-[3-(pyrido[2,3-d]pyrimidin-4-ylamino)-phenyl]-benzamide

Example 83A

N-(3-Amino-phenyl)-3-fluoro-benzamide

The title compound was prepared according to the procedure of Example 254A substituting 3-fluoro-benzoyl chloride for 4-bromo-benzoyl chloride followed by reduction of the nitro group using the procedure from Example 255B to provide the title product.

Example 83B

3-Fluoro-N-[3-(pyrido[2,3-d]pyrimidin-4-ylamino)-phenyl]-benzamide

The product from Example 83A was reacted with the product from Example 57A using the procedure from Example 254C substituting the product from Example 83A for the product from Example 254B to provide the crude product which was purified by HPLC with TFA to provide the title compound as a trifluoroacetic acid salt (21 mg, 28%). 1H NMR (300 MHz, DMSO-D6) δ ppm: 7.41-7.53 (m, 2H), 7.54-7.65 (m, 3H), 7.77-7.86 (m, 3H), 8.33 (s, 1H), 8.89 (s, 1H), 9.10-9.16 (m, 2H), 10.48 (s, 1H), 10.97 (s, 1H); MS ESI+ m/z 360 (M+H)+, ESI– m/z 358 (M–H)–.

Example 84

4-[4-Benzylamino-2-(7-methyl-pyrido[2,3-d]pyrimidin-4-ylamino)-phenylsulfanyl]-phenol Example 84A 4-(4-Amino-2-nitro-phenylsulfanyl)-phenol A solution of 4-chloro-3-nitro aniline (1.0 g, 5.79 mmol), 4-hydroxythiophenol (0.75 g, 6.00 mmol), cesium carbonate (3.9 g, 12 mmol) in dimethylsulfoxide (10 ml) was heated at 100° C. for 16 hours. Afterwards ice water (50 mL) was added to the solution and the resultant slurry was treated with ethyl acetate (100 ml). The layers were separated and the organic layer was washed with 10% sodium bicarbonate and 10% sodium chloride, then dried over anhydrous sodium sulfate. The drying agent was filtered and solvent was removed under vacuum leaving a red solid as the title compound, (1.45 g, 92%).

Example 84B 4-(4-Benzylamino-2-nitro-phenylsulfanyl)-phenol

A solution of the product of Example 84A (0.63 g, 2.4 mmol), benzaldehyde (0.24 g, 2.3 mmol) and sodium cyanoborohydride (0.15 g, 2.4 mmol) in methanol (10 mL) containing 1% acetic acid was stirred at room temperature for 16 hours. The reaction mixture was quenched with water (20 mL) and the resultant solution was concentrated under vacuum to a yellow solid. The solid was dissolved in ethyl acetate (50 mL), and washed with water, 10% sodium bicarbonate and 10% sodium chloride. The organic layer was dried over anhydrous sodium sulfate, filtered and solvent removed under vacuum leaving a light yellow oil. The oil was purified by silica gel chromatography eluting with 1% methanol in methylene chloride to provide the title compound (0.63 g, 77%).

Example 84C 4-(2-Amino-4-benzylamino-phenylsulfanyl)-phenol

A solution of the product of Example 84B (0.5 g, 1.4 mmol), iron powder (0.49 g, 8.74 mmol) and ammonium chloride (0.50 g, 9.3 mmol) in a methanol (10 mL), tetrahydrofuran (10 mL), and water (5 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (0.30 g, 66%).

Example 84D

4-[4-Benzylamino-2-(7-methyl-pyrido[2,3-d]pyrimidin-4-ylamino)-phenylsulfanyl]-phenol A solution of the product from Example 10B (30 mg, 0.159 mmol), and the product from Example 84C (56.5 mg, 0.17 mmol) in acetic acid (2 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (12 mg, 10%). 1H NMR (300 MHz, DMSO-D6) δ ppm: 2.71 (s, 3H), 4.50 (s, 2H), 6.60-6.69 (m, 2H), 6.73-6.85 (m, 2H), 7.04-7.29 (m, 6H), 7.31-7.40 (m, 2H), 7.46 (d, J=7.35 Hz, 2H), 8.54 (s, 1H), 8.75 (s, 1H), 9.74 (s, 1H); MS (ESI) m/z 466 (M+H)+, (ESI–) m/z 464 (M–H)–.

Example 85

N1-Benzyl-4-(4-benzyloxy-phenylsulfanyl)-N3-(7-methyl-pyrido[2,3-d]pyrimidin-4-yl)-benzene-1,3-diamine Example 85A 4-(2-Amino-4-nitro-phenylsulfanyl)-phenol A solution of 2-Chloro-5-nitroaniline (3 g, 17.4 mmole), 4-hydroxythiophenol (2.4 g, 19.0 mmol), cesium carbonate (12.35 g, 38 mmol) in dimethylformamide (35 ml) was heated at 100° C. for 16 hours. Afterwards ice water (200 mL) was added to the solution and to the resultant slurry was added ethyl acetate (200 ml). The layers were separated and the organic layer was washed with 10% sodium bicarbonate and 10% sodium chloride, dried over anhydrous sodium sulfate. The drying agent was filtered and solvent was removed under vacuum leaving a yellow oil. The oil was purified by silica gel chromatography eluting with methylene chloride/methanol (97:3), to provide a yellow solid as the title compound (2.1 g, 46%).

Example 85B 2-(4-Benzyloxy-phenylsulfanyl)-5-nitro-phenylamine

A slurry containing of the product from Example 85A (0.2 g, 0.763 mmole) and cesium carbonate (0.25 g, 0.763 mmole) in dimethylformamide (5 ml) was treated with benzyl bromide (0.091 ml, 0.763 mmole) and the resulting slurry was stirred 18 hours at room temperature. Afterwards ice water (50 mL) was added to the solution and to the resultant slurry was added ethyl acetate (50 ml). The layers were separated and the organic layer was washed with 10% sodium bicarbonate and 10% sodium chloride, dried over anhydrous sodium sulfate. The drying agent was filtered and solvent was removed under vacuum leaving a yellow solid as the title compound (0.24 g, 89%).

Example 85C

[2-(4-Benzyloxy-phenylsulfanyl)-5-nitro-phenyl]-(7-methyl-pyrido[2,3-d]pyrimidin-4-yl)-amine A solution of the product from Example 10B (62 mg, 0.331 mmol), and the product of Example 85B (120 mg, 0.331 mmol) in acetic acid (1 mL) was stirred in an oil bath preheated to 130° C. for 20 minutes. The mixture was then cooled to room temperature, the acetic acid removed under vacuum leaving a brown oil as the title compound (0.15 g, 92%). The compound was used without purification in the next step.

Example 85D 4-(4-Benzyloxy-phenylsulfanyl)-N3-(7-methyl-pyrido[2,3-d]pyrimidin-4-yl)-benzene-1,3-diamine A solution of the product from Example 85C (0.150 g, 0.303 mmole), iron powder (0.10 g, 1.86 mmol) and ammonium chloride (0.10 g, 1.98 mmol) in a methanol (2 mL), tetrahydrofuran (2 mL), and water (1 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (0.06 g, 42%).

Example 85E

N1-Benzyl-4-(4-benzyloxy-phenylsulfanyl)-N3-(7-methyl-pyrido[2,3-d]pyrimidin-4-yl)-benzene-1,3-diamine A mixture of the compound prepared in Example 85D (0.06 g, 0.130 mmole), benzaldehyde (0.013 g, 0.130 mmole) and sodium cyanoborohydride (0.0081 g, 0.13 mmole) in methanol (1 ml) containing 1 drop acetic acid was stirred 18 hr at room temperature. The solvent was removed under vacuum and the resultant residue purified by HPLC with TFA to provide the title compound as a trifluoroacetic acid salt (12 mg, 17%). 1H NMR (300 MHz, DMSO-D6) δ ppm: 2.69 (s, 3H), 4.30 (s, 2H), 4.96 (s, 2H), 6.60 (dd, J=8.46, 2.57 Hz, 1H), 6.72-6.89 (m, 3H), 6.94-7.09 (m, 2H), 7.19-7.29 (m, 1H), 7.29-7.46 (m, 11H), 7.63 (d, J=8.46 Hz, 1H), 8.61 (s, 1H), 8.71 (d, J=8.82 Hz, 1H), 10.69 (s, 1H).

Example 86

4-[4-[(Furan-3-ylmethyl)-amino]-2-(7-methyl-pyrido[2,3-d]pyrimidin-4-ylamino)-phenylsulfanyl]-phenol

Example 86A

4-[2-(7-Methyl-pyrido[2,3-d]pyrimidin-4-ylamino)-4-nitro-phenylsulfanyl]-phenol

A solution of the product from Example 10B (340 mg, 1.80 mmol), and the product of Example 85A (480 mg, 1.80 mmol) in acetic acid (10 mL) was stirred in an oil bath preheated to 130° C. for 30 minutes. The mixture was then cooled to room temperature, the acetic acid removed under vacuum leaving a brown oil as the title compound (0.65 g, 89%).

Example 86B

4-[4-Amino-2-(7-methyl-pyrido[2,3-d]pyrimidin-4-ylamino)-phenylsulfanyl]-phenol

A slurry of the product from Example 86A (0.19 g, 0.469 mmol) and 10% Pd/C (0.025 g) in acetic acid (3 ml) was placed under a hydrogen atmosphere with stirring for 2 hr at room temperature. The slurry was filtered and the solvent removed under vacuum leaving a brown solid as an acetate salt of the title compound (0.21 g, 91%).

Example 86C

4-[4-[(Furan-3-ylmethyl)-amino]-2-(7-methyl-pyrido[2,3-d]pyrimidin-4-ylamino)-phenylsulfanyl]-phenol A solution of the product from Example 86B (69.7 mg, 0.141 mmol), 3-furaldehyde (13.5 mg, 0.141 mmol) and sodium cyanoborohydride (8.7 mg, 0.141 mmol) in 2 ml methanol was stirred 18 hr at room temperature. The solvent was evaporated under vacuum and the resultant residue purified by HPLC with TFA to provide the title compound as a trifluoroacetic acid salt (16 mg, 14%). 1H NMR (300 MHz, DMSO-D6) δ ppm: 2.75 (s, 3H), 3.85 (s, 1H), 4.09 (s, 2H), 6.47 (s, 1H), 6.53 (d, J=8.82 Hz, 2H), 6.62-6.75 (m, 2H), 6.94 (d, J=8.46 Hz, 3H), 7.21-7.32 (m, 1H), 7.61 (s, 1H), 7.83 (d, J=8.46 Hz, 1H), 8.77 (s, 1H), 8.88 (s, 1H), 9.51 (s, 1H), 11.68 (s, 1H).

Example 87

4-{2-(7-Methyl-pyrido[2,3-d]pyrimidin-4-ylamino)-4-[(thiophen-3-ylmethyl)-amino]-phenylsulfanyl}-phenol A solution of the product from Example 86B and 3-thiophene carboxaldehyde were reacted according to the procedure from Example 86C substituting 3-thiophene carboxaldehyde for 3-furaldehyde to provide the crude product which was purified by HPLC with TFA to provide the title compound as a trifluoroacetic acid salt (26 mg, 37%). 1H NMR (300 MHz, DMSO-D6) δ ppm: 2.74 (s, 3H), 3.74 (s, 1H), 4.26 (s, 2H), 6.52 (d, J=8.82 Hz, 3H), 6.64-6.76 (m, 1H), 6.86-6.99 (m, 3H), 7.02-7.14 (m, 1H), 7.19-7.34 (m, 1H), 7.42-7.54 (m, 1H), 7.82 (d, J=8.09 Hz, 1H), 8.76 (s, 1H), 8.90 (s, 1H), 9.51 (s, 1H), 11.65 (s, 1H).

Example 88

4-{2-(7-Methyl-pyrido[2,3-d]pyrimidin-4-ylamino)-4-[(naphthalen-1-ylmethyl)-amino]-phenylsulfanyl}-phenol A solution of the product from Example 86B and 1-naphthaldehyde were reacted according to the procedure from Example 86C substituting 1-naphthaldehyde for 3-furaldehyde to provide the crude product which was purified by HPLC with TFA to provide the title compound as a trifluoroacetic acid salt (18 mg, 12%). 1H NMR (300 MHz, DMSO-D6) δ ppm: 2.73 (s, 3H), 4.73 (s, 1H), 6.39 (s, 1H), 6.45-6.60 (m, 2H), 6.67-6.80 (m, 1H), 6.88-6.98 (m, 2H), 7.17-7.34 (m, 1H), 7.43-7.54 (m, 1H), 7.51-7.71 (m, 4H), 7.71-7.83 (m, 1H), 7.83 (d, J=8.82 Hz, 1H), 7.95-8.09 (m, 2H), 8.10-8.18 (m, 1H), 8.22 (d, J=8.09 Hz, 1H), 8.76 (s, 1H), 8.82-8.89 (m, 1H), 9.51 (s, 1H), 11.64 (s, 1H).

Example 89

4-[4-[(Furan-2-ylmethyl)-amino]-2-(7-methyl-pyrido[2,3-d]pyrimidin-4-ylamino)-phenylsulfanyl]-phenol A solution of the product from Example 86B and 2-furaldehyde were reacted according to the procedure from Example 86C substituting 2-furaldehyde for 3-furaldehyde to provide the crude product which was purified by HPLC with TFA to provide the title compound as a trifluoroacetic acid salt (18 mg, 16%). 1H NMR (300 MHz, DMSO-D6) δ ppm: 2.69-2.81 (m, 3H), 4.26 (s, 2H), 6.27-6.44 (m, 1H), 6.45-6.59

(m, 2H), 6.46-6.60 (m, 3H), 6.68-6.78 (m, 2H), 6.89-7.00 (m, 2H), 7.20-7.33 (m, 1H), 7.59 (s, 1H), 7.84 (d, J=8.09 Hz, 1H), 8.77 (s, 1H), 8.89 (s, 1H), 11.73 (s, 1H).

Example 90

4-{2-(7-Methyl-pyrido[2,3-d]pyrimidin-4-ylamino)-4-[(thiophen-2-ylmethyl)-amino]-phenylsulfanyl}-phenol A solution of the product from Example 86B and 2-thiophene carboxaldehyde were reacted according to the procedure from Example 86C substituting 2-thiophene carboxaldehyde for 3-furaldehyde to provide the crude product which was purified by HPLC with TFA to provide the title compound as a trifluoroacetic acid salt (11 mg, 16%). 1H NMR (300 MHz, DMSO-D6) δ ppm: 2.64-2.86 (m, 3H), 4.47 (s, 2H), 6.46-6.57 (m, 2H), 6.64-6.78 (m, 3H), 6.87-7.00 (m, 3H), 7.02-7.13 (m, 2H), 7.19-7.31 (m, 2H), 7.32-7.48 (m, 1H), 7.82 (d, J=8.82 Hz, 1H), 8.77 (s, 1H), 8.89 (s, 1H), 9.50 (s, 1H), 11.68 (s, 1H).

Example 91

4-[4-(4-Bromo-benzylamino)-2-(7-methyl-pyrido[2,3-d]pyrimidin-4-ylamino)-phenysulfanyl]-phenol Example 91A 4-[4-(4-Bromo-benzylamino)-2-nitro-phenylsulfanyl]-phenol A solution of the product from Example 84A and 4-Bromobenzaldehyde were reacted according to the procedure from Example 84B substituting 4-Bromobenzaldehyde for the product from Example 84A to provide the crude product which was purified by silica gel chromatography eluting with 2% methanol in methylene chloride to provide the title compound as a yellow solid (0.11 g, 73%).

Example 91B

4-[2-Amino-4-(4-bromo-benzylamino)-phenylsulfanyl]-phenol

A solution of the product from Example 91A was reacted according to the procedure from Example 84C to provide the title compound (0.17 g, 76%).

Example 91C

4-[4-(4-Bromo-benzylamino)-2-(7-methyl-pyrido[2,3-d]pyrimidin-4-ylamino)-phenysulfanyl]-phenol A solution of the product of Example 10B (50 mg, 0.266 mmol), and the product of Example 91B (110 mg, 0.266 mmol) in acetic acid (2 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (22 mg, 15%). 1H NMR (300 MHz, DMSO-D6) δ ppm: 2.73 (s, 3H), 4.26 (s, 2H), 6.53 (d, J=8.46 Hz, 2H), 6.54-6.69 (m, 2H), 6.85-7.03 (m, 2H), 7.23 (d, J=8.46 Hz, 1H), 7.30 (d, J=8.46 Hz, 3H), 7.46-7.61 (m, 2H), 7.78 (d, J=8.46 Hz, 1H), 8.73 (s, 1H), 8.89 (d, J=19.12 Hz, 1H), 9.51 (s, 1H), 11.46 (s, 1H).

Example 92

N1-Benzyl-4-(4-methoxy-phenylsulfanyl)-N3-(7-methyl-pyrido[2,3-d]pyrimidin-4-yl)-benzene-1,3-diamine 4-(4-Methoxy-phenylsulfanyl)-3-nitro-phenylamine Example 92A A solution of 4-chloro-3-nitro aniline (1.0 g, 5.79 mmol), 4-methoxythiophenol (0.84 g, 6.00 mmol), cesium carbonate (1.95 g, 6.00 mmol) in dimethylformamide (10 ml) was heated at 100° C. for 16 hours. Afterwards ice water (50 mL) was added to the solution and the resultant slurry was treated with ethyl acetate (100 ml). The layers were separated and the organic layer was washed with 10% sodium bicarbonate and 10% sodium chloride, then dried over anhydrous sodium sulfate. The drying agent was filtered and solvent was removed under vacuum leaving a red solid as the title compound (1.5 g, 94%).

Example 92B

Benzyl-[4-(4-methoxy-phenylsulfanyl)-3-nitro-phenyl]-amine

A solution of the product of Example 92A (0.50 g, 1.81 mmol), benzaldehyde (0.19 g, 1.81 mmol) and sodium cyanoborohydride (0.11 g, 1.8 mmol) in methanol (10 mL) containing 1% acetic acid was stirred at room temperature for 16 hours. The reaction mixture was quenched with water (20 mL) and the resultant solution was concentrated under vacuum to a yellow solid. The solid was dissolved in ethyl acetate (50 mL), and washed with water, 10% sodium bicarbonate and 10% sodium chloride. The organic layer was dried over anhydrous sodium sulfate, filtered and solvent removed under vacuum leaving a light yellow oil. The oil was purified by silica gel chromatography eluting with 1% methanol in methylene chloride to provide the title compound as a brick red solid (0.62 g, 91%).

Example 92C

N1-Benzyl-4-(4-methoxy-phenylsulfanyl)-benzene-1,3-diamine

A solution of the product of Example 92B was reacted according to the procedure from Example 84C to provide the title compound (0.49 g, 89%).

Example 92D

N1-Benzyl-4-(4-methoxy-phenylsulfanyl)-N3-(7-methyl-pyrido[2,3-d]pyrimidin-4-yl)-benzene-1,3-diamine A solution of the product of Example 10B (27.8 mg, 0.148 mmol), and the product of Example 92C (49 mg, 0.148 mmol) in acetic acid (2 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (15 mg, 14%). 1H NMR (300 MHz, DMSO-D6) δ ppm: 2.64-2.81, (m, 3H) 3.56-3.71, (m, 3H) 4.29 (s, 2H), 6.61-6.75 (m, 3H), 6.95-7.07

(m, 2H), 7.16-7.45 (m, 8H), 7.76 (d, J=8.46 Hz, 1H), 8.69 (s, 1H), 8.80 (d, 1H), 11.34 (s, 1H).

Example 93

N1-Benzyl-4-(4-methoxy-phenoxy)-N3-(7-methyl-pyrido[2,3-d]pyrimidin-4-yl)-benzene-1,3-diamine

Example 93A 4-(4-Methoxy-phenoxy)-3-nitro-phenylamine

A solution of 4-chloro-3-nitro aniline (1.0 g, 5.79 mmol), 4-methoxyphenol (0.74 g, 6.00 mmol), cesium carbonate (1.95 g, 6.00 mmol) in dimethylformamide (10 ml) was heated at 100° C. for 16 hours. Afterwards ice water (50 mL) was added to the solution and the resultant slurry was treated with ethyl acetate (100 ml). The layers were separated and the organic layer was washed with 10% sodium bicarbonate and 10% sodium chloride, then dried over anhydrous sodium sulfate. The drying agent was filtered and solvent was removed under vacuum leaving a red solid as the title compound (1.1 g, 73%).

Example 93B

N1-Benzyl-4-(4-methoxy-phenoxy)-benzene-1,3-diamine

A solution of the product from Example 93A was reacted according to the procedure from Example 92B substituting the product from Example 93A for the product from Example 92A which was reduced according to the procedure from Example 84C to provide the title compound (0.05 g, 12%).

Example 93C

N1-Benzyl-4-(4-methoxy-phenoxy)-N3-(7-methyl-pyrido[2,3-d]pyrimidin-4-yl)-benzene-1,3-diamine A solution of the product of Example 10B and the product from Example 93B was reacted according to the procedure from Example 92D substituting the product from Example 93B for the product from Example 92C which was purified by HPLC with TFA to provide the title compound as a trifluoro-acetic acid salt (8 mg, 18%). 1H NMR (300 MHz, DMSO-D6) δ ppm: 2.55-2.68 (m, 3H), 3.61 (s, 3H), 4.26 (d, J=5.88 Hz, 2H), 6.27 (t, J=5.88 Hz, 1H), 6.50 (dd, J=8.64, 2.76 Hz, 1H), 6.64-6.87 (m, 6H), 7.18-7.45 (m, 6H), 8.48 (s, 1H), 8.57 (d, J=8.46 Hz, 1H), 9.59 (s, 1H).

Example 94

N1-Benzyl-4-(4-benzyloxy-phenoxy)-N3-(7-methyl-pyrido[2,3-d]pyrimidin-4-yl)-benzene-1,3-diamine

Example 94A 4-(4-Benzyloxy-phenoxy)-3-nitro-phenylamine

A solution of 4-chloro-3-nitro aniline (2.0 g, 11.16 mmol), 4-benzyloxyphenol (2.55 g, 12.76 mmol), powdered potassium hydroxide (0.94 g, 16.80 mmol) in dimethylformamide (15 ml) was heated at 120° C. for 20 hours. Afterwards ice water (50 mL) was added to the solution and the resultant slurry was treated with ethyl acetate (100 ml). The layers were separated and the organic layer was washed with 10% sodium bicarbonate and 10% sodium chloride, then dried over anhydrous sodium sulfate. The drying agent was filtered and solvent was removed under vacuum leaving a dark red solid as the title compound, (2.07 g, 53%).

Example 94B

N1-Benzyl-4-(4-benzyloxy-phenoxy)-benzene-1,3-diamine

A solution of the product from Example 94A was reacted according to the procedure from Example 92B substituting the product from Example 94A for the product from Example 92A which was reduced according to the procedure from Example 84C to provide the title compound (0.6 g, 91%).

Example 94C

N1-Benzyl-4-(4-benzyloxy-phenoxy)-N3-(7-methyl-pyrido[2,3-d]pyrimidin-4-yl)-benzene-1,3-diamine A solution of the product of Example 10B and the product from Example 94B was reacted according to the procedure from Example 92D substituting the product from Example 94B for the product from Example 92C which was purified by HPLC with TFA to provide the title compound as a trifluoro-acetic acid salt (12 mg, 10%). 1H NMR (300 MHz, DMSO-D6) δ ppm: 2.70 (s, 3H), 4.27 (s, 2H), 4.94 (s, 2H), 4.99-5.12 (m, 1H), 6.64 (dd, J=8.82, 2.94 Hz, 1H), 6.70-6.92 (m, 9H), 6.90-7.00 (m, 1H), 7.16-7.29 (m, 1H), 7.31-7.42 (m, 5H), 7.70 (d, J=8.46 Hz, 1H), 8.67-8.86 (m, 2H), 11.22 (s, 1H).

Example 95

4-[4-Amino-2-(7-isopropyl-pyrido[2,3-d]pyrimidin-4-ylamino)-phenylsulfanyl]-phenol

Example 95A

4-[2-(7-Isopropyl-pyrido[2,3-d]pyrimidin-4-ylamino)-4-nitro-phenylsulfanyl]-phenol A solution of the product from Example 10B (340 mg, 2.31 mmol), and the product of Example 85A (610 mg, 2.30 mmol) in acetic acid (10 mL) was stirred in an oil bath preheated to 130° C. for 10 minutes. The mixture was then cooled to room temperature, the acetic acid removed under vacuum providing a brown oil as the title compound (0.92 g, 92%).

Example 95B

4-[4-Amino-2-(7-isopropyl-pyrido[2,3-d]pyrimidin-4-ylamino)-phenylsulfanyl]-phenol A slurry of the compound prepared in Example 95A (0.7 g, 1.73 mmol) and 10% Pd/C (100 mg) in acetic acid (10 ml) and methanol (10 mL) was placed under a hydrogen balloon atmosphere with stirring for 20 hours at room temperature. The slurry was filtered and the solvent removed under vacuum to provide the title compound as an acetic acid salt (540 mg, 63%). 1H NMR (300 MHz, DMSO-D6) δ ppm: 1.35 (d, J=7.0 Hz, 6H), 1.91 (s, 6H), 3.27 (m, 1H), 6.55 (d, J=8.8 Hz, 2H), 6.62 (m, 1H), 6.69 (m, 1H), 6.95 (d, J=8.8 Hz, 2H), 7.20 (d, J=8.5 Hz, 1H), 7.87 (d, J=8.5 Hz, 1H), 7.95 (s, 1H), 8.75 (s, 1H), 8.99 (m, 1H), 9.52 (s, 1H), 11.57 (bs, 1H); MS (ESI+) m/z 404 (M+H)+.

Example 96

4-[2-(7-Isopropyl-pyrido[2,3-d]pyrimidin-4-ylamino)-4-phenethylamino-phenylsulfanyl]-phenol A solution containing the product from Example 95B (65 mg, 0.124 mmole), phenylacetaldehyde (15 mg, 0.124 mmole) and sodium cyanoborohydride (10 mg, 0.199 mmole) in 2 ml methanol was stirred 18 hr at room temperature. The solvent was evaporated under vacuum and the resultant residue purified by HPLC with TFA to provide the title compound as a trifluoroacetic acid salt (25 mg, 32%). 1H NMR (300 MHz, DMSO-D6) δ ppm: 1.28 (d, 6H), 2.31-2.48 (m, 1H), 2.78-2.93 (m, 2H), 3.16-3.35 (m, 2H), 4.17-4.36 (m, 2H), 4.73-4.91 (m, 1H), 6.47-6.59 (m, 2H), 6.61-6.74 (m, 1H), 6.86-7.01 (m, 2H), 7.10 (d, J=6.99 Hz, 1H), 7.15-7.27 (m, 1H), 7.19-7.39 (m, 6H), 7.89 (d, J=8.46 Hz, 1H), 8.77 (s, 1H), 8.96 (s, 1H), 9.50 (s, 1H), 11.61 (s, 1H).

Example 97

4-[4-(Cyclopentylmethyl-amino)-2-(7-isopropyl-pyrido[2,3-d]pyrimidin-4-ylamino)-phenylsulfanyl]-phenol A solution containing the product from Example 95B was reacted with cyclopentanecarbaldehyde according to the procedure from Example 96 substituting cyclopentanecarbaldehyde for phenylacetaldehyde which was purified by HPLC with TFA to provide the title compound as a trifluoroacetic acid salt (11 mg, 9%). 1H NMR (300 MHz, DMSO-D6) δ ppm: 1.26-1.43 (m, 6H), 1.53 (s, 4H), 1.75 (d, J=3.31 Hz, 4H), 2.01-2.19 (m, 1H), 2.92 (d, J=6.99 Hz, 2H), 3.20-3.36 (m, 1H), 6.53 (d, J=8.82 Hz, 2H), 6.58-6.73 (m, 1H), 6.87-7.00 (m, 2H), 6.98-7.13 (m, 1H), 7.17-7.36 (m, 1H), 7.89 (s, 1H), 8.15 (s, 1H), 8.77 (s, 1H), 8.95 (s, 1H), 9.49 (s, 1H), 10.98 (s, 1H), 11.68 (s, 1H).

Example 98

N1-Benzyl-N3-(7-isopropyl-pyrido[2,3-d]pyrimidin-4-yl)-4-(4-methoxy-phenylsulfanyl)-benzene-1,3-diamine A solution of the product from Example 36E (40.4 mg, 0.187 mmol) and the product of Example 92C (62.8 mg, 0.187 mmol) in acetic acid (2 mL) was stirred in an oil bath preheated to 140° C. for 45 minutes. The reaction was cooled to room temperature, diluted with hexanes (50 mL), concentrated by rotary evaporation, and co-evaporated with methylene chloride/hexanes (4×). The residue was dried on under vacuum, then purified by silica gel flash chromatography with a gradient of 15% to 20% ethyl acetate/methylene chloride as eluent to afford the title compound as a yellow solid (29.6 mg, 31%). 1H NMR (300 MHz, DMSO-D6) δ ppm: 1.31 (d, J=6.99 Hz, 6H) 3.11-3.26 (m, 1H) 3.64 (s, 3H) 4.30 (d, J=5.88 Hz, 2H) 6.53 (dd, J=8.46, 2.57 Hz, 1H) 6.66-6.78 (m, 3H) 6.95 (d, J=2.21 Hz, 1H) 7.03 (d, J=8.82 Hz, 2H) 7.12-7.28 (m, 2H) 7.28-7.44 (m, 4H) 7.54 (d, J=8.46 Hz, 1H) 8.50 (s, 1H) 8.65 (d, J=8.46 Hz, 1H) 9.75 (s, 1H); MS (DCI/NH$_3$) m/z 508 (M+H)$^+$.

Example 99

4-[2-(7-Methyl-pyrido[2,3-d]pyrimidin-4-ylamino)-4-pyrrol-1-yl-phenylsulfanyl]-phenol To a solution of the product from Example 86B (50 mg, 0.101 mmol) and succinic dialdehyde (40% in water solution) (0.065 mL, 0.303 mmol) in toluene (5 mL) and methanol (3 mL) was added 4A molecular sieves (100 mg). The mixture was then heated to 60° C. for 7 hours, cooled to room temperature, the solvent removed under vacuum, a solution of 0.1 N aqueous hydrochloric acid (20 mL) added and the mixture extracted with dichloromethane (2×25 mL) and dioxane (25 mL). The combined organic extracts were dried and concentrated under vacuum then the resultant residue purified by HPLC with TFA to provide the title compound as a trifluoroacetic acid salt (14 mg, 26%). 1H NMR (300 MHz, DMSO-D6) δ ppm: 2.68 (s, 3H), 6.26 (m, 2H), 6.77 (d, J=8.5 Hz, 2H), 7.05 (d, J=8.5 Hz, 1H), 7.24 (d, J=8.5 Hz, 2H), 7.37 (m 2H), 7.48 (dd, J=8.6, 2.4 Hz, 1H), 7.57 (d, J=8.5 Hz, 1H), 7.73 (d, J=2.6 Hz, 1H), 8.57 (s, 1H), 8.80 (d, J=8.4 Hz, 1H), 9.81 (s, 1H), 10.11 (s, 1H); MS (ESI+) m/z 426 (M+H)+.

Example 100

4-[2,4-Bis-(7-methyl-pyrido[2,3-d]pyrimidin-4-ylamino)-phenylsulfanyl]-phenol To a solution of the product from Example 86B (50 mg, 0.101 mmol) and the product from Example 10B (19 mg, 0.101 mmol) in acetic acid (1 mL) was heated to 120° C. for 2 hours. After cooling to room temperature, the solvent was removed under vacuum and methanol (2 mL) was added. The resultant solid was collected and triturated with methanol to provide the title compound as a light brown solid (12 mg, 23%). $^1$H NMR (300 MHz, DMSO-D6) δ ppm: 2.67 (s, 3H), 2.68 (m, 3H), 6.75 (d, J=8.8 Hz, 2H), 6.83 (m, 1H), 7.12 (m, 1H), 7.21 (d, J=8.8 Hz, 2H), 7.34 (m, 1H), 7.58 (m, J=8.8 Hz, 2H), 8.73 (s, 1H), 8.81 (m, 1H), 8.88 (m, 1H), 9.76 (s, 1H), 10.13 (s, 1H), 11.95 (bs, 1H); MS (ESI+) m/z 519 (M+H)+.

Example 101

4-[4-(4-Bromo-benzylamino)-2-(7-isopropyl-pyrido[2,3-d]pyrimidin-4-ylamino)-phenylsulfanyl]-phenol A solution containing the product from Example 95B was reacted with 4-Bromo-benzaldehyde according to the procedure from Example 96 substituting 4-Bromo-benzaldehyde for phenylacetaldehyde which was purified by HPLC with TFA to provide the title compound as a trifluoroacetic acid salt (7 mg, 3%). 1H NMR (300 MHz, DMSO-D6) δ ppm: 1.35 (d, J=6.6 Hz, 6H), 3.30 (m, 1H), 6.55 (d, J=8.5 Hz, 2H), 6.68 (m, 1H), 6.76 (d, J=8.8 Hz, 2H), 6.91 (m, 1H), 6.98 (d, J=8.5 Hz, 2H), 7.27 (d, J=8.8 Hz, 2H), 7.32 (m, 1H), 7.56 (m, 2H), 8.78 (s, 1H), 9.53 (m, 1H); MS (ESI+) m/z 574 (M+H)+.

Example 102

4-[4-Methyl-2-(7-methyl-pyrido[2,3-d]pyrimidin-4-ylamino)-phenylsulfanyl]-phenol To a solution of the product from Example 10B (100 mg, 0.575 mmol) and the product from Example 6c (146 mg, 0.632 mmol) in acetic acid (1 mL) was heated at 130° C. for 1 hour. The mixture was then allowed to cool to room temperature, then methanol (5 mL) added to the solution and the resulting solid collected and washed with methanol to provide the title compound (120 mg, 56%). 1H NMR (300 MHz, DMSO-D6) δ ppm: 2.29 (s, 3H), 2.66 (s, 3H), 6.73 (d, J=8.8 Hz, 1H), 6.93 (m, 1H), 7.03 (m, 1H), 7.18 (d, J=8.5 Hz, 2H), 7.26, (s, 1H), 7.53 (d, J=8.5 Hz, 1H), 8.53 (s, 1H), 8.77 (m, 1H), 9.76 (bs, 1H), 9.96 (bs, 1H); MS (ESI)+ m/z 375 (M+H)+.

Example 103

(5-Methyl-2-phenylsulfanyl-phenyl)-(7-methyl-pyrido[2,3-d]pyrimidin-4-yl)-amine

To a solution of the product from Example 10B (90 mg, 0.517 mmol) and the product from Example 5I (122 mg, 0.569 mmol) in acetic acid (1 mL) was heated at 130° C. for 1 hour. The mixture was then allowed to cool to room temperature, the resulting solid collected and washed with methanol, then dissolved 50 mg of the material in dioxane (2 mL) and added hydrochloric acid followed by removal of the solvent under vacuum to provide the title compound as a hydrochloride salt. 1H NMR (300 MHz, DMSO-D6) δ ppm: 2.37 (s, 3H), 2.74 (s, 3H), 7.18 (m, 5H), 7.24 (m, 1H), 7.37 (m, 2H), 7.81 (d, J=8.5 Hz, 1H), 8.80 (s, 1H), 8.99 (d, J=8.5 Hz, 1H), 11.82 (bs, 1H); MS (ESI)+ m/z 359 (M+H)+.

Example 104

[3-(3-Bromo-phenoxymethyl)-phenyl]-(7-methyl-pyrido[2,3-d]pyrimidin-4-yl)-amine

Example 104A

1-Nitro-3-(3-bromo-phenoxymethyl)-benzene

To a solution of 3-nitrobenzyl chloride (1.0 g, 5.83 mmol), 3-bromophenol (1.01 g, 5.83 mmol) and potassium carbonate (806 mg, 5.83 mmol) in acetone (25 mL) was heated to reflux for 23 hours. After cooling the solid was filtered off and the filtrate was concentrated under vacuum to a yellow residue which was dissolved in ethyl acetate (50 mL) and washed with 1N aqueous sodium hydroxide solution (25 mL) and water (25 mL) then dried and concentrated under vacuum to the title compound as a white solid (1.64 g, 91%).

Example 104B 3-(3-Bromo-phenoxymethyl)-phenylamine

To a solution of the product from Example 104A (1.64 g, 5.32 mmol), iron powder (1.49 g, 26.62 mmol) and ammonium chloride (430 mg, 7.98 mmol) in a mixture of tetrahydrofuran (20 mL), water (6 mL) and ethanol (20 mL) was heated to reflux for 3 hours. The mixture was cooled to room temperature, filtered through a pad of celite, which was washed with ethanol and the resultant filtrate concentrated under vacuum. The material was then dissolved in water (50 mL) and extracted with ethyl acetate (50 mL), the organic layer dried and concentrated under vacuum to provide the title compound as a yellow oil (1.43 g, 97%).

Example 104C

[3-(3-Bromo-phenoxymethyl)-phenyl]-(7-methyl-pyrido[2,3-d]pyrimidin-4-yl)-amine

To a solution of the product from Example 10C (50 mg, 0.266 mmol) and the product from Example 104B (74 mg, 0.266 mol) in acetic acid (3 mL) was heated to 130° C. for 30 minutes. After cooling to room temperature the solution was concentrated under vacuum and purified by HPLC with TFA to provide the title compound as a trifluoroacetic acid salt (62 mg, 44%). 1H NMR (300 MHz, DMSO-D6) δ ppm: 2.71 (s, 3H), 5.20 (s, 2H), 7.05 (m, 1H), 7.16 (m, 1H), 7.24 (m, 2H), 7.33 (m, 1H), 7.49 (t, J=7.7 Hz, 1H), 7.70 (d, J=8.5 Hz, 1H), 7.79 (m, 1H), 7.84 (s, 1H), 8.83 (s, 1H), 8.96 (d, J=8.4 Hz, 1H), 10.75 (bs, 1H); MS (ESI)+ m/z 421/423 (M+H)+.

Example 105

(3'-Methoxy-5-methyl-biphenyl-3-yl)-(7-methyl-pyrido[2,3-d]pyrimidin-4-yl)-amine

Example 105A

3-Bromo-5-methyl-phenylamine

The title compound was prepared from 3-Bromo-5-nitrotoluene (1.08 g, 5.0 mmol) using the conditions from Example 104B to provide the title compound as an orange oil (0.8 g, 86%).

Example 105B (3-Bromo-5-methyl-phenyl)-(7-methyl-pyrido[2,3-d]pyrimidin-4-yl)-amine The product from Example 105A (0.8 g, 4.3 mmol) was reacted with the product from Example 10C using the procedure from Example 104C substituting the product from Example 105A for the product from Example 104B to provide the crude residue which was purified by chromatography on silica eluting with 99:1 dichloromethane/methanol to provide the title compound as a yellow powder (1.1 g, 77%).

Example 105C (3'-Methoxy-5-methyl-biphenyl-3-yl)-(7-methyl-pyrido[2,3-d]pyrimidin-4-yl)-amine The product of Example 105B (0066 g, 0.2 mmol), 3-Methoxy phenylboronic acid (0.043 g, 0.28 mmol), cesium carbonate (0.1 g, 0.3 mmol) and dichlorobis(triphenylphosphine)palladium(II) (0.014 g, 0.02 mmol) were combined in N,N-dimethylformamide (1 mL) and heated to 100° C. for 24 hours. After cooling to room temperature the mixture was poured into ice water (20 mL) and the resultant solution acidified with 1N aqueous hydrochloric acid. The solution was then extracted with ethyl acetate (3×10 mL), the combined extracts dried over sodium sulfate, filtered and concentrated under vacuum. The crude product was purified by HPLC with TFA to provide the title compound as a trifluoroacetic acid salt (12 mg, 13%). 1H NMR (300 MHz, DMSO-D6) δ ppm: 2.45 (s, 3H), 2.75 (s, 3H), 3.83 (s, 3H), 6.98 (dd, J=7.72, 2.21 Hz, 1H), 7.20 (d, J=2.21 Hz, 1H), 7.25 (d, J=8.09 Hz, 1H), 7.41 (t, J=7.91 Hz, 1H), 7.48 (s, 1H), 7.56 (s, 1H), 7.82 (d, J=5.15 Hz, 1H), 7.83 (d, J=3.31 Hz, 1H), 8.96 (s, 1H), 9.03 (d, J=8.46 Hz, 1H), 11.34 (s, 1H); MS (ESI)+ m/z 357 (M+H)+.

Example 106

{2-2-(4-Methoxy-phenyl)-ethyl]-5-methyl-phenyl}-(7-methyl-pyrido[2,3-d]pyrimidin-4-yl)amine

Example 106A

1-[2-(4-Methoxy-phenyl)-vinyl-4-methyl-2-nitrobenzene

To a solution of 1-Bromo-4-methyl-2-nitro-benzene (0.76 g, 3.5 mmol), 1-methoxy-4-vinyl-benzene (0.59 g, 4.4 mmol), triethylamine (0.88 g, 8.8 mmol), tri-o-tolylphosphine (0.022 g) and palladium acetate (0.008 g) in N,N-dimethylformamide (7 mL) was placed in a high-pressure tube and purged with nitrogen for 10 mins. The tube was sealed and heated at 120° C. for 16 hours. The mixture was partitioned with water and ethyl acetate adjusting the pH to 3. The organic layer was washed with brine, dried (sodium sulfate) and filtered through a plug of silica. The filtrate was evaporated under vacuum and the residue was triturated with hexane/ethyl acetate (9:1) to provide the title compound (0.55 g, 58%).

Example 106B

2-[2-(4-Methoxy-phenyl)-ethyl]-5-methyl-phenylamine

To a solution of the product from Example 106A (164 mg, 0.6 mmol) and 10% palladium on charcoal (50 mg) in ethanol (20 ml) was hydrogenated with a hydrogen balloon for three days. The solvent was filtered through celite, washed with ethanol and evaporated under vacuum to provide the title compound (140 mg, 97%).

Example 106C

{2-2-(4-Methoxy-phenyl)-ethyl]-5-methyl-phenyl}-(7-methyl-pyrido[2,3-d]pyrimidin-4-yl)amine The product from Example 106B was reacted with the product from Example 10C using the procedure from Example 104C substituting the product from Example 106B for the product from Example 104B to provide the crude residue which was purified by chromatography on silica eluting with 99:1 dichloromethane/methanol to provide the title compound (53 mg, 69%). 1H NMR (300 MHz, DMSO-D6) δ ppm: 2.30 (s, 3H), 2.69 (m, 7H), 3.64 (s, 3H), 6.69 (d, J=8.8 Hz, 2H), 6.89 (d, J=8.8 Hz, 2H), 7.08 (d, J=7.7 Hz, 1H), 7.13 (s, 1H), 7.22 (d, J=7.7 Hz, 1H), 7.53 (d, J=8.5 Hz, 1H), 8.50 (s, 1H), 8.79 (d, J=8.5 Hz, 1H), 9.83 (s, 1H); (ESI+) m/z 385 (M+H)+.

Example 107

4-[4-Methyl-2-(pyrido[2,3-d]pyrimidin-4-ylamino)-phenylsulfanyl]-phenol

The product from Example 6c was reacted with the product from Example 57A using the procedure from Example 10F substituting the product from Example 6c for the product from Example 10E and substituting the product from Example 57A for the product from Example 10B to provide the crude residue which was purified by HPLC with TFA to provide the title compound as a trifluoroacetic acid salt. 1H NMR (300 MHz, DMSO-D6) δ ppm: 2.31 (s, 3H), 6.61-6.78 (m, 2H), 7.02 (d, J=8.09 Hz, 1H), 7.11-7.20 (m, 3H), 7.24 (s, 1H), 7.87 (dd, J=8.46, 4.41 Hz, 1H), 8.79 (s, 1H), 9.03 (d, J=8.46 Hz, 1H), 9.14-9.19 (m, 1H), 9.79 (s, 1H); MS (ESI+) m/z 361 (M+H)+.

Example 108

(5-Methyl-2-phenylsulfanyl-phenyl)-pyrido[2,3-d]pyrimidin-4-yl-amine

The product from Example 5I was reacted with the product from Example 57A using the procedure from Example 10F substituting the product from Example 5I for the product from Example 10E and substituting the product from Example 57A for the product from Example 10B to provide the crude residue which was purified by HPLC with TFA to provide the title compound as a trifluoroacetic acid salt. 1H NMR (300 MHz, DMSO-D6) δ ppm: 2.37 (s, 3H), 7.09-7.27 (m, 6H), 7.35 (d, J=7.72 Hz, 2H), 7.83 (dd, J=8.09, 4.41 Hz, 1H), 8.75 (s, 1H), 8.96 (d, J=7.72 Hz, 1H), 9.13 (d, J=3.31 Hz, 1H); MS (ESI+) m/z 345 (M+H)+.

Example 109

N-{4-[4-Methyl-2-(pyrido[2,3-d]pyrimidin-4-ylamino)-phenylsulfanyl]-phenyl}-acetamide The product from Example 7b was reacted with the product from Example 57A using the procedure from Example 10F substituting the product from Example 7b for the product from Example 10E and substituting the product from Example 57A for the product from Example 10B to provide the crude residue which was purified by HPLC with TFA to provide the title compound as a trifluoroacetic acid salt. 1H NMR (300 MHz, DMSO-D6) δ ppm: 2.02 (s, 3H), 2.34 (s, 3H), 7.13-7.35 (m, 5H), 7.46 (d, J=8.46 Hz, 2H), 7.87 (dd, J=8.09, 4.41 Hz, 1H), 8.80 (s, 1H), 9.01 (d, J=8.09 Hz, 1H), 9.15 (d, J=3.31 Hz, 1H), 9.99 (s, 1H); MS (ESI+) m/z 402 (M+H)+.

Example 110

4-[2-(7-Isopropyl-pyrido[2,3-d]pyrimidin-4-ylamino)-4-methyl-phenylsulfanyl]-phenol The product from Example 6c was reacted with the product from Example 36E using the procedure from Example 36I substituting the product from Example 6c for the product from Example 36H to provide the crude residue which was purified by HPLC with TFA to provide the title compound as a trifluoroacetic acid salt. 1H NMR (300 MHz, DMSO-D6) δ ppm: 1.35 (d, J=6.62 Hz, 6H), 2.31 (s, 3H), 3.29 (t, J=6.89 Hz, 1H), 6.70 (d, J=8.82 Hz, 2H), 7.01 (d, J=8.09 Hz, 1H), 7.17 (d, J=8.82 Hz, 2H), 7.13-7.22 (m, 2H), 7.23 (s, 1H), 7.87 (d, J=8.82 Hz, 1H), 8.79 (s, 1H), 8.97 (d, J=8.82 Hz, 1H), 9.80 (s, 1H), 11.42 (s, 1H); MS (ESI+) m/z 403 (M+H)+.

Example 111

2-Chloro-4-[2-(7-isopropyl-pyrido[2,3-d]pyrimidin-4-ylamino)-4-methyl-phenylsulfanyl]-phenol To a solution of the product from Example 110 (50 mg, 0.124 mmol) in acetic acid (1.5 mL) was added sulfuryl chloride (0.01 mL, 0.124 mmol) dropwise at room temperature. The mixture was stirred for an additional 30 minutes then was concentrated under vacuum and purified by HPLC with TFA to provide the title compound as a trifluoroacetic acid salt (19 mg, 28%). 1H NMR (300 MHz, DMSO-D6) δ ppm: 1.35 (d, J=6.6 HZ, 6H), 2.34 (s, 3H), 3.30 (m, 1H), 6.82 (d, J=8.5 Hz, 1H), 7.08 (dd, J=8.5, 2.2 Hz, 1H), 7.17 (m, 1H), 7.24 (m, 3H), 8.74 (s, 1H), 8.94 (d, J=8.5 Hz, 1H), 10.50 (s, 1H), 11.42 (bs, 1H); MS (ESI+) m/z 437 (M+H)+.

Example 112

2,6-Dichloro-4-[2-(7-isopropyl-pyrido[2,3-d]pyrimidin-4-ylamino)-4-methyl-phenylsulfanyl]-phenol To a solution of the product from Example 110 (50 mg, 0.124 mmol) in acetic acid (1.5 mL) was added sulfuryl chloride (0.02 mL, 0.248 mmol) dropwise at room temperature. The mixture was stirred for an additional 30 minutes then was concentrated under vacuum and purified by HPLC with TFA to provide the title compound as a trifluoroacetic acid salt (17 mg, 23%). 1H NMR (300 MHz, DMSO-D6) δ ppm: 1.35 (d, J=6.6 Hz, 6H), 2.37 (s, 3H), 3.28 (m, 1H), 7.12 (s, 1H), 7.28 (m, 2H), 7.46 (d, J=8.1 Hz, 1H), 7.83 (d, J=8.5 Hz, 1H), 8.70 (s, 1H), 8.88 (d, J=8.8 Hz, 1H), 10.38 (s, 1H), 11.22 (bs, 1H); MS (ESI+) m/z 472 (M+H)+.

Example 113

4-[4-Hydroxymethyl-2-(7-isopropyl-pyrido[2,3-d]pyrimidin-4-ylamino)-phenylsulfanyl]-phenol Example 113A 4-(4-Hydroxy-phenylsulfanyl)-3-nitro-benzoic acid methyl ester A solution of 4-Chloro-3-nitro-benzoic acid methyl ester (4.0 g, 18.55 mmol) in anhydrous N,N-dimethylformamide (25 mL) was treated with 4-mercaptophenol (2.34 g, 18.55 mmol) and cesium carbonate (9.07 g, 27.83 mmol) at room temperature for 23 hours. The solvent was then removed by rotary evaporation under vacuum, the residue taken up in water (100 mL) and the pH adjusted to 3 with 1N aqueous HCl. The aqueous solution was extracted with ethyl acetate (2×100 mL), and the combined organic extracts washed with brine (50 mL). The organic layer was dried over magnesium sulfate, filtered, and concentrated by rotary evaporation to provide the product as an orange oil contaminated with N,N-dimethylformamide (7.28 g).

Example 113B

3-Amino-4-(4-hydroxy-phenylsulfanyl)-benzoic acid methyl ester

A suspension of the product of Example 113A (as a mono DMF adduct)(7.25 g, 19.23 mmol) ammonium chloride (1.54 g, 28.8 mmol) and iron powder (5.37 g, 96.15 mmol) in tetrahydrofuran (75 mL), water (25 mL) and ethanol (75 mL) was heated at reflux for 3 hours. The reaction was cooled to room temperature, and the mixture was filtered through a pad of celite, which was then washed with methanol, and the filtrate concentrated to a solid under vacuum. The residue was then dissolved in water (100 mL) and extracted with dichloromethane (2×50 mL). The combined organic extracts were washed with brine (25 mL), dried over magnesium sulfate, filtered, and concentrated under vacuum to provide the title compound as a white solid (4.2 g, 79%).

Example 113C 4-(2-Amino-4-hydroxymethyl-phenylsulfanyl)-phenol

To the product from Example 113B (500 mg, 1.82 mmol) in tetrahydrofuran (50 mL) was added a solution of lithium aluminum hydride (1.0M in THF, 1.8 mL, 1.82 mmol) dropwise at room temperature followed by heating the mixture to 70° C. for 4 hours. Water (25 mL) was then carefully added to the solution and the organic layer separated, dried and concentrated under vacuum to provide the title compound (295 mg, 66%).

Example 113D

4-[4-Hydroxymethyl-2-(7-isopropyl-pyrido[2,3-d]pyrimidin-4-ylamino)-phenylsulfanyl]-phenol The product from Example 113C was reacted with the product from Example 36E using the procedure from Example 36I substituting the product from Example 113C for the product from Example 36H to provide the crude residue which was purified by HPLC with TFA to provide the title compound as a trifluoroacetic acid salt (30 mg, 31%). 1H NMR (300 MHz, DMSO-D6) δ ppm: 1.36 (d, J=7.0 Hz, 6H), 3.30 (m, 1H), 4.50 (s, 2H), 6.72 (d, J=8.5 Hz, 2H), 7.05 (d, J=8.1 Hz, 1H), 7.19 (d, J=8.5 Hz, 2H), 7.27 (m, 1H), 7.35 (s, 1H), 7.87 (d, J=8.5 Hz, 1H), 8.79 (s, 1H), 8.98 (m, 1H), 9.82 (s, 1H), 11.43 (bs, 1H); MS (ESI+) m/z 419 (M+H)+.

Example 114

Acetic acid 4-(4-hydroxy-phenylsulfanyl)-3-(7-isopropyl-pyrido[2,3-d]pyrimidin-4-ylamino)-benzyl ester The product from Example 113C was reacted with the product from Example 36E using the procedure from Example 36I substituting the product from Example 113C for the product from Example 36H to provide the crude residue which was purified by HPLC with TFA to provide the title compound as a trifluoroacetic acid salt (12 mg, 11%). 1H NMR (300 MHz, DMSO-D6) δ ppm: 1.36 (d, J=6.6 Hz, 6H), 2.05 (s, 3H), 3.30 (m, 1H), 5.07 (s, 2H), 6.71 (d, J=8.5 Hz, 2H), 7.03 (d, J=8.1 Hz, 1H), 7.19 (d, J=8.5 Hz, 2H), 7.27 (m, 1H), 7.40 (m, 1H), 7.95 (d, J=8.8 Hz, 1H), 8.89 (s, 1H), 9.02 (d, J=8.8 Hz, 1H), 9.75 (bs, 1H), 11.79 (bs, 1H); MS (ESI+) m/z 461 (M+H)+.

Example 115

N-{4-[2-(7-Isopropyl-pyrido[2,3-d]pyrimidin-4-ylamino)-4-methyl-phenylsulfanyl]-phenyl}-acetamide The product from Example 7b was reacted with the product from Example 36E using the procedure from Example 36I substituting the product from Example 7b for the product from Example 36H to provide the crude residue which was purified by HPLC with TFA to provide the title compound as a trifluoroacetic acid salt. 1H NMR (300 MHz, DMSO-D6) δ ppm: 1.35 (d, J=6.99 Hz, 6H), 2.02 (s, 3H), 2.33 (s, 3H), 3.28 (t, J=6.89 Hz, 1H), 7.18 (s, 1H), 7.20 (d, J=8.46 Hz, 2H), 7.28 (s, 1H), 7.46 (d, J=8.46 Hz, 2H), 7.86 (d, J=8.46 Hz, 1H,) 8.79 (s, 1H), 8.93 (d, J=8.82 Hz, 1H), 9.99 (s, 1H), 11.46 (s, 1H); MS (ESI+) m/z 444 (M+H)+.

Example 116

(7-Isopropyl-pyrido[2,3-d]pyrimidin-4-yl)-[2-(4-methoxy-phenoxy)-5-methyl-phenyl]-amine Example 116A 1-(4-Methoxy-phenoxy)-4-methyl-2-nitro-benzene 4-Methoxy-phenol was reacted with 1-fluoro-4-methyl-2-nitrobenzene according to the procedure from Example 122a substituting 4-methoxy-phenol for hydroquinone to provide the title compound.

Example 116B 2-(4-Methoxy-phenoxy)-5-methyl-phenylamine

The product from Example 116A was reduced according to the procedure of Example 104B substituting the product from Example 116A for the product from Example 104A to provide the title compound.

Example 116C (7-Isopropyl-pyrido[2,3-d]pyrimidin-4-yl)-[2-(4-methoxy-phenoxy)-5-methyl-phenyl]-amine The product from Example 116B was reacted with the product from Example 36E using the procedure from Example 36I substituting the product from Example 116B for the product from Example 36H to provide the crude residue which was purified by HPLC with TFA to provide the title compound as a trifluoroacetic acid salt. 1H NMR (300 MHz, DMSO-D6) δ ppm: 1.33 (d, J=6.99 Hz, 6H), 2.33 (s, 3H), 3.26 (dt, J=13.74, 6.85 Hz, 1H), 3.67 (s, 3H), 6.77-6.96 (m, 5H), 7.18 (dd, J=8.46, 2.21 Hz, 1H), 7.33 (d, J=1.84 Hz, 1H), 7.83 (d, J=8.46 Hz, 1H), 8.84 (s, 1H), 8.91 (d, J=8.82 Hz, 1H), 11.33 (s, 1H); MS (ESI)+ m/z 401 (M+H)+.

Example 117

4-[2-(7-Isopropyl-pyrido[2,3-d]pyrimidin-4-ylamino)-4-methyl-phenoxy]-phenol

The product from Example 122b was reacted with the product from Example 36E using the procedure from Example 36I substituting the product from Example 122b for the product from Example 36H to provide the crude residue which was purified by HPLC with TFA to provide the title compound as a trifluoroacetic acid salt. 1H NMR (300 MHz, DMSO-D6) δ ppm: 1.33 (d, J=6.99 Hz, 6H), 2.32 (s, 3H), 3.27 (t, J=6.89 Hz, 1H), 6.67 (m, 2H), 6.75-6.85 (m, 3H), 7.16 (dd, J=8.46, 1.84 Hz, 1H), 7.31 (d, J=1.47 Hz, 1H), 7.84 (d, J=8.46 Hz, 1H), 8.85 (s, 1H), 8.94 (d, J=8.46 Hz, 1H), 9.28 (s, 1H); MS (ESI)+ m/z 387 (M+H)+.

Example 118

(7-Isopropyl-pyrido[2,3-d]pyrimidin-4-yl)-[2-(4-methoxy-phenylsulfanyl)-5-methyl-phenyl]-amine The product from Example 6a (5.0 g, 175 mmol) was reacted with 4-methoxy-benzenethiol (2.45 g, 175 mmol) for 18 h following the procedure from Example 6b giving 1-(4-methoxy-phenylsulfanyl)-4-methyl-2-nitro-benzen, which was reduced with SnCl$_2$ following the procedure from Example 5I giving 2-(4-Methoxy-phenylsulfanyl)-5-methyl-phenylamine.
2-(4-Methoxy-phenylsulfanyl)-5-methyl-phenylamine was reacted with the product from Example 36E using the procedure from Example 36I substituting 2-(4-methoxy-phenylsulfanyl)-5-methyl-phenylamine for the product from Example 36H to provide the crude residue which was purified by HPLC with TFA to provide the title compound as a trifluoroacetic acid salt. 1H NMR (300 MHz, DMSO-D6) δ ppm: 1.35 (d, J=6.62 Hz, 6H), 2.33 (s, 3H), 3.28 (t, J=6.89 Hz, 1H), 3.69 (s, 3H), 6.81 (d, J=9.19 Hz, 2H), 7.06-7.20 (m, 2H), 7.23 (d, J=8.82 Hz, 2H), 7.26 (s, 1H), 7.85 (d, J=8.46 Hz, 1H), 8.76 (s, 1H), 8.94 (d, J=8.46 Hz, 1H), 11.36 (s, 1H); MS (ESI)+ m/z 417 (M+H)+.

Example 119

(7-Cyclopropyl-pyrido[2,3-d]pyrimidin-4-yl)-(5-methyl-2-phenylsulfanyl-phenyl)-amine

Example 119A

N'-(3-Cyano-6-cyclopropyl-pyridin-2-yl)-N,N-dimethyl-formamidine

Cyclopropyl methyl ketone was reacted according to the procedures described in Examples 36A-36E to provide the title compound.

Example 119B (7-Cyclopropyl-pyrido[2,3-d]pyrimidin-4-yl)-(5-methyl-2-phenylsulfanyl-phenyl)-amine The product from Example 5I was reacted with the product from Example 119A using the procedure from Example 102 substituting the product from Example 5I for the product from Example 6c and substituting the product from Example 119A for the product from Example 10B to provide the crude residue which was purified by trituration with methanol to provide the title compound. 1H NMR (300 MHz, DMSO-D6) δ ppm: 1.05-1.19 (m, 4H), 2.22-2.41 (m, 1H), 2.35 (s, 3H), 7.05-7.31 (m, 7H), 7.37 (s, 1H), 7.58 (d, J=8.46 Hz, 1H), 8.50 (s, 1H), 8.65 (d, J=8.46 Hz, 1H), 10.21 (s, 1H); MS (ESI)+ m/z 385 (M+H)+.

Example 120

4-[2-(7-Cyclopropyl-pyrido[2,3-d]pyrimidin-4-ylamino)-4-methyl-phenylsulfanyl]-phenol The product from Example 6c was reacted with the product from Example 119A using the procedure from Example 102 substituting the product from Example 119A for the product from Example 10B to provide the crude residue which was purified by trituration with methanol to provide the title compound. 1H NMR (300 MHz, DMSO-D6) δ ppm: 1.05-1.22 (m, J=1.84 Hz, 4H), 2.24-2.39 (m, 1H), 2.29 (s, 3H), 6.73 (d, J=8.82 Hz, 2H), 6.91 (d, J=8.09 Hz, 1H), 7.04 (dd, J=8.09, 1.47 Hz, 1H), 7.17 (d, J=8.82 Hz, 2H), 7.25 (s, 1H), 7.57 (d, J=8.82 Hz, 1H), 8.49 (s, 1H), 8.71 (d, J=8.46 Hz, 1H), 9.74 (s, 1H), 9.92 (s, 1H); MS (ESI)+ m/z 401 (M+H)+.

Example 121

N-{4-[2-(7-Cyclopropyl-pyrido[2,3-d]pyrimidin-4-ylamino)-4-methyl-phenylsulfanyl]-phenyl}-acetamide The product from Example 7b was reacted with the product from Example 119A using the procedure from Example 102 substituting the product from Example 7b for the product from Example 6c and substituting the product from Example 119A for the product from Example 10B to provide the crude residue which was purified by trituration with methanol to provide the title compound. 1H NMR (300 MHz, DMSO-D6) δ ppm: 1.13 (d, J=6.25 Hz, 4H), 2.02 (s, 3H), 2.22-2.38 (m, 1H), 2.31 (s, 3H), 7.07 (s, 2H), 7.20 (d, J=8.82 Hz, 2H), 7.30 (s, 1H), 7.50 (d, J=8.82 Hz, 2H), 7.56 (d, J=8.46 Hz, 1H), 8.49 (s, 1H), 8.68 (d, J=8.82 Hz, 1H), 9.99 (s, 2H); MS (ESI+) m/z 442 (M+H)+.

Example 122

4-[2-(7-Cyclopropyl-pyrido[2,3-d]pyrimidin-4-ylamino)-4-methyl-phenoxy]-phenol

Example 122a 4-(4-methyl-2-nitrophenoxy)phenol

A solution of hydroquinone (3.2 g, 29.0 mmol) and $K_2CO_3$ (8.0 g, 54.0 mmol) in 40 mL of DMF was heated at 100° C. with 1-fluoro-4-methyl-2-nitrobenzene (3.0 g, 19.3 mmol) with stirring for 24 hours. Cooled to room temperature and diluted with EtOAc. Washed with water and dried the organic layer over $MgSO_4$. Filtered and concentrated under vacuum giving the title compound, which was purified by silica gel column chromatography eluting with 5% EtOAc/hexane giving an orange oil (1.89 g, 40%).

Example 122b 4-(2-amino-4-methylphenoxy)phenol

The product from Example 122a (1.89 g, 7.71 mmol) was reduced with $SnCl_2$ following the procedure from Example 5I giving the title compound as a white solid (1.42 g, 86%).

Example 122c 4-(2-(7-cyclopropylpyrido[2,3-d]pyrimidin-4-ylamino)-4-methylphenoxy)phenol The product from Example 122b was reacted with the product from Example 119A using the procedure from Example 102 substituting the product from Example 122b for the product from Example 6c and substituting the product from Example 119A for the product from Example 10B to provide the crude residue which was purified by trituration with methanol to provide the title compound. 1H NMR (300 MHz, DMSO-D6) δ ppm: 1.03-1.18 (m, J=6.25 Hz, 4H), 2.20-2.35 (m, 1H), 2.30 (s, 3H), 6.57-6.85 (m, 5H), 7.03 (dd, J=8.27, 1.65 Hz, 1H), 7.36 (d, J=1.84 Hz, 1H), 7.52 (d, J=8.46 Hz, 1H), 8.50 (s, 1H), 8.65 (d, J=8.46 Hz, 1H), 9.18 (s, 1H), 9.70 (s, 1H); MS (ESI)+ m/z 385 (M+H)+.

Example 123

(7-Cyclopropyl-pyrido[2,3-d]pyrimidin-4-yl)-[2-(4-methoxy-phenoxy)-5-methyl-phenyl]-amine The product from Example 116B was reacted with the product from Example 119A using the procedure from Example 102 substituting the product from Example 116B for the product from Example 6c and substituting the product from Example 119A for the product from Example 10B to provide the crude residue which was purified by trituration with methanol to provide the title compound. 1H NMR (300 MHz, DMSO-D6) δ ppm: 1.02-1.20 (m, J=6.25 Hz, 4H), 2.21-2.37 (m, 1H), 2.31 (s, 3H), 3.66 (s, 3H), 6.75-6.92 (m, 5H), 7.06 (dd, J=8.64, 0.92 Hz, 1H), 7.37 (s, 1H), 7.51 (d, J=8.46 Hz, 1H), 8.49 (s, 1H), 8.63 (d, J=8.82 Hz, 1H), 9.74 (s, 1H); MS (ESI)+ m/z 399 (M+H)+.

Example 124

(7-Cyclopropyl-pyrido[2,3-d]pyrimidin-4-yl)-[2-(4-fluoro-phenylsulfanyl)-5-methyl-phenyl]-amine The product from Example 6a (5.00 g, 17.53 mmol) was reacted with 4-fluorothiophenol (2.24 g, 17.53 mmol) in place of thiophenol following the procedure from Example 5H for 18 h giving 1-(4-Fluoro-phenylsulfanyl)-4-methyl-2-nitrobenzene which was purified by silica gel column chromatography eluting with 5% EtOAc/hexane providing a solid (3.39 g, 74%). 1-(4-Fluoro-phenylsulfanyl)-4-methyl-2-nitro-benzene was reduced with $SnCl_2$ following the procedure from Example 5I giving 2-(4-Fluoro-phenylsulfanyl)-5-methylphenylamine.

2-(4-Fluoro-phenylsulfanyl)-5-methyl-phenylamine was reacted with the product from Example 119A using the procedure from Example 102 substituting 2-(4-Fluoro-phenylsulfanyl)-5-methyl-phenylamine for the product from Example 6c and substituting the product from Example 119A for the product from Example 10B to provide the crude residue which was purified by trituration with methanol to provide the title compound. 1H NMR (300 MHz, DMSO-D6) δ ppm: 0.96-1.19 (m, J=6.25 Hz, 4H), 2.22-2.42 (m, 1H), 2.33 (s, 3H), 7.02-7.28 (m, 6H), 7.33 (s, 1H), 7.56 (d, J=8.46 Hz, 1H), 8.46 (s, 1H), 8.66 (d, J=8.09 Hz, 1H), 10.03 (s, 1H); MS (ESI)+ m/z 403 (M+H)+.

Example 125

(7-Cyclopropyl-pyrido[2,3-d]pyrimidin-4-yl)-[2-(4-methoxy-phenylsulfanyl)-5-methyl-phenyl]-amine 2-(4-Methoxy-phenylsulfanyl)-5-methyl-phenylamine (Example 118) was reacted with the product from Example 119A using the procedure from Example 102 substituting 2-(4-Methoxy-phenylsulfanyl)-5-methyl-phenylamine for the product from Example 6c and substituting the product from Example 119A for the product from Example 10B to provide the crude residue which was purified by trituration with methanol to provide the title compound. 1H NMR (300 MHz, DMSO-D6) δ ppm: 0.96-1.30 (m, J=5.52 Hz, 4H), 2.21-2.42 (m, 1H), 2.31 (s, 3H), 3.71 (s, 3H), 6.85 (d, J=8.82 Hz, 2H), 6.99-7.12 (m, 2H), 7.24 (d, J=8.82 Hz, 2H), 7.63 (d, J=8.46 Hz, 1H), 8.53 (s, 1H), 8.72 (d, J=8.46 Hz, 1H), 10.33 (s, 1H); MS (ESI)+ m/z 415 (M+H)+.

Example 126

[2-(4-Methoxy-phenoxy)-5-methyl-phenyl]-(7-methyl-pyrido[2,3-d]pyrimidin-4-yl)-amine The product from Example 116B was reacted with the product from Example 10C using the procedure from Example 104C substituting the product from Example 116B for the product from Example 104B to provide the crude residue which was purified by HPLC with TFA to provide the title compound as a trifluoroacetic acid salt. 1H NMR (300 MHz, DMSO-D6) δ ppm: 2.33 (s, 3H), 2.72 (s, 3H), 3.68 (s, 3H), 6.80-6.95 (m, 5H), 7.18 (dd, J=8.46, 2.21 Hz, 1H), 7.34 (d, J=1.84 Hz, 1H), 7.76 (d, J=8.46 Hz, 1H), 8.85 (s, 2H), 11.32 (s, 1H).

Example 127

4-[2-(7-tert-Butyl-pyrido[2,3-d]pyrimidin-4-ylamino)-4-methyl-phenylsulfanyl]-phenol

Example 127A

N'-(6-tert-Butyl-3-cyano-pyridin-2-yl)-N,N-dimethyl-formamidine 3,3-Dimethyl-2-butanone was reacted according to the procedures described in Examples 36A-36E to provide the title compound.

Example 127B

4-[2-(7-tert-Butyl-pyrido[2,3-d]pyrimidin-4-ylamino)-4-methyl-phenylsulfanyl]-phenol The product from Example 6c was reacted with the product from Example 127A using the procedure from Example 36I substituting the product from Example 6c for the product from Example 36H and substituting the product from Example 127A for the product from 276E to provide the crude residue which was purified by HPLC with TFA to provide the title compound as a trifluoroacetic acid salt (40 mg, 29%). 1H NMR (300 MHz, DMSO-D6) δ ppm: 1.44 (s, 9H), 2.31 (s, 3H), 6.71 (d, J=8.5 Hz, 2H), 7.00 (d, J=8.1 Hz, 1H), 7.16 (m, 1H), 7.18 (d, J=8.8 Hz, 2H), 7.23 (s, 1H), 8.01 d, J=7.6 Hz, 1H), 8.75 (s, 1H), 8.97 (d, J=8.8 Hz, 1H), 9.79 (s, 1H), 11.22 (bs, 1H); MS (ESI)+ m/z 417 (M+H)+.

Example 128

(5-Methyl-2-phenylsulfanyl-phenyl)-(7-propyl-pyrido[2,3-d]pyrimidin-4-yl)-amine The product was prepared using the procedure from Example 36A substituting 2-pentanone for methyl isopropyl ketone to give the intermediate that was then reacted according to the sequential procedures from Examples 36A-36E.

Example 128A

N'-(3-Cyano-6-propyl-pyridin-2-yl)-N,N-dimethyl-formamidine

The product was prepared using the procedure from Example 36A substituting 2-pentanone for methyl isopropyl ketone to give the intermediate that was then reacted according to the sequential procedures from Examples 36A-36E.

Example 128B

(5-Methyl-2-phenylsulfanyl-phenyl)-(7-propyl-pyrido[2,3-d]pyrimidin-4-yl)-amine The product from Example 5I (49 mg 0.231 mmol) and the product from Example 128A (50 mg, 0.231 mmol) were dissolved in acetic acid (1 mL) and heated to 130° C. for 1.5 hours. After cooling to room temperature a solid in the acetic acid solvent appeared which was collected by filtration to provide the title compound as an acetic acid salt (68 mg, 62%). 1H NMR (300 MHz, DMSO-D6) δ ppm: 0.94 (t, J=7.4 Hz, 3H), 1.79 (m, 2H), 1.88 (s, 6H), 2.35 (s, 3H), 2.88 (t, J=7.6 Hz, 2H), 7.18 (m, 5H), 7.23 (m, 2H), 7.37 (s, 1H), 7.51 (d, J=8.1 Hz, 1H), 8.48 (s, 1H), 8.69 (d, J=8.5 Hz, 1H); MS (ESI)+ m/z 387 (M+H)+.

Example 129

3-[4-Methyl-2-(7-propyl-pyrido[2,3-d]pyrimidin-4-ylamino)-phenylsulfanyl]-phenol The product from Example 6a (10.14 g, 35.6 mmol) was reacted with 3-(4-methyl-2-nitro-phenylsulfanyl)-phenol (4.48 g, 35.6 mmol) for 18 h following the procedure from Example 6b giving 3-(4-Methyl-2-nitro-phenylsulfanyl)-phenol (7.88 g, 85%), which was reduced with SnCl₂ following the procedure from Example 5I giving 3-(2-amino-4-methyl-phenylsulfanyl)-phenol.

3-(2-amino-4-methyl-phenylsulfanyl)-phenol (49 mg 0.231 mmol) and the product from Example 128A (50 mg, 0.231 mmol) were dissolved in acetic acid (1 mL) and heated to 130° C. for 1.5 hours. After cooling to room temperature a solid in the acetic acid solvent appeared which was collected by filtration to provide the title compound as an acetic acid salt (78 mg, 68%). 1H NMR (300 MHz, DMSO-D6) δ ppm: 0.95 (t, J=7.3 Hz, 3H), 1.79 (m, 2H), 1.88 (s, 6H), 2.40 (s, 3H), 2.88 (t, J=7.6 Hz, 2H), 6.57 (m, 3H), 7.00 (t, J=7.7 Hz, 1H), 7.13 (m, 1H), 7.26 (d, J=7.7 Hz, 1H), 7.38 (s, 1H), 7.51 (d, J=8.5 Hz, 1H), 8.50 (s, 1H), 8.70 (d, J=8.5 Hz, 1H); MS (ESI)+ m/z 403 (M+H)+.

Example 130

N-{4-[4-Methyl-2-(7-propyl-pyrido[2,3-d]pyrimidin-4-ylamino)-phenylsulfanyl]-phenyl}-acetamide The product from Example 7b (49 mg 0.231 mmol) and the product from Example 128A (50 mg, 0.231 mmol) were dissolved in acetic acid (1 mL) and heated to 130° C. for 1.5 hours. After cooling to room temperature and removal of the acetic acid solvent under vacuum methanol (3 mL) was added to the oil which caused a solid to form which was triturated with methanol to provide the title compound 80 mg, 78%). 1H NMR (300 MHz, DMSO-D6) δ ppm: 0.95 (t, J=7.4 Hz, 3H), 1.89 (m, 2H), 2.02 (s, 3H), 2.32 (s, 3H), 2.89 (t, J=7.5 Hz, 2H), 7.06 (s, 2H), 7.21 (t, J=8.5 Hz, 2H), 7.30 (s, 1H), 7.50 (d, J=8.8 Hz, 2H), 7.52 (m, 1H), 8.52 (s, 1H), 8.74 (d, J=7.7 Hz, 1H), 10.00 (s, 1H); MS (ESI)+ m/z 444 (M+H)+.

Example 131

4-[4-Methyl-2-(7-propyl-pyrido[2,3-d]pyrimidin-4-ylamino)-phenylsulfanyl]-phenol The product from Example 6c (49 mg 0.231 mmol) and the product from Example 128A (50 mg, 0.231 mmol) were dissolved in acetic acid (1 mL) and heated to 130° C. for 1.5 hours. After cooling to room temperature a solid in the acetic acid solvent appeared which was collected by filtration to provide the title compound as an acetic acid salt (77 mg, 68%). 1H NMR (300 MHz, DMSO-D6) δ ppm: 0.96 (t, J=7.4 Hz, 3H), 1.80 (m, 2H), 1.88 (s, 6H), 2.40 (s, 3H), 2.90 (t, J=7.6 Hz, 2H), 6.74 (d, J=8.5 Hz, 2H), 6.90 (d, J=8.1 Hz, 1H), 7.03 (m, 1H), 7.18 (d, J=8.8 Hz, 2H), 7.22 (s, 1H), 7.54 (d, J=8.1 Hz, 1H), 8.53 (s, 1H), 8.78 (d, J=8.5 Hz, 1H); MS (ESI)+ m/z 403 (M+H)+.

Example 132

N-{4-[5-Hydroxy-2-(7-isopropyl-pyrido[2,3-d]pyrimidin-4-ylamino)-4-methyl-phenylsulfanyl]-phenyl}-acetamide A mixture of 2-methyl-4-nitro-5-chloro phenol (1.5 g, 8.0 mmol), 4-Acetamido thiophenol (1.6 g, 8.8 mmol) and cesium carbonate (5.74 g, 17.6 mmol) in DMF (10 mL) was heated 2.5 h at 100° C. The mixture was cooled, diluted with ethyl acetate (100 mL) and the organic layer was washed with water and aqueous 10% sodium chloride solution, then, dried over anhydrous sodium sulfate. The drying agent was filtered and the solvent removed under vacuum leaving N-[4-(5-Hydroxy-4-methyl-2-nitro-phenylsulfanyl)-phenyl]-acetamide as a solid (2.5 g, 81%). A solution of N-[4-(5-Hydroxy-4-methyl-2-nitro-phenylsulfanyl)-phenyl]-acetamide (2.5 g, 6.45 mmol), iron powder (1.79 g, 32 mmol) and ammonium chloride (0.514 g, 9.6 mmol) in a methanol (10 mL), tetrahydrofuran (10 mL), and water (5 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide N-[4-(2-Amino-5-hydroxy-4-methyl-phenylsulfanyl)-phenyl]-acetamide (1.7 g, 91%).

N-[4-(2-Amino-5-hydroxy-4-methyl-phenylsulfanyl)-phenyl]-acetamide was reacted with the product from Example 36E using the procedure from Example 36I substituting N-[4-(2-amino-5-hydroxy-4-methyl-phenylsulfanyl)-phenyl]-acetamide for the product from Example 36H to provide the crude residue which was purified by HPLC with TFA to provide the title compound as a trifluoroacetic acid salt. 1H NMR (300 MHz, DMSO-D6) δ ppm: 1.34 (d, J=6.99 Hz, 6H), 2.03 (s, 3H), 2.11 (s, 3H), 3.27 (s, 1H), 6.63 (s, 1H), 7.12 (s, 1H), 7.25 (d, J=8.82 Hz, 2H), 7.51 (d, J=8.82 Hz, 2H), 7.85 (d, J=8.46 Hz, 1H), 8.80 (s, 1H), 8.94 (d, J=8.46 Hz, 1H), 9.75 (s, 1H), 10.02 (s, 1H), 11.36 (s, 1H); MS (ESI)+ m/z 460 (M+H)+.

Example 133

$N^1$-(4-Benzyloxy-phenyl)-$N^2$-(7-isopropyl-pyrido[2,3-d]pyrimidin-4-yl)-4,$N^1$-dimethyl-benzene-1,2-diamine Example 133A (4-Benzyloxy-phenyl)-(4-methyl-2-nitro-phenyl)-amine A mixture of 4-methyl-2-nitroaniline (1.006 g, 6.612 mmol), 4-benzyloxybromobenzene (5.794 g, 22.02 mmol), cuprous iodide (62.9 mg, 0.3306 mmol), potassium carbonate (0.914 g, 6.612 mmol) and anhydrous o-xylene (18 mL) was heated at 150° for 24 hours. Added additional cuprous iodide (30 mg) and heated an additional 6 hours at 160°. The reaction was cooled to room temperature and the solvent removed by rotary evaporation under vacuum. The residue was purified by silica gel flash chromatography using 1:1 methylene chloride/hexanes as eluent to afford the title compound as a red oil which slowly crystallized (1.23 g, 56%).

Example 133B (4-Benzyloxy-phenyl)-methyl-(4-methyl-2-nitro-phenyl)-amine

A solution of the product from Example 133A (229.4 mg, 0.6861 mmol) in anhydrous N,N-dimethylformamide (3 mL) was added to a suspension of sodium hydride (60% dispersion in mineral oil, 55 mg, 1.372 mmol) in N,N-dimethylformamide (3 mL) at room temperature under a nitrogen atmosphere. The reaction was stirred at room temperature for 1 hour, then added methyl iodide (0.171 mL, 2.744 mmol) and let stir at room temperature for 2 hours. The solvent was removed by rotary evaporation under vacuum. The residue was taken up in water (30 mL) and extracted with methylene chloride (50 mL). The organic phase was washed with water (30 mL), dried over anhydrous magnesium sulfate, filtered, and concentrated by rotary evaporation under vacuum to afford the title compound as a maroon-colored solid (239 mg, 100%).

Example 133C (4-Benzyloxy-phenyl)-methyl-(4-methyl-2-amino-phenyl)-amine

A mixture of the product from Example 133B (129.4 mg, 0.3714 mmol), iron powder (128 mg, 2.284 mmol), ammonium chloride (130 mg, 2.433 mmol) in water (1 mL) and ethanol (2 mL) was heated at 70° under a nitrogen atmosphere for 1 hour. The reaction was cooled to room temperature and vacuum filtered, washing the residue with methanol. The filtrate was concentrated under vacuum and azeotroped with toluene (50 mL). The residue was purified by silica gel flash chromatography using methylene chloride as eluent to provide the title compound as a waxy solid (85 mg, 72%).

Example 133D $N^1$-(4-Benzyloxy-phenyl)-$N^2$-(7-isopropyl-pyrido[2,3-d]pyrimidin-4-yl)-4,$N^1$-dimethyl-benzene-1,2-diamine A solution of the product from Example 36E (28 mg, 0.1297 mmol) and the product from Example 133C (41.3 mg, 0.1297 mmol) in acetic acid (1 mL) was stirred in an oil bath preheated to 140° C. for 1 hour. The reaction was cooled to room temperature, diluted with hexanes (50 mL), concentrated by rotary evaporation under vacuum, and co-evaporated with methylene chloride/hexanes (4×). The residue was dried, then purified by silica gel flash chromatography using 20% ethyl acetate/methylene chloride as eluent to afford the title compound as a yellow solid (35 mg, 55%). $^1$H NMR (300 MHz, DMSO-D6) δ ppm: 1.27 (d, J=6.62 Hz, 6H), 2.34 (s, 3H), 3.08 (s, 3H), 3.06-3.22 (m, 1H), 4.79 (s, 21H), 6.50 (d, J=9.19 Hz, 21H), 6.60 (d, J=8.82 Hz, 21H), 7.05-7.17 (m, 2H), 7.25-7.37 (m, 5H), 7.41 (d, J=8.46 Hz, 1H), 7.47 (s, 1H), 8.42 (d, J=8.46 Hz, 1H), 8.52 (s, 1H), 9.33 (s, 1H); MS (DCI/NH$_3$) m/z 490 (M+H)$^+$.

Example 134

(2-Benzyl-5-methyl-phenyl)-(7-isopropyl-pyrido[2,3-d]pyrimidin-4-yl)-amine

Example 134A

2-Benzyl-5-methyl-phenylamine

A solution of lithium aluminum hydride in tetrahydrofuran (1.0 M, 2.54 mL, 2.54 mmol) was added via syringe to a flask containing aluminum chloride (534 mg, 4.005 mmol) under a nitrogen atmosphere and cooled in a 0° bath. After letting the mixture cool for 5 minutes, a solution of 2-amino-4-methyl-benzophenone (200 mg, 0.9467 mmol) in tetrahydrofuran (4 mL) was added slowly dropwise at 0°. The reaction was then heated at 50° for 30 minutes. The reaction was cooled to room temperature and moist ethyl ether (5 mL) was added. The reaction was carefully poured into water (20 mL) and extracted with ethyl ether (2×50 mL). The combined ethereal extracts were washed with brine (20 mL), dried over anhydrous sodium sulfate, filtered, and concentrated by rotary evaporation under vacuum. Purification by silica gel flash chromatography using 40:60 hexanes/methylene chloride as eluent provided the title compound as an oil (94 mg, 50%).

Example 134B (2-Benzyl-5-methyl-phenyl)-(7-isopropyl-pyrido[2,3-d]pyrimidin-4-yl)-amine A solution of the product from Example 36E (34.6 mg, 0.160 mmol) and the product from Example 134A (31.6 mg, 0.160 mmol) in acetic acid (1 mL) was stirred in an oil bath preheated to 140° C. for 1 hour. The reaction was cooled to room temperature, diluted with hexanes (50 mL), concentrated by rotary evaporation under vacuum, and co-evaporated with methylene chloride/hexanes (4×). The residue was dried, then purified by silica gel flash chromatography using 2% methanol/methylene chloride as eluent to provide the title compound as a light yellow solid (50 mg, 85%). $^1$H NMR (300 MHz, DMSO-D6) δ ppm: 1.32 (d, J=6.99 Hz, 6H) 2.30 (s, 3H) 3.12-3.28 (m, 1H) 3.87 (s, 2H) 6.95-7.20 (m, 8H) 7.57 (s, 1H) 8.47 (s, 1H) 8.74 (d, J=8.46 Hz, 1H) 9.81 (s, 1H); MS (DCI/NH$_3$) m/z 369 (M+H)$^+$.

Example 135

(7-Cyclohexyl-pyrido[2,3-d]pyrimidin-4-yl)-(5-methyl-2-phenylsulfanyl-phenyl)-amine

Example 135A

N'-(3-Cyano-6-cyclohexyl-pyridin-2-yl)-N,N-dimethyl-formamidine

1-Cyclohexyl-ethanone was reacted according to the procedures described in Examples 36A-36E to provide the title compound.

Example 135B (7-Cyclohexyl-pyrido[2,3-d]pyrimidin-4-yl)-(5-methyl-2-phenylsulfanyl-phenyl)-amine To a solution of the product from Example 135A (56.0 mg, 0.2322 mmol) in acetic acid (4 mL) was added the product from Example 5I (50.0 mg, 0.2322 mmol) and the mixture stirred in an oil bath preheated to 130° C. for 15 minutes. The mixture was then cooled to room temperature, the acetic acid removed under vacuum, and the resultant residue purified by HPLC with TFA to provide the title compound as a trifluoroacetic acid salt (20 mg, 20%). 1H NMR (300 MHz, DMSO-D6) δ ppm: 1.38-1.51 (m, 2H), 1.57-1.69 (m, 2H), 1.70-1.80 (m, 2H), 1.80-1.99 (m, 6H), 2.33-2.40 (m, 3H), 7.12-7.17 (m, 1H), 7.12-7.26 (m, 3H), 7.30-7.33 (m, 1H), 7.33-7.38 (m, 2H), 8.68-8.75 (m, 1H), 8.82-8.90 (m, 1H); MS (DCI/NH3) m/z 427 (M+H)+.

Example 136

4-[2-(7-Cyclohexyl-pyrido[2,3-d]pyrimidin-4-ylamino)-4-methyl-phenylsulfanyl]-phenol The product from Example 135A was reacted with the product from Example 6c according to the procedure from Example 135B substituting the product from Example 6c for the product from Example 5I to provide the title compound as a trifluoroacetic acid salt (20 mg, 20%). 1H NMR (300 MHz, DMSO-D6) δ ppm: 1.38-1.52 (m, 2H), 1.55-1.80 (m, 3H), 1.80-1.91 (m, 2H), 1.91-2.03 (m, 3H), 2.30 (s, 3H), 3.26-3.47 (m, 1H), 6.66-6.74 (m, 2H), 6.74-6.81 (m, 1H), 6.96-7.03 (m, 1H), 7.10-7.14 (m, 1H), 7.14-7.21 (m, 3H), 7.21-7.26 (m, 1H), 8.72-8.80 (m, 1H), 8.90-8.97 (m, 1H), 9.78 (s, 1H); MS (DCI/NH3) m/z 443 (M+H)+.

Example 137

N-{4-[2-(7-Cyclohexyl-pyrido[2,3-d]pyrimidin-4-ylamino)-4-methyl-phenylsulfanyl]-phenyl}-acetamide The product from Example 135A was reacted with the product from Example 7b according to the procedure from Example 135B substituting the product from Example 7b for the product from Example 5I to provide the title compound as a trifluoroacetic acid salt (21 mg, 25%). 1H NMR (300 MHz, DMSO-D6) δ ppm: 1.28-1.52 (m, 3H), 1.53-1.79 (m, 3H), 1.79-1.97 (m, 4H), 2.02 (s, 3H), 2.32 (s, 3H), 2.79-2.94 (m, 1H), 7.03-7.12 (m, 1H), 7.20 (d, J=8.46 Hz, 2H), 7.31 (s, 1H), 7.50 (d, J=8.82 Hz, 2H), 7.56 (d, J=8.46 Hz, 1H), 8.54 (s, 1H), 8.76 (d, J=8.82 Hz, 1H), 9.99 (s, 2H); MS (DCI/NH3) m/z 484 (M+H)+.

Example 138

N-{4-[2-(7-Cyclobutyl-pyrido[2,3-d]pyrimidin-4-ylamino)-4-methyl-phenylsulfanyl]-phenyl}-acetamide

Example 138A

N'-(3-Cyano-6-cyclobutyl-pyridin-2-yl)-N,N-dimethyl-formamidine

1-Cyclobutyl-ethanone was reacted according to the procedures described in Examples 36A-36E to provide the title compound.

Example 138B

N-{4-[2-(7-Cyclobutyl-pyrido[2,3-d]pyrimidin-4-ylamino)-4-methyl-phenylsulfanyl]-phenyl}-acetamide The product from Example 138A was reacted with the product from Example 7b according to the procedure from Example 135B substituting the product from Example 7b for the product from Example 5I and substituting the product from Example 138A for the product from Example 135A to provide the title compound as a trifluoroacetic acid salt (30 mg, 36% yield). 1H NMR (500 MHz, DMSO-D6) δ ppm: 0.86 (t, J=7.02 Hz, 1H), 1.86-1.98 (m, 1H), 2.02 (s, 3H), 2.06-2.18 (m, 1H), 2.34 (s, 3H), 2.37-2.47 (m, 4H), 3.80-4.02 (m, 1H), 7.13-7.25 (m, 4H), 7.29 (s, 1H), 7.45 (d, J=8.54 Hz, 2H), 7.78 (d, J=8.54 Hz, 1H), 8.80 (s, 1H), 8.92 (d, J=8.54 Hz, 1H), 9.98 (s, 1H); MS (DCI/NH$_4$) m/z 456 (M+H)+.

Example 139

4-[2-(7-Cyclobutyl-pyrido[2,3-d]pyrimidin-4-ylamino)-4-methyl-phenylsulfanyl]-phenol The product from Example 138A was reacted with the product from Example 6c according to the procedure from Example 135B substituting the product from Example 6c for the product from Example 5I and substituting the product from Example 138A for the product from Example 135A to provide the title compound as a trifluoroacetic acid salt (30 mg, 33%). 1H NMR (300 MHz, DMSO-D6) δ ppm: 1.85-2.01 (m, 1H), 2.03-2.24 (m, 1H), 2.31 (s, 3H), 2.36-2.46 (m, 4H), 3.81-4.13 (m, 2H), 6.70 (d, J=8.46 Hz, 2H), 7.02 (d, J=8.09 Hz, 1H), 7.17 (d, J=8.46 Hz, 3H), 7.24 (s, 1H), 7.82 (d, J=8.46 Hz, 1H), 8.82 (s, 1H), 8.97 (d, J=8.46 Hz, 1H), 9.72-9.93 (m, 1H); MS (DCI/NH$_4$) m/z 415 (M+H)+.

Example 140

(7-sec-Butyl-pyrido[2,3-d]pyrimidin-4-yl)-(5-methyl-2-phenylsulfanyl-phenyl)-amine Example 140A N'-(6-sec-Butyl-3-cyano-pyridin-2-yl)-N,N-dimethyl-formamidine 3-Methyl-pentan-2-one was reacted according to the procedures described in Examples 36A-36E to provide the title compound.

Example 140B (7-sec-Butyl-pyrido[2,3-d]pyrimidin-4-yl)-(5-methyl-2-phenylsulfanyl-phenyl)-amine The product from Example 140A was reacted with the product from Example 5I according to the procedure from Example 135B substituting the product from Example 140A for the product from Example 135A to provide the title compound as a trifluoroacetic acid salt. 1H NMR (300 MHz, DMSO-D6) δ ppm: 0.83 (t, J=7.35 Hz, 3H), 1.32 (d, J=6.99 Hz, 3H), 1.59-1.75 (m, 1H), 1.75-1.95 (m, 1H), 2.37 (s, 3H), 2.95-3.12 (m, 2H), 7.11-7.22 (m, 5H), 7.25 (d, J=6.62 Hz, 1H), 7.31-7.46 (m, 2H), 7.81 (d, J=8.82 Hz, 1H), 8.76 (s, 1H), 8.91 (d, J=8.46 Hz, 1H); MS (DCI/NH$_4$) M/Z 401 (M+H)+.

Example 141

N-{4-[2-(7-sec-Butyl-pyrido[2,3-d]pyrimidin-4-ylamino)-4-methyl-phenylsulfanyl]-phenyl}-acetamide The product from Example 140A was reacted with the product from Example 7b according to the procedure from Example 135B substituting the product from Example 7b for the product from Example 5I and substituting the product from Example 140A for the product from Example 135A to provide the title compound as a trifluoroacetic acid salt (37 mg, 45%). 1H NMR (500 MHz, DMSO-D6) δ ppm: 0.84 (t, J=7.32 Hz, 3H), 1.33 (d, J=6.71 Hz, 3H), 1.62-1.76 (m, 1H), 1.77-1.91 (m, 1H), 2.34 (s, 3H), 2.49 (s, 3H), 2.96-3.14 (m, 1H), 7.11-7.25 (m, 4H), 7.28 (s, 1H), 7.46 (d, J=9.16 Hz, 2H), 7.83 (d, J=8.54 Hz, 1H), 8.79 (s, 1H), 8.94 (d, J=7.93 Hz, 1H), 9.97 (s, 1H), 11.31-11.69 (m, 1H); MS (DCI/NH$_4$) m/z 458 (M+H)+.

Example 142

N-(4-{4-Methyl-2-[7-(1-methyl-cyclopropyl)-pyrido[2,3-d]pyrimidin-4-ylamino]-phenylsulfanyl}-phenyl)-acetamide Example 142A N'-[3-Cyano-6-(1-methyl-cyclopropyl)-pyridin-2-yl]-N,N-dimethyl-formamidine 1-(1-Methyl-cyclopropyl)-ethanone was reacted according to the procedures described in Examples 36A-36E to provide the title compound.

Example 142B

N-(4-{4-Methyl-2-[7-(1-methyl-cyclopropyl)-pyrido[2,3-d]pyrimidin-4-ylamino]-phenylsulfanyl}-phenyl)-acetamide The product from Example 142A was reacted with the product from Example 7b according to the procedure from Example 135B substituting the product from Example 7b for the product from Example 5I and substituting the product from Example 142A for the product from Example 135A to provide the title compound as a trifluoroacetic acid salt (30 mg, 50%). 1H NMR (300 MHz, DMSO-D6) δ ppm: 0.79-0.91 (m, 1H), 1.08-1.19 (m, 2H), 1.19-1.30 (m, 1H), 1.37-1.50 (m, 2H), 1.61 (s, 3H), 2.02 (s, 1H), 2.33 (s, 3H), 7.10-7.24 (m, 4H), 7.28 (s, 1H), 7.45 (d, J=8.82 Hz, 2H), 7.85 (d, J=8.46 Hz, 1H), 8.78 (s, 1H), 8.89 (d, J=9.19 Hz, 1H), 9.99 (s, 1H); MS (DCI/NH$_4$) m/z 456 (M+H)+.

Example 143

4-{4-Methyl-2-[7-(1-methyl-cyclopropyl)-pyrido[2,3-d]pyrimidin-4-ylamino]-phenylsulfanyl}-phenol The product from Example 142A was reacted with the product from Example 6c according to the procedure from Example 135B substituting the product from Example 6c for the product from Example 5I and substituting the product from Example 142A for the product from Example 135A to provide the title compound as a trifluoroacetic acid salt (20 mg, 37%). 1H NMR (300 MHz, DMSO-D6) δ ppm: 0.77-0.91 (m, 1H), 1.07-1.18 (m, 2H), 1.38-1.52 (m, 2H), 1.61 (s, 3H), 2.31 (s, 3H), 6.70 (d, J=8.46 Hz, 2H), 7.02 (d, J=8.09 Hz, 1H), 7.10-7.21 (m, J=8.46 Hz, 3H), 7.23 (s, 1H), 7.86 (d, J=8.82 Hz, 1H), 8.78 (s, 1H), 8.93 (d, J=8.82 Hz, 1H), 9.82 (s, 1H); MS (DCI/NH$_4$) m/z 415 (M+H)+.

Example 144

3-{4-Methyl-2-[7-(1-methyl-cyclopropyl)-pyrido[2,3-d]pyrimidin-4-ylamino]-phenylsulfanyl}-phenol The product from Example 142A was reacted with 3-(2-amino-4-methyl-phenylsulfanyl)-phenol (Example 129) according to the procedure from Example 135B substituting 3-(2-amino-4-methyl-phenylsulfanyl)-phenol for the product from Example 5I and substituting the product from Example 142A for the product from Example 135A to provide the title compound as a trifluoroacetic acid salt (20 mg, 37%). 1H NMR (300 MHz, DMSO-D6) δ ppm: 0.77-0.92 (m, 1H), 1.35-1.48 (m, 2H), 1.60 (s, 3H), 2.36 (s, 3H), 6.41-6.68 (m, 3H), 6.90-7.05 (m, 1H), 7.23 (d, J=6.62 Hz, 1H), 7.29-7.42 (m, 2H), 7.77 (d, J=9.56 Hz, 1H), 8.68 (s, 1H), 8.82 (d, J=7.72 Hz, 1H), 9.52 (s, 1H); MS (DCI/NH$_4$) m/z 415 (M+H)+.

Example 145

(7-Ethyl-pyrido[2,3-d]pyrimidin-4-yl)-(5-methyl-2-phenylsulfanyl-phenyl)-amine

Example 145A

N'-(3-Cyano-6-ethyl-pyridin-2-yl)-N,N-dimethyl-formamidine

A solution of the product from Example 10B (0.942 g, 5.0 mmol) in anhydrous tetrahydrofuran (50 mL) was cooled to −78° C. under a nitrogen atmosphere. To this solution was added slowly dropwise a solution of lithium diisopropylamide (3.0 mL of a 2.0 M solution in toluene/hexane/heptane, 6.0 mmol, 1.2 eq). After the addition was complete the reaction mixture was stirred at −78° C. for 1 h, and then methyl iodide (1.42 g, 10.0 mmol, 2.0 eq) was added dropwise. The reaction mixture was stirred for an additional 1.5 h at −78° C., during which time all solids dissolved. The reaction flask was then removed from the cooling bath and saturated aqueous ammonium chloride (25 mL) and water (25 mL) was added. The reaction mixture was extracted with ethyl acetate (3×100 mL) and the combined organic layers were washed with brine, dried over anhydrous magnesium sulfate, filtered, and evaporated under vacuum. The residue was purified by chromatography on silica gel, eluting with a 3/2 hexane:ethyl acetate to provide the title compound (0.87 g, 86% yield).

Example 145B (7-Ethyl-pyrido[2,3-d]pyrimidin-4-yl)-(5-methyl-2-phenylsulfanyl-phenyl)-amine The product from Example 145A was reacted with the product from Example 5I according to the procedure from Example 135B substituting the product from Example 145A for the product from Example 135A to provide the title compound as a trifluoroacetic acid salt (20 mg, 33%). 1H NMR (500 MHz, DMSO-D6) δ ppm: 1.34 (t, J=7.93 Hz, 3H), 2.35 (s, 3H), 3.01 (q, J=7.93 Hz, 2H), 7.09-7.29 (m, 6H), 7.36 (s, 1H), 7.78 (d, J=8.54 Hz, 1H), 8.75 (s, 1H), 8.88 (d, J=8.54 Hz, 1H); MS (DCI/NH$_4$) m/z 373 (M+H)+.

Example 146

N-{4-[2-(7-Ethyl-pyrido[2,3-d]pyrimidin-4-ylamino)-4-methyl-phenylsulfanyl]-phenyl}-acetamide The product from Example 145A was reacted with the product from Example 7b according to the procedure from Example 135B substituting the product from Example 7b for the product from Example 5I and substituting the product from Example 145A for the product from Example 135A to provide the title compound as a trifluoroacetic acid salt (20 mg, 29%). 1H NMR (500 MHz, DMSO-D6) δ ppm: 1.34 (m, 3H), 2.37 (s, 3H), 3.01 (q, J=7.93 Hz, 2H), 7.12-7.28 (m, 5H), 7.35 (s, 1H), 7.36 (s, 1H), 7.78 (d, J=8.54 Hz, 1H), 8.75 (s, 1H), 8.88 (d, J=8.54 Hz, 1H); MS (DCI/NH$_4$) m/z 430 (M+H)+.

Example 147

4-[4-(6-Bromo-1H-benzoimidazol-2-yl)-2-(7-isopropyl-pyrido[2,3-d]pyrimidin-4-ylamino)-phenoxy]-phenol

Example 147A 4-(4-Benzyloxy-phenoxy)-3-nitro-benzaldehyde

A mixture of 4-chloro-3-nitrobenzaldehyde (1.00 g, 5.389 mmol), 4-(benzyloxy)phenol (1.187 g, 5.928 mmol), and potassium carbonate (0.744 g, 5.389 mmol) in anhydrous pyridine (10 mL) was heated at reflux under a nitrogen atmosphere for 30 minutes. The reaction was cooled to room temperature and the solvent removed by rotary evaporation under vacuum. The residue was taken up in ethyl acetate (100 mL) and washed with 1N aqueous hydrochloric acid (2×50 mL), water (50 mL), and brine (50 mL). The organic phase was dried over anhydrous sodium sulfate, filtered, and concentrated under vacuum. Purification by silica gel flash chromatography using methylene chloride as eluent provided the title compound as a yellow solid (1.625 g, 86%).

Example 147B

2-[4-(4-Benzyloxy-phenoxy)-3-nitro-phenyl]-6-bromo-1H-benzoimidazole

A solution of 4-bromo-1,2-benzenediamine (214 mg, 1.145 mmol) in N,N-dimethylformamide (12 mL) containing water (0.4 mL) was treated with the product of Example 147A (400 mg, 1.145 mmol) and OXONE (458 mg, 0.7443 mmol), and the reaction stirred at room temperature for 30 minutes. Water (40 mL) was then added and the reaction stirred for 10 minutes. The mixture was vacuum filtered and the solid washed with water, then dried under vacuum. Purification by silica gel chromatography using a gradient of 3% to 4% ethyl acetate/methylene chloride as eluent provided the title compound as a yellow solid (305 mg, 51%).

Example 147C 2-(4-Benzyloxy-phenoxy)-5-(6-bromo-1H-benzoimidazol-2-yl)-phenylamine The product of Example 147B (374 mg, 0.723 mmol), iron powder (248 mg, 4.45 mmol), and ammonium chloride (253 mg, 4.74 mmol) in water (5 mL) and ethanol (10 mL) were heated at 80° for 45 minutes. The reaction mixture was cooled to room temperature, diluted with ethyl acetate (100 mL), and washed with water (2×50 mL) and brine (50 mL). The organic phase was dried over anhydrous sodium sulfate, filtered, and concentrated by rotary evaporation under vacuum provided the title compound as a golden solid (327 mg, 93%).

Example 147D

[2-(4-Benzyloxy-phenoxy)-5-(6-bromo-1H-benzoimidazol-2-yl)-phenyl]-(7-isopropyl-pyrido[2,3-d]pyrimidin-4-yl)-amine A solution of the product from Example 36E (26.7 mg, 0.123 mmol) and the product of Example 147C (60 mg, 0.123 mmol) in acetic acid (2 mL) was stirred in an oil bath preheated to 140° C. for 30 minutes. The reaction was cooled to room temperature, diluted with hexanes (50 mL), concentrated by rotary evaporation under vacuum, and co-evaporated with methylene chloride/hexanes (4×). The residue was dried under vacuum, then purified by silica gel chromatography using 3% methanol/methylene chloride as eluent to provide the title compound as an off-white solid (59 mg, 73%).

Example 147E

4-[4-(6-Bromo-1H-benzoimidazol-2-yl)-2-(7-isopropyl-pyrido[2,3-d]pyrimidin-4-ylamino)-phenoxy]-phenol A solution of the product from Example 147D (38.8 mg, 0.059 mmol) and pentamethylbenzene (87 mg, 0.5901 mmol) in trifluoroacetic acid (5 mL) was stirred at room temperature for 2 hours. The solvent was removed by rotary evaporation under vacuum and co-evaporated with methylene chloride/ hexanes (2×). The resulting solid was triturated with hexanes (3×) and purified by HPLC with TFA to provide the title compound as a trifluoroacetic acid salt (22 mg, 47%). $^1$H NMR (300 MHz, DMSO-D6) δ ppm: 1.36 (d, J=6.99 Hz, 6H), 3.20-3.39 (m, 1H), 6.78 (d, J=8.82 Hz, 2H), 6.95 (d, J=9.19 Hz, 2H), 7.02 (d, J=8.82 Hz, 1H), 7.36 (dd, J=8.64, 2.02 Hz, 1H), 7.55 (d, J=8.46 Hz, 1H), 7.78 (d, J=1.47 Hz, 1H), 7.91 (d, J=8.82 Hz, 1H), 8.11 (dd, J=8.64, 2.02 Hz, 1H), 8.35 (d, J=1.84 Hz, 1H), 8.94 (s, 1H), 9.03 (d, J=8.82 Hz, 1H), 9.46 (br s, 1H), 11.63 (br s, 1H); MS (APCI+) m/z 567/569 (M+H)$^+$.

Example 148

4-[4-(6-Bromo-1H-benzoimidazol-2-yl)-2-(7-methyl-pyrido[2,3-d]pyrimidin-4-ylamino)-phenoxy]-phenol The product from Example 147C was reacted with the product from Example 10B using the procedure described in Example 147D substituting the product from Example 10B for the product from Example 36E to provide [2-(4-Benzyloxy-phenoxy)-5-(6-bromo-1H-benzoimidazol-2-yl)-phenyl]-(7-methyl-pyrido[2,3-d]pyrimidin-4-yl)-amine which was debenzylated according to the procedure described in Example 147E to provide the crude product which was purified by HPLC with TFA to provide the title compound as a trifluoroacetic acid salt. $^1$H NMR (300 MHz, DMSO-D6) δ ppm: 2.74 (s, 3H), 6.77 (d, J=9.19 Hz, 2H), 6.95 (d, J=8.82 Hz, 2H), 7.01 (d, J=8.82 Hz, 1H), 7.35 (dd, J=8.46, 1.84 Hz, 1H), 7.54 (d, J=8.82 Hz, 1H), 7.74-7.85 (m, 2H), 8.10 (dd, J=8.82, 2.21 Hz, 1H), 8.36 (d, J=2.21 Hz, 1H), 8.90 (s, 1H), 8.95 (d, J=8.46 Hz, 1H), 9.45 (bs, 1H), 11.35 (bs, 1H); MS (ESI+) m/z 539/541 (M+H)+.

Example 149

4-(4-Amino-phenylsulfanyl)-N-(4-bromo-phenyl)-3-(7-isopropyl-pyrido[2,3-d]pyrimidin-4-ylamino)-benzenesulfonamide Example 149A N-(4-Bromo-phenyl)-4-chloro-3-nitro-benzene-sulfonamide A solution of 4-chloro-3-nitrobenzenesulfonyl chloride (2.561 g, 10 mmol) in acetic acid (20 mL) was treated with 4-bromoaniline (1.72 g, 10 mmol) and anhydrous sodium acetate (1.23 g, 15 mmol), then heated at 100° for 30 minutes. The reaction was cooled to room temperature and the acetic acid removed by rotary evaporation under vacuum. The residue was taken up in ethyl acetate (100 mL) and washed with water (2×25 mL) and brine (25 mL). The organic phase was dried over anhydrous sodium sulfate, filtered, and concentrated under vacuum, co-evaporating the oil with methylene chloride/hexanes. Purification by silica gel chromatography using methylene chloride followed by 5% ethyl acetate/methylene chloride as eluent provided the title compound as a yellow solid (2.038 g, 52%).

Example 149B 4-(4-Amino-phenylsulfanyl)-N-(4-bromo-phenyl)-3-nitro-benzenesulfonamide A mixture of the product of Example 149A (500 mg, 1.277 mmol), 4-aminothiophenol (240 mg, 1.915 mmol) and anhydrous sodium acetate (524 mg, 6.384 mmol) in anhydrous ethanol (9 mL) was heated at reflux under a nitrogen atmosphere for 1 hour. The reaction was cooled to room temperature and the ethanol removed by rotary evaporation under vacuum. The residue was taken up in ethyl acetate (100 mL) and washed with water (2×50 mL) and brine (50 mL). The organic phase was dried over anhydrous sodium sulfate, filtered, and concentrated under vacuum, co-evaporating the oil with methylene chloride/hexanes to obtain the title compound as an orange foam (613 mg, 100%).

Example 149C

{4-[4-(4-Bromo-phenylsulfamoyl)-2-nitro-phenyl-sulfanyl]-phenyl}-carbamic acid tert-butyl ester A solution of the product of Example 149B (613 mg, 1.277 mmol) in anhydrous 1,4-dioxane (10 mL) was treated with di-tert-butyl dicarbonate (418 mg, 1.92 mmol) at room temperature, then the reaction was heated at reflux under a nitrogen atmosphere for 3 hours. The reaction was cooled to room temperature, additional di-tert-butyl dicarbonate (500 mg) was added, and the reaction refluxed for 17 hours. The reaction was cooled to room temperature and the solvent removed by rotary evaporation under vacuum. Purification of the residue by silica gel chromatography using 3% ethyl acetate/methylene chloride as eluent provided the title compound as a yellow solid (512 mg, 69%).

Example 149D

{4-[2-Amino-4-(4-bromo-phenylsulfamoyl)-phenyl-sulfanyl]-phenyl}-carbamic acid tert-butyl ester The product of Example 149C (510 mg, 0.879 mmol), iron powder (302 mg, 5.40 mmol), and ammonium chloride (308 mg, 5.76 mmol) in water (4 mL) and ethanol (8 mL) were heated at 80° for 40 minutes. The reaction was cooled to room temperature, diluted with ethyl acetate (100 mL), and washed with water (2×50 mL) and brine (50 mL). The organic phase was dried over anhydrous sodium sulfate, filtered, and concentrated by rotary evaporation under vacuum to provide the title compound as a white foam (436 mg, 90%).

Example 149E

{4-[4-(4-Bromo-phenylsulfamoyl)-2-(7-isopropyl-pyrido[2,3-d]pyrimidin-4-ylamino)-phenylsulfanyl]-phenyl}-carbamic acid tert-butyl ester A solution of the product from Example 36E (59 mg, 0.2725 mmol) and the product from Example 149D (150 mg, 0.2725 mmol) in acetic acid (4 mL) was stirred in an oil bath preheated to 140° C. for 25 minutes. The reaction was cooled to room temperature, diluted with hexanes (100 mL), concentrated by rotary evaporation under vacuum, and co-evaporated with methylene chloride/hexanes (4×). The residue was dried under vacuum, then purified by silica gel chromatography using 4% methanol/methylene chloride as eluent to provide the title compound as a tan solid (67 mg, 34%).

Example 149F 4-(4-Amino-phenylsulfanyl)-N-(4-bromo-phenyl)-3-(7-isopropyl-pyrido[2,3-d]pyrimidin-4-ylamino)-benzenesulfonamide The product from Example 149E (44 mg, 0.061 mmol) was treated with trifluoroacetic acid (2 mL) in methylene chloride (2 mL) at room temperature for 30 minutes. The solvents were removed by rotary evaporation under vacuum and the residual oil dried under hi-vacuum. Purification by silica gel chromatography using 5% methanol/methylene chloride as eluent provided the title compound as a trifluoroacetic acid salt (25 mg, 48%). $^1$H NMR (300 MHz, DMSO-D6) δ ppm: 1.35 (d, J=6.62 Hz, 6H), 3.13-3.38 (m, 1H), 6.63 (d, J=8.46 Hz, 2H), 6.87 (d, J=7.72 Hz, 1H), 7.01-7.09 (d, J=8.82 Hz, 2H), 7.12 (d, J=8.46 Hz, 2H), 7.44 (d, J=8.82 Hz, 2H), 7.61 (dd, J=7.72, 1.47 Hz, 1H), 7.71 (s, 1H), 7.81 (dd, J=6.62, 1.47 Hz, 1H), 8.66-8.80 (m, 1H), 8.90 (d, J=6.99 Hz, 1H), 10.55 (s, 1H); MS (ESI+) m/z 621/623 (M+H)$^+$.

Example 150

4-(4-Amino-phenylsulfanyl)-N-(4-bromo-phenyl)-3-(7-methyl-pyrido[2,3-d]pyrimidin-4-ylamino)-benzenesulfonamide The product from Example 149D was reacted with the product from Example 10B using the procedure described in Example 149E substituting the product from Example 10B for the product from Example 36E to provide {4-[4-(4-Bromo-phenylsulfamoyl)-2-(7-methyl-pyrido[2,3-d]pyrimidin-4-ylamino)-phenylsulfanyl]-phenyl}-carbamic acid tert-butyl ester which was deprotected according to the procedure described in Example 149F, followed by silica gel chromatography provided the title compound as a trifluoroacetic acid salt. $^1$H NMR (300 MHz, DMSO-D6) δ ppm: 2.74 (s, 3H), 6.64 (d, J=8.46 Hz, 2H), 6.89 (d, J=8.09 Hz, 1H), 7.05 (d, J=9.19 Hz, 2H), 7.12 (d, J=8.82 Hz, 2H), 7.44 (d, J=8.82 Hz, 2H), 7.63 (dd, J=7.72, 0.74 Hz, 1H), 7.74 (s, 1H), 7.79 (dd, J=7.72, 1.10 Hz, 1H), 8.70-8.83 (m, 1H), 8.88 (d, J=8.09 Hz, 1H), 10.55 (s, 1H); MS (ESI+) m/z 593/595 (M+H)+.

Example 151

4-[4-Chloro-2-(7-isopropyl-pyrido[2,3-d]pyrimidin-4-ylamino)-phenoxy]-phenol

Example 151A 4-(4-Chloro-2-nitro-phenoxy)-phenol

A solution of hydroquinone (1.21 g, 0.011 mol) and potassium hydroxide (0.894 g, 0.0159 mol) in anhydrous dimethylsulfoxide (7 mL) was heated at 120° for 30 minutes under a nitrogen atmosphere. A solution of 2,5-dichloronitrobenzene (1.90 g, 0.0099 mol) in dimethylsulfoxide (3 mL) was added dropwise over a 30 minute period at 120° then let the reaction stir for 1 hour at the same temperature. The reaction was then cooled in an ice bath and poured into 30 mL of ice water. The mixture was acidified with concentrated hydrochloric acid to pH 1 and extracted with ethyl ether (2×50 mL). The combined ethereal extracts were washed with water (3×150 mL), dried over anhydrous sodium sulfate, filtered, and concentrated by rotary evaporation under vacuum. Purification of the residue by silica gel chromatography using methylene chloride as eluent provided the product as a tan solid (1.34 g, 51%).

Example 151B 4-(2-Amino-4-chloro-phenoxy)-phenol

A mixture of the product of Example 151A (400 mg, 1.506 mmol) and iron powder (336 mg, 6.02 mmol) in acetic acid (10 mL) and ethanol (10 mL) was heated at reflux under a nitrogen atmosphere for 25 minutes. The reaction was cooled to room temperature, diluted with water (50 mL), and treated with solid sodium carbonate until the pH was 6. Extracted with ethyl acetate (2×50 mL) and washed the organic with brine (50 mL), dried over anhydrous sodium sulfate, filtered, and concentrated by rotary evaporation under vacuum. Co-evaporating the resulting oil with methylene chloride/hexanes provided the title compound as a tan solid (355 mg, 100%).

Example 151C

4-[4-Chloro-2-(7-isopropyl-pyrido[2,3-d]pyrimidin-4-ylamino)-phenoxy]-phenol

A solution of the product from Example 36E (38 mg, 0.177 mmol) and the product from Example 151B (42 mg, 0.177 mmol) in acetic acid (2 mL) was stirred in an oil bath preheated to 140° C. for 1.5 hour. The reaction was cooled to room temperature, diluted with hexanes (100 mL), concentrated by rotary evaporation under vacuum, and co-evaporated with methylene chloride/hexanes (4×). The residue was dried under hi-vacuum, then purified by triturating with 40% ethyl acetate/methylene chloride to provide the title compound as a beige solid (49 mg, 65%). $^1$H NMR (300 MHz, DMSO-D6) δ ppm: 1.31 (d, J=6.99 Hz, 6H), 3.10-3.29 (m, 1H), 6.70 (d, J=8.82 Hz, 2H), 6.76-6.90 (m, 3H), 7.24 (dd, J=8.64, 2.39 Hz, 1H), 7.55 (d, J=8.82 Hz, 1H), 7.71 (bs, 1H), 8.59 (bs, 1H), 8.73 (d, J=8.09 Hz, 1H), 9.31 (bs, 1H), 9.89 (bs, 1H); MS (DCI/NH$_3$) m/z 407 (M+H)+.

Example 152

4-(4-Hydroxy-phenoxy)-3-(7-isopropyl-pyrido[2,3-d]pyrimidin-4-ylamino)-benzonitrile Example 152A 4-(4-Hydroxy-phenoxy)-3-nitro-benzonitrile A solution of hydroquinone (1.21 g, 0.011 mol) and potassium hydroxide (0.894 g, 0.0159 mol) in anhydrous dimethylsulfoxide (8 mL) was heated at 90° C. for 30 minutes under a nitrogen atmosphere. A solution of 4-chloro-3-nitrobenzonitrile (1.806 g, 0.0099 mol) in dimethylsulfoxide (8 mL) was added dropwise over a 30 minute period at 90°, then let the reaction stir for 1 hour at the same temperature. The reaction was then cooled in an ice bath and poured into 30 mL of ice-water. The mixture was acidified with concentrated hydrochloric acid to pH 3 and extracted with ethyl ether (3×100 mL). The combined ethereal extracts were washed with water (3×150 mL) and brine (50 mL), dried over anhydrous sodium sulfate, filtered, and concentrated by rotary evaporation under vacuum. Purification by silica gel chromatography using 4% ethyl acetate/methylene chloride as eluent provided the product as an orange solid (0.984 g, 39%).

Example 152B

3-Amino-4-(4-hydroxy-phenoxy)-benzonitrile

The product of Example 152A (500 mg, 1.952 mmol) was hydrogenated in methanol (20 mL) with hydrogen (1 atmosphere, balloon) and 10% palladium on carbon (50 mg) for 30 minutes. The reaction was vacuum filtered through a 0.45☐ PTFE membrane and the catalyst washed with methanol. The filtrate was concentrated by rotary evaporation under vacuum to provide the title compound as a pinkish-beige solid (437 mg, 99%).

Example 152C 4-(4-Hydroxy-phenoxy)-3-(7-isopropyl-pyrido[2,3-d]pyrimidin-4-ylamino)-benzonitrile A solution of the product from Example 36E (41 mg, 0.1896 mmol) and the product from Example 152B (42.9 mg, 0.1896 mmol) in acetic acid (2 mL) was stirred in an oil bath preheated to 140° C. for 1.5 hour. The reaction was cooled to room temperature, diluted with hexanes (100 mL), concentrated by rotary evaporation under vacuum, and co-evaporated with methylene chloride/hexanes (4×). The residue was dried under hi-vacuum. Purification by silica gel chromatography using 30% ethyl acetate/methylene chloride as eluent provided the title compound as an white solid (16 mg, 21%). $^1$H NMR (300 MHz, DMSO-D6) δ ppm: 1.31 (d, J=6.99 Hz, 6H), 3.11-3.28 (m, 1H), 6.77 (d, J=8.82 Hz, 2H), 6.85 (d, J=8.46 Hz, 1H), 6.93 (d, J=8.46 Hz, 2H), 7.64 (dd, J=17.28, 8.46 Hz, 2H), 8.12 (s, 1H), 8.66 (s, 1H), 8.81 (d, J=8.09 Hz, 1H), 9.47 (s, 1H), 9.99 (s, 1H); MS (DCI/NH$_3$) m/z 398 (M+H)+.

Example 153

(5-Bromo-2-phenoxy-phenyl)-pyrido[2,3-d]pyrimidin-4-yl-amine 5-bromo-2-phenoxybenzenamine was reacted with the product from Example 57A using the procedure described in Example 57E substituting 5-bromo-2-phenoxybenzenamine for the product from Example 57D to provide the crude product which was purified by HPLC with TFA to provide the title compound as a trifluoroacetic acid salt. 1H NMR (300 MHz, DMSO-D6) δ ppm: 6.94-7.03 (m, J=8.09, 5.88 Hz, 3H), 7.07 (t, J=7.35 Hz, 1H), 7.24-7.36 (m, 2H), 7.54 (dd, J=8.82, 2.21 Hz, 1H), 7.77 (dd, J=8.46, 4.41 Hz, 1H), 7.83 (d, J=2.21 Hz, 1H), 8.82 (s, 1H), 8.89 (d, J=7.35 Hz, 1H), 9.10 (d, J=2.57 Hz, 1H); MS (ESI)+ m/z 394 (M+2)+.

Example 154

(5-Chloro-2-phenoxy-phenyl)-pyrido[2,3-d]pyrimidin-4-yl-amine

5-Chloro-2-phenoxy-phenylamine was reacted with the product from Example 57A using the procedure described in Example 57E substituting 5-chloro-2-phenoxy-phenylamine for the product from Example 57D to provide the crude product which was purified by HPLC with TFA to provide the title compound as a trifluoroacetic acid salt. 1H NMR (300 MHz, DMSO-D6) δ ppm: 6.97 (d, J=7.72 Hz, 2H), 7.00-7.11 (m, 2H), 7.24-7.34 (m, J=8.09, 8.09 Hz, 2H), 7.41 (dd, J=8.82, 2.57 Hz, 1H), 7.69-7.77 (m, 2H), 8.77 (s, 1H), 8.85 (d, J=8.46 Hz, 1H), 9.08 (d, J=3.31 Hz, 1H); MS (ESI)+ m/z 349 (M+H)+.

Example 155

1-{3-[4-Chloro-2-(7-isopropyl-pyrido[2,3-d]pyrimidin-4-ylamino)-phenoxy]-phenyl}-ethanol 1-[4-(2-Amino-4-chloro-phenoxy)-phenyl]-ethanol was reacted with the product from Example 36E according to the procedure from Example 152C substituting 1-[4-(2-Amino-4-chloro-phenoxy)-phenyl]-ethanol for the product from Example 152B to provide the crude product which was purified by HPLC with TFA to provide the title compound as a trifluoro acetic acid salt. 1H NMR (300 MHz, DMSO-D6) δ ppm: 1.16 (d, J=6.62 Hz, 3H), 1.31 (d, J=6.99 Hz, 6H), 3.17-3.28 (m, 1H), 4.60 (q, 1H), 6.81 (m, 1H), 6.94 (s, 1H), 7.01 (d, J=7.72 Hz, 1H), 7.06 (d, J=8.82 Hz, 1H), 7.23 (t, J=7.91 Hz, 1H), 7.43 (dd, J=8.82, 2.57 Hz, 1H), 7.72 (m, 1H), 7.76 (s, 1H), 8.79 (s, 1H), 8.82 (s, 1H); MS (ESI–) m/z 433 (M–H)–.

Example 156

4-[2-(7-Ethylsulfanyl-pyrimido[4,5-d]pyrimidin-4-ylamino)-4-methyl-phenylsulfanyl]-phenol

Example 156A

4-Amino-2-ethylsulfanyl-pyrimidine-5-carbonitrile

A solution of 2-Ethyl-2-thiopsuedourea hydrobromide (1.52 g, 8.19 mmol), (Ethoxymethylene) malononitrile (1.0 g, 8.19 mmol) and N,N-diisopropylethylamine (3.57 mL, 20.05 mmol) in ethanol (20 mL) was stirred at room temperature for 3.5 hours. The resultant solid was collected, washed with ethanol, and the dried under vacuum to provide the title compound as a light yellow solid (580 mg, 39%).

Example 156B

N'-(5-Cyano-2-ethylsulfanyl-pyrimidin-4-yl)-N,N-dimethyl-formamidine

A solution of the product from Example 156A (200 mg, 1.11 mmol) and N,N-dimethylformamide dimethyl acetal (0.15 mL, 1.11 mmol) in toluene (10 mL) was refluxed for 2.5 hours. After cooling to room temperature the solution was concentrated under vacuum to provide the title compound as a colorless solid (260 mg, 100%).

Example 156C

4-[2-(7-Ethylsulfanyl-pyrimido[4,5-d]pyrimidin-4-ylamino)-4-methyl-phenylsulfanyl]-phenol A solution of the product from Example 6c (54 mg, 0.234 mmol) and the product from Example 156B (50 mg, 0.213 mmol) in acetic acid (2 mL) was heated at 130° C. for 1.5 hours. The solution was then allowed to cool to room temperature, the acetic acid removed under vacuum and the resultant residue purified by HPLC with TFA to provide the title compound as a trifluoroacetic acid salt (51 mg, 45%). $^1$H NMR (300 MHz, DMSO-d$_6$) δ ppm: 1.38 (t, J=7.4 Hz, 3H), 2.30 (s, 3H), 3.23 (q, J=7.3 Hz, 2H), 6.72 (d, J=8.8 Hz, 2H), 6.98 (d, J=8.1 Hz, 1H), 7.10 (m, 1H), 7.18 (d, J=8.7 Hz, 2H), 7.21 (s, 1H), 8.62 (s, 1H), 9.70 (s, 1H), 9.78 (bs, 1H), 10.85 (s, 1H); MS (ESI)+ m/z 422 (M+H)+.

Example 157

(7-Ethylsulfanyl-pyrimido[4,5-d]pyrimidin-4-yl)-[5-methyl-2-(4-phenoxy-phenylsulfanyl)-phenyl]-amine

Example 157a

5-Methyl-2-(4-phenoxy-phenylsulfanyl)-phenylamine

The product from Example 6c (0.500 g, 1.91 mmol) was dissolved in CH$_2$Cl$_2$ along with phenyl boronic acid (0.701 g, 5.74 mmol), copper(II) acetate (0.659 g, 3.83 mmol), and triethylamine (0.387 g, 3.83 mmol). Stirred at room temperature for 48 h, at which time 2 more equivalents of each reagent was added. Stirred at room temperature for another 16 h at which time another 2 eq of each reagent was added. Stirred at room temperature for another 16 h. The reaction was diluted with water and extracted with ethyl acetate Dried over $Na_2SO_4$, filtered and concentrated under vacuum giving the crude product which was purified silica gel column chromatography eluting with 20% EtOAc/hexane (0.100 g, 15%). The product was reduced with $SnCl_2$ following the procedure from Example 5I to give the title compound (90 mg, 98%).

Example 157b 7-(ethylthio)-N-(5-methyl-2-(4-phenoxyphenylthio) phenyl)pyrimido[4,5-d]pyrimidin-4-amine A solution of the product from Example 156B and the product from Example 157a was reacted according to the procedure from Example 156C substituting the product from Example 157a for the product from Example 6c to provide the crude product which was purified by HPLC with TFA to provide the title compound as a trifluoroacetic acid salt (16 mg, 21%). 1H NMR (300 MHz, DMSO-D6) δ ppm: 1.37 (t, J=7.35 Hz, 3H), 2.34 (s, 3H), 3.22 (q, J=7.35 Hz, 2H), 6.82 (m, 2H), 6.93 (m, 2H), 7.29 (m, 8H), 8.57 (s, 1H), 9.64 (s, 1H), 10.66 (s, 1H); MS (ESI+) m/z 498 (M+H)+.

Example 158

4-[4-Methyl-2-(7-piperidin-1-yl-pyrimido[4,5-d] pyrimidin-4-ylamino)-phenylsulfanyl]-phenol To a solution of the product from Example 156C (42 mg, 0.1 mmol) in piperidine (1 ml) was microwaved (CEM Discover microwave) at 180° C. for 2 hours. The solution was concentrated under vacuum and the residue was purified by HPLC with TFA to provide the title compound as a trifluoroacetic acid salt (17 mg, 38%). 1H NMR (300 MHz, DMSO-D6) δ ppm: 1.64 (m, 6H), 2.30 (s, 3H), 3.96 (m, 4H), 6.72 (m, 2H), 7.01 (d, J=7.72 Hz, 1H), 7.17 (m, 4H), 8.59 (s, 1H), 9.53 (s, 1H), 9.83 (s, 1H), 11.43 (s, 1H); (ESI+) m/z 445 (M+H)+.

Example 159

Propane-2-sulfonic acid 4-[2-(7-ethylsulfanyl-pyrimido[4,5-d]pyrimidin-4-ylamino)-4-methyl-phenylsulfanyl]-phenyl ester The product from Example 156C (0.042 g, 0.1 mmol), isopropyl sulfonyl chloride (0.014 g, 0.105 mmol), 4-dimethylaminopyridine (0.002 g, 0.01 mmol) and diisopropylethylamine (0.04 g, 0.3 mmol) in 1,2-dichloroethane (2.0 mL) was stirred for 1 hour, poured into water (20 mL) and extracted with ethyl acetate (3×10 mL). The combined extracts were dried over sodium sulfate, filtered and concentrated under vacuum. The crude product was purified by HPLC with TFA to provide the title compound as a trifluoroacetic acid salt (15 mg, 23%). 1H NMR (300 MHz, DMSO-D6) δ ppm: 1.27-1.46 (m, 9H), 2.37 (s, 3H), 3.20 (q, J=7.35 Hz, 2H), 3.56-3.70 (m, 1H), 7.09-7.20 (m, 2H), 7.19-7.29 (m, 3H), 7.34 (s, 1H), 7.39 (d, J=8.09 Hz, 2H), 8.56 (s, 1H), 9.61 (s, 1H), 10.72 (s, 1H); MS (ESI)+ m/z 528 (M+H)+.

Example 160

4-Acetylamino-benzenesulfonic acid 4-[2-(7-ethyl-sulfanyl-pyrimido[4,5-d]pyrimidin-4-ylamino)-4-methyl-phenylsulfanyl]-phenyl ester The product from Example 156C was reacted with 4-Acetylamino-benzenesulfonyl chloride according to the procedure from Example 159 substituting 4-Acetylamino-benzenesulfonyl chloride for isopropyl sulfonyl chloride to provide the crude product which was purified by HPLC with TFA to provide the title compound as a trifluoroacetic acid salt (31 mg, 50%). 1H NMR (300 MHz, DMSO-D6) δ ppm: 1.36 (t, J=7.35 Hz, 3H), 2.10 (s, 3H), 2.35 (s, 3H), 3.20 (q, J=7.35 Hz, 2H), 6.85 (d, J=8.82 Hz, 2H), 7.13 (d, J=8.82 Hz, 2H), 7.26 (m, 3H), 7.71 (m, 2H), 7.81 (m, 2H), 8.52 (s, 1H), 9.59 (s, 1H), 10.48 (s, 1H), 10.71 (s, 1H); MS (ESI+) m/z 619 (M+H)+.

Example 161

4-[4-Methyl-2-(7-morpholin-4-yl-pyrimido[4,5-d] pyrimidin-4-ylamino)-phenylsulfanyl]-phenol To a solution of the product from Example 156C in morpholine (1 ml) was microwaved (CEM Discover microwave) at 180° C. for 2 hours. The solution was concentrated under vacuum and the residue was purified by HPLC with TFA to provide the title compound as a trifluoroacetic acid salt (29 mg, 65%). 1H NMR (300 MHz, DMSO-D6) δ ppm: 2.30 (s, 3H), 3.73 (t, J=4.41 Hz, 4H), 3.94 (bs, 4H), 6.72 (d, J=8.82 Hz, 2H), 7.02 (d, J=8.09 Hz, 1H), 7.18 (m, 4H), 8.61 (s, 1H), 9.57 (s, 1H), 9.85 (s, 1H), 11.47 (s, 1H); MS (ESI+) m/z 447 (M+H)+.

Example 162

Benzenesulfonic acid 4-[2-(7-ethylsulfanyl-pyrimido [4,5-d]pyrimidin-4-ylamino)-4-methyl-phenylsulfanyl]-phenyl ester The product from Example 156C was reacted with benzenesulfonyl chloride according to the procedure from Example 159 substituting benzenesulfonyl chloride for isopropyl sulfonyl chloride to provide the crude product which was purified by HPLC with TFA to provide the title compound as a trifluoroacetic acid salt (27 mg, 48%). 1H NMR (300 MHz, DMSO-D6) δ ppm: 1.36 (t, J=7.35 Hz, 3H), 2.36 (s, 3H), 3.20 (q, J=7.35 Hz, 2H), 6.85 (m, 2H), 7.11 (m, 2H), 7.20 (d, J=7.72 Hz, 1H), 7.35 (m, 2H), 7.65 (m, 2H), 7.86 (m, 3H), 8.51 (s, 1H), 9.58 (s, 1H), 10.65 (s, 1H); MS (ESI+) 562 (M+H)+.

Example 163

4-Bromo-benzenesulfonic acid 4-[2-(7-ethylsulfanyl-pyrimido[4,5-d]pyrimidin-4-ylamino)-4-methyl-phenylsulfanyl]-phenyl ester The product from Example 156C was reacted with 4-bromo-benzenesulfonyl chloride according to the procedure from Example 159 substituting 4-bromo-benzenesulfonyl chloride for isopropyl sulfonyl chloride to provide the crude product which was purified by HPLC with TFA to provide the title compound as a trifluoroacetic acid salt. 1H NMR (300 MHz, DMSO-D6) δ ppm: 1.36 (t, J=7.35 Hz, 3H), 2.37 (s, 3H), 3.20 (q, J=7.35 Hz, 2H), 6.87 (m, 2H), 7.12 (m, 2H), 7.19 (d, J=7.05 Hz, 1H), 7.36 (m, 2H), 7.71 (m, 2H), 7.87 (m, 2H), 8.51 (s, 1H), 9.60 (s, 1H), 10.61 (s, 1H); MS (ESI+) m/z 640/642 (M+H)+.

Example 164

(7-Ethylsulfanyl-pyrimido[4,5-d]pyrimidin-4-yl)-[2-(4-hydroxy-phenylsulfanyl)-5-methyl-phenyl]-carbamic acid tert-butyl ester The product of Example 156C was reacted with Di-tert-butyl dicarbonate and triethyl amine in tetrahydrofuran at room temperature for 16 hours. Afterwards, the mixture was poured into water (10 mL) and the resultant solution extracted with ethyl acetate (3×10 mL), the combined extracts dried over magnesium sulfate, filtered and concentrated under vacuum to provide the title compound. 1H NMR (300 MHz, DMSO-D6) δ ppm: 1.52 (t, J=7.35 Hz, 3H), 1.62 (s, 9H), 2.50 (s, 3H), 3.35 (q, J=7.35 Hz, 2H), 7.21 (d, J=8.46 Hz, 2H), 7.41 (m, 5H), 8.71 (s, 1H), 9.80 (s, 1H), 10.72 (s, 1H); MS (ESI+) m/z 522 (M+H)+.

Example 165

{4-[2-(7-Ethylsulfanyl-pyrimido[4,5-d]pyrimidin-4-ylamino)-4-methyl-phenylsulfanyl]-phenoxy}-acetonitrile The product from Example 164 (52 mg, 0.1 mmol), bromo-acetonitrile (0.008 ml, 0.12 mmol), cesium carbonate (0.065 g, 0.2 mmol) and tetrabutylammonium iodide (0.001 g) in N,N-dimethylformamide (2 ml) was stirred at room temperature for 2 hours. The mixture was partitioned between water and ethyl acetate. The organic layer was washed with brine, dried (sodium sulfate), filtered and evaporated under vacuum. To the residue was added dichloromethane (2.5 ml) and trifluoroacetic acid (2.5 ml) then stirred at room temperature for 1 hour. The solvent was evaporated under vacuum and the residue was purified by HPLC with TFA to provide the title compound (9 mg, 20%). 1H NMR (300 MHz, DMSO-D6) δ ppm: 1.42 (t, J=7.35 Hz, 3H), 2.24 (s, 3H), 3.29 (q, J=7.35 Hz, 2H), 5.25 (s, 2H), 6.81 (m, 5H), 7.20 (d, J=8.46 Hz, 2H), 8.34 (s, 1H), 9.25 (s, 1H), 9.75 (s, 1H); MS (ESI+) m/z 461 (M+H)+.

Example 166

[2-(4-Benzyloxy-phenylsulfanyl)-5-methyl-phenyl]-(7-ethylsulfanyl-pyrimido[4,5-d]pyrimidin-4-yl)-amine The product from Example 164 was reacted with benzyl bromide according to the procedure from Example 165 substituting benzyl bromide for bromo-acetonitrile to provide the crude product which was purified by silica gel chromatography using 98/2 dichloromethane/methanol as eluent to provide the title compound (15 mg, 29%). 1H NMR (300 MHz, DMSO-D6) δ ppm: 1.20 (t, J=7.35 Hz, 3H), 2.27 (s, 3H), 3.08 (q, J=7.35 Hz, 2H), 5.44 (s, 2H), 6.74 (d, J=8.46 Hz, 2H), 6.95 (m, 3H), 7.20 (d, J=8.46 Hz, 2H), 7.35 (m, 5H), 8.77 (s, 1H), 9.42 (s, 1H), 9.81 (s, 1H); MS (ESI+) m/z 512 (M+H)+.

Example 167

4-[4-(3-Bromo-benzyloxy)-2-(2-methylsulfanyl-thiazolo[4,5-d]pyrimidin-7-ylamino)-phenylsulfanyl]-phenol Example 167A N'-(5-Cyano-2-methylsulfanyl-thiazol-4-yl)-N,N-dimethyl-formamidine The title compound was prepared from the reaction of 4-Amino-2-methylsulfanyl-thiazole-5-carbonitrile with N,N-dimethylformamide dimethyl acetal using the procedure from Example 156B to provide the title compound as a white foam (0.132, g, 99%).

Example 167B

4-[4-(3-Bromo-benzyloxy)-2-(2-methylsulfanyl-thiazolo[4,5-d]pyrimidin-7-ylamino)-phenylsulfanyl]-phenol A solution of the product from Example 167A (66.0 mg, 0.29 mmol) and the product from Example 15A (118 mg, 0.29 mmol) in acetic acid (1 mL) was stirred in a preheated 140° C. oil bath for 20 minutes. The mixture was cooled and concentrated under vacuum. The resultant residue was then purified by HPLC with TFA to provide the title compound as a trifluoroacetic acid salt (34 mg, 17%). 1H NMR (300 MHz, DMSO-D6) δ ppm: 2.75 (s, 3H), 5.12 (s, 2H), 6.70 (d, J=8.82 Hz, 1H), 6.96-7.05 (m, 2H), 7.07-7.16 (m, 3H), 7.33 (t, J=7.72 Hz, 1H), 7.41-7.46 (m, 1H), 7.51 (d, J=7.72 Hz, 1H), 7.63 (s, 1H), 8.47 (s, 1H), 9.73 (s, 2H); MS (ESI)+ m/z 583/585 (M+H)+.

Example 168

4-[4-(4-Bromo-benzyloxy)-2-(2-methylsulfanyl-thiazolo[4,5-d]pyrimidin-7-ylamino)-phenylsulfanyl]-phenol A solution of the product from Example 167A and the product from Example 16A were reacted according to the procedure from Example 167B substituting the product from Example 16A for the product from Example 15A to provide the crude material which was purified by trituration with methanol to provide the title compound as a white solid (46 mg, 27%). 1H NMR (300 MHz, DMSO-D6) δ ppm: 2.76 (s, 3H), 5.09 (s, 2H), 6.70 (d, J=8.46 Hz, 2H), 6.91-7.24 (m, 5H), 7.38 (d, J=8.09 Hz, 2H), 7.56 (d, J=8.09 Hz, 2H), 8.46 (s, 1H), 9.71 (s, 2H); MS (ESI)+ m/z 583/585 (M+H)+.

Example 169

4-[4-Methyl-2-(2-methylsulfanyl-thiazolo[4,5-d]pyrimidin-7-ylamino)-phenylsulfanyl]-phenol A solution of the product from Example 167A and the product from Example 6c were reacted according to the procedure from Example 167B substituting the product from Example 6c for the product from Example 15A to provide the crude material which was purified by HPLC with TFA to provide the title compound as a trifluoroacetic acid salt (17 mg, 11%). 1H NMR (300 MHz, DMSO-D6) δ ppm: 2.27 (s, 3H), 2.76 (s, 3H), 6.76 (d, J=8.46 Hz, 2H), 6.82 (d, J=8.09 Hz, 1H), 7.06-7.22 (m, 4H), 8.49 (s, 1H), 9.86 (s, 2H); MS (ESI)+ m/z 413 (M+H)+.

Example 170

N-{4-[4-Methyl-2-(2-methylsulfanyl-thiazolo[4,5-d]pyrimidin-7-ylamino)-phenylsulfanyl]-phenyl}-acetamide A solution of the product from Example 167A and the product from Example 7b were reacted according to the procedure from Example 167B substituting the product from Example 7b for the product from Example 15A to provide the crude material which was purified by trituration with methanol to provide the title compound (110 mg, 83%). 1H NMR (300 MHz, DMSO-D6) δ ppm: 2.03 (s, 3H), 2.29 (s, 3H), 2.76 (s, 3H), 6.96 (d, J=8.09 Hz, 1H), 7.14 (d, J=8.09 Hz, 1H), 7.18-7.26 (m, J=8.82 Hz, 3H), 7.54 (d, J=8.46 Hz, 2H), 8.45 (s, 1H), 9.74 (s, 1H), 10.04 (s, 1H); MS (ESI)+ m/z 454 (M+H)+.

Example 171

N-{4-[2-(1-tert-Butyl-1H-pyrazolo[3,4-d]pyrimidin-4-ylamino)-4-methyl-phenylsulfanyl]-phenyl}-acetamide Example 171A N'-(2-tert-Butyl-4-cyano-2H-pyrazol-3-yl)-N,N-dimethyl-formamidine The title compound was prepared from the reaction of 5-Amino-1-tert-butyl-1H-pyrazole-4-carbonitrile with N,N-dimethylformamide dimethyl acetal using the procedure from Example 156B to provide the title compound.

Example 171B

N-{4-[2-(1-tert-Butyl-1H-pyrazolo[3,4-d]pyrimidin-4-ylamino)-4-methyl-phenylsulfanyl]-phenyl}-acetamide A solution of the product from Example 171A and the product from Example 7b were reacted according to the procedure from Example 167B substituting the product from Example 7b for the product from Example 15A and substituting the product from Example 171A for the product from Example 167A to provide the crude material which was purified by HPLC with TFA to provide the title compound as a trifluoroacetic acid salt (54 mg, 32%). 1H NMR (300 MHz, DMSO-D6) δ ppm: 1.74 (s, 9H), 2.03 (s, 3H), 2.41 (s, 3H), 7.13 (d, J=8.82 Hz, 2H), 7.49 (m, 4H), 7.62 (s, 1H), 8.41 (s, 1H), 8.47 (s, 1H), 8.76 (s, 1H), 10.06 (s, 1H), 10.39 (s, 1H); MS (ESI+) m/z 447 (M+H)+.

Example 172

4-[2-(1-tert-Butyl-1H-pyrazolo[3,4-d]pyrimidin-4-ylamino)-4-methyl-phenylsulfanyl]-phenol A solution of the product from Example 171A and the product from Example 6c were reacted according to the procedure from Example 167B substituting the product from Example 6c for the product from Example 15A and substituting the product from Example 171A for the product from Example 167A to provide the crude material which was purified by HPLC with TFA to provide the title compound as a trifluoroacetic acid salt (40 mg, 25%). 1H NMR (300 MHz, DMSO-D6) δ ppm: 1.76 (s, 9H), 2.38 (s, 3H), 6.67 (d, J=8.82 Hz, 2H), 7.07 (d, J=8.82 Hz, 2H), 7.34 (d, J=8.09 Hz, 1H), 7.50 (d, J=8.09 Hz, 1H), 7.58 (s, 1H), 8.43 (s, 1H), 8.49 (s, 1H), 8.75 (s, 1H), 9.91 (s, 1H), 10.40 (s, 1H); MS (ESI+) m/z 406 (M+H)+.

Example 173

4-[2-(7-Isopropyl-pyrimido[4,5-d]pyrimidin-4-ylamino)-4-methyl-phenylsulfanyl]-phenol Example 173A N'-(5-Cyano-2-isopropyl-pyrimidin-4-yl)-N,N-dimethyl-formamidine The title compound was prepared from the reaction of 4-Amino-2-isopropyl-pyrimidine-5-carbonitrile with N,N-dimethylformamide dimethyl acetal using the procedure from Example 156B to provide the title compound.

Example 173B

4-[2-(7-Isopropyl-pyrimido[4,5-d]pyrimidin-4-ylamino)-4-methyl-phenylsulfanyl]-phenol A solution of the product from Example 173A and the product from Example 6c were reacted according to the procedure from Example 167B substituting the product from Example 6c for the product from Example 15A and substituting the product from Example 173A for the product from Example 167A to provide the crude material which was purified by HPLC with TFA to provide the title compound as a trifluoroacetic acid salt (39 mg, 38%). 1H NMR (300 MHz, DMSO-D6) δ ppm: 1.36 (d, J=6.62 Hz, 6H), 2.30 (s, 3H), 3.29 (m, 1H), 6.70 (d, J=8.46 Hz, 2H), 6.98 (d, J=8.09 Hz, 1H), 7.17 (m, 4H), 8.72 (s, 1H), 9.76 (s, 1H), 9.90 (s, 1H), 11.13 (s, 1H); MS (ESI+) m/z 404 (M+H)+.

Example 174

4-[4-Benzyloxy-2-(7-isopropyl-pyrimido[4,5-d]pyrimidin-4-ylamino)-phenylsulfanyl]-phenol A solution of the product from Example 173A and the product from Example 27A were reacted according to the procedure from Example 167B substituting the product from Example 27A for the product from Example 15A and substituting the product from Example 173A for the product from Example 167A to provide the crude material which was purified by HPLC with TFA to provide the title compound as a trifluoroacetic acid salt (10 mg, 20%). 1H NMR (300 MHz, DMSO-D6) δ ppm: 1.35 (d, J=6.99 Hz, 6H), 3.27 (m, 1H), 5.11 (s, 2H), 6.64 (d, J=8.46 Hz, 2H), 7.06 (m, 5H), 7.40 (m, 5H), 8.64 (s, 1H), 9.65 (s, 1H), 9.84 (s, 1H), 10.88 (s, 1H); MS (ESI+) m/z 496 (M+H)+.

Example 175

N-{4-[2-(7-Ethylsulfanyl-5-methylsulfanyl-pyrimido[4,5-d]pyrimidin-4-ylamino)-4-methyl-phenylsulfanyl]-phenyl}-acetamide

Example 175A

N'-(5-Cyano-2-ethylsulfanyl-6-methylsulfanyl-pyrimidin-4-yl)-N,N-dimethyl-formamidine The title compound was prepared from the reaction of 4-Amino-2-ethylsulfanyl-6-methylsulfanyl-pyrimidine-5-carbonitrile with N,N-dimethylformamide dimethyl acetal using the procedure from Example 156B to provide the title compound.

Example 175B

N-{4-[2-(7-Ethylsulfanyl-5-methylsulfanyl-pyrimido[4,5-d]pyrimidin-4-ylamino)-4-methyl-phenylsulfanyl]-phenyl}-acetamide A solution of the product from Example 175A and the product from Example 7b were reacted according to the procedure from Example 167B substituting the product from Example 7b for the product from Example 15A and substituting the product from Example 175A for the product from Example 167A to provide the crude material which was purified by HPLC with TFA to provide the title compound as a trifluoroacetic acid salt (23 mg, 35%). 1H NMR (300 MHz, DMSO-D6) δ ppm: 1.36 (t, J=7.35 Hz, 3H), 2.03 (s, 3H), 2.24 (s, 3H), 2.40 (s, 3H), 3.18 (q, J=7.35 Hz, 2H), 6.84 (m, 3H), 7.19 (d, J=8.46 Hz, 2H), 7.49 (d, J=8.46 Hz, 2H), 7.82 (s, 1H), 9.97 (s, 1H), 12.25 (s, 1H); MS (ESI+) m/z 509 (M+H)+.

Example 176

4-[2-(7-Ethylsulfanyl-5-methylsulfanyl-pyrimido[4,5-d]pyrimidin-4-ylamino)-4-methyl-phenylsulfanyl]-phenol A solution of the product from Example 175A and the product from Example 6c were reacted according to the procedure from Example 167B substituting the product from Example 6c for the product from Example 15A and substituting the product from Example 175A for the product from Example 167A to provide the crude material which was purified by HPLC with TFA to provide the title compound as a trifluoroacetic acid salt (19 mg, 31%). 1H NMR (300 MHz, DMSO-D6) δ ppm: 1.36 (t, J=7.35 Hz, 3H), 2.21 (s, 3H), 2.44 (s, 3H), 3.19 (q, J=7.11 Hz, 2H), 6.70 (m, 5H), 7.18 (d, J=8.46 Hz, 2H), 7.84 (s, 1H), 9.67 (s, 1H), 12.24 (s, 1H); MS (ESI+) m/z 468 (M+H)+.

Example 177

N-{4-[2-(2-Cyanomethylsulfanyl-thiazolo[4,5-d]pyrimidin-7-ylamino)-4-methyl-phenylsulfanyl]-phenyl}-acetamide

Example 177A

N'-(5-Cyano-2-cyanomethylsulfanyl-thiazol-4-yl)-N,N-dimethyl-formamidine

The title compound was prepared from the reaction of 4-Amino-2-cyanomethylsulfanyl-thiazole-5-carbonitrile with N,N-dimethylformamide dimethyl acetal using the procedure from Example 156B to provide the title compound.

Example 177B

N-{4-[2-(2-Cyanomethylsulfanyl-thiazolo[4,5-d]pyrimidin-7-ylamino)-4-methyl-phenylsulfanyl]-phenyl}-acetamide A solution of the product from Example 177A and the product from Example 7b were reacted according to the procedure from Example 167B substituting the product from Example 7b for the product from Example 15A and substituting the product from Example 177A for the product from Example 167A to provide the crude material which was purified by HPLC with TFA to provide the title compound as a trifluoroacetic acid salt (64 mg, 52%). 1H NMR (300 MHz, DMSO-D6) δ ppm: 2.03 (s, 3H), 2.30 (s, 3H), 4.54 (s, 2H), 6.95 (d, J=8.09 Hz, 1H), 7.15 (d, J=8.09 Hz, 1H), 7.23 (m, 3H), 7.55 (d, J=8.46 Hz, 2H), 8.51 (s, 1H), 9.91 (s, 1H), 10.04 (s, 1H); MS (ESI+) m/z 479 (M+H)+.

Example 178

{7-[2-(4-Hydroxy-phenylsulfanyl)-5-methyl-phenylamino]-thiazolo[4,5-d]pyrimidin-2-ylsulfanyl}-acetonitrile A solution of the product from Example 177A and the product from Example 6c were reacted according to the procedure from Example 167B substituting the product from Example 6c for the product from Example 15A and substituting the product from Example 177A for the product from Example 167A to provide the crude material which was purified by HPLC with TFA to provide the title compound as a trifluoroacetic acid salt (62 mg, 56%). 1H NMR (300 MHz, DMSO-D6) δ ppm: 2.27 (s, 3H), 4.54 (s, 2H), 6.77 (m, 3H), 7.18 (m, 4H), 8.53 (s, 1H), 9.85 (s, 1H), 9.97 (s, 1H); MS (ESI+) m/z 438 (M+H)+.

Example 179

4-[4-Benzyloxy-2-(7-heptafluoropropyl-pyrimido[4,5-d]pyrimidin-4-ylamino)-phenylsulfanyl]-phenol

Example 179A

N'-(5-Cyano-2-heptafluoropropyl-pyrimidin-4-yl)-N,N-dimethyl-formamidine

The title compound was prepared from the reaction of 4-Amino-2-heptafluoropropyl-pyrimidine-5-carbonitrile with N,N-dimethylformamide dimethyl acetal using the procedure from Example 156B to provide the title compound.

Example 179B

4-[4-Benzyloxy-2-(7-heptafluoropropyl-pyrimido[4,5-d]pyrimidin-4-ylamino)-phenylsulfanyl]-phenol A solution of the product from Example 179A and the product from Example 27A were reacted according to the procedure from Example 167B substituting the product from Example 27A for the product from Example 15A and substituting the product from Example 179A for the product from Example 167A to provide the crude material which was purified by HPLC with TFA to provide the title compound as a trifluoroacetic acid salt (24 mg, 39%). 1H NMR (300 MHz, DMSO-D6) δ ppm: 5.11 (s, 2H), 6.61 (d, J=8.46 Hz, 2H), 7.04 (dd, J=8.82, 2.57 Hz, 1H), 7.10 (d, J=8.46 Hz, 2H), 7.17 (d, J=2.57 Hz, 1H), 7.23 (d, J=8.82 Hz, 1H), 7.40 (m, 5H), 8.79 (s, 1H), 9.63 (s, 1H), 10.12 (s, 1H), 11.01 (s, 1H); MS (ESI+) m/z 622 (M+H)+.

Example 180

(7-Isopropyl-pyrimido[4,5-d]pyrimidin-4-yl)-[5-methyl-2-(4-phenoxy-phenylsulfanyl)-phenyl]-amine A solution of the product from Example 173A and the product from Example 157a were reacted according to the procedure from Example 167B substituting the product from Example 157a for the product from Example 15A and substituting the product from Example 173A for the product from Example 167A to provide the crude material which was purified by HPLC with TFA to provide the title compound as a trifluoroacetic acid salt. 1H NMR (300 MHz, DMSO-D6) δ ppm: 1.34 (d, J=6.99 Hz, 6H), 2.34 (s, 3H), 3.24 (m, 1H), 6.81 (d, J=8.82 Hz, 2H), 6.94 (d, J=7.72 Hz, 2H), 7.28 (m, 8H), 8.63 (s, 1H), 9.83 (s, 1H), 10.78 (s, 1H); MS (ESI+) m/z 480 (M+H)+.

Example 181

(7-Ethylsulfanyl-pyrimido[4,5-d]pyrimidin-4-yl)-[3-(4-methoxy-phenylsulfanyl)-5-methyl-phenyl]-amine

Example 181A

1-(4-Methoxy-phenylsulfanyl)-3-methyl-5-nitro-benzene

Cuprous 4-methoxy thiophenolate (0.94 g, 4.63 mmol), which was prepared by refluxing excess 4-methoxythiophenol with copper oxide in ethyl alcohol overnight and isolating the desired product by filtration, and 3-bromo-5-nitrotoluene (1.0 g, 4.63 mmol), prepared in two steps from 3-nitro-4-aminotoluene as described in J. Am. Chem. Soc. Vol. 78, pp 1992, 1956, were heated to 165° C. in a mixture of quinoline (5 mL) and pyridine (1 mL) for 2 hours. After quenching with aqueous HCl the desired product was isolated by chromatography on silica using ethyl acetate/hexane as eluent to provide the title compound (0.96 g, 75%).

Example 181B

3-(4-Methoxy-phenylsulfanyl)-5-methyl-phenylamine

The product from Example 181A was reduced according to the procedure from Example 147C substituting the product from Example 181A for the product from Example 147B to provide the title compound.

Example 181C

(7-Ethylsulfanyl-pyrimido[4,5-d]pyrimidin-4-yl)-[3-(4-methoxy-phenylsulfanyl)-5-methyl-phenyl]-amine The product from Example 181B was reacted with the product from Example 156B according to the procedure from Example 156C substituting the product from Example 181B for the product from Example 6c to provide the crude product which was purified by HPLC with TFA to provide the title compound as a trifluoroacetic acid salt. 1H NMR (500 MHz, DMSO-D6) δ ppm: 1.37 (t, J=7.32 Hz, 3H), 2.28 (s, 3H), 3.21 (q, J=7.32 Hz, 2H), 3.79 (s, 3H), 6.83 (s, 1H), 7.03 (d, J=9.16 Hz, 2H), 7.42-7.53 (m, 4H), 8.71 (s, 1H), 9.72 (s, 1H), 10.39 (s, 1H); MS (ESI+) m/z 436 (M+H)+.

Example 182

(7-Ethylsulfanyl-pyrimido[4,5-d]pyrimidin-4-yl)-[3-(3-methoxy-phenylsulfanyl)-5-methyl-phenyl]-amine

Example 182A

3-(3-Methoxy-phenylsulfanyl)-5-methyl-phenylamine

Cuprous 3-methoxy thiophenolate was reacted with 3-bromo-5-nitrotoluene according to the procedure from Example 181A substituting cuprous 3-methoxy thiophenolate for cuprous 4-methoxy thiophenolate to provide 1-(3-Methoxy-phenylsulfanyl)-3-methyl-5-nitro-benzene which was reduced according to the procedure from Example 181B to provide the title compound.

Example 182B

(7-Ethylsulfanyl-pyrimido[4,5-d]pyrimidin-4-yl)-[3-(3-methoxy-phenylsulfanyl)-5-methyl-phenyl]-amine The product from Example 182A was reacted with the product from Example 156B according to the procedure from Example 156C substituting the product from Example 182A for the product from Example 6c to provide the crude product which was purified by HPLC with TFA to provide the title compound as a trifluoroacetic acid salt. 1H NMR (300 MHz, DMSO-D6) δ ppm: 1.37 (t, J=7.35 Hz, 3H), 2.33 (s, 3H), 3.21 (q, J=7.11 Hz, 2H), 3.74 (s, 3H), 6.84-6.96 (m, J=1.10 Hz, 3H), 7.05 (s, 1H), 7.32 (dd, J=9.01, 7.17 Hz, 1H), 7.60 (s, 1H), 7.65 (s, 1H), 8.74 (s, 1H), 9.74 (s, 1H), 10.47 (s, 1H); MS (ESI+) m/z 436 (M+H)+.

Example 183

(7-Benzylsulfanyl-pyrimido[4,5-d]pyrimidin-4-yl)-(5-ethyl-2-phenylsulfanyl-phenyl)-amine

Example 183A

5-Ethyl-2-phenylsulfanyl-phenylamine

Sodium thiophenolate was reacted with 1-Chloro-4-ethyl-2-nitro-benzene according to the procedure from Example 5H substituting 1-Chloro-4-ethyl-2-nitro-benzene for 4-chloro-3-nitrotoluene to provide 4-Ethyl-2-nitro-1-phenylsulfanyl-benzene which was reduced according to the procedure from Example 5I to provide the title compound.

Example 183B

4-Amino-2-benzylsulfanyl-pyrimidine-5-carbonitrile

A solution of 2-Benzyl-2-thiopsuedourea hydrochloride (5.0 g, 24.67 mmol), (Ethoxymethylene) malononitrile (3.01 g, 24.67 mmol) and N,N-diisopropylethylamine (10.75 mL, 61.68 mmol) in ethanol (50 mL) was stirred at room temperature for 18 hours. The resultant solid was collected, washed with ethanol, and the dried under vacuum to provide the title compound (2.69 g, 45%).

Example 183C

N'-(2-Benzylsulfanyl-5-cyano-pyrimidin-4-yl)-N,N-dimethyl-formamidine

A solution of the product from Example 183B was reacted with N,N-dimethylformamide dimethyl acetal according to the procedure from Example 156B substituting the product from Example 183B for the product from Example 156B to provide the title compound.

Example 183D (7-Benzylsulfanyl-pyrimido[4,5-d]pyrimidin-4-yl)-(5-ethyl-2-phenylsulfanyl-phenyl)-amine The product from Example 183A was reacted with the product from Example 183C according to the procedure from Example 156C substituting the product from Example 183A for the product from Example 6c and substituting the product from Example 183C for the product from Example 156B to provide the crude product which was purified by HPLC with TFA to provide the title compound as a trifluoroacetic acid salt. MS (ESI+) m/z 482 (M+H)+.

Example 184

(7-Benzylsulfanyl-pyrimido[4,5-d]pyrimidin-4-yl)-[2-(4-methoxy-phenylsulfanyl)-5-methyl-phenyl]-amine The product from Example 183C was reacted with 2-(4-Methoxy-phenylsulfanyl)-5-methyl-phenylamine (Example 118) according to the procedure from Example 156C substituting 2-(4-Methoxy-phenylsulfanyl)-5-methyl-phenylamine for the product from Example 6c and substituting the product from Example 183C for the product from Example 156B to provide the crude product which was purified by HPLC with TFA to provide the title compound as a trifluoroacetic acid salt. MS (ESI+) m/z 498 (M+H)+.

Example 185

(7-Benzylsulfanyl-pyrimido[4,5-d]pyrimidin-4-yl)-(5-fluoro-2-phenylsulfanyl-phenyl)-amine

Example 185A

5-Fluoro-2-phenylsulfanyl-phenylamine

4-Fluoro-2-nitrophenol was reacted according to procedures similar to those described in Examples 6a, 6b, and 6c substituting benzenethiol for 4-mercaptophenol and 4-fluoro-2-nitrophenol for 4-methyl-2-nitro phenol to provide the title compound.

Example 185B (7-Benzylsulfanyl-pyrimido[4,5-d]pyrimidin-4-yl)-(5-fluoro-2-phenylsulfanyl-phenyl)-amine The product from Example 185A was reacted with the product from Example 203A according to the procedure from Example 156C substituting the product from Example 203A for the product from Example 6c and substituting the product from Example 185A for the product from Example 156B to provide the crude product which was purified by HPLC with TFA to provide the title compound as a trifluoroacetic acid salt. MS (ESI+) m/z 472 (M+H)+.

Example 186

(7-Benzylsulfanyl-pyrimido[4,5-d]pyrimidin-4-yl)-[2-(4-fluoro-phenylsulfanyl)-5-methyl-phenyl]-amine The product from Example 183C was reacted with 2-(4-Fluoro-phenylsulfanyl)-5-methyl-phenylamine (Example 124) according to the procedure from Example 156C substituting 2-(4-Fluoro-phenylsulfanyl)-5-methyl-phenylamine for the product from Example 6c and substituting the product from Example 183C for the product from Example 156B to provide the crude product which was purified by HPLC with TFA to provide the title compound as a trifluoroacetic acid salt. MS (ESI+) m/z 486 (M+H)+.

Example 187

(7-Benzylsulfanyl-pyrimido[4,5-d]pyrimidin-4-yl)-(5-methyl-2-m-tolylsulfanyl-phenyl)-amine The product from Example 183C was reacted with 5-Methyl-2-m-tolylsulfanyl-phenylamine according to the procedure from Example 156C substituting 5-Methyl-2-m-tolylsulfanyl-phenylamine for the product from Example 6c and substituting the product from Example 183C for the product from Example 156B to provide the crude product which was purified by HPLC with TFA to provide the title compound as a trifluoroacetic acid salt. MS (ESI+) m/z 482 (M+H)+.

Example 188

(7-Benzylsulfanyl-pyrimido[4,5-d]pyrimidin-4-yl)-(5-methyl-2-phenylsulfanyl-phenyl)-amine The product from Example 183C was reacted with the product from Example 5I according to the procedure from Example 156C substituting the product from Example 5I for the product from Example 6c and substituting the product from Example 183C for the product from Example 156B to provide the crude product which was purified by HPLC with TFA to provide the title compound as a trifluoroacetic acid salt. MS (ESI+) m/z 468 (M+H)+.

Example 189

3-[2-(7-Benzylsulfanyl-pyrimido[4,5-d]pyrimidin-4-ylamino)-4-methyl-phenylsulfanyl]-phenol The product from Example 183C was reacted with 3-(2-amino-4-methyl-phenylsulfanyl)-phenol (Example 129) according to the procedure from Example 156C substituting 3-(2-amino-4-methyl-phenylsulfanyl)-phenol for the product from Example 6c and substituting the product from Example 183C for the product from Example 156B to provide the crude product which was purified by HPLC with TFA to provide the title compound as a trifluoroacetic acid salt. MS (ESI+) m/z 484 (M+H)+.

Example 190

(7-Benzylsulfanyl-pyrimido[4,5-d]pyrimidin-4-yl)-[3-(3-methoxy-phenylsulfanyl)-5-methyl-phenyl]-amine The product from Example 183C was reacted with the product from Example 182A according to the procedure from Example 156C substituting the product from Example 182A for the product from Example 6c and substituting the product from Example 183C for the product from Example 156B to provide the crude product which was purified by HPLC with TFA to provide the title compound as a trifluoroacetic acid salt. 1H NMR (300 MHz, DMSO-D6) δ ppm: 2.34 (s, 3H), 3.74 (s, 3H), 4.52 (s, 2H), 6.84-6.97 (m, J=1.10 Hz, 3H), 7.05 (s, 1H), 7.21-7.39 (m, 4H), 7.46-7.53 (m, 2H), 7.61 (s, 1H), 7.66 (s, 1H), 8.76 (s, 1H), 9.77 (s, 1H), 10.47 (s, 1H); MS (ESI+) m/z=498 (M+H)+.

Example 191

(7-Benzylsulfanyl-pyrimido[4,5-d]pyrimidin-4-yl)-[3-(4-methoxy-phenylsulfanyl)-5-methyl-phenyl]-amine The product from Example 183C was reacted with the product from Example 181B according to the procedure from Example 156C substituting the product from Example 181B for the product from Example 6c and substituting the product from Example 183C for the product from Example 156B to provide the crude product which was purified by HPLC with TFA to provide the title compound as a trifluoroacetic acid salt. 1H NMR (300 MHz, DMSO-D6) δ ppm: 2.28 (s, 3H), 3.79 (s, 3H), 4.52 (s, 2H), 6.83 (s, 1H), 7.04 (d, J=8.82 Hz, 2H), 7.19-7.38 (m, 2H), 7.41-7.55 (m, 5H), 8.74 (s, 1H), 9.75 (s, 1H), 10.42 (s, 1H); MS (ESI+) m/z 497 (M+H)+.

Example 192

(7-Benzylsulfanyl-pyrimido[4,5-d]pyrimidin-4-yl)-[2-(4-methoxy-phenoxy)-5-methyl-phenyl]-amine The product from Example 183C was reacted with the product from Example 116B according to the procedure from Example 156C substituting the product from Example 116B for the product from Example 6c and substituting the product from Example 183C for the product from Example 156B to provide the crude product which was purified by HPLC with TFA to provide the title compound as a trifluoroacetic acid salt. MS (ESI+) m/z 482 (M+H)+.

Example 193

(7-Benzylsulfanyl-pyrimido[4,5-d]pyrimidin-4-yl)-(5-methyl-2-p-tolylsulfanyl-phenyl)-amine The product from Example 183C was reacted with 5-methyl-2-p-tolylsulfanyl-phenylamine according to the procedure from Example 156C substituting 5-methyl-2-p-tolylsulfanyl-phenylamine for the product from Example 6c and substituting the product from Example 183C for the product from Example 156B to provide the crude product which was purified by HPLC with TFA to provide the title compound as a trifluoroacetic acid salt. MS (ESI+) m/z 482 (M+H)+.

Example 194

4-[4-(3-Bromo-benzyloxy)-2-(pyrimido[4,5-d]pyrimidin-4-ylamino)-phenylsulfanyl]-phenol

Example 194A

N'-(5-Cyano-pyrimidin-4-yl)-N,N-dimethyl-formamidine

The title compound was prepared from the reaction of 4-Amino-5-pyrimidinecarbonitrile (Aldrich) with N,N-dimethylformamide dimethyl acetal using the procedure from Example 156B to provide the title compound.

Example 194B

4-[4-(3-Bromo-benzyloxy)-2-(pyrimido[4,5-d]pyrimidin-4-ylamino)-phenylsulfanyl]-phenol The product from Example 194A was reacted with the product from Example 15A according to the procedure from Example 156C substituting the product from Example 15A for the product from Example 6c and substituting the product from Example 194A for the product from Example 156B to provide the crude product which was purified by HPLC with NH4OAc to provide the title compound. 1H NMR (300 MHz, DMSO-D6) δ ppm: 5.12 (s, 2H), 6.64 (d, J=8.82 Hz, 2H), 6.93-7.04 (m, 1H), 7.10 (d, J=8.82 Hz, 2H), 7.14-7.23 (m, 2H), 7.36 (t, J=7.72 Hz, 1H), 7.43-7.49 (m, 1H), 7.54 (dt, J=7.81, 1.61 Hz, 1H), 7.65 (d, J=1.47 Hz, 1H), 9.04 (m, 1H), 9.63 (s, 1H), 10.29 (m, 1H); MS (ESI−) m/z 531 (M−H)−.

Example 195

4-[4-Benzyloxy-2-(pyrimido[4,5-d]pyrimidin-4-ylamino)-phenylsulfanyl]-phenol

The product from Example 194A was reacted with the product from Example 27A according to the procedure from Example 156C substituting the product from Example 27A for the product from Example 6c and substituting the product from Example 194A for the product from Example 156B to provide the crude product which was purified by HPLC with NH4OAc to provide the title compound. 1H NMR (300 MHz, DMSO-D6) δ ppm: 5.10 (s, 2H), 6.63 (d, J=8.46 Hz, 2H), 6.94-7.05 (m, 1H), 7.10 (d, J=8.82 Hz, 2H), 7.18 (d, J=7.72 Hz, 2H), 7.29-7.51 (m, 5H), 9.05 (m, 1H), 9.63 (s, 1H), 9.92 (s, 1H), 10.66 (s, 1H); MS (ESI−) m/z 452 (M−H)−.

Example 196

(7-Isopropyl-pyrido[2,3-d]pyrimidin-4-yl)-[3-(4-methoxy-phenylsulfanyl)-5-methyl-phenyl]-amine The product from Example 181B was reacted with the product from Example 36E using the procedure from Example 36I substituting the product from Example 181B for the product from Example 36H to provide the crude material which was purified by HPLC with TFA to provide the title compound as a trifluoroacetic acid salt. 1H NMR (500 MHz, DMSO-D6) δ ppm: 1.33 (d, J=6.71 Hz, 6H), 2.29 (s, 3H) 3.25 (qq, J=7.02, 6.90 Hz, 1H), 3.79 (s, 3H), 6.88 (s, 1H), 7.03 (d, J=9.16 Hz, 2H), 7.42 (d, J=7.93 Hz, 2H), 7.45 (d, J=8.54 Hz, 2H), 7.77 (d, J=8.54 Hz, 1H), 8.81 (s, 1H), 8.95 (d, J=8.54 Hz, 1H), 10.74 (s, 1H); MS (ESI+) m/z 417 (M+H)+.

Example 197

4-[3-(7-Isopropyl-pyrido[2,3-d]pyrimidin-4-ylamino)-5-methyl-phenylsulfanyl]-phenol

Example 197A 4-(3-Amino-5-methyl-phenylsulfanyl)-phenol

To the product from Example 181B (0.5 g, 2.0 mmol) in dichloromethane was treated with boron tribromide (10 mmol) at room temperature for 1 hour. The solution was the extracted with water, then the organic solution dried and concentrated to provide the title compound.

Example 197B

4-[3-(7-Isopropyl-pyrido[2,3-d]pyrimidin-4-ylamino)-5-methyl-phenylsulfanyl]-phenol The product from Example 197A was reacted with the product from Example 36E using the procedure from Example 36I substituting the product from Example 197A for the product from Example 36H to provide the crude material which was purified by HPLC with TFA to provide the title compound as a trifluoroacetic acid salt. 1H NMR (300 MHz, DMSO-D6) δ ppm: 1.35 (s, 3H), 1.33 (s, 3H), 2.28 (s, 3H), 3.27 (qq, J=6.86 Hz, 1H), 6.79-6.91 (m, 1H), 6.86 (d, J=8.82 Hz, 2H), 7.30 (s, 1H), 7.36 (d, J=8.46 Hz, 2H), 7.35 (s, 1H), 7.83 (d, J=8.46 Hz, 1H), 8.87 (s, 1H), 8.98 (d, J=8.82 Hz, 1H), 9.92 (s, 1H), 11.06 (s, 1H); MS (ESI−) m/z 403 (M+H)+.

Example 198

4-[5-(3-Fluoro-benzyloxy)-2-(4-hydroxy-phenylsulfanyl)-phenylamino]-7-methyl-pyrido[2,3-d]pyrimidine-6-carbonitrile

Example 198A

N'-(3,5-Dicyano-6-methyl-pyridin-2-yl)-N,N-dimethyl-formamidine

A solution of 2-Amino-6-methyl-pyridine-3,5-dicarbonitrile (0.158 g, 1.0 mmol) and N,N-Dimethylformamide dimethyl acetal (0.119 g, 1.0 mmol) in toluene (10 mL) was heated at reflux for 6 hours. After cooling to room temperature, the solution was concentrated under vacuum to provide the title compound as a brown solid (0.2 g, 94%).

Example 198B

4-[5-(3-Fluoro-benzyloxy)-2-(4-hydroxy-phenylsulfanyl)-phenylamino]-7-methyl-pyrido[2,3-d]pyrimidine-6-carbonitrile The product of Example 198A was reacted with the product of Example 10B using the procedure of Example 10F substituting the product of Example 198A for the product of Example 10E to provide the crude material which was purified by HPLC with TFA to provide the title compound as a trifluoroacetic acid salt (18 mg, 29%). 1H NMR (300 MHz, DMSO-D6) δ ppm: 2.82 (s, 3H), 5.13 (s, 2H), 6.64 (d, J=8.46 Hz, 2H), 6.99 (d, J=9.56 Hz, 1H), 7.09 (d, J=8.82 Hz, 2H), 7.12-7.21 (m, 3H), 7.29 (d, J=7.72 Hz, 2H), 7.39-7.53 (m, 1H), 8.63 (s, 1H), 9.36 (s, 1H), 9.64 (s, 1H), 10.33 (s, 1H).

Example 199

[3-(3-Fluoro-benzyloxy)-phenyl]-(7-methyl-pyrido[2,3-d]pyrimidin-4-yl)-amine

Example 199A (3-Fluoro-benzyloxy)-3-nitro-benzene

A solution of 3-nitro-phenol (0.278 g, 2.0 mmol), 1-bromomethyl-3-fluoro-benzene (0.258 ml, 2.1 mmol), potassium carbonate (0.553 g, 4.0 mmol) and tetrabutylammonium iodide (0.001 g) in N,N-dimethylformamide (5 ml) was stirred at room temperature for 16 hours. Afterwards, ice water (10 mL) was added to the solution and the resultant solid was collected by filtration and dried in a vacuum oven to provide the title compound in quantitative yield.

Example 199B (3-Fluoro-benzyloxy)-3-amino-benzene

To a solution of the product from Example 199A (0.494 g, 2.0 mmol), iron powder (0.56 g, 10.0 mmol) and ammonium chloride (0.54 g, 10.0 mmol) in a methanol (20 mL), tetrahydrofuran (20 mL), and water (10 mL) solution was heated to reflux for 2 hours. The resultant mixture was filtered through a pad of celite, and the filtrate was concentrated. Then ethyl acetate was added, stirred for 30 minutes, filtered and concentrated under vacuum to provide the title compound (0.405 g, 93%).

Example 199C

[3-(3-Fluoro-benzyloxy)-phenyl]-(7-methyl-pyrido[2,3-d]pyrimidin-4-yl)-amine

The product of Example 199B was reacted with the product of Example 10B using the procedure of Example 10F substituting the product of Example 199B for the product of Example 10E to provide the crude material which was purified by HPLC with TFA to provide the title compound as a trifluoroacetic acid salt (32 mg, 89%). 1H NMR (300 MHz, DMSO-D6) δ ppm: 2.74 (s, 3H), 5.18 (s, 2H), 6.98 (m, 1H), 7.18 (m, 1H), 7.42 (m, 6H), 7.79 (d, J=8.46 Hz, 1H), 8.92 (s, 1H), 9.00 (d, J=8.82 Hz, 1H), 11.16 (s, 1H); MS (ESI+) m/z 361 (M+H)+.

Example 200

[3-(3-Fluoro-benzyloxy)-phenyl]-(7-isopropyl-pyrido[2,3-d]pyrimidin-4-yl)-amine

The product from Example 199B was reacted with the product from Example 36E using the procedure from Example 36I substituting the product from Example 199B for the product from Example 36H to provide the crude material which was purified by HPLC with TFA to provide the title compound as a trifluoroacetic acid salt. 1H NMR (300 MHz, DMSO-D6) δ ppm: 1.34 (d, J=6.99 Hz, 6H), 3.26 (m, 1H), 5.18 (s, 2H), 6.93 (m, 1H), 7.17 (m, 1H), 7.42 (m, 6H), 7.79 (d, J=8.46 Hz, 1H), 8.85 (s, 1H), 9.00 (d, J=8.46 Hz, 1H), 10.76 (s, 1H); MS (ESI+) m/z 389 (M+H)+.

Example 201

[3-(3-Fluoro-benzyloxy)-phenyl]-pyrido[2,3-d]pyrimidin-4-yl-amine

The product of Example 199B was reacted with the product of Example 57A using the procedure of Example 57E substituting the product of Example 199B for the product of Example 57D to provide the crude title compound which was purified by HPLC with TFA to provide the title compound as a trifluoroacetic acid salt. 1H NMR (300 MHz, DMSO-D6) δ ppm: 5.18 (s, 2H), 6.98 (m, 1H), 7.18 (m, 1H), 7.42 (m, 6H), 7.87 (dd, J=8.27, 4.60 Hz, 1H), 8.93 (s, 1H), 9.14 (m, 2H), 11.12 (s, 1H); MS (ESI+) m/z 347 (M+H)+.

Example 202

[3-(4-Fluoro-benzyloxy)-phenyl]-pyrido[2,3-d]pyrimidin-4-yl-amine

Example 202A

3-(4-Fluoro-benzyloxy)-phenylamine

3-Nitro-phenol was reacted with 1-bromomethyl-4-fluoro-benzene according to the procedure from Example 199A substituting 1-bromomethyl-4-fluoro-benzene for 1-bromomethyl-3-fluoro-benzene then reduced according to the procedure from Example 199B to provide the title compound.

Example 202B

[3-(4-Fluoro-benzyloxy)-phenyl]-pyrido[2,3-d]pyrimidin-4-yl-amine

The product of Example 202A was reacted with the product of Example 57A using the procedure of Example 57E substituting the product of Example 202A for the product of Example 57D to provide the crude title compound which was purified by HPLC with TFA to provide the title compound as a trifluoroacetic acid salt (20 mg, 58%). 1H NMR (300 MHz, DMSO-D6) δ ppm: 5.13 (s, 2H), 6.92 (m, 1H), 7.24 (m, 2H), 7.38 (m, 2H), 7.55 (m, 3H), 7.80 (dd, J=8.27, 4.60 Hz, 1H), 8.87 (s, 1H), 9.07 (dd, J=8.27, 1.65 Hz, 1H), 9.12 (dd, J=4.41, 1.84 Hz, 1H), 10.69 (s, 1H); MS (ESI+) m/z 347 (M+H)+.

Example 203

[3-(3,5-Difluoro-benzyloxy)-phenyl]-(7-isopropyl-pyrido[2,3-d]pyrimidin-4-yl)-amine

Example 203A

3-(3,5-Difluoro-benzyloxy)-phenylamine

3-Nitro-phenol was reacted with 1-bromomethyl-3,5-difluoro-benzene according to the procedure from Example 199A substituting 1-bromomethyl-3,5-difluoro-benzene for 1-bromomethyl-3-fluoro-benzene then reduced according to the procedure from Example 199B to provide the title compound.

Example 203B

[3-(3,5-Difluoro-benzyloxy)-phenyl]-(7-isopropyl-pyrido[2,3-d]pyrimidin-4-yl)-amine The product from Example 203A was reacted with the product from Example 36E using the procedure from Example 36I substituting the product from Example 203A for the product from Example 36H to provide the crude material which was purified by HPLC with TFA to provide the title compound as a trifluoroacetic acid salt (26 mg, 67%). 1H NMR (300 MHz, DMSO-D6) δ ppm: 1.35 (d, J=6.99 Hz, 6H), 3.26 (m, 1H), 5.19 (s, 2H), 6.95 (m, 1H), 7.20 (m, 3H), 7.38 (m, 2H), 7.54 (s, 1H), 7.82 (d, J=8.46 Hz, 1H), 8.86 (s, 1H), 9.02 (d, J=8.46 Hz, 1H), 10.89 (s, 1H); MS (ESI+) m/z 407 (M+H)+.

Example 204

[3-(3,5-Difluoro-benzyloxy)-phenyl]-(7-methyl-pyrido[2,3-d]pyrimidin-4-yl)-amine The product of Example 203A was reacted with the product of Example 10B using the procedure of Example 10F substituting the product of Example 203A for the product of Example 10E to provide the crude material which was purified by HPLC with TFA to provide the title compound as a trifluoroacetic acid salt. 1H NMR (300 MHz, DMSO-D6) δ ppm: 2.73 (s, 3H), 5.19 (s, 2H), 6.95 (m, 1H), 7.21 (m, 3H), 7.38 (m, 2H), 7.55 (s, 1H), 7.75 (d, J=8.46 Hz, 1H), 8.87 (s, 1H), 8.98 (d, J=8.46 Hz, 1H), 10.90 (s, 1H); MS (ESI+) m/z 379 (M+H)+.

Example 205

[3-(3,5-Difluoro-benzyloxy)-phenyl]-pyrido[2,3-d]pyrimidin-4-yl-amine

The product of Example 203A was reacted with the product of Example 57A using the procedure of Example 57E substituting the product of Example 203A for the product of Example 57D to provide the crude title compound which was purified by HPLC with TFA to provide the title compound as a trifluoroacetic acid salt. 1H NMR (300 MHz, DMSO-D6) δ ppm: 5.19 (s, 2H), 6.94 (m, 1H), 7.21 (m, 3H), 7.39 (d, J=5.15 Hz, 2H), 7.58 (s, 1H), 7.81 (dd, J=8.09, 4.41 Hz, 1H), 8.87 (s, 1H), 9.10 (m, 2H), 10.79 (s, 1H); MS (ESI+) m/z 365 (M+H)+.

Example 206

4-[3-(7-Methyl-pyrido[2,3-d]pyrimidin-4-ylamino)-phenoxymethyl]-benzonitrile

Example 206A

4-(3-Amino-phenoxymethyl)-benzonitrile

3-Nitro-phenol was reacted with 4-bromomethyl-benzonitrile according to the procedure from Example 199A substituting 4-bromomethyl-benzonitrile for 1-bromomethyl-3-fluoro-benzene then reduced according to the procedure from Example 199B to provide the title compound.

Example 206B

4-[3-(7-Methyl-pyrido[2,3-d]pyrimidin-4-ylamino)-phenoxymethyl]-benzonitrile The product of Example 206A was reacted with the product of Example 10B using the procedure of Example 10F substituting the product of Example 206A for the product of Example 10E to provide the crude material which was purified by HPLC with TFA to provide the title compound as a trifluoroacetic acid salt. 1H NMR (300 MHz, DMSO-D6) δ ppm: 2.71 (s, 3H), 5.27 (s, 2H), 6.92 (m, 1H), 7.38 (m, 2H), 7.59 (s, 1H), 7.68 (m, 3H), 7.89 (d, J=8.46 Hz, 2H), 8.83 (s, 1H), 8.95 (d, J=8.82 Hz, 1H), 10.64 (s, 1H); MS (ESI+) m/z 368 (M+H)+.

Example 207

4-[3-(Pyrido[2,3-d]pyrimidin-4-ylamino)-phenoxymethyl]-benzonitrile

The product of Example 206A was reacted with the product of Example 57A using the procedure of Example 57E substituting the product of Example 206A for the product of Example 57D to provide the crude title compound which was purified by HPLC with TFA to provide the title compound as a trifluoroacetic acid salt. 1H NMR (300 MHz, DMSO-D6) δ ppm: 5.27 (s, 2H), 6.93 (m, 1H), 7.38 (m, 2H) 7.60 (s, 1H), 7.67 (d, J=8.46 Hz, 2H), 7.80 (dd, J=8.46, 4.41 Hz, 1H), 7.90 (d, J=8.46 Hz, 2H), 8.86 (s, 1H), 9.07 (dd, J=8.46, 1.65 Hz, 1H), 9.13 (dd, J=4.41, 1.65 Hz, 1H), 10.72 (s, 1H); MS (ESI+) m/z 354 (M+H)+.

Example 208

3-[3-(7-Isopropyl-pyrido[2,3-d]pyrimidin-4-ylamino)-phenoxymethyl]-benzonitrile

Example 208A 3-(3-Amino-phenoxymethyl)-benzonitrile

3-Nitro-phenol was reacted with 3-bromomethyl-benzonitrile according to the procedure from Example 199A substituting 3-bromomethyl-benzonitrile for 1-bromomethyl-3-fluoro-benzene then reduced according to the procedure from Example 199B to provide the title compound.

Example 208B

3-[3-(7-Isopropyl-pyrido[2,3-d]pyrimidin-4-ylamino)-phenoxymethyl]-benzonitrile

The product from Example 208A was reacted with the product from Example 36E using the procedure from Example 36I substituting the product from Example 208A for the product from Example 36H to provide the crude material which was purified by HPLC with TFA to provide the title compound as a trifluoroacetic acid salt (22 mg, 56%). 1H NMR (300 MHz, DMSO-D6) δ ppm: 1.34 (d, J=6.99 Hz, 6H), 3.26 (m, 1H), 5.22 (s, 2H), 6.93 (m, 1H), 7.38 (m, 2H), 7.62 (m, 2H), 7.77 (d, J=8.46 Hz, 1H), 7.84 (m, 2H), 7.95 (s, 1H), 8.83 (s, 1H), 8.99 (d, J=8.46 Hz, 1H), 10.67 (s, 1H); MS (ESI+) m/z 396 (M+H)+.

Example 209

2-[3-(Pyrido[2,3-d]pyrimidin-4-ylamino)-phenoxymethyl]-benzonitrile

Example 209A 2-(3-Amino-phenoxymethyl)-benzonitrile

3-Nitro-phenol was reacted with 2-bromomethyl-benzonitrile according to the procedure from Example 199A substituting 2-bromomethyl-benzonitrile for 1-bromomethyl-3-fluoro-benzene then reduced according to the procedure from Example 199B to provide the title compound.

Example 209B

2-[3-(Pyrido[2,3-d]pyrimidin-4-ylamino)-phenoxymethyl]-benzonitrile

The product from Example 209A was reacted with the product from Example 36E using the procedure from Example 36I substituting the product from Example 209A for the product from Example 36H to provide the crude material which was purified by HPLC with TFA to provide the title compound as a trifluoroacetic acid salt. 1H NMR (300 MHz, DMSO-D6) δ ppm: 5.30 (s, 2H), 7.02 (m, 1H), 7.42 (m, 2H), 7.59 (m, 2H), 7.78 (m, 2H), 7.85 (dd, J=8.46, 4.41 Hz, 1H), 7.94 (d, J=7.72 Hz, 1H), 8.92 (s, 1H), 9.14 (m, 2H), 11.03 (s, 1H); MS (ESI+) m/z 354 (M+H)+.

Example 210

(3-Benzyloxy-phenyl)-(7-isopropyl-pyrido[2,3-d]pyrimidin-4-yl)-amine

Example 210A

3-Benzyloxy-phenylamine

3-Nitro-phenol was reacted with bromomethyl-benzene according to the procedure from Example 199A substituting bromomethyl-benzene for 1-bromomethyl-3-fluoro-benzene then reduced according to the procedure from Example 199B to provide the title compound.

Example 210B (3-Benzyloxy-phenyl)-(7-isopropyl-pyrido[2,3-d]pyrimidin-4-yl)-amine The product from Example 210A was reacted with the product from Example 36E using the procedure from Example 36I substituting the product from Example 210A for the product from Example 36H to provide the crude material which was purified by HPLC with TFA to provide the title compound as a trifluoroacetic acid salt (5 mg, 10%). 1H NMR (500 MHz, DMSO-D6) δ ppm: 1.33 (d, J=6.84 Hz, 6H), 3.25 (qt, J=6.84 Hz, 1H), 5.13 (s, 2H), 6.89-6.94 (m, J=2.20, 2.20 Hz, 1H), 7.33-7.41 (m, 5H), 7.45-7.48 (m, J=7.32 Hz, 2H), 7.54-7.58 (m, J=2.44, 2.44 Hz, 1H), 7.76 (d, J=8.30 Hz, 1H), 8.84 (s, 1H), 9.02 (d, J=8.30 Hz, 1H); MS ESI+ m/z 371 (M+H)+, ESI− m/z 369 (M−H)−.

Example 211

[3-(3-Bromo-benzyloxy)-phenyl]-(7-isopropyl-pyrido[2,3-d]pyrimidin-4-yl)-amine

Example 211A 3-(3-Bromo-benzyloxy)-phenylamine

3-Nitro-phenol was reacted with 1-bromo-3-bromomethyl-benzene according to the procedure from Example 199A substituting 1-bromo-3-bromomethyl-benzene for 1-bromomethyl-3-fluoro-benzene then reduced according to the procedure from Example 199B to provide the title compound.

Example 211B

[3-(3-Bromo-benzyloxy)-phenyl]-(7-isopropyl-pyrido[2,3-d]pyrimidin-4-yl)-amine

The product from Example 211A was reacted with the product from Example 36E using the procedure from Example 36I substituting the product from Example 211A for the product from Example 36H to provide the crude material which was purified by HPLC with TFA to provide the title compound as a trifluoroacetic acid salt (1 mg, 1%). 1H NMR (300 MHz, DMSO-D6) δ ppm: 1.34 (d, J=6.99 Hz, 6H), 5.16 (s, 2H), 6.94 (td, J=4.50, 2.39 Hz, 1H), 7.39 (td, J=7.63, 3.86 Hz, 3H), 7.46-7.51 (m, 1H), 7.53-7.57 (m, 2H), 7.69 (s, 1H), 7.80 (d, J=8.46 Hz, 1H), 8.86 (s, 1H), 9.01 (d, J=8.46 Hz, 1H), 10.84 (s, 1H); MS ESI+ m/z 451 (M+H)+, ESI− m/z 449 (M−H)−.

Example 212

(7-Isopropyl-pyrido[2,3-d]pyrimidin-4-yl)-[3-(3-methoxy-benzyloxy)-phenyl]-amine

Example 212A 3-(3-Methoxy-benzyloxy)-phenylamine

3-Nitro-phenol was reacted with 1-Bromomethyl-3-methoxy-benzene according to the procedure from Example 199A substituting 1-Bromomethyl-3-methoxy-benzene for 1-bromomethyl-3-fluoro-benzene then reduced according to the procedure from Example 199B to provide the title compound.

Example 212B (7-Isopropyl-pyrido[2,3-d]pyrimidin-4-yl)-[3-(3-methoxy-benzyloxy)-phenyl]-amine The product from Example 212A was reacted with the product from Example 36E using the procedure from Example 36I substituting the product from Example 212A for the product from Example 36H to provide the crude material which was purified by HPLC with TFA to provide the title compound as a trifluoroacetic acid salt (8 mg, 9%). 1H NMR (300 MHz, DMSO-D6) δ ppm: 1.35 (d, J=6.99 Hz, 6H), 3.76 (s, 3H), 5.12 (s, 2H), 6.87-6.98 (m, 2H), 7.00-7.06 (m, 2H), 7.36 (dt, J=19.85, 8.09 Hz, 3H), 7.52 (s, 1H), 7.82 (d, J=8.82 Hz, 1H), 8.88 (s, 1H), 9.02 (d, J=8.46 Hz, 1H), 10.94 (s, 1H); MS ESI+ m/z 401 (M+H)+, ESI− m/z 399 (M−H)−.

Example 213

[3-(4-Bromo-benzyloxy)-phenyl]-pyrido[2,3-d]pyrimidin-4-yl-amine

Example 213A 3-(4-Bromo-benzyloxy)-phenylamine

3-Nitro-phenol was reacted with 1-bromo-4-bromomethyl-benzene according to the procedure from Example 199A substituting 1-bromo-4-bromomethyl-benzene for 1-bromomethyl-3-fluoro-benzene then reduced according to the procedure from Example 199B to provide the title compound.

Example 213B

[3-(4-Bromo-benzyloxy)-phenyl]-pyrido[2,3-d]pyrimidin-4-yl-amine

The product from Example 213A was reacted with the product from Example 36E using the procedure from Example 36I substituting the product from Example 213A for the product from Example 36H to provide the crude material which was purified by HPLC with TFA to provide the title compound as a trifluoroacetic acid salt. 1H NMR (300 MHz, DMSO-D6) δ ppm: 5.13 (s, 2H), 6.82 (dd, J=8.09, 1.84 Hz, 1H), 7.32 (t, J=8.09 Hz, 1H), 7.45 (d, J=8.46 Hz, 3H), 7.61 (d, J=8.46 Hz, 2H), 7.64-7.71 (m, 2H), 9.01 (dd, J=8.46, 1.84 Hz, 1H), 9.08 (dd, J=4.23, 1.65 Hz, 1H), 10.01 (s, 1H); MS ESI+ m/z 407 (M+H)+, ESI+ m/z 429 (M+Na)+, ESI− m/z 405 (M−H)−.

Example 214

[2-(4-Amino-phenylsulfanyl)-5-benzyloxy-phenyl]-(7-methyl-pyrido[2,3-d]pyrimidin-4-yl)-amine

Example 214A

4-Benzyloxy-1-chloro-2-nitro-benzene

A solution of 4-chloro-3-nitro-phenol (2.0 g, 11.5 mmol), 1-bromomethyl-benzene (2.01 g, 11.5 mmol), potassium carbonate (1.65 g, 12.0 mmol) and tetrabutylammonium iodide (0.005 g, 0.0135 mmol) in N,N-dimethylformamide (5 ml) was stirred at room temperature for 16 hours. Afterwards, ice water (10 mL) was added to the solution and the resultant solid was collected by filtration and dried in a vacuum oven to provide the title compound (3.0 g, 99%).

Example 214B 4-(4-Benzyloxy-2-nitro-phenylsulfanyl)-phenylamine

A solution of the compound prepared in Example 214A (1.0 g, 3.80 mmol), 4-aminothiophenol (0.5 g, 4.00 mmol), cesium carbonate (1.3 g, 4 mmol) in dimethylformamide (10 ml) was heated at 40° C. for 16 hours. Afterwards, ice water (50 mL) was added to the solution and the resultant slurry was treated with ethyl acetate (100 ml). The layers were separated and the organic layer was washed with 10% sodium bicarbonate and 10% sodium chloride, then dried over anhydrous sodium sulfate. The drying agent was filtered and solvent was removed under vacuum leaving an orange oil as the title compound, (1.1 g, 83%).

Example 214C

[4-(4-Benzyloxy-2-nitro-phenylsulfanyl)-phenyl]-carbamic acid tert-butyl ester

A solution of the compound from Example 214B (1.1 g, 3.1 mmole) was treated with Boc anhydride (0.9 g, 4.00 mmole) in dioxane (15 ml) and heated at reflux hours. The next day, the solvent was removed under vacuum leaving the title compound as a light tan oil (1.4 g, 100%).

Example 214D

[4-(2-Amino-4-benzyloxy-phenylsulfanyl)-phenyl]-carbamic acid tert-butyl ester

A solution of the product of Example 214C (1.4 g, 3.09 mmol), iron powder (0.70 g, 12 mmol) and ammonium chloride (0.18 g, 3.41 mmol) in a methanol (10 mL), tetrahydrofuran (10 mL), and water (5 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (1.1 g, 90%).

Example 214E

[2-(4-Amino-phenylsulfanyl)-5-benzyloxy-phenyl]-(7-methyl-pyrido[2,3-d]pyrimidin-4-yl)-amine A solution of the product from Example 10B (67 mg, 0.355 mmol), and the product from Example 214D (150 mg, 0.355 mmol) in acetic acid (1 mL) was stirred in an oil bath preheated to 130° C. for 10 minutes. The mixture was then cooled to room temperature, the acetic acid removed under vacuum, and the resultant residue was treated with 50% TFA in $CH_2Cl_2$ (2 ml) for 30 minutes at room temperature. The solvent was evaporated under vacuum and the resultant residue was purified by HPLC with TFA to provide the title compound as a trifluoroacetic acid salt (25 mg, 12%). 1H NMR (300 MHz, DMSO-D6) δ ppm: 2.76 (s, 3H), 5.10 (s, 2H), 6.46-6.61 (m, 2H), 6.97-7.12 (m, 3H), 7.10-7.22 (m, 2H), 7.29-7.51 (m, 6H), 7.85 (d, J=8.46 Hz, 1H), 8.80-8.90 (m, 2H), 8.95 (d, J=8.46 Hz, 1H), 11.70 (s, 1H).

Example 215

[2-(4-Amino-phenylsulfanyl)-5-benzyloxy-phenyl]-(7-isopropyl-pyrido[2,3-d]pyrimidin-4-yl)-amine A solution of the product from Example 36E (80 mg, 0.368 mmol), and the product from Example 214D (160 mg, 0.368 mmol) in acetic acid (2 mL) was stirred in an oil bath preheated to 130° C. for 10 minutes. The mixture was then cooled to room temperature, the acetic acid removed under vacuum and the residue was treated with 50% TFA in $CH_2Cl_2$ (2 ml) for 30 minutes at room temperature. The solvent was evaporated under vacuum and the resultant residue was purified by HPLC with TFA to provide the title compound as a trifluoroacetic acid salt (22 mg, 10%). 1H NMR (300 MHz, DMSO-D6) δ ppm: 1.36 (d, J=6.62 Hz, 6H), 3.19-3.38 (m, 1H), 5.10 (s, 2H), 6.41-6.61 (m, 2H), 6.92-7.18 (m, 5H), 7.27-7.52 (m, 6H), 7.91 (d, J=8.46 Hz, 1H), 8.84 (s, 1H), 9.01 (s, 1H), 11.64 (s, 2H).

Example 216

[2-(4-Amino-phenylsulfanyl)-5-(1-phenyl-ethoxy)-phenyl]-(7-isopropyl-pyrido[2,3-d]pyrimidin-4-yl)-amine Example 216A 1-Chloro-2-nitro-4-(1-phenyl-ethoxy)-benzene A solution of 4-chloro-3-nitro-phenol (2.0 g, 11.5 mmol), 1-bromoethyl-benzene (3.2 g, 17.3 mmol), sodium carbonate (1.80 g, 17.0 mmol) in acetone (20 ml) was heated at reflux for 18 hours. The reaction mixture was cooled, the solids filtered off and the filtrate concentrated to a thick syrup under vacuum. The residue was dissolved in ether (80 ml) and washed with water (20 ml) and 30% KOH solution (2×20 ml) and the solvent is concentrated under vacuum leaving an oily residue as the title compound (3.01 g, 94%).

Example 216B

4-[2-Nitro-4-(1-phenyl-ethoxy)-phenylsulfanyl]-phenylamine

A solution of the compound from Example 216A (1.86 g, 6.95 mmol), 4-aminothiophenol (0.88 g, 7.00 mmol), cesium carbonate (2.3 g, 7.00 mmol) in dimethylformamide (10 ml) was heated at 40° C. for 16 hours. Afterwards ice water (50 mL) was added to the solution and the resultant slurry was treated with ethyl acetate (100 ml). The layers were separated and the organic layer was washed with 10% sodium bicarbonate and 10% sodium chloride, and dried over anhydrous sodium sulfate. The drying agent was filtered and solvent was removed under vacuum leaving an orange oil as the title compound, (2.35 g, 92%).

Example 216C

{4-[2-Nitro-4-(1-phenyl-ethoxy)-phenylsulfanyl]-phenyl}-carbamic acid tert-butyl ester A solution of the compound from Example 216B (2.35 g, 6.4 mmole) was treated with Boc anhydride (1.7 g, 7.70 mmole) in dioxane (20 ml) and heated at reflux for 18 hours. The next day, the solvent was removed under vacuum leaving the title compound as a light tan oil (1.78 g, 60%).

Example 216D

{4-[2-Amino-4-(1-phenyl-ethoxy)-phenylsulfanyl]-phenyl}-carbamic acid tert-butyl ester A solution of the product from Example 216C (1.78 g, 3.80 mmol), iron powder (0.85 g, 15.3 mmol) and ammonium chloride (0.25 g, 4.57 mmol) in a methanol (10 mL), tetrahydrofuran (10 mL), and water (5 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (0.53 g, 32%).

Example 216E

[2-(4-Amino-phenylsulfanyl)-5-(1-phenyl-ethoxy)-phenyl]-(7-isopropyl-pyrido[2,3-d]pyrimidin-4-yl)-amine A solution of the product from Example 36E (57 mg, 0.265 mmol), and the product from Example 216D (116 mg, 0.265 mmol) in acetic acid (2 mL) was stirred in an oil bath preheated to 130° C. for 10 minutes. The mixture was then cooled to room temperature, the acetic acid removed under vacuum and the residue was treated with 50% TFA in $CH_2Cl_2$ (2 ml) for 30 minutes at room temperature. The solvent was evaporated under vacuum and the resultant residue was purified by HPLC with TFA to provide the title compound as a trifluoroacetic acid salt (18 mg, 11%). 1H NMR (300 MHz, DMSO-D6) δ ppm: 1.30 (m, 3H), 1.31 (d, 6H), 3.18-3.34 (m, 1H), 5.48 (s, 1H), 6.50 (s, 1H), 6.86-7.08 (m, 3H), 7.10 (d, J=5.15 Hz, 2H), 7.22-7.50 (m, 5H), 7.86 (s, 1H), 8.37 (s, 1H), 8.48 (s, 1H), 8.78 (s, 1H), 8.94 (s, 1H), 11.19 (s, 1H).

Example 217

[2-(2-Amino-6-chloro-pyrimidin-4-ylsulfanyl)-5-benzyloxy-phenyl]-(7-methyl-pyrido[2,3-d]pyrimidin-4-yl)-amine Example 217A 4-Benzyloxy-2-nitro-phenylamine A solution containing 4-amino-3-nitro phenol (1.09 g, 7.07 mmole), benzylbromide (1.28 g, 7.5 mmole and cesium carbonate (2.43 g, 7.5 mmole) were stirred for 4 days at room temperature. After the reaction was complete, the reaction mixture was poured into ice water (500 ml), stirred 1 hour, and the resultant solid was filtered and dried under vacuum to provide the title compound (1.1 g, 64%).

Example 217B 4-benzyloxy-2-nitrobenzenediazonium tetrafluoroborate

The product from Example 217A (0.5 g, 2.05 mmole) was dissolved in THF (10 ml) and added dropwise to a cold (−20° C.) solution containing boron trifluoride etherate (1.1 ml, 8.20 mmole), and tert-butyl nitrite (0.6 ml, 4.92 mmole) over a 5 min period. The resultant mixture was stirred for 10 minutes at −20° C., then 2 hr at 10° C. The reaction mixture was then poured into hexane (100 ml) and the solid was filtered, washed with ether and dried under vacuum to provide the title compound (0.61 g, 87%).

Example 217C 4-(4-Benzyloxy-2-nitro-phenylsulfanyl)-6-chloro-pyrimidin-2-ylamine A solution of the product from Example 217B (0.1 g, 0.290 mmol) in dimethylsulfoxide (1 ml) was added dropwise to a solution containing potassium thioacetate (0.04 g, 0.350 mmol) in dimethylsulfoxide (1 ml). The reaction mixture immediately began bubbling. The mixture was stirred 90 minutes at room temperature when the bubbling had subsided. The resultant dark green mixture was then treated with an aqueous 3M potassium hydroxide solution (0.1 ml) and stirred an additional 80 minutes, whereupon, solid 4,6 dichloro-2-aminopyrimidine was added and the mixture stirred an additional 60 minutes. The reaction mixture was diluted with ethyl acetate (50 ml), washed with water (20 ml), 10% sodium bicarbonate and 10% sodium chloride solution, dried over sodium sulfate, filtered and the solvent removed under vacuum to provide a tan solid as the title compound (0.1 g, 88%).

Example 217D 4-(2-Amino-4-benzyloxy-phenylsulfanyl)-6-chloro-pyrimidin-2-ylamine A solution of the product from Example 217C (0.1 g, 0.257 mmol), iron powder (0.058 g, 1.03 mmol) and ammonium chloride (0.017 g, 0.310 mmol) in a methanol (5 mL), tetrahydrofuran (5 mL), and water (2 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (0.04 g, 43%).

Example 217E

[2-(2-Amino-6-chloro-pyrimidin-4-ylsulfanyl)-5-benzyloxy-phenyl]-(7-methyl-pyrido[2,3-d]pyrimidin-4-yl)-amine A solution of the product from Example 10B (21 mg, 0.112 mmol), and the product from Example 217D (40 mg, 0.112 mmol) in acetic acid (1 mL) was stirred in an oil bath preheated to 130° C. for 10 minutes. The mixture was then cooled to room temperature, the acetic acid removed under vacuum, and the resultant residue was treated with 50% TFA in $CH_2Cl_2$ (2 ml) for 30 minutes at room temperature. The solvent was evaporated under vacuum and the resultant residue was purified by HPLC with TFA to provide the title compound as a trifluoroacetic acid salt (5 mg, 7%). 1H NMR (300 MHz, DMSO-D6) δ ppm: 2.66 (s, J=6.25 Hz, 3H), 5.21 (s, 2H), 6.53 (s, 1H), 7.07 (s, 1H), 7.14 (dd, J=8.64, 2.76 Hz, 1H), 7.25-7.61 (m, 6H), 7.62-7.72 (m, 1H), 8.52 (s, 1H), 8.66 (d, J=8.82 Hz, 1H), 8.71 (s, 1H), 8.88 (d, J=8.46 Hz, 1H), 10.05 (s, 1H).

Example 218

4-[4-(3-Bromo-benzyloxy)-2-(7-isopropyl-pyrido[2,3-d]pyrimidin-4-ylamino)-phenoxy]-phenol Example 218A 4-[4-(3-Bromo-benzyloxy)-2-nitro-phenoxy]-phenol A solution of hydroquinone (276.4 mg, 2.510 mmol) in anhydrous 3.64 mmol) and heated under a nitrogen atmosphere at 120° for 30 minutes. A solution of 4-(3-Bromo-benzyloxy)-1-chloro-2-nitro-benzene (from Example 15A) (774 mg, 2.259 mmol) in dimethylsulfoxide (4 mL) was added dropwise from an addition funnel over a period of 30 minutes at 120°, the mixture was then stirred at this temperature for 1 hour. The reaction was cooled in an ice bath, then poured into ice water (20 mL) and adjusted the pH to 2 with concentrated hydrochloric acid. The mixture was extracted with ethyl ether (3×100 mL), the combined ethereal extracts were washed with water (3×100 mL) and brine (50 mL), dried over anhydrous sodium sulfate, filtered and concentrated by rotary evaporation under vacuum. Purification of the residue by silica gel flash chromatography using 3% ethyl acetate/methylene chloride as eluent afforded the title compound as a dark yellow solid (386 mg, 0.927 mmol, 41%).

Example 218B

4-[2-Amino-4-(3-bromo-benzyloxy)-phenoxy]-phenol

A mixture of the product from Example 218A (384.6 mg, 0.924 mmol), iron powder (317.4 mg, 5.683 mmol), and ammonium chloride (323.7 mg, 6.052 mmol) in water (3 mL) and ethanol (6 mL) was heated at 70° under a nitrogen atmosphere for 1 hour. The reaction was cooled to room temperature and vacuum filtered, washing the residue with methanol. The filtrate was concentrated under vacuum and azeotroped with toluene (50 mL). The residue was purified by silica gel flash chromatography using a gradient of 7% to 10% ethyl acetate/methylene chloride as eluent to provide the title compound as a beige solid (272 mg, 0.704 mmol, 76%).

Example 218C

4-[4-(3-Bromo-benzyloxy)-2-(7-isopropyl-pyrido[2,3-d]pyrimidin-4-ylamino)-phenoxy]-phenol A solution of the product from Example 36E (25 mg, 0.116 mmol) and the product from Example 218B (44.6 mg, 0.116 mmol) in acetic acid (1 mL) was stirred in an oil bath preheated to 140° C. for 1 hour. The reaction was cooled to room temperature, diluted with hexanes (50 mL), concentrated by rotary evaporation, and co-evaporated with methylene chloride/hexanes (4×). The residue was dried under hi-vacuum overnight, then purified by silica gel flash chromatography using 3% methanol/methylene chloride as eluent to provide the title compound as a light yellow solid (34 mg, 0.0613 mmol, 53%). 1H NMR (300 MHz, DMSO-D6) δ ppm: 1.30 (d, J=6.62 Hz, 6H), 3.09-3.28 (m, 1H), 5.12 (s, 2H), 6.62 (d, J=9.20 Hz, 2H), 6.76 (d, J=8.82 Hz, 2H), 6.82-6.97 (m, 2H), 7.32-7.36 (m, 1H), 7.39 (d, J=7.72 Hz, 1H), 7.45-7.58 (m, 3H), 7.68 (s, 1H), 8.57 (s, 1H), 8.72 (d, J=8.82 Hz, 1H), 9.14 (s, 1H), 9.75 (s, 1H); MS (ESI+) m/z 557/559 (M+H)+.

Example 219

4-[4-(4-Bromo-benzyloxy)-2-(7-isopropyl-pyrido[2,3-d]pyrimidin-4-ylamino)-phenoxy]-phenol Example 219A 4-[2-Amino-4-(4-bromo-benzyloxy)-phenoxy]-phenol 4-(4-Bromo-benzyloxy)-1-chloro-2-nitro-benzene (from Example 16A) was reacted with hydroquinone according to the procedure from Example 39A and reduced according to the procedure from Example 39B to provide the title product.

Example 219B

4-[4-(4-Bromo-benzyloxy)-2-(7-isopropyl-pyrido[2,3-d]pyrimidin-4-ylamino)-phenoxy]-phenol The product from Example 219A was reacted with the product from Example 36E according to the procedure from Example 39C substituting the product from Example 219A for the product from Example 218B to provide the title compound after silica gel chromatography (38 mg, 59%). 1H NMR (300 MHz, DMSO-D6) δ ppm: 1.30 (d, J=6.99 Hz, 6H), 3.10-3.27 (m, 1H), 5.09 (s, 2H), 6.56-6.66 (m, 2H), 6.70-6.79 (m, 2H), 6.81-6.97 (m, 2H), 7.32 (d, J=2.57 Hz, 1H), 7.43 (d, J=8.46 Hz, 2H), 7.53 (d, J=8.46 Hz, 1H), 7.60 (d, J=8.46 Hz, 2H), 8.57 (s, 1H), 8.72 (d, J=8.46 Hz, 1H), 9.14 (s, 1H), 9.74 (s, 1H); MS (ESI+) m/z 557/559 (M+H)+.

Example 220

4-[4-Benzyloxy-2-(7-isopropyl-pyrido[2,3-d]pyrimidin-4-ylamino)-phenoxy]-phenol

Example 220A 4-(2-Amino-4-benzyloxy-phenoxy)-phenol

4-Benzyloxy-1-chloro-2-nitro-benzene (from Example 27A) was reacted with hydroquinone according to the procedure from Example 39A and reduced according to the procedure from Example 39B to provide the title product.

Example 220B

4-[4-Benzyloxy-2-(7-isopropyl-pyrido[2,3-d]pyrimidin-4-ylamino)-phenoxy]-phenol

The product from Example 220A was reacted with the product from Example 36E according to the procedure from Example 39C substituting the product from Example 220A for the product from Example 218B to provide the title compound after silica gel chromatography (58 mg, 65%). 1H NMR (300 MHz, DMSO-D6) δ ppm: 1.30 (d, J=6.99 Hz, 6H), 3.08-3.27 (m, 1H), 5.10 (s, 2H), 6.62 (d, J=9.2 Hz, 2H), 6.74 (d, J=9.2 Hz, 2H), 6.81-6.98 (m, 2H), 7.26-7.61 (m, 7H), 8.57 (s, 1H), 8.72 (d, J=8.46 Hz, 1H), 9.13 (s, 1H), 9.75 (s, 1H); MS (DCI/NH$_3$) m/z 479 (M+H)+.

Example 221

4-[4-Benzyloxy-2-(7-ethyl-pyrido[2,3-d]pyrimidin-4-ylamino)-phenylsulfanyl]-phenol The product from Example 27A was reacted with the product from Example 145A using the procedure from Example 10F substituting the product from Example 27A for the product from Example 10E and substituting the product from Example 145A for the product from Example 10B to provide the title product. 1H NMR (300 MHz, DMSO-D6) δ ppm: 1.32 (t, J=7.72 Hz, 3H), 2.95 (q, J=7.72 Hz, 2H), 5.11 (s, 2H), 6.65 (d, J=8.82 Hz, 2H), 6.91-7.05 (m, 1H), 7.10 (d, J=8.46 Hz, 2H), 7.32-7.50 (m, 6H), 8.12 (d, J=6.99 Hz, 1H), 8.66-8.77 (m, 1H), 9.04 (d, J=8.82 Hz, 1H), 9.63 (s, 1H), 10.28 (s, 1H); MS (APCI) m/z 481 (M+H)+.

Example 222

4-[4-Benzyloxy-2-(7-cyclohexyl-pyrido[2,3-d]pyrimidin-4-ylamino)-phenylsulfanyl]-phenol The product from Example 27A was reacted with the product from Example 135A using the procedure from Example 10F substituting the product from Example 27A for the product from Example 10E and substituting the product from Example 135A for the product from Example 10B to provide the title product. 1H NMR (300 MHz, DMSO-D6) δ ppm: 1.23-1.51 (m, 4H), 1.53-1.79 (m, 4H), 1.80-2.00 (m, 2H), 2.77-3.02 (m, 1H), 5.10 (s, 2H), 6.67 (d, J=8.46 Hz, 2H), 6.88-7.01 (m, 1H), 7.11 (d, J=8.82 Hz, 2H), 7.22-7.31 (m, 1H), 7.32-7.49 (m, 6H), 7.56 (d, J=7.72 Hz, 1H), 8.55 (s, 1H), 8.73 (d, J=8.09 Hz, 1H), 9.94 (s, 1H); MS (APCI) m/z 535 (M+H)+.

Example 223

4-[4-Benzyloxy-2-(7-sec-butyl-pyrido[2,3-d]pyrimidin-4-ylamino)-phenylsulfanyl]-phenol The product from Example 27A was reacted with the product from Example 140A using the procedure from Example 10F substituting the product from Example 27A for the product from Example 10E and substituting the product from Example 140A for the product from Example 10B to provide the title product. 1H NMR (300 MHz, DMSO-D6) δ ppm: 0.82 (t, J=7.35 Hz, 3H), 1.30 (d, J=6.62 Hz, 3H), 1.58-1.73 (m, 1H), 1.75-1.87 (m, 1H), 2.89-3.08 (m, 1H), 5.11 (s, 2H), 6.67 (d, J=8.82 Hz, 2H), 6.85-7.03 (m, 1H), 7.11 (d, J=8.46 Hz, 2H), 7.30-7.50 (m, 6H), 7.56 (d, J=8.82 Hz, 1H), 8.56 (s, 1H), 8.75 (d, J=8.46 Hz, 1H), 9.64 (s, 1H), 9.95 (s, 1H); MS (APCI) m/z

Example 224

4-[4-(2-Chloro-thiazol-5-ylmethoxy)-2-(7-isopropyl-pyrido[2,3-d]pyrimidin-4-ylamino)-phenylsulfanyl]-phenol

Example 224A

4-[2-Amino-4-(2-chloro-thiazol-5-ylmethoxy)-phenylsulfanyl]-phenol

The title compound was prepared as described in Example 16A substituting benzyl bromide with 2-chloro-5-bromomethyl thiazole to provide the title compound (0.38 g, 64%).

Example 224b

4-[4-(2-Chloro-thiazol-5-ylmethoxy)-2-(7-isopropyl-pyrido[2,3-d]pyrimidin-4-ylamino)-phenylsulfanyl]-phenol A solution of the product of Example 36E (40.4 mg, 0.187 mmol), and the product of Example 224A (68 mg, 0.187 mmol) in acetic acid (1 mL) was stirred in an oil bath preheated to 130° C. for 10 minutes. The mixture was then cooled to room temperature, the acetic acid removed under vacuum, and the resultant residue purified by HPLC with TFA to provide the title compound as a trifluoroacetic acid salt (31 mg, 30%). $^1$H NMR (300 MHz, DMSO-$d_6$) δ ppm: 1.35 (d, J=6.99 Hz, 6H) 3.17-3.36 (m, 1H) 5.35 (s, 2H) 6.55 (d, J=7.72 Hz, 1H) 6.58-6.74 (m, 2H) 7.00-7.30 (m, 4H) 7.68-7.95 (m, 2H) 8.76 (s, 1H) 8.94 (d, J=8.46 Hz, 1H) 9.73 (s, 1H) 11.34 (s, 1H); MS (ESI+) m/z 536 (M+H)+, (ESI−) m/z 534 (M−H)−.

Example 225

4-[4-(6-Chloro-pyridin-2-ylmethoxy)-2-(7-methyl-pyrido[2,3-d]pyrimidin-4-ylamino)-phenylsulfanyl]-phenol

Example 225a

4-[2-Amino-4-(6-chloro-pyridin-2-ylmethoxy)-phenylsulfanyl]-phenol

The title compound was prepared as described in Example 16A substituting benzyl bromide with 2-chloro-5-bromomethyl pyridine to provide the title compound (0.63 g, 73%).

Example 225b

4-[4-(6-Chloro-pyridin-2-ylmethoxy)-2-(7-methyl-pyrido[2,3-d]pyrimidin-4-ylamino)-phenylsulfanyl]-phenol A solution of the product of Example 10B (37 mg, 0.197 mmol), and the product of Example 225a (70.7 mg, 0.197 mmol) in acetic acid (2 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (20 mg, 20%). $^1$H NMR (300 MHz, DMSO-$d_6$) δ ppm: 2.70 (s, 3H) 5.18 (s, 2H) 6.65 (d, J=8.82 Hz, 2H) 7.02 (d, J=8.09 Hz, 1H) 7.11 (d, J=8.82 Hz, 2H) 7.19 (d, J=8.82 Hz, 1H) 7.25 (s, 1H) 7.52 (dd, J=13.60, 7.72 Hz, 2H) 7.67 (d, J=8.09 Hz, 1H) 7.93 (t, J=7.72 Hz, 2H) 8.65 (s, 1H) 8.80 (d, J=8.09 Hz, 1H) 9.68 (s, 1H); MS (ESI+) m/z 502 (M+H)+, (ESI−) m/z 500 (M−H)−.

Example 226

4-[4-(6-Chloro-pyridin-2-ylmethoxy)-2-(7-isopropyl-pyrido[2,3-d]pyrimidin-4-ylamino)-phenylsulfanyl]-phenol A solution of the product of Example 36E (36 mg, 0.168 mmol), and the product of Example 225a (60 mg, 0.168 mmol) in acetic acid (1 mL) was stirred in an oil bath preheated to 130° C. for 10 minutes. The mixture was then cooled to room temperature, the acetic acid removed under vacuum, and the resultant residue purified by HPLC with TFA to provide the title compound as a trifluoroacetic acid salt (31 mg, 30%). $^1$H NMR (300 MHz, DMSO-$d_6$) δ ppm: 1.16 (d, J=6.99 Hz, 3H) 1.36 (d, J=6.62 Hz, 3H) 3.20-3.40 (m, 1H) 5.18 (s, 1H) 6.55 (d, J=7.72 Hz, 1H) 6.64 (d, J=8.82 Hz, 2H) 6.77 (s, 1H) 7.04-7.18 (m, 2H) 7.15-7.29 (m, 2H) 7.52 (dd, J=10.48, 7.91 Hz, 2H) 7.77 (d, J=7.72 Hz, 1H) 7.93 (t, J=7.72 Hz, 2H) 8.82 (s, 1H) 8.97 (s, 1H) 9.72 (s, 1H) 11.66 (s, 1H); MS (ESI+) m/z 530 (M+H)+, (ESI−) m/z 528 (M−H)−.

Example 227

4-[2-(7-tert-Butyl-pyrido[2,3-d]pyrimidin-4-ylamino)-4-(3-fluoro-benzyloxy)-phenylsulfanyl]-phenol The product from Example 127A (110 mg, 0.478 mmol) was reacted with the product from Example 28A (164 mg, 0.48 mmol) in 1 mL of glacial acetic acid was heated at 120° C. for 13 min. Cooled to room temperature and removed the acetic acid under vacuum. The crude product was purified by HPLC with TFA to give the title compound as a trifluoroacetic acid salt (134 mg, 44%). $^1$H NMR (300 MHz, DMSO-$d_6$) δ ppm: 1.43 (s, 9H) 5.14 (s, 2H) 6.65 (d, J=8.45 Hz, 2H) 7.17 (m, 4H) 7.29 (d, J=8.45 Hz, 2H) 7.44 (d, J=8.45 Hz, 2H) 7.99 (d, J=7.80 Hz, 1H) 8.72 (s, 1H) 8.93 (d, J=8.45 Hz, 1H) 9.68 (s, 1H) 10.90 (br s, 1H); MS (ESI+) m/z, 527 (M+H−TFA)+; (ESI−) m/z, 525 (M−H−TFA)−.

Example 228

4-[4-[1-(3-Bromo-phenyl)-ethoxy]-2-(pyrido[2,3-d]pyrimidin-4-ylamino)-phenylsulfanyl]-phenol

Example 228a 1-(1-Bromo-ethyl)-4-fluoro-benzene

To a solution of 1-(3-Bromo-phenyl)-ethanol (7.0 g, 34.0 mmol) in dichloromethane (40 mL) was added drop wise phosphorus tribromide (77 g, 34.0 mmol). The mixture was stirred at room temperature for 16 h. The reaction was poured onto ice/water. The aqueous phase was made basic with sodium bicarbonate. The aqueous phase was extracted with dichloromethane. The organic phase was washed with water, brine, and dried over sodium sulfate, filtered and concentrated under vacuum giving the title compound (7.8 g, 80%).

Example 228b

4-[1-(3-Bromo-phenyl)-ethoxy]-1-chloro-2-nitro-benzene

To Example 228a (7.8 g, 30 mmol) in DMF (50 mL) was added 4-chloro-3-nitro-phenol (5.14 g, 30.0 mmol), and K$_2$CO$_3$ (8.18 g, 60 mmol). The mixture was heated at 80° C. for 16 hr. The reaction was cooled and poured into water. The aqueous phase was extracted with ethyl acetate (2×) and the combined phases were washed with water, brine, and dried over sodium sulfate. The organic phase was concentrated under reduced pressure. The residue was purified by silica gel chromatography eluting with (hexanes/ethyl acetate 90:10) to give the title compound (7.0 g, 66%).

Example 228c

4-{4-[1-(3-Bromo-phenyl)-ethoxy]-2-nitro-phenyl-sulfanyl}-phenol

To Example 228b (5.0 g, 14.0 mmol) in DMF (50 mL) was added 4-mercaptophenol (1.7 g, 14.0 mmol), and K$_2$CO$_3$ (3.8 g, 28 mmol). The mixture was heated at 80° C. for 16 hr. The reaction was cooled and poured into water. The aqueous phase was extracted with ethyl acetate (2×) and the combined phases were washed with water, brine, and dried over sodium sulfate. The organic phase was concentrated under reduced pressure. The residue was purified by silica gel chromatography eluting with (hexanes/ethyl acetate/methanol 75:15:5) to give the title compound (5.2 g, 83%).

Example 228d

4-{2-Amino-4-[1-(3-bromo-phenyl)-ethoxy]-phenyl-sulfanyl}-phenol

The product from Example 228c (5.4 g, 12.2 mmol) was reacted with Fe and NH$_4$Cl as described in Example 10E to give the title compound (3.6 g, 76%).

Example 228e

4-[4-[1-(3-Bromo-phenyl)-ethoxy]-2-(pyrido[2,3-d]pyrimidin-4-ylamino)-phenylsulfanyl]-phenol The product from Example 57A (125 mg, 0.72 mmol) was reacted with Example 228d (298 mg, 0.72 mmol) in acetic acid (10 mL) at 125° C. in a sealed tube for 5 minute giving the crude title compound which was purified by HPLC with TFA providing the product as the trifluoroacetic acid (120 mg, 31%). $^1$H NMR (300 MHz, DMSO-d$_6$) δ ppm: 1.54 (d, J=6.25 Hz, 3H) 5.52 (q, J=6.25 Hz, 1H) 6.66 (d, J=8.82 Hz, 2H) 6.85 (s, 1H) 7.07-7.12 (m, 3H) 7.19 (s, 1H) 7.32 (t, J=7.72 Hz, 1H) 7.39-7.49 (m, 2H) 7.61 (s, 2H) 8.57 (s, 1H) 8.80 (s, 1H) 9.06 (s, 1H) 9.65 (s, 1H); MS (ESI−) m/z 545 (M−H)−.

Example 229

4-[4-[1-(3-Bromo-phenyl)-ethoxy]-2-(7-methyl-pyrido[2,3-d]pyrimidin-4-ylamino)-phenylsulfanyl]-phenol The product from Example 10B (110 mg, 0.58 mmol) was reacted with Example 228d (243 mg, 0.58 mmol) in acetic acid (10 mL) at 125° C. in a sealed tube for 5 minute giving the crude title compound which was purified by HPLC with TFA providing the product as the trifluoroacetic acid (100 mg, 30%). $^1$H NMR (300 MHz, DMSO-d$_6$) δ ppm: 1.33 (d, J=6.25 Hz, 3H) 2.53 (s, 3H) 5.31 (q, J=6.43 Hz, 1H) 6.44 (d, J=8.82 Hz, 2H) 6.68 (dd, J=8.82, 2.57 Hz, 1H) 6.85-6.92 (m, 3H) 6.95 (d, J=2.57 Hz, 1H) 7.11 (t, J=7.72 Hz, 1H) 7.19-7.27 (m, 2H) 7.40 (s, 1H) 7.44 (d, J=8.46 Hz, 1H) 8.44 (s, 1H) 8.56 (d, J=8.46 Hz, 1H); MS (ESI+) m/z 560 (M+H)+.

Example 230

4-[4-[1-(3-Bromo-phenyl)-ethoxy]-2-(7-isopropyl-pyrido[2,3-d]pyrimidin-4-ylamino)-phenylsulfanyl]-phenol The product from Example 36E (130 mg, 0.60 mmol) was reacted with Example 228d (250 mg, 0.60 mmol) in acetic acid (10 mL) at 125° C. in a sealed tube for 5 minute giving the crude title compound which was purified by HPLC with TFA providing the product as the trifluoroacetic acid (140 mg, 39%). $^1$H NMR (300 MHz, DMSO-d$_6$) δ ppm: 1.34 (d, J=6.99 Hz, 6H) 1.54 (d, J=6.25 Hz, 3H) 3.26 (q, 1H) 5.52 (q, J=6.62 Hz, 1H) 6.65 (d, J=8.46 Hz, 2H) 6.92 (dd, J=8.82, 2.94 Hz, 1H) 7.10 (m, 4H) 7.32 (t, J=7.72 Hz, 1H) 7.39-7.50 (m, 2H) 7.60 (s, 1H) 7.79 (d, J=8.46 Hz, 1H) 8.70 (s, 1H) 8.86 (d, J=8.46 Hz, 1H) 9.72 (s, 1H); MS (ESI+) m/z 588 (M+H)+.

Example 231

4-[4-(3-Bromo-benzyloxy)-2-(7-tert-butyl-pyrido[2,3-d]pyrimidin-4-ylamino)-phenylsulfanyl]-phenol The product from Example 127A (147 mg, 0.63 mmol) and the product from Example 15A (256 mg, 0.63 mmol) were heated in 2 mL of glacial acetic acid at 120° C. for 15 min. Cooled to room temperature and the acetic acid was removed under vacuum. The crude product was purified by HPLC with TFA to provide the title compound as a trifluoroacetic acid salt 45 mg, 10%). $^1$H NMR (300 MHz, DMSO-d$_6$) δ ppm: 1.43 (s, 9H) 5.13 9 (s, 2H) 6.66 (d, J=8.83 Hz, 2H) 7.01 (d, J=6.62 Hz, 1H) 7.11 (d, J=8.83 Hz, 2H) 7.19 (m, 1H) 7.37 (m, 1H) 7.46 (d, J=7.72 Hz, 1H) 7.54 (D, J=6.62 Hz, 1H) 7.66 (s, 1H) 7.95 (d, J=8.09 Hz, 1H) 8.69 (s, 1H) 8.88 (D, J=8.83 Hz, 1H) 9.68 (s, 1H); MS (ESI+) m/z, 587, 589 (M+H−TFA)+; (ESI−) m/z, 585, 587 (M−H−TFA)−.

Example 232

4-[4-(3-Bromo-phenoxymethyl)-2-(7-isopropyl-pyrido[2,3-d]pyrimidin-4-ylamino)-phenylsulfanyl]-phenol

Example 232A

4-[2-Amino-4-(3-bromo-phenoxymethyl)-phenylsulfanyl]-phenol

A solution of 4-[4-(3-Bromo-phenoxymethyl)-2-nitro-phenylsulfanyl]-phenol (325 mg, 0.752 mmol), iron dust (210 mg, 3.76 mmol) and ammonium chloride (60 mg, 1.13 mmol) in tetrahydrofuran (5 mL), water (1.5 mL) and ethanol (5 mL) was heated at reflux for 2.5 hours. After cooling to room temperature, the solution was filtered through a pad of celite, which was washed with methanol. The filtrate was then concentrated under vacuum, then dissolved in water (20 mL) and extracted with ethyl acetate (2×20 mL). The organic extracts were dried and concentrated under vacuum to provide the title compound as a light yellow solid (240 mg, 79%).

Example 232B

4-[4-(3-Bromo-phenoxymethyl)-2-(7-isopropyl-pyrido[2,3-d]pyrimidin-4-ylamino)-phenylsulfanyl]-phenol A solution of the product from Example 232A (85 mg, 0.211 mmol) and the product from Example 36E (46 mg, 0.211 mmol) in acetic acid (3 mL) was heated at 130° C. for 15 minutes. The solution was then allowed to cool to room temperature, the acetic acid removed under vacuum and the resultant residue purified by HPLC with TFA to provide the title compound as a trifluoroacetic acid salt (63 mg, 43%). $^1$H NMR (300 MHz, DMSO-$d_6$) δ ppm: 1.35 (d, J=7.0 Hz, 6H), 3.25 (m, 1H), 5.13 (s, 2H), 6.77 (d, J=8.8 Hz, 2H), 7.02 (d, J=8.1 Hz, 2H), 7.15 (m, 1H), 7.23 (m, 4H), 7.36 (m 1H), 7.46 (s, 1H), 7.83 (d, J=8.8 Hz, 1H), 8.76 (s, 1H), 8.95 (d, J=8.8 Hz, 1H), 9.88 (s, 1H), 11.22 (bs, 1H); MS (ESI)+ m/z 573/575 (M+H)+.

Example 233

4-[4-(3-Bromo-phenoxymethyl)-2-(7-methyl-pyrido[2,3-d]pyrimidin-4-ylamino)-phenylsulfanyl]-phenol A solution of the product from Example 232A (60 mg, 0.149 mmol) and the product from Example 10B (28 mg, 0.149 mmol) in acetic acid (3 mL) was heated at 130° C. for 15 minutes. The solution was then allowed to cool to room temperature, the acetic acid removed under vacuum and the resultant residue purified by HPLC with TFA to provide the title compound as a trifluoroacetic acid salt (46 mg, 47%). $^1$H NMR (300 MHz, DMSO-$d_6$) δ ppm: 2.72 (s, 3H), 5.12 (s, 2H), 6.77 (d, J=8.5 Hz, 2H), 7.02 (m, 2H), 7.16 (m, 1H), 7.23 (m, 4H), 7.36 (m 1H), 7.47 (s, 1H), 7.70 (d, J=8.8 Hz, 1H), 8.70 (s, 1H), 8.86 (d, J=8.5 Hz, 1H), 9.87 (s, 1H), 10.95 (bs, 1H); MS (ESI)+ m/z 545/547 (M+H)+.

Example 234

4-[4-(2,5-Difluoro-benzyloxy)-2-(pyrido[2,3-d]pyrimidin-4-ylamino)-phenylsulfanyl]-phenol

Example 234a

2-Bromomethyl-1,4-difluoro-benzene

To a solution of (2,5-difluoro-phenyl)-methanol (4.8 g, 33.6 mmol) in dichloromethane (40 mL) was added drop wise phosphorus tribromide (94 g, 33.6 mmol). The mixture was stirred at room temperature for 16 h. The reaction was poured onto ice/water. The aqueous phase was made basic with sodium bicarbonate. The aqueous phase was extracted with dichloromethane. The organic phase was concentrated under reduced pressure. The residue was purified by silica gel chromatography eluting with (hexanes/ethyl acetate 90:10) to give the title compound (3.5 g, 50%).

Example 234b

1-Chloro-4-(2,5-fluoro-benzyloxy)-2-nitro-benzene

To Example 234a (2.2 g, 10.4 mmol) in DMF (50 mL) was added 4-chloro-3-nitro-phenol (1.8 g, 10.4 mmol), and K$_2$CO$_3$ (2.87 g, 20.8 mmol). The mixture was heated at 80° C. for 16 h. The reaction was cooled and poured into water. The aqueous phase was extracted with ethyl acetate (2×) and the combined phases were washed with water, brine, and dried over sodium sulfate. The organic phase was concentrated under reduced pressure. The residue was purified by silica gel chromatography eluting with (hexanes/ethyl acetate 90:10) to give the title compound (2.48 g, 66%).

Example 234c

4-[4-(2,5-Difluoro-benzyloxy)-2-nitro-phenylsulfanyl]-phenol

To Example 234b (2.5 g, 8.3 mmol) in DMF (50 mL) was added 4-mercaptophenol (1.0 g, 8.3 mmol), and K$_2$CO$_3$ (2.3 g, 16.5 mmol). The mixture was heated at 80° C. for 16 h. The reaction was cooled and poured into water. The aqueous phase was extracted with ethyl acetate (2×) and the combined phases were washed with water, brine, and dried over sodium sulfate. The organic phase was concentrated under reduced pressure. The residue was purified by flash chromatography eluting with (hexanes/ethyl acetate/methanol 75:15:5) to give the title compound (1.7 g, 52%).

Example 234d

4-[2-Amino-4-(2,5-difluoro-benzyloxy)-phenylsulfanyl]-phenol

The product from Example 234c (1.70 g, 4.2 mmol) was reacted with Fe and NH$_4$Cl as described in Example 10E to give the title compound (1.3 g, 84%).

Example 234e

4-[4-(2,5-Difluoro-benzyloxy)-2-(pyrido[2,3-d]pyrimidin-4-ylamino)-phenylsulfanyl]-phenol The product from Example 57A (100 mg, 0.57 mmol) was reacted with Example 234d (206 mg, 0.57 mmol) in acetic acid (10 mL) at 125° C. in a sealed tube for 5 minute giving the crude title compound which was purified by HPLC with TFA providing the product as the trifluoroacetic acid (140 mg, 39%). $^1$H NMR (300 MHz, DMSO-$d_6$) δ ppm: 5.13 (s, 2H) 6.67 (d, J=8.46 Hz, 2H) 6.93-7.01 (m, 1H) 7.10-7.16 (m, 3H) 7.22-7.37 (m, 4H) 7.41-7.52 (m, J=5.79, 5.79, 2.76 Hz, 1H) 7.64 (dd, J=8.09, 4.41 Hz, 1H) 8.53 (s, 1H) 8.84 (d, J=7.72 Hz, 1H) 9.05 (s, 1H); MS (ESI+) m/z 489 (M+H)+.

Example 235

4-[4-(2,5-Difluoro-benzyloxy)-2-(7-isopropyl-pyrido[2,3-d]pyrimidin-4-ylamino)-phenylsulfanyl]-phenol The product from Example 36E (100 mg, 0.46 mmol) was reacted with Example 234d (206 mg, 0.46 mmol) in acetic acid (10 mL) at 125° C. in a sealed tube for 5 minute giving the crude title compound which was purified by HPLC with TFA providing the product as the trifluoroacetic acid (140 mg, 39%). $^1$H NMR (300 MHz, DMSO-$d_6$) δ ppm: 1.34 (d, J=6.62 Hz, 6H) 5.14 (s, 2H) 6.66 (d, J=8.46 Hz, 2H) 7.06 (d, J=2.57 Hz, 1H) 7.12 (d, J=8.46 Hz, 2H) 7.21-7.35 (m, 4H) 7.44 (s, 1H) 7.77 (d, J=8.46 Hz, 1H) 8.69 (s, 1H) 8.88 (d, J=8.46 Hz, 1H) 9.70 (s, 1H); MS (ESI+) m/z 531 (M+H)+.

Example 236

4-[4-(2-Chloro-5-fluoro-benzyloxy)-2-(7-isopropyl-pyrido[2,3-d]pyrimidin-4-ylamino)-phenylsulfanyl]-phenol

Example 236a

2-Bromomethyl-1-chloro-4-fluoro-benzene

To a solution of (2-chloro-5-fluoro-phenyl)-methanol (5.0 g, 31.1 mmol) in dichloromethane (40 mL) was added drop wise phosphorus tribromide (87 g, 31.1 mmol). The mixture was stirred at room temperature for 16 h. The reaction was poured onto ice/water. The aqueous phase was made basic with sodium bicarbonate. The aqueous phase was extracted with dichloromethane. The organic phase was concentrated under reduced pressure. The residue was purified by silica gel chromatography eluting with (hexanes/ethyl acetate 90:10) to give the title compound (5.75 g, 82.5%).

Example 236b

1-Chloro-4-(2-chloro-5 0flouro-benzyloxy)-2-nitro-benzene

To Example 236a (5.7 g, 25.7 mmol) in DMF (50 mL) was added 4-chloro-3-nitro-phenol (4.46 g, 25.7 mmol), and $K_2CO_3$ (7.10 g, 51.4 mmol). The mixture was heated at 80° C. for 16 h. The reaction was cooled and poured into water. The aqueous phase was extracted with ethyl acetate (2×) and the combined phases were washed with water, brine, and dried over sodium sulfate. The organic phase was concentrated under reduced pressure. The residue was purified by silica gel chromatography eluting with (hexanes/ethyl acetate 90:10) to give the title compound (7.0 g, 86%).

Example 236c

4-[4-(2-Chloro-5-fluoro-benzyloxy)-2-nitro-phenylsulfanyl]-phenol

To Example 236b (2.5 g, 8.3 mmol) in DMF (50 mL) was added 4-mercaptophenol (1.0 g, 8.3 mmol), and $K_2CO_3$ (2.3 g, 16.5 mmol). The mixture was heated at 80° C. for 16 h. The reaction was cooled and poured into water. The aqueous phase was extracted with ethyl acetate (2×) and the combined phases were washed with water, brine, and dried over sodium sulfate. The organic phase was concentrated under reduced pressure. The residue was purified by silica gel chromatography eluting with (hexanes/ethyl acetate/methanol (70:25:5) to give the title compound (5.0 g, 78%).

Example 236d

4-[2-Amino-4-(2-chloro-5-fluoro-benzyloxy)-phenylsulfanyl]-phenol

The product from Example 236c (4.2 g, 10.2 mmol) was reacted with Fe and $NH_4Cl$ as described in Example 10E to give the title compound (3.0 g, 77%).

Example 236e

4-[4-(2-Chloro-5-fluoro-benzyloxy)-2-(7-isopropyl-pyrido[2,3-d]pyrimidin-4-ylamino)-phenylsulfanyl]-phenol The product from Example 36E (125 mg, 0.72 mmol) was reacted with Example 236d (298 mg, 0.72 mmol) in acetic acid (10 mL) at 125° C. in a sealed tube for 5 minute giving the crude title compound which was purified by adding ethyl ether to the residue providing the desired product as the acetic acid (225 mg, 66%). $^1H$ NMR (300 MHz, DMSO-$d_6$) δ ppm: 1.32 (d, J=6.99 Hz, 6H) 3.21 (q, 1H) 5.15 (s, 2H) 6.69 (d, J=8.46 Hz, 2H) 6.99 (dd, 1H) 7.13 (d, J=8.46 Hz, 4H) 7.25-7.35 (m, 2H) 7.49 (dd, J=9.38, 3.13 Hz, 1H) 7.54-7.62 (m, J=8.82, 5.15 Hz, 3H) 8.55 (1H, s)(1 8.74 (s, 1H) 9.66 (s, 1H) 9.98 (s, 1H); MS (ESI−) m/z 547 (M+H)+.

Example 237

4-[5-Benzyloxy-2-(7-isopropyl-pyrido[2,3-d]pyrimidin-4-ylamino)-phenylsulfanyl]-phenol

Example 237A

4-Benzyloxy-2-fluoro-1-nitro-benzene

A mixture of 3-fluoro-4-nitrophenol (0.30 g, 1.91 mmol), benzyl bromide (0.36 g, 2.10 mmol, 1.1 eq), potassium carbonate (0.792 g, 5.73 mmol, 3.0 eq) and tetrabutylammonium iodide (5.0 mg, 0.014 mmol, 0.007 eq) in dimethylformamide (5 mL) was stirred at room temperature for 16 h. Water (20 mL) was added to the reaction mixture and the resulting solid precipitate was isolated by vacuum filtration and dried to provide the title compound (0.455 g, 96%) as a yellow solid.

Example 237B 4-(5-Benzyloxy-2-nitro-phenylsulfanyl)-phenol

The product of Example 237A (0.301 g, 1.22 mmol), 4-mercaptophenol (0.184 g, 1.46 mmol, 1.2 eq) and cesium carbonate (0.952 g, 2.92 mmol, 2.4 eq) in dimethylformamide (10 mL) was heated in a 100° C. oil bath for 3 hours and then cooled to room temperature. Water (20 mL) was added and the mixture was stirred at room temperature for 2 hours, and the resulting solid was isolated by vacuum filtration and dried to provide the title compound (0.405 g, 94%) as a yellow solid.

Example 237C 4-(2-Amino-5-benzyloxy-phenylsulfanyl)-phenol

The product of Example 237B (0.390 g, 1.10 mmol), iron powder (0.248 g, 4.41 mmol, 4.0 eq) and ammonium chloride (0.071 g, 1.32 mmol, 1.2 eq) in tetrahydrofuran (6 mL), methanol (6 mL) and water (2 mL) was heated under reflux for 16 hours and then cooled to room temperature. The reaction mixture was filtered through Celite, rinsing with methanol, and the filtrate was evaporated under reduced pressure to provide the title compound (0.340 g, 95%) as a gray powder that was used in subsequent reactions without further purification.

Example 237D

4-[5-Benzyloxy-2-(7-isopropyl-pyrido[2,3-d]pyrimidin-4-ylamino)-phenylsulfanyl]-phenol The product of Example 237C (0.0908 g, 0.281 mmol) and the product of Example 36E (0.0607 g, 0.281 mmol) in glacial acetic acid (2 mL) was heated in a 140° C. oil bath for 10 min, cooled to room temperature, and evaporated under reduced pressure. The residue was purified by column chromatography on silica gel eluting with 5% methanol/dichloromethane to provide the title compound (0.0368 g, 27%) as a tan solid. 1H NMR (300 MHz, DMSO-D6) δ ppm: 9.88 (s, 2H), 8.82 (d, J=8.46 Hz, 1H), 8.52 (s, 1H), 7.58 (d, J=8.46 Hz, 1H), 7.28-7.42 (m, 5H), 7.19-7.28 (m, 3H), 6.87 (dd, J=8.64, 2.76 Hz, 1H), 6.75-6.84 (m, 2H), 6.38 (d, J=2.57 Hz, 1H), 4.99 (s, 2H), 3.14-3.27 (m, 1H), 1.32 (d, J=6.99 Hz, 6H); MS (ESI+) m/z 495.2 (M+H)+, (ESI−) m/z 493.2 (M−H)−.

Example 238

4-[2-(7-Methyl-pyrido[2,3-d]pyrimidin-4-ylamino)-4-styryl-phenylsulfanyl]-phenol Example 238A 4-(4-Bromo-2-nitro-phenylsulfanyl)-phenol A mixture of 4-bromo-1-fluoro-2-nitrobenzene (0.44 g, 2.0 mmol), 4-mercaptophenol (0.303 g, 2.4 mmol), and cesium carbonate (1.56 g, 4.8 mmol, 2.4 eq) in dimethylformamide (10 mL) was heated in a 100° C. oil bath for 3 hours and then cooled to room temperature. The reaction mixture was poured over ice water (50 mL), adjusted to pH 3 by the addition of 1N aqueous hydrochloric acid, and extracted with ethyl acetate (3×100 mL). The combined organic layers were dried over anhydrous magnesium sulfate, filtered and evaporated to provide the title compound as a thick yellow oil (0.70 g, >100%) that was utilized without further purification.

Example 238B 4-(2-Amino-4-bromo-phenylsulfanyl)-phenol

A mixture of the product from Example 238A (0.302 g, 0.926 mmol), iron powder (0.208 g, 3.7 mmol, 4.0 eq) and ammonium chloride (0.059 g, 1.11 mmol, 1.2 eq) in a mixture of methanol (6 mL), tetrahydrofuran (6 mL), and water (2 mL) was heated under reflux for 5 hours and then cooled to room temperature. The reaction mixture was filtered through Celite and the filter pad was rinsed with methanol (25 mL). The filtrate was evaporated under reduced pressure to leave a brown glassy solid (0.27 g, 99%) that was utilized without further purification.

Example 238C

4-[4-Bromo-2-(7-methyl-pyrido[2,3-d]pyrimidin-4-ylamino)-phenylsulfanyl]-phenol

A mixture of the product from Example 238B (0.158 g, 0.533 mmol) and the product from Example 10B (0.100 g, 0.533 mmol) in glacial acetic acid (2 mL) was heated in a 130° C. oil bath for 30 min. An additional amount of the product from Example 10B (0.060 g, 0.319 mmol) was added and the reaction mixture was heated for an additional 30 min at 130° C. The reaction mixture was then cooled to room temperature and the solvent evaporated under reduced pressure. The residue was triturated with 2-propanol, and the resulting solid isolated by vacuum filtration and dried to provide the title compound (0.083 g, 36% yield) as a beige solid.

Example 238D

4-[2-(7-Methyl-pyrido[2,3-d]pyrimidin-4-ylamino)-4-styryl-phenylsulfanyl]-phenol A mixture of the product from Example 238C (0.0791 g, 0.180 mmol), styrene (0.176 g, 1.69 mmol, 9.4 eq), palladium (II) acetate (6.2 mg, 0.0276 mmol, 0.15 eq), tri-o-tolylphosphine (13.3 mg, 0.0437 mmol, 0.24 eq), and di-isopropyl ethylamine (0.697 g, 0.539 mmol, 3.0 eq) in dimethylformamide (2 mL) was heated in a 130° C. oil bath for 98 hours. The mixture was then cooled to room temperature and the solvent evaporated under a stream of nitrogen gas. The residue was partitioned between ethyl acetate and water and the aqueous layer further extracted with ethyl acetate. The combined organic layers were dried over anhydrous magnesium sulfate, filtered and evaporated. The residue was purified by HPLC with TFA to provide the title compound as a trifluoroacetic acid salt (6.1 mg, 10% yield). 1H NMR (300 MHz, DMSO-D6) δ ppm: 11.27 (s, 1H), 9.89 (s, 1H), 8.93 (d, J=8.09 Hz, 1H), 8.79 (s, 1H), 7.78 (d, J=8.82 Hz, 1H), 7.66 (s, 1H), 7.58 (d, J=7.35 Hz, 2H), 7.52 (dd, J=8.09, 1.47 Hz, 1H), 7.37 (t, J=7.35 Hz, 2H), 7.19-7.31 (m, 5H), 7.00 (d, J=8.09 Hz, 1H), 6.73-6.81 (m, 2H), 2.75 (s, 3H).

Example 239

(7-Methyl-pyrido[2,3-d]pyrimidin-4-yl)-(2-phenylsulfanyl-5-styryl-phenyl)-amine

Example 239A (5-Bromo-2-phenylsulfanyl-phenyl)-(7-methyl-pyrido[2,3-d]pyrimidin-4-yl)-amine 5-bromo-2-(phenylthio)benzenamine was prepared according to procedures similar to those described in Examples 6a, 6b, and 6c substituting benzenethiol for 4-mercaptophenol and 4-bromo-2-nitrophenol for 4-methyl-2-nitro phenol.

A mixture of the product from Example 10B (0.188 g, 1.0 mmol) and 5-bromo-2-(phenylthio)benzenamine (0.280 g, 1.0 mmol) in glacial acetic acid (2 mL) was heated in a 130° C. oil bath for 30 min. The reaction mixture was then cooled to room temperature and the solvent evaporated under reduced pressure. The residue was triturated with methanol, and the resulting solid isolated by vacuum filtration and dried to provide the title compound (0.276 g, 65% yield) as a beige solid.

Example 239B (7-Methyl-pyrido[2,3-d]pyrimidin-4-yl)-(2-phenylsulfanyl-5-styryl-phenyl)-amine A mixture of the product from Example 239A (0.127 g, 0.30 mmol), styrene (0.133 g, 1.27 mmol, 4.3 eq), palladium (II) acetate (5.3 mg, 0.0236 mmol, 0.08 eq), tri-o-tolylphosphine (17.7 mg, 0.058 mmol, 0.19 eq), and triethylamine (0.0913 g, 0.90 mmol, 3.0 eq) in dimethylformamide (3 mL) was heated in a 130° C. oil bath for 98 hours. The mixture was then cooled to room temperature and the solvent evaporated under a stream of nitrogen gas. The residue was partitioned between ethyl acetate and water and the aqueous layer further extracted with ethyl acetate. The combined organic layers were dried over anhydrous magnesium sulfate, filtered and evaporated. The residue was purified by HPLC with TFA to provide the title compound as a trifluoroacetic acid salt (4.0 mg, 2.4%). 1H NMR (300 MHz, DMSO-D6) δ ppm: 11.21 (s, 1H), 8.85 (d, J=8.46 Hz, 1H), 8.74 (s, 1H), 7.68-7.78 (m, 2H), 7.55-7.65 (m, J=7.35 Hz, 3H), 7.19-7.46 (m, 1H), 2.72 (s, 3H); MS (ESI+) m/z 447.2 (M+H)+, (ESI−) m/z 445.2 (M−H)−.

Example 240

(7-Methyl-pyrido[2,3-d]pyrimidin-4-yl)-(3-styryl-phenyl)-amine

Example 240A

(3-Bromo-phenyl)-(7-methyl-pyrido[2,3-d]pyrimidin-4-yl)-amine

A mixture of the product from Example 10B (0.206 g, 1.09 mmol) and 3-bromoaniline (0.188 g, 1.09 mmol) in glacial acetic acid (1 mL) was heated in a 130° C. oil bath for 15 min. The reaction mixture was then cooled to room temperature and the solvent evaporated under reduced pressure. The residue was triturated with methanol, and the resulting solid isolated by vacuum filtration and dried to provide the title compound (0.126 g, 37%) as a beige solid.

Example 240B

(7-Methyl-pyrido[2,3-d]pyrimidin-4-yl)-(3-styryl-phenyl)-amine

A mixture of the product from Example 240A (0.063 g, 0.20 mmol), styrene (0.0412 g, 0.40 mmol, 2.0 eq), palladium (II) acetate (0.9 mg, 0.004 mmol, 0.02 eq), tri-o-tolylphosphine (2.4 mg, 0.008 mmol, 0.04 eq), and triethylamine (0.0607 g, 0.60 mmol, 3.0 eq) in dimethylformamide (2 mL) was heated in a 120° C. oil bath for 4 hours. The mixture was then cooled to room temperature and the solvent evaporated under a stream of nitrogen gas. The residue was partitioned between ethyl acetate and water and the aqueous layer further extracted with ethyl acetate. The combined organic layers were dried over anhydrous magnesium sulfate, filtered and evaporated. The residue was recrystallized from methanol and dried to provide the title compound as yellow crystals (11.8 mg, 17%). 1H NMR (300 MHz, DMSO-D6) δ ppm: 10.01 (s, 1H), 8.89 (d, J=8.46 Hz, 1H), 8.72 (s, 1H), 8.03 (s, 1H), 7.72-7.85 (m, J=6.07, 2.76 Hz, 1H), 7.64 (d, J=6.99 Hz, 2H), 7.57 (d, J=8.82 Hz, 1H), 7.35-7.49 (m, 4H), 7.24-7.35 (m, 3H), 2.63-2.74 (m, 3H); MS (ESI$^+$) m/z 339.1 (M+H)$^+$, (ESI$^-$) m/z 337.1 (M−H)$^-$.

Example 241

(2-Methyl-5-phenethyl-phenyl)-(7-methyl-pyrido[2,3-d]pyrimidin-4-yl)-amine

Example 241A

1-Methyl-2-nitro-4-styryl-benzene

A mixture of 4-bromo-2-nitrotoluene (0.432 g, 2.0 mmol), styrene (0.250 g, 2.40 mmol, 1.2 eq), palladium(II) acetate (4.5 mg, 0.020 mmol, 0.01 eq), tri-o-tolylphosphine (12.2 mg, 0.04 mmol, 0.02 eq), and triethylamine (0.405 g, 4.0 mmol, 2.0 eq) in dimethylformamide (2 mL) was heated in a 120° C. oil bath for 4 hours. The mixture was then cooled to room temperature and the solvent evaporated under a stream of nitrogen gas. The residue was partitioned between ethyl acetate and water and the aqueous layer further extracted with ethyl acetate. The combined organic layers were dried over anhydrous magnesium sulfate, filtered and evaporated. The residue was purified by chromatography on silica gel, eluting with a hexane/ethyl acetate gradient to provide the title compound as a yellow solid (166 mg, 35% yield).

Example 241B

2-Methyl-5-phenethyl-phenylamine

A mixture of the product from Example 241A (0.166 g, 0.694 mmol) and 10% palladium on charcoal (18.4 mg, 0.025 eq), in ethanol (10 mL) was stirred under one atmosphere of hydrogen for 16 hours. The reaction mixture was then filtered through Celite and the solvent evaporated under reduced pressure to provide the title compound as a slightly red oil (0.141 g, 96% yield).

Example 241C

(2-Methyl-5-phenethyl-phenyl)-(7-methyl-pyrido[2,3-d]pyrimidin-4-yl)-amine

A mixture of the product from Example 10B (0.041 g, 0.22 mmol) and the product from Example 241B (0.046 g, 0.22 mmol) in glacial acetic acid (1 mL) was heated in a 130° C. oil bath for 15 min. The reaction mixture was then cooled to room temperature and the solvent evaporated under reduced pressure. The residue was triturated with methanol, and the resulting solid isolated by vacuum filtration and dried to provide the title compound (0.0121 g, 16% yield) as a slightly orange solid. 1H NMR (300 MHz, CHCl$_3$-d) δ ppm: 8.84 (s, 1H), 8.23 (d, J=8.46 Hz, 1H), 7.44 (s, 1H), 7.15-7.37 (m, 8H), 7.07 (dd, J=7.72, 1.47 Hz, 1H), 2.93 (s, 4H), 2.78 (s, 3H), 2.28 (s, 3H); MS (ESI$^+$) m/z 355.3 (M+H)$^+$, (ESI$^-$) m/z 353.2 (M−H)$^-$.

Example 242

(7-Isopropyl-pyrido[2,3-d]pyrimidin-4-yl)-(2-methyl-5-phenethyl-phenyl)-amine A mixture of the product from Example 241B (46.2 mg, 0.219 mmol) and the product from Example 36E (47.3 mg, 0.219 mmol) in glacial acetic acid (1 mL) was heated in a 130° C. oil bath for 15 min. The reaction mixture was then cooled to room temperature and the solvent evaporated under reduced pressure. The residue was purified by HPLC with TFA to provide the title compound as a trifluoroacetic acid salt (0.0131 g, 10%). 1H NMR (300 MHz, DMSO-D6) δ ppm: 11.09 (s, 1H), 8.94 (d, J=8.46 Hz, 1H), 8.74 (s, 1H), 7.82 (d, J=8.46 Hz, 1H), 7.12-7.35 (m, 8H), 3.21-3.33 (m, 1H), 2.89 (s, 4H), 2.15 (s, 3H), 1.35 (d, J=6.62 Hz, 6H); MS (ESI$^+$) m/z 383.2 (M+H)$^+$, (ESI$^-$) m/z 381.3 (M−H)$^-$.

Example 243

(5-Methyl-2-phenylsulfanyl-phenyl)-(7-propyl-pteridin-4-yl)-amine

Example 243A

N'-(3-Cyano-6-propylpyrazin-2-yl)-N,N-dimethylformamidine

A mixture of 3-amino-5-propylpyrazine-2-carbonitrile (0.140 g, 0.863 mmol) (prepared according to the method of Taylor and LaMattina, JOC 1977, 47, 1523) and dimethylformamide dimethylacetal (0.123 g, 1.04 mmol, 1.2 eq) in toluene (10 mL) was heated under reflux for 2 h. The mixture was cooled to room temperature and the solvent evaporated under reduced pressure to provide the title compound (0.188 mg, 100%) as a thick oil.

Example 243B (5-Methyl-2-phenylsulfanyl-phenyl)-(7-propyl-pteridin-4-yl)-amine A mixture of the product from Example 243A (38.2 mg, 0.176 mmol) and the product of Example 5I (41.6 mg, 0.193 mmol, 1.1 eq) in acetic acid (1 mL) was heated under reflux for 1.5 h. The reaction mixture was cooled to room temperature and the solvent evaporated under reduced pressure. The resulting residue was triturated with methanol to provide the title compound (19 mg, 28% yield) as a beige solid. 1H NMR (300 MHz, DMSO-D6) δ ppm: 0.97 (t, J=7.35 Hz, 3H), 1.76-1.90 (m, 2H), 2.42 (s, 3H), 2.94-3.05 (m, 2H), 7.08-7.28 (m, 6H), 7.55 (d, J=8.09 Hz, 1H), 8.45 (s, 1H), 8.81 (s, 1H), 8.89 (s, 1H), 10.32 (s, 1H). MS (ESI$^+$) m/z 388.1 (M+H)$^+$ (ESI$^-$) m/z 386.1 (M−H)$^-$.

Example 244

4-[4-Benzyloxy-2-(7-isopropyl-pteridin-4-ylamino)-phenylsulfanyl]-phenol

Example 244A

3-Amino-5-isopropyl-4-oxy-pyrazine-2-carbonitrile

A mixture of 2-hydroxyimino-3-methylbutyraldehyde (1.93 g, 16.8 mmol)(prepared by the procedure of Nakamura, *Agric. Biol. Chem.* 1961, 25, 665-670) and 2-aminomalononitrile tosylate (4.25 g, 16.8 mmol) in i-propanol (40 mL) was stirred at room temperature for 18 h. The resulting solid was isolated by vacuum filtration and rinsed with i-propanol and air dried to provide the title compound (0.525 g, 18% yield) as a white solid.

Example 244B

3-Amino-5-isopropyl-pyrazine-2-carbonitrile

A solution of the product from Example 244A (0.525 g, 2.95 mmol) in tetrahydrofuran (30 mL) was stirred at ice water bath temperature. To this solution was added quickly dropwise phosphorus trichloride (4.0 g, 2.6 mL, 29.5 mmol, 10 eq). The reaction mixture was stirred at room temperature for 16 h and then the solvent and excess reagent was evaporated. The resulting residue was partitioned between ethyl acetate and half-saturated aqueous sodium bicarbonate. The aqueous phase was extracted with ethyl acetate (3×100 mL) and the combined organic layers dried over anhydrous magnesium sulfate, filtered, and evaporated to provide the title compound (0.370 g, 77% yield) as a light brown solid.

Example 244C

N'-(3-Cyano-6-isopropyl-pyrazin-2-yl)-N,N-dimethyl-formamidine

A mixture of the product from Example 244B (0.37 g, 2.28 mmol) and dimethylformamide dimethylacetal (0.30 g, 2.5 mmol, 1.1 eq) in toluene (25 mL) was heated under reflux for 1.75 h. The reaction mixture was then cooled to room temperature and the solvent evaporated under reduced pressure to provide the title compound (0.50 g, 100%) as a thick red/brown oil that was used in subsequent reactions without further purification.

Example 244D

4-[4-Benzyloxy-2-(7-isopropyl-pteridin-4-ylamino)-phenylsulfanyl]-phenol

A mixture of the product from Example 244C (56.2 mg, 0.259 mmol) and the product from Example 27A in acetic acid (1 mL) was heated under reflux for 2 h. The reaction mixture was cooled to room temperature and evaporated under reduced pressure. The resulting residue was triturated with methanol to provide the title compound (55.5 mg, 53% yield) as a beige solid. 1H NMR (300 MHz, DMSO-D6) δ ppm: 10.37 (s, 1H), 9.65 (s, 1H), 9.03 (s, 1H), 8.80 (s, 1H), 8.31 (s, 1H), 7.38 (d, J=8.09 Hz, 1H), 7.21 (d, J=8.82 Hz, 2H), 7.03 (dd, J=8.09, 1.47 Hz, 1H), 6.68 (d, J=8.82 Hz, 2H), 3.35-3.46 (m, 1H), 2.37 (s, 3H), 1.38 (d, J=6.62 Hz, 6H). MS (ESI$^+$) m/z 404.2 (M+H)$^+$ (ESI$^-$) m/z 402.3 (M−H)$^-$.

Example 245

[2-(4-Amino-phenoxy)-5-(6-bromo-1H-benzoimidazol-2-yl)-phenyl]-(7-isopropyl-pyrido[2,3-d]pyrimidin-4-yl)-amine

Example 245A

[4-(4-Formyl-2-nitro-phenoxy)-phenyl]-carbamic acid tert-butyl ester

A mixture of 4-chloro-3-nitrobenzaldehyde and (4-Hydroxy-phenyl)-carbamic acid tert-butyl ester were reacted together in DMSO with addition of KOH to provide the title product.

Example 245B

{4-[2-Amino-4-(6-bromo-1H-benzoimidazol-2-yl)-phenoxy]-phenyl}-carbamic acid tert-butyl ester The product from Example 245A was reacted according to the procedures from Examples 147B and 147C to provide the title product.

Example 245C

[2-(4-Amino-phenoxy)-5-(6-bromo-1H-benzoimidazol-2-yl)-phenyl]-(7-isopropyl-pyrido[2,3-d]pyrimidin-4-yl)-amine The product from Example 245B was reacted with the product from Example 36E in HOAc and placed in a preheated 120° C. oil bath. The solvent was removed under a stream of N$_2$. The product was deprotected by dissolving in a 1:1 mixture of TFA in DCM and stirred at room temperature. The crude material was purified by HPLC with TFA to provide the title product as a trifluoroacetic acid salt. 1H NMR (300 MHz, DMSO-D6) δ ppm: 1.35 (d, J=6.99 Hz, 6H) 3.21-3.39 (m, 1H) 6.87-7.04 (m, 4H) 7.09 (d, J=8.46 Hz, 1H) 7.36 (dd, J=8.82, 1.84 Hz, 1H) 7.56 (d, J=8.46 Hz, 1H) 7.78 (d, J=1.47 Hz, 1H) 7.89 (d, J=8.46 Hz, 1H) 8.14 (dd, J=8.82, 1.84 Hz, 1H) 8.37 (d, J=1.84 Hz, 1H) 8.90 (s, 1H) 9.00 (d, J=8.09 Hz, 1H); MS (ESI+) m/z 568.2 (M+H)+.

Example 246

4-[4-Benzyloxy-2-(7-tert-butyl-pyrido[2,3-d]pyrimidin-4-ylamino)-phenylsulfanyl]-phenol

The product from Example 27A was heated at 130° C. in acetic acid with the product from Example 127A for 15 minutes, the mixture was then cooled to room temperature, the solvent removed and the residue purified by column chromatography on silica gel to provide the title product. 1H NMR (300 MHz, DMSO-D6) δ ppm: 1.38 (s, 9H) 5.11 (s, 2H) 6.60-6.74 (m, 2H) 6.94 (d, J=7.35 Hz, 1H) 7.06-7.19 (m, 3H) 7.27-7.50 (m, 6H) 7.78 (d, J=8.09 Hz, 1H) 8.56 (s, 1H) 8.75 (s, 1H) 9.64 (s, 1H) 9.95 (s, 1H); MS (ESI+) m/z 509 (M+H)+.

Example 247

2-(4-Amino-phenylsulfanyl)-5-(2-chloro-thiazol-5-ylmethoxy)-phenyl]-(7-isopropyl-pyrido[2,3-d]pyrimidin-4-yl)-amine

Example 247A

{4-[2-Amino-4-(2-chloro-thiazol-5-ylmethoxy)-phenylsulfanyl]-phenyl}-carbamic acid tert-butyl ester

2-Chloro-5-(4-chloro-3-nitro-phenoxymethyl)-thiazole (from Example 25A) was reacted with 4-aminothiophenol in anhydrous ethanol and at reflux under a nitrogen atmosphere. The reaction was cooled to room temperature and the ethanol removed by rotary evaporation. The residue was taken up in water and extracted with ethyl acetate. The combined organic extracts were washed with brine, dried over anhydrous sodium sulfate, filtered, and concentrated in vacuo. Trituration of the solid with 4% ethyl acetate/methylene chloride afforded 4-(4-((2-chlorothiazol-5-yl)methoxy)-2-nitrophenylthio)aniline. A mixture of 4-(4-((2-chlorothiazol-5-yl)methoxy)-2-nitrophenylthio)aniline and di-tert-butyl dicarbonate in 1,4-dioxane was heated at reflux under a nitrogen atmosphere, and then additional Boc anhydride was added and the reaction allowed to reflux. The reaction was cooled to room temperature and the solvent removed by rotary evaporation in vacuo. The resulting solid was triturated with 2.5% ethyl acetate/methylene chloride to obtain tert-butyl 4-(4-((2-chlorothiazol-5-yl)methoxy)-2-nitrophenylthio)phenylcarbamate. A suspension of 4-(4-((2-chlorothiazol-5-yl)methoxy)-2-nitrophenylthio)phenylcarbamate, iron powder, and ammonium chloride in water and ethanol was heated. The reaction was cooled to room temperature. The mixture was diluted with ethyl acetate and washed with water and brine. The organic phase was dried, filtered, and concentrated under vacuum to provide the title compound.

Example 247B

[2-(4-Amino-phenylsulfanyl)-5-(2-chloro-thiazol-5-ylmethoxy)-phenyl]-(7-isopropyl-pyrido[2,3-d]pyrimidin-4-yl)-amine

The product from Example 247A was heated at 130° C. in acetic acid with the product from Example 36E for 15 minutes, the mixture was then cooled to room temperature, the solvent removed under vacuum and a mixture of dichloromethane/trifluoroacetic acid 1/1 was added and the residue then stirred at room temperature for 2 hours followed by removal of the solvent under vacuum and the residue purified by HPLC with TFA to provide the title product as a trifluoroacetic acid salt. 1H NMR (300 MHz, DMSO-D6) δ ppm: 1.36 (d, J=6.99 Hz, 6H) 3.20-3.37 (m, 1H) 3.75 (s, 2H) 5.33 (s, 2H) 6.53 (d, J=8.46 Hz, 2H) 6.99-7.12 (m, 5H) 7.14 (s, 1H) 7.80 (s, 1H) 7.92 (d, J=8.82 Hz, 1H) 8.83 (s, 1H) 9.01 (s, 1H) 11.62 (s, 1H); MS (ESI+) m/z 535 (M+H)+.

Example 248

{4-[2-(7-tert-Butyl-pyrido[2,3-d]pyrimidin-4-ylamino)-4-(2-chloro-thiazol-5-ylmethoxy)-phenylsulfanyl]-phenyl}-carbamic acid tert-butyl ester

The product from Example 247A was heated at 130° C. in acetic acid with the product from Example 127A for 15 minutes, the mixture was then cooled to room temperature, the solvent removed and the residue purified by HPLC with TFA to provide the title product as a trifluoroacetic acid salt. 1H NMR (300 MHz, DMSO-D6) δ ppm: 1.43 (d, J=11.40 Hz, 15H) 2.73 (s, 1H) 5.36 (s, 2H) 7.00 (d, 1H) 7.13 (d, J=8.46 Hz, 2H) 7.25 (d, 1H) 7.33 (d, J=8.46 Hz, 3H) 7.81 (s, 2H) 8.62 (s, 1H) 8.78 (s, 1H) 9.39 (s, 1H) 10.49 (bs, 1H); MS (ESI+) m/z 649 (M+H)+.

Example 249

[2-(4-Amino-phenylsulfanyl)-5-(2-chloro-thiazol-5-ylmethoxy)-phenyl]-(7-tert-butyl-pyrido[2,3-d]pyrimidin-4-yl)-amine

The product from Example 248 was added to a mixture of dichloromethane/trifluoroacetic acid 1/1 and the solution stirred at room temperature for 2 hours followed by removal of the solvent under vacuum and the resultant residue was purified by HPLC with TFA to provide the title product as a trifluoroacetic acid salt. 1H NMR (300 MHz, DMSO-D6) δ ppm: 1.44 (s, 6H) 2.51-2.59 (m, 1H) 3.72 (s, 2H) 5.33 (s, 2H) 6.24 (dd, J=8.82, 2.94 Hz, 1H) 6.42 (d, J=2.94 Hz, 1H) 6.53 (d, J=8.46 Hz, 2H) 6.98-7.12 (m, 3H) 7.14 (s, 1H) 7.74-7.85 (m, 1H) 8.09 (d, J=8.46 Hz, 1H) 8.83 (s, 1H) 9.03 (s, 1H) 11.65 (s, 1H); MS (ESI+) m/z 549 (M+H)+.

Example 250

[2-(4-Amino-phenylsulfanyl)-5-(6-bromo-1H-benzoimidazol-2-yl)-phenyl]-(7-isopropyl-pyrido[2,3-d]pyrimidin-4-yl)-amine

Example 250A

[4-(4-Formyl-2-nitro-phenylsulfanyl)-phenyl]-carbamic acid tert-butyl ester

A mixture of 4-chloro-3-nitrobenzaldehyde and 4-aminothiophenol were reacted together according to the procedure of Example 216B substituting 4-chloro-3-nitrobenzaldehyde for the product from Example 216A which was then subjected to the conditions from Example 216C to provide the title product.

Example 250B

[2-(4-Amino-phenylsulfanyl)-5-(6-bromo-1H-benzoimidazol-2-yl)-phenyl]-(7-isopropyl-pyrido[2,3-d]pyrimidin-4-yl)-amine

The product from Example 250A was reacted according to the procedures from Examples 147B, 147C and 147C to provide a crude residue which was purified by HPLC with TFA to provide the title product as a trifluoroacetic acid salt. 1H NMR (300 MHz, DMSO-D6) δ ppm: 1.38 (d, J=6.62 Hz, 6H) 3.26-3.40 (m, 1H) 6.64 (d, J=8.46 Hz, 2H) 7.03 (d, J=8.46 Hz, 1H) 7.17 (d, J=8.46 Hz, 2H) 7.35 (dd, J=8.46, 1.84 Hz, 1H) 7.54 (d, J=8.82 Hz, 1H) 7.77 (d, J=1.84 Hz, 1H) 7.94 (d, J=8.46 Hz, 1H) 8.03 (dd, J=8.46, 1.84 Hz, 1H) 8.18 (s, 1H) 8.89 (s, 1H) 9.05 (d, J=8.82 Hz, 1H); MS (ESI+) m/z 584 (M+H)+.

Example 251

[2-(4-Amino-phenylsulfanyl)-5-(3-fluoro-benzyloxy)-phenyl]-(7-isopropyl-pyrido[2,3-d]pyrimidin-4-yl)-amine Example 251A {4-[2-Amino-4-(3-fluoro-benzyloxy)-phenylsulfanyl]-phenyl}-carbamic acid tert-butyl ester The product from Example 57B was reacted with 4-aminothiophenol according to the procedure from Example 214B followed by reaction according to the procedures from Examples 214C and 214D to provide the title product.

Example 251B

[2-(4-Amino-phenylsulfanyl)-5-(3-fluoro-benzyloxy)-phenyl]-(7-isopropyl-pyrido[2,3-d]pyrimidin-4-yl)-amine The product from Example 251A was heated at 130° C. in acetic acid with the product from Example 36E for 15 minutes, the mixture was then cooled to room temperature, the solvent removed under vacuum and a mixture of dichloromethane/trifluoroacetic acid 1/1 was added and the residue then stirred at room temperature for 2 hours followed by removal of the solvent under vacuum and the residue purified by column chromatography on silica gel to provide the title product. 1H NMR (300 MHz, DMSO-D6) δ ppm: 1.26-1.44 (d, 6H) 3.23-3.37 (m, 1H) 5.13 (s, 2H) 6.44-6.61 (m, 2H) 6.96-7.10 (m, 3H) 7.10-7.22 (m, 2H) 7.24-7.35 (m, 3H) 7.35 (d, J=6.25 Hz, 1H) 7.43 (dd, J=7.91, 5.70 Hz, 2H) 7.92 (s, 1H) 8.18 (d, J=8.82 Hz, 1H) 8.83 (s, 1H) 9.03 (s, 1H); MS (ESI+) m/z 512 (M+H)+.

Example 252

[2-(4-Amino-phenylsulfanyl)-5-(3-fluoro-benzyloxy)-phenyl]-(7-tert-butyl-pyrido[2,3-d]pyrimidin-4-yl)-amine The product from Example 251A was heated at 130° C. in acetic acid with the product from Example 127A for 15 minutes, the mixture was then cooled to room temperature, the solvent removed under vacuum and a mixture of dichloromethane/trifluoroacetic acid 1/1 was added and the residue then stirred at room temperature for 2 hours followed by removal of the solvent under vacuum and the residue purified by HPLC with TFA to provide the title product as a trifluoroacetic acid salt. 1H NMR (300 MHz, DMSO-D6) δ ppm: 1.38-1.50 (m, 9H) 5.12 (s, 2H) 6.44-6.61 (m, 3H) 6.96-7.12 (m, 3H) 7.19 (s, 3H) 7.23-7.33 (m, 3H) 7.38-7.50 (m, 2H) 8.00 (s, 1H) 8.76 (s, 1H) 8.96 (s, 1H); MS (ESI+) m/z 526 (M+H)+.

Example 253

[5-Benzyloxy-2-(4-dimethylamino-phenylsulfanyl)-phenyl]-(7-isopropyl-pyrido[2,3-d]pyrimidin-4-yl)-amine Example 253A 5-Benzyloxy-2-(4-dimethylamino-phenylsulfanyl)-phenylamine The product from Example 214B (1.0 g, 0.284 mmol) was placed in a tube along with formic acid (5 mL), dioxane (5 mL), and 37% aqueous formaldehyde (5 mL). The tube was sealed and heated to 110° C. for 20 minutes. The mixture was cooled to room temperature, the solvent removed and the resultant residue purified with column chromatography on silica gel followed by reduction of the nitro group according to the procedure of Example 214D to provide the title product (411 mg, 43%).

Example 253B

[5-Benzyloxy-2-(4-dimethylamino-phenylsulfanyl)-phenyl]-(7-isopropyl-pyrido[2,3-d]pyrimidin-4-yl)-amine A mixture of the product from Example 253A and the product from Example 36E in glacial acetic acid was heated in a preheated 130° C. oil bath for 20 min. The reaction mixture was then cooled to room temperature and the solvent evaporated under vacuum to provide the title compound as an acetic acid salt. 1H NMR (300 MHz, DMSO-D6) δ ppm: 1.36 (d, J=7.0 Hz, 6H), 2.81 (s, 6H), 3.30 (m, 1H), 5.10 (s, 2H), 6.45 (d, J=9.2 Hz, 2H), 7.07 (d, J=8.8 Hz, 2H), 7.12 (m, 2H), 7.25 (d, J=8.8 Hz, 1H), 7.40 (m, 5H), 7.94 (m, 1H), 8.78 (s, 1H), 8.99 (m, 1H), 11.70 (bs, 1H); MS (ESI) m/z 522 (M+H)+.

Example 254

4-Bromo-N-[3-(pyrido[2,3-d]pyrimidin-4-ylamino)-phenyl]-benzamide

Example 254A

4-Bromo-N-(3-nitro-phenyl)-benzamide

The title compound was prepared according to the procedure of Example 255A substituting 3-nitro-phenylamine for 4-Fluoro-3-nitro-aninline and substituting 4-bromo-benzoyl chloride for 3-Trifluoromethyl-benzoyl chloride to provide the title product (3.373 g, 90%).

Example 254B

4-Bromo-N-(3-amino-phenyl)-benzamide

The title compound was prepared according to the procedure of Example 255B substituting the product from Example 254A for the product from Example 255A to provide the title product (1.8 g, 80%).

Example 254C

4-Bromo-N-[3-(pyrido[2,3-d]pyrimidin-4-ylamino)-phenyl]-benzamide

A solution of the product from Example 57A (40.0 mg, 0.212 mmol), and the product of Example 254B (61.0 mg, 0.212 mmol) in acetic acid (1 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (25.0 mg, 30%). 1H NMR (300 MHz, DMSO-D) δ ppm: 7.45 (t, J=8.09 Hz, 1H), 7.52-7.61 (m, 2H), 7.74-7.86 (m, 3H), 7.94 (d, J=8.82 Hz, 2H), 8.33 (t, J=1.84 Hz, 1H), 8.88 (s, 1H), 9.09-9.17 (m, 2H), 10.48 (s, 1H), 10.94 (s, 1H); MS (ESI+) m/z 420 (M+H)+, (ESI−) m/z 417 (M−H)−.

Example 255

N-[4-(4-Hydroxy-phenylsulfanyl)-3-(7-methyl-pyrido[2,3-d]pyrimidin-4-ylamino)-phenyl]-3-trifluoromethyl-benzamide

Example 255A

N-(4-Fluoro-3-nitro-phenyl)-3-trifluoromethyl-benzamide

A solution of 4-Fluoro-3-nitro-aniline (2.00 g, 12.8 mmol), 3-Trifluoromethyl-benzoyl chloride (1.895 mL, 12.8 mmol), Hunig's base (4.463 mL, 25.6 mmol) in tetrahydrofuran (50 ml) was stirred at room temperature for 1 hour. Afterwards water (450 mL) was added to the solution and the resultant solid was collected by filtration and dried in a vacuum oven to provide the title compound (3.311 g, 97%).

Example 255B

N-[4-(4-Hydroxy-phenylsulfanyl)-3-nitro-phenyl]-3-trifluoromethyl-benzamide

A solution of the product of Example 255A (2.00 g, 5.80 mmol), 4-hydroxythiophenol (0.732 g, 5.80 mmol) and potassium carbonate (1.604 g, 11.6 mmol) in N,N-dimethylformamide (40 mL) was heated to 80° C. for 2 hours. After cooling to room temperature the mixture was poured into ice water (100 mL). The solution was then extracted with ethyl acetate (3×150 mL), the combined extracts dried over magnesium sulfate, filtered and concentrated under vacuum to provide the title compound (2.52 g, 100%).

Example 255C

N-[3-Amino-4-(4-hydroxy-phenylsulfanyl)-phenyl]-3-trifluoromethyl-benzamide

A solution of the product of Example 255B (0.660 g, 1.52 mmol), iron powder (0.339 g, 6.07 mmol) and ammonium chloride (0.099 g, 1.82 mmol), tetrahydrofuran (18 mL), and water (6 mL) solution was heated to reflux for 3 hours. The resultant mixture was diluted with methanol (50 mL) and filtered through a pad of celite. The filtrate was diluted with water (50 mL) and extracted with dichloromethane (2×100 mL). The combined extracts were dried over magnesium sulfate, filtered and concentrated under vacuum to provide the title compound (0.60 g, 97%).

Example 255D

N-[4-(4-Hydroxy-phenylsulfanyl)-3-(7-methyl-pyrido[2,3-d]pyrimidin-4-ylamino)-phenyl]-3-trifluoromethyl-benzamide A solution of the product from Example 10B (40.0 mg, 0.212 mmol), and the product from Example 255C (86.0 mg, 0.212 mmol) in acetic acid (1 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (11 mg, 10%). $^1$H NMR (300 MHz, DMSO-D6) δ ppm: 2.74 (s, 3H), 6.70 (d, J=8.82 Hz, 2H), 7.18 (d, J=8.46 Hz, 3H), 7.64 (dd, J=8.46, 2.21 Hz, 1H), 7.79 (t, J=7.72 Hz, 2H), 7.93-8.07 (m, J=6.62 Hz, 2H), 8.21-8.30 (m, 2H), 8.78 (s, 1H), 8.92 (d, J=7.72 Hz, 1H), 9.79 (s, 1H), 10.67 (s, 1H), 11.17-11.50 (m, 1H) MS (ESI+) m/z 548.2 (M+H)+, (ESI−) m/z 546.2 (M−H)−.

Biological Evaluation

Representative compounds of the invention were analyzed according to the assays described below.

The following acronyms are used herein:

| | |
|---|---|
| $IC_{50}$ | 50% inhibitory concentration |
| $TC_{50}$ | 50% toxicity concentration |
| DMEM | Dulbecco's Modified Essential Medium ™ |
| RNA | ribonucleic acid |
| RT-PCR | reverse transcriptase polymerase chain reaction |
| SEAP | secreted alkaline phosphatase |

The hepatitis C virus genome encodes a large polyprotein, which after processing produces the necessary functional components to synthesize progeny RNA. Selectable cell lines that produce high and sustained levels of subgenomic HCV RNA (replicons) have been derived from human hepatoma cells (Huh7) as described in Ikeda et al., *J. Virology*, 76(6): 2997-3006 (2002), and Blight et al., *Science*, 290:1972-1974 (2000). The mechanism of RNA replication in these cell lines is considered to be identical to the replication of full length HCV RNA in infected hepatocytes. The compounds of this invention are inhibitors of HCV RNA replication in the replicon assay systems described below.

Evaluation of the HCV Inhibitors in HCV Replicon

Representative compounds of the invention were evaluated for their inhibitory effect on HCV genotype 1a and 1b replicons. They were also evaluated by MTT assay for cytotoxicity to the host cells. The cell lines were maintained according to the methods described by Yi et al., *Virology*, 304(2):197-210 (2002).

A. RNA Assay and SEAP Assay

The purpose of these assays was to evaluate the efficacy of the compounds in inhibiting the replication of HCV genotype 1a and 1b replicons in vitro.

Genotype 1a and/or 1b replicon cells were plated at 3-5× $10^3$ cells per well in 96-well plate in DMEM medium containing 5% fetal calf serum. The next day, the culture medium was removed and replaced with fresh medium containing eight serial dilutions of compound. The untreated control culture was treated in an identical manner except no inhibitor was added to the medium. Plates were incubated in a $CO_2$ incubator at 37° C. On day 4, 100 μl lysis buffer (RTL) (Qiagen) was added to each well after removal of culture medium. RNA was purified according to manufacturer's recommendations (Qiagen RNAeasy) and eluted in 200 μl of water. The HCV RNA level was quantified from a portion (5 μl out of 200 μl) of the purified RNA by real-time RT-PCR method. The primers and probe were derived from specific sequence in the 5'-Untranslated Region (5'UTR). RT-PCR reaction was performed at 48° C. for 30 min, followed by 40 cycles set to 95° C., 15 s; 54° C., 30 s; and 72° C., 40 s.

Alternatively, the activity of SEAP was measured in each culture supernatant after four days incubation with compound according to the manufacturer's instructions. The percentage reduction of HCV RNA or SEAP in the presence of compound was calculated and the 50% inhibitory concentration ($IC_{50}$) was calculated by non-linear regression analysis using the Prism program (version 4.0, GraphPad software, San Diego, Calif.).

When tested using the above method, representative compounds of the present invention inhibited HCV replicon replication with $IC_{50}$ values in the range of from about 0.3 nM to about 100 µM.

B. Cytotoxicity Assay

The purpose of this assay was to determine the toxicity of the compounds on viral host cells in vitro.

Cytotoxicity of the compounds was measured using a mitochondrial enzyme-based cell proliferation/viability assay in replicon cells. Briefly, HCV replicon cells were plated at $3-5 \times 10^3$ cells per well in 96-well plate in DMEM medium containing 5% FCS. At day 1, culture medium was removed and replaced with fresh medium containing eight serial dilutions of compound. The untreated control culture was treated in an identical manner except no inhibitor was added to the medium. Plates were incubated in a $CO_2$ incubator at 37° C. On day 4, stock solution of the tetrazolium salt, MTT (4 mg/ml in PBS, Sigma cat.# M 2128) was added to each well at 25 µl per well. Plates were further incubated for 4 hours, treated with 20% SDS plus 0.02 N HCl at 50 µl per well to lyse the cells. After an overnight incubation, optical density was measured by reading the plates at 570/650 nm wavelengths. The percent reduction of formazan blue color formed relative to control was calculated and the 50% toxicity concentration ($TC_{50}$) was calculated by non-linear regression analysis using the Prism program (version 4.0, GraphPad software, San Diego, Calif.).

When tested using the above method, the $TC_{50}$ values of representative compounds of the present invention were greater than the corresponding $IC_{50}$ values of these compounds.

Pharmaceutical Compositions and Uses

The present invention features pharmaceutical compositions comprising the compounds of the invention. As a non-limiting example, a pharmaceutical composition of the present invention comprises one or more compounds of this invention, wherein each compound is independently selected from Formulae I, II, III, IV, V, VI, VII or VIII. Preferably, each compound is independently selected from Examples 1-255.

The present invention also features pharmaceutical compositions comprising pharmaceutically acceptable salts, solvates, or prodrugs of the compounds of this invention. Pharmaceutically acceptable salts can be zwitterions or derived from pharmaceutically acceptable inorganic or organic acids or bases. Preferably, a pharmaceutically acceptable salt of a compound of the invention retains the biological effectiveness of the free acid or base of the compound without undue toxicity, irritation, or allergic response, has a reasonable benefit/risk ratio, and is effective for their intended use and not biologically or otherwise undesirable. Non-limiting examples of pharmaceutically acceptable salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. The basic nitrogen-containing groups can also be quaternized with such agents as loweralkyl halides (e.g., methyl, ethyl, propyl or butyl chlorides, bromides or iodides), dialkyl sulfates (e.g., dimethyl, diethyl, dibutyl or diamyl sulfates), long chain halides (e.g., decyl, lauryl, myristyl or stearyl chlorides, bromides or iodides), aralkyl halides (e.g., benzyl or phenethyl bromides). Other salts that can be used in the present invention include salts with alkali or alkaline earth metals, such as sodium, potassium, calcium or magnesium, or with organic bases. Examples of acids which can be used to form pharmaceutically acceptable acid addition salts include, but are not limited to, hydrochloric acid, sulphuric acid, phosphoric acid, oxalic acid, maleic acid, succinic acid, citric acid, or other suitable inorganic or organic acids.

The present invention further features pharmaceutical compositions comprising a compound of the invention (or a salt, solvate or prodrug thereof) and another therapeutic agent. In a non-limiting example, a pharmaceutical composition of the present invention includes 1, 2, 3 or more compounds of the invention (or salts, solvates or prodrugs thereof), and 1, 2, 3 or more other therapeutic agents. By way of illustration not limitation, these other therapeutic agents can be selected from antiviral agents (e.g., anti-HIV agents or other anti-HCV agents), immunomodulators, anti-cancer or chemotherapeutic agents, or anti-inflammation agents. Specific examples of these other therapeutic agents include, but are not limited to, ribavirin; interferons (e.g., IFN alpha 2a or 2b); protease inhibitors; immunosuppressants; antibodies (e.g., therapeutic monoclonal or chimeric antibodies); antisense or siRNA; HIV inhibitors; hepatitis B (HBV) inhibitors; agents for treating cirrhosis and inflammation of the liver; Omega IFN (BioMedicines Inc., Emeryville, Calif.); BILN-2061 serine protease inhibitor (Boehringer Ingelheim Pharma KG, Ingelheim, Germany); Summetrel antiviral (Endo Pharmaceuticals Holdings Inc., Chadds Ford, Pa.); Roferon A IFN-alpha 2a (F. Hoffmann-La Roche LTD, Basel, Switzerland); Pegasys PEGylated IFN-alpha 2a (F. Hoffmann-La Roche LTD, Basel, Switzerland); Pegasys and Ribavirin PEGylated IFN-alpha 2a/ribavirin (F. Hoffmann-La Roche LTD, Basel, Switzerland); CellCept HCV IgG immunosuppressant (F. Hoffmann-La Roche LTD, Basel, Switzerland); Wellferon lymphoblastoid IFN-alpha n1 (GlaxoSmithKline plc, Uxbridge, UK); Albuferon-alpha albumin IFN-alpha 2b (Human Genome Sciences Inc., Rockville, Md.); Levovirin ribavirin (ICN Pharmaceuticals, Costa Mesa, Calif.); IDN-6556 caspase inhibitor (Idun Pharmaceuticals Inc., San Diego, Calif.); IP-501 antifibrotic (Indevus Pharmaceuticals Inc., Lexington, Mass.); Actimmune INF-gamma (InterMune Inc., Brisbane, Calif.); Infergen A IFN alfacon-1 (InterMune Pharmaceuticals Inc., Brisbane, Calif.); ISIS 14803 antisense (ISIS Pharmaceuticals Inc., Carlsbad, Calif./Elan Pharmaceuticals Inc., New York, N.Y.); JTK-003 RdRp inhibitor (Japan Tobacco Inc., Tokyo, Japan); Pegasys and Ceplene PEGylated IFN-alpha 2a/immune modulator (Maxim Pharmaceuticals inc., San Diego, Calif.); Ceplene immune modulator (Maxim Pharmaceuticals Inc., San Diego, Calif.); Civacir HCV IgG immunosuppressant (Nabi Biopharmaceuticals Inc., Boca Raton, Fla.); Intron A and Zadaxin IFN-alpha 2b/alpha 1-thymosin (RegeneRx Biopharmiceuticals Inc., Bethesda, Md./SciClone Pharmaceuticals Inc., San Mateo, Calif.); Levovirin IMPDH inhibitor (Ribapharm Inc., Costa Mesa, Calif.); Viramidine IMPDH inhibitor (Ribapharm Inc., Costa Mesa, Calif.); Heptazyme ribozyme (Ribozyme Pharmaceuticals Inc., Boulder, Colo.); Intron A IFN-alpha 2b (Schering-Plough Corporation, Kenilworth, N.J.); PEG-Intron PEGylated IFN-alpha 2b (Schering-Plough Corporation, Kenilworth, N.J.); Rebetron IFN-alpha 2b/ribavirin (Schering-Plough Corporation, Kenilworth, N.J.); Ribavirin (Schering-Plough Corporation, Kenilworth, N.J.); PEG-Intron/Ribavirin PEGylated IFN-alpha 2b/ribavirin (Schering-Plough Corporation, Kenilworth, N.J.); Zadazim immune modulator (SciClone Pharmaceuticals Inc., San Mateo, Calif.); Rebif IFN-beta 1a (Serono, Geneva, Switzerland); IFN-beta and EMZ701 IFN-beta and EMZ701 (Transition Therapeutics Inc., Ontario, Canada); T67 beta-tubulin inhibitor (Tularik Inc., South San Francisco, Calif.); VX-497 IMPDH inhibitor (Vertex Pharmaceuticals Inc., Cambridge, Mass.); VX-950/LY-570310 serine protease inhibitor (Vertex Pharmaceuticals Inc., Cambridge, Mass./Eli Lilly and Co., Inc., Indianapolis, Ind.); Omniferon natural IFN-alpha (Viragen Inc., Plantation, Fla.); XTL-002 monoclonal antibody (XTL Biopharmaceuticals);

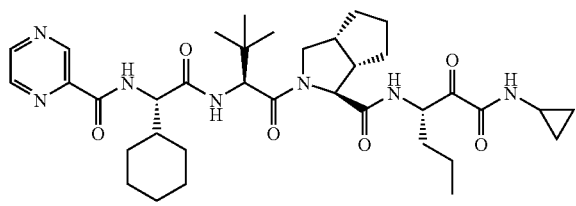

(hereinafter compound VX-950, Vertex Pharmaceuticals Inc.);

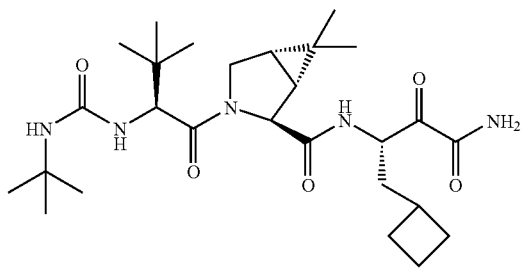

(hereinafter compound SCH503034, Schering-Plough Co.); and

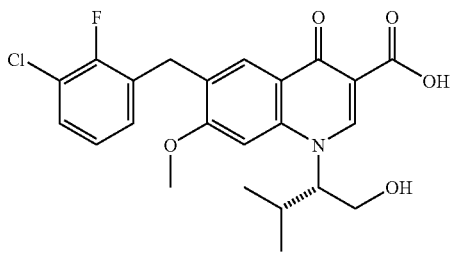

(hereinafter compound GS9137, Gilead Sciences, Inc., Foster City, Calif.). Any other desirable therapeutic agent(s) can also be included in a pharmaceutical composition of the present invention.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents. In one example, each of the compounds of the present invention is independently selected from Formulae I, II, III, IV, V, VI, VII or VIII, or Examples 1-255, and each of the other anti-HCV agents is independently selected from HCV RNA dependent RNA polymerase inhibitors (e.g., nucleoside or non-nucleoside type polymerase inhibitors), HCV protease inhibitors, or HCV helicase inhibitors.

In a further embodiment, a pharmaceutical composition of the present invention comprises one or more compounds of the present invention (or salts, solvates or prodrugs thereof), and two or more other anti-HCV inhibitors. Preferably, each compound of the present invention is independently selected from Formulae I, II, III, IV, V, VI, VII or VIII, or from Examples 1-255. The other anti-HCV inhibitors can be selected from the same inhibitor class (e.g., all of them are selected from HCV RNA dependent RNA polymerase inhibitors, or from HCV protease inhibitors), or selected from different inhibitor classes (e.g., one or more are selected from HCV RNA dependent RNA polymerase inhibitor and the other or others are selected from HCV protease inhibitors).

In still another embodiment, a pharmaceutical composition of the present invention comprises at least one compound of the present invention (or a salt, solvate or prodrug thereof), and at least one HCV RNA dependent RNA polymerase inhibitor. Preferably, each compound of the present invention is independently selected from Formulae I, II, III, IV, V, VI, VII or VIII, or Examples 1-255.

In another embodiment, a pharmaceutical composition of the present invention comprises at least one compound of the present invention (or a salt, solvate or prodrug thereof), and at least one HCV protease inhibitor. Preferably, the compound of the present invention is selected from Formulae I, II, III, IV, V, VI, VII or VIII, or Examples 1-255.

In yet another embodiment, a pharmaceutical composition of the present invention comprises at least one compound of the present invention (or a salt, solvate or prodrug thereof), at least one HCV RNA dependent RNA polymerase inhibitor, and at least one HCV protease inhibitor. Preferably, the compound of the present invention is selected from Formulae I, II, III, IV, V, VI, VII or VIII, or Examples 1-255.

In still yet another embodiment, a pharmaceutical composition of the present invention comprises at least one compound of the present invention (or a salt, solvate or prodrug thereof), and two or more anti-HCV agents each of which is independently selected from HCV RNA dependent RNA polymerase inhibitors or HCV protease inhibitors. Preferably, the compound of the present invention is selected from Formulae I, II, III, IV, V, VI, VII or VIII, or Examples 1-255.

In still another embodiment, a pharmaceutical composition of the present invention comprises at least one compound of the present invention (or a salt, solvate or prodrug thereof), and three or more other anti-HCV agents each of which is independently selected from HCV RNA dependent RNA polymerase inhibitors or HCV protease inhibitors. Preferably, the compound of the present invention is selected from Formulae I, II, III, IV, V, VI, VII or VIII, or Examples 1-255.

Non-limiting examples of HCV RNA dependent RNA polymerase inhibitors include those described in WO0190121(A2), U.S. Pat. No. 6,348,587B1, WO0160315, WO0132153, EP1162196A1 and WO0204425. Non-limiting examples of HCV protease inhibitors include BILN-2061, VX-950, and SCH503034.

In another embodiment, a pharmaceutical composition of the present invention comprises at least one compound of the present invention (or a salt, solvate or prodrug thereof), and one or more other antiviral agents, such as anti-HBV or anti-HIV agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, and other HIV protease, reverse transcriptase, integrase or fusion inhibitors. Other desirable antiviral agents can also be included in a pharmaceutical composition of the present invention, as appreciated by those skilled in the art.

In one embodiment, a pharmaceutical composition of the present invention comprises at least one compound of the present invention selected from Formulae I, II, III, IV, V, VI, VII or VIII or from Examples 1-255, or a salt, solvate or prodrug thereof, and at least one anti-HBV agent. In another embodiment, a pharmaceutical composition of the present invention comprises at least one compound of the present invention selected from Formulae I, II, III, IV, V, VI, VII or VIII or from Examples 1-255, or a salt, solvate or prodrug thereof, and at least one anti-HIV agent. In yet another embodiment, a pharmaceutical composition of the present invention comprises at least one compound of the present invention selected from Formulae I, II, III, IV, V, VI, VII or VIII or from Examples 1-255, or a salt, solvate or prodrug thereof, and at least one anti-hepatitis A, anti-hepatitis D, anti-hepatitis E or anti-hepatitis G agent.

In still yet another embodiment, a pharmaceutical composition of the present invention comprises at least one compound of the present invention selected from Formulae I, II, III, IV, V, VI, VII or VIII or from Examples 1-255, or a salt, solvate or prodrug thereof, and at least one agent suitable for treating liver inflammation.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention, as appreciated by those of ordinary skill in the art.

A pharmaceutical composition of the present invention can be administered to a patient in need thereof via a variety of routes, such as orally, parenterally, sublingually, rectally, topically or by inhalation spray. Topical administration may involve the use of transdermal administration such as transdermal patches or iontophoresis devices. Parenteral administration includes, but is not limited to, subcutaneous, intravenous, intramuscular or intrastemal injections, and infusion techniques.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

The present invention further features methods of using the compounds of the present invention (or salts, solvates or prodrugs thereof) to inhibit HCV replication. In one embodiment, the methods comprise contacting HCV virus with an effective amount of a compound of the present invention (or a salt, solvate or prodrug thereof), thereby inhibiting the replication of the HCV virus. In another embodiment, the methods comprise contacting cells infected with HCV virus with an effective amount of a compound of the present invention (or a salt, solvate or prodrug thereof), thereby inhibiting the replication of the HCV virus in the cells. In still another embodiment, the methods comprise contacting HCV virus or infected cells with an effective amount of two or more compounds of the present invention (or salts, solvates or prodrugs thereof), thereby inhibiting the replication of the HCV virus. As used herein, "inhibiting" means significantly reducing, or abolishing, the activity being inhibited (e.g., viral replication). In many cases, representative compounds of the present invention can reduce the replication of HCV virus (e.g., in HCV replicon assays as described above) by at least 10%, 20%, 30%, 40%, 50%, 60%, 70%, 80%, 90%, 95% or more.

The compounds of the present invention may inhibit all HCV subtypes. Examples of HCV subtypes that are amenable to the present invention include, but are not be limited to, HCV genotypes 1, 2, 3, 4, 5 and 6, including HCV genotypes 1a, 1b, 2a, 2b, 2c or 3a. In one embodiment, a compound or compounds of the present invention (or salts, solvates or prodrugs thereof) are used to inhibit the replication of HCV genotype 1a. In another embodiment, a compound or compounds of the present invention (or salts, solvates or prodrugs thereof) are used to inhibit the replication of HCV genotype 1b. In still another embodiment, a compound or compounds of the present invention (or salts, solvates or prodrugs thereof) are used to inhibit the replication of both HCV genotypes 1a and 1b.

The present invention also features methods of using the compounds of the present invention (or salts, solvates or prodrugs thereof) to treat HCV infection. These methods typically comprise administering a therapeutic effective amount of a compound of the present invention (or a salt, solvate or prodrug thereof) to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts, solvates or prodrugs thereof) to an HCV patient, thereby reducing the HCV viral level in the blood or liver of the patient. Preferably, the compound(s) employed in these methods has Formulae I, II, III, IV, V, VI, VII or VIII or is selected from Examples 1-255, or is a salt, solvate or prodrug thereof.

In another aspect, the present invention features methods of using a pharmaceutical composition of the present invention to treat HCV infection. Any pharmaceutical composition described herein can be used for this purpose. These methods typically comprise administering a therapeutic effective amount of a pharmaceutical composition of the present invention to an HCV patient, thereby reducing the HCV viral level in the blood or liver of the patient. Where the pharmaceutical composition includes other therapeutic agent(s), it may also treat other diseases, disorders or conditions in the patient.

In one embodiment, the pharmaceutical composition being administered comprises at least one compound of the present invention selected from Formulae I, II, III, IV, V, VI, VII or VIII or from Examples 1-255, or a salt, solvate or prodrug thereof, and at least another anti-HCV agent selected from HCV RNA dependent RNA polymerase inhibitors, HCV protease inhibitors or HCV helicase inhibitors. In another embodiment, the pharmaceutical composition being administered comprises at least one compound of the present invention selected from Formulae I, II, III, IV, V, VI, VII or VIII or from Examples 1-255, or a salt, solvate or prodrug thereof, and at least two other anti-HCV agents each of which is independently selected from HCV RNA dependent RNA polymerase inhibitors, HCV protease inhibitors or HCV helicase inhibitors. In still another embodiment, the pharmaceutical composition being administered comprises at least one compound of the present invention selected from Formulae I, II, III, IV, V, VI, VII or VIII or from Examples 1-255, or a salt, solvate or prodrug thereof, and 1, 2 or more HCV RNA dependent RNA polymerase inhibitors (e.g., those described in WO0190121(A2), U.S. Pat. No. 6,348,587B1, WO0160315, WO0132153, EP1162196A1 and WO0204425). In yet another embodiment, the pharmaceutical composition being administered comprises at least one compound of the present invention selected from Formulae I, II, III, IV, V, VI, VII or VIII or from Examples 1-255, or a salt, solvate or prodrug thereof, and 1, 2 or more HCV protease inhibitors (e.g., BILN-2061, VX-950, and SCH503034).

In a further embodiment, the pharmaceutical composition being administered comprises at least one compound of the present invention selected from Formulae I, II, III, IV, V, VI, VII or VIII or from Examples 1-255, or a salt, solvate or prodrug thereof, and at least one antiviral agent selected from anti-HIV agents, anti-HBV agents, anti-hepatitis A agents, anti-hepatitis D agents, anti-hepatitis E agents, or anti-hepatitis G agents.

In yet another aspect, the present invention provides methods of using a compound(s) of the present invention and another therapeutic agent(s) to treat HCV infection. The methods comprise administering a therapeutic effective amount of a compound(s) of the present invention and another therapeutic agent(s) to an HCV patient, thereby reducing the HCV viral level in the blood or liver of the patient. Each compound of the present invention (or a salt, solvate or prodrug thereof) and the other therapeutic agent(s) can be combined in a single formulation and administered simultaneously to the patient. They can also be administered simultaneously but in different formulations. In addition, they can be administered sequentially.

In one embodiment, the compound(s) of the present invention being administered includes one or more compounds selected from Formulae I, II, III, IV, V, VI, VII or VIII or from Examples 1-255, or salts, solvates or prodrugs thereof, and the other therapeutic agent(s) being administered includes one or more agents selected from HCV RNA dependent RNA polymerase inhibitors, HCV protease inhibitors or HCV helicase inhibitors. In another embodiment, the compound(s) of the present invention being administered includes one or more compounds selected from Formulae I, II, III, IV, V, VI, VII or VIII or from Examples 1-255, or salts, solvates or prodrugs thereof, and the other therapeutic agent(s) being administered includes two or more agents selected from HCV RNA dependent RNA polymerase inhibitors, HCV protease inhibitors or HCV helicase inhibitors. In yet another embodiment, the compound(s) of the present invention being administered includes one or more compounds selected from Formulae I, II, III, IV, V, VI, VII or VIII or from Examples 1-255, or salts, solvates or prodrugs thereof, and the other therapeutic agent(s) being administered includes one, two or more HCV RNA dependent RNA polymerase inhibitors (e.g., those described in WO0190121(A2), U.S. Pat. No. 6,348,587B1, WO0160315, WO0132153, EP1162196A1 and WO0204425). In still yet another embodiment, the compound(s) of the present invention being administered includes one or more compounds selected from Formulae I, II, III, IV, V, VI, VII or VIII or from Examples 1-255, or salts, solvates or prodrugs thereof, and the other therapeutic agent(s) being administered includes one, two or more HCV protease inhibitors (e.g., BILN-2061, VX-950, and SCH503034).

A compound of the present invention (or a salt, solvate or prodrug thereof) can also be coadministered with other desired drugs, such as anti-HIV agents, anti-HBV agents, anti-hepatitis A agents, anti-hepatitis D agents, anti-hepatitis E agents, anti-hepatitis G agents, or other antiviral drugs.

A compound of the present invention (or a salt, solvent or prodrug thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or the active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

In still another aspect, the compounds of Formulae I, II, III, IV, V, VI, VII or VIII, or their pharmaceutically acceptable salts, stereoisomers or tautomers, can be administered as the sole active pharmaceutical agent, or used in combination with one or more other agents, to treat infections or symptoms associated with other RNA-containing viruses.

Treatment or prevention of infection caused by RNA-containing viruses can be provided by a combination therapy comprising a therapeutically effective amount of a first antiviral agent provided by one or more compounds, or salts thereof, of Formulae I, II, III, IV, V, VI, VII or VIII, along with a therapeutically-effective amount of a second agent provided by one or more compounds selected from the group consisting of another anti-viral agent; a host immune modulator; interferon derivative, such as interferon-alpha, pegylated-interferon-alpha, interferon-beta, and interferon-gamma; a cytokine; a vaccine; a nucleoside analog; inhibitors of key enzymes which result in HCV dysfunction, examples of such enzymes being HCV metalloprotease, HCV serine protease, inosine monophosphate dehydrogenase (IMPDH), and HCV helicase; inhibitors of viral particle proteins such as HCV NS4B protein, and HCV NS5a protein; and agents which inhibit HCV function, such as HCV entry, HCV assembly, and HCV egress. Also included are vaccines comprising HCV antigens or antigen adjuvant combinations directed against HCV. Further included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7.

In one embodiment, the present invention is directed to a method of treating or preventing infection caused by an RNA-containing virus comprising administering to a patient in need of such treatment a therapeutically effective amount of a compound of Formulae I, II, III, IV, V, VI, VII or VIII, or a pharmaceutically acceptable salt thereof.

In another embodiment, the present invention is directed to a method of treating or preventing infection caused by an RNA-containing virus comprising co-administering to a patient in need of such treatment one or more agents selected from the group consisting of a host immune modulator and a second antiviral agent, or a combination thereof, with a therapeutically effective amount of a compound of Formulae I, II, III, IV, V, VI, VII or VIII, or a pharmaceutically acceptable salt thereof.

In yet another embodiment, the present invention is directed to a method of treating or preventing infection caused by an RNA-containing virus comprising co-administering to a patient in need of such treatment one or more agents selected from the group consisting of interferon-alpha, pegylated-interferon-alpha, interferon-beta, interferon-gamma, a cytokine, a vaccine, and a vaccine comprising an antigen and an adjuvant, and a second antiviral agent, or a combination thereof, with a therapeutically effective amount of a compound of Formulae I, II, III, IV, V, VI, VII or VIII, or a pharmaceutically acceptable salt thereof.

In still another embodiment, the present invention provides a method of treating or preventing infection caused by an RNA-containing virus comprising co-administering to a patient in need of such treatment one or more agents selected from the group consisting of a host immune modulator and a second antiviral agent which inhibits replication of HCV by inhibiting host cellular functions associated with viral replication, or a combination thereof, with a therapeutically effective amount of a compound of Formulae I, II, III, IV, V, VI, VII or VIII, or a pharmaceutically acceptable salt thereof.

In a further embodiment, the present invention provides a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound of Formulae I, II, III, IV, V, VI, VII or VIII, or a pharmaceutically acceptable salt thereof.

In another embodiment, the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound of Formulae I, II, III, IV, V, VI, VII or VIII, or a pharmaceutically acceptable salt thereof.

In yet another embodiment, the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound of Formulae I, II, III, IV, V, VI, VII or VIII, or a pharmaceutically acceptable salt thereof.

The phrase "combination therapy" (or "co-therapy"), is intended to embrace administration of each agent in a sequential manner in a regimen that will provide beneficial effects of the drug combination, and is intended as well to embrace co-administration of these agents in a substantially simultaneous manner, such as by oral ingestion or a single capsule having a fixed ratio of these active agents or ingestion of multiple, separate capsules for each agent. "Combination therapy" will also include simultaneous or sequential administration by oral, intravenous, intramuscular or other parenteral routes into the body, including direct absorption through mucous membrane tissues, as found in the sinus passages. Sequential administration also includes drug combinations where the individual agents may be administered at different times and/or by different routes but which act in combination to provide a beneficial effect, for example, by co-action of pharmacokinetic or pharmacodynamic effects of each agent.

The present invention also features use of the compounds of the invention, or pharmaceutically acceptable salts, solvates or prodrugs thereof, for the manufacture of medicaments for the treatment of HCV or other viral infections. In one embodiment, the present invention features the use of a compound of the present invention selected from Formulae I, II, III, IV, V, VI, VII or VIII, or a salt, solvate or prodrug thereof, for the manufacture of a medicament for the treatment of HCV infection. In another embodiment, the present invention features the use of two or more compounds of the present invention (or salts, solvates or prodrugs thereof) for the manufacture of a medicament for the treatment of HCV infection, wherein each of the two or more compounds is independently selected from Formulae I, II, III, IV, V, VI, VII or VIII.

In still another embodiment, the present invention features the use of at least one compound of the present invention (or a salt, solvate or prodrug thereof) and at least one additional therapeutic agent for the manufacture of a medicament for the treatment of HCV infection. Preferably, the compound(s) of the present invention is selected from Formulae I, II, III, IV, V, VI, VII or VIII, and the additional therapeutic agent(s) can be selected, by way of illustration not limitation, from antiviral agents (e.g., anti-HIV agents or other anti-HCV agents), immunomodulators, anti-cancer or chemotherapeutic agents, and anti-inflammation agents. Specific examples of additional therapeutic agents include, but are not limited to, ribavirin; interferons (e.g., IFN alpha 2a or 2b); protease inhibitors; immunosuppressants; antibodies (e.g., therapeutic monoclonal or chimeric antibodies); antisense or siRNA; HIV inhibitors; hepatitis B (HBV) inhibitors; agents for treating cirrhosis and inflammation of the liver; Omega IFN (BioMedicines Inc., Emeryville, Calif.); BILN-2061 serine protease inhibitor (Boehringer Ingelheim Pharma KG, Ingelheim, Germany); Summetrel antiviral (Endo Pharmaceuticals Holdings Inc., Chadds Ford, Pa.); Roferon A IFN-alpha 2a (F. Hoffmann-La Roche LTD, Basel, Switzerland); Pegasys PEGylated IFN-alpha 2a (F. Hoffmann-La Roche LTD, Basel, Switzerland); Pegasys and Ribavirin PEGylated IFN-alpha 2a/ribavirin (F. Hoffmann-La Roche LTD, Basel, Switzerland); CellCept HCV IgG immunosuppressant (F. Hoffmann-La Roche LTD, Basel, Switzerland); Wellferon lymphoblastoid IFN-alpha n1 (GlaxoSmithKline plc, Uxbridge, UK); Albuferon-alpha albumin IFN-alpha 2b (Human Genome Sciences Inc., Rockville, Md.); Levovirin ribavirin (ICN Pharmaceuticals, Costa Mesa, Calif.); IDN-6556 caspase inhibitor (Idun Pharmaceuticals Inc., San Diego, Calif.); IP-501 antifibrotic (Indevus Pharmaceuticals Inc., Lexington, Mass.); Actimmune INF-gamma (InterMune Inc., Brisbane, Calif.); Infergen A IFN alfacon-1 (InterMune Pharmaceuticals Inc., Brisbane, Calif.); ISIS 14803 antisense (ISIS Pharmaceuticals Inc., Carlsbad, Calif./Elan Pharmaceuticals Inc., New York, N.Y.); JTK-003 RdRp inhibitor (Japan Tobacco Inc., Tokyo, Japan); Pegasys and Ceplene PEGylated IFN-alpha 2a/immune modulator (Maxim Pharmaceuticals inc., San Diego, Calif.); Ceplene immune modulator (Maxim Pharmaceuticals Inc., San Diego, Calif.); Civacir HCV IgG immunosuppressant (Nabi Biopharmaceuticals Inc., Boca Raton, Fla.); Intron A and Zadaxin IFN-alpha 2b/alpha 1-thymosin (RegeneRx Biopharmiceuticals Inc., Bethesda, Md./SciClone Pharmaceuticals Inc., San Mateo, Calif.); Levovirin IMPDH inhibitor (Ribapharm Inc., Costa Mesa, Calif.); Viramidine IMPDH inhibitor (Ribapharm Inc., Costa Mesa, Calif.); Heptazyme ribozyme (Ribozyme Pharmaceuticals Inc., Boulder, Colo.); Intron A IFN-alpha 2b (Schering-Plough Corporation, Kenilworth, N.J.); PEG-Intron PEGylated IFN-alpha 2b (Schering-Plough Corporation, Kenilworth, N.J.); Rebetron IFN-alpha 2b/ribavirin (Schering-Plough Corporation, Kenilworth, N.J.); Ribavirin (Schering-Plough Corporation, Kenilworth, N.J.); PEG-Intron/Ribavirin PEGylated IFN-alpha 2b/ribavirin (Schering-Plough Corporation, Kenilworth, N.J.); Zadazim immune modulator (SciClone Pharmaceuticals Inc., San Mateo, Calif.); Rebif IFN-beta 1a (Serono, Geneva, Switzerland); IFN-beta and EMZ701 IFN-beta and EMZ701 (Transition Therapeutics Inc., Ontario, Canada); T67 beta-tubulin inhibitor (Tularik Inc., South San Francisco, Calif.); VX-497 IMPDH inhibitor (Vertex Pharmaceuticals Inc., Cambridge, Mass.); VX-950/LY-570310 serine protease inhibitor (Vertex Pharmaceuticals Inc., Cambridge, Mass./Eli Lilly and Co., Inc., Indianapolis, Ind.); Omniferon natural IFN-alpha (Viragen Inc., Plantation, Fla.); XTL-002 monoclonal antibody (XTL Biopharmaceuticals); compound VX-950 (Vertex Pharmaceuticals Inc.); compound SCH503034 (Schering-Plough Co.); and compound GS9137 (Gilead Sciences, Inc., Foster City, Calif.).

In yet another embodiment, the present invention features the use of at least one compound of the present invention (or a salt, solvate or prodrug thereof) and at least one additional anti-viral agent for the manufacture of a medicament for the treatment of viral infection. Preferably, the compound(s) of the present invention is selected from Formulae I, II, III, IV, V, VI, VII or VIII, and the additional anti-viral agent(s) can be selected, without limitation, from anti-HCV or anti-HIV agents. In one example, the present invention features the use of at least one compound of the present invention selected from Formulae I, II, III, IV, V, VI, VII or VIII (or a salt, solvate or prodrug thereof), and at least one additional anti-HCV agent for the manufacture of a medicament for the treatment of HCV infection. Non-limiting examples of anti-HCV agents include HCV RNA dependent RNA polymerase inhibitors (e.g., nucleoside or non-nucleoside type polymerase inhibitors) or HCV protease inhibitors. In another example, the present invention features the use of at least one compound of the present invention selected from Formulae I, II, III, IV, V, VI, VII or VIII (or a salt, solvate or prodrug thereof), and at least two or more additional anti-HCV agents for the manufacture of a medicament for the treatment of HCV infection. Each of the additional anti-HCV agents can be independently selected from HCV RNA dependent RNA polymerase inhibitors or HCV protease inhibitors.

In still another embodiment, the present invention features the use of at least one compound of the present invention selected from Formulae I, II, III, IV, V, VI, VII or VIII (or a salt, solvate or prodrug thereof), and at least one anti-HIV agent for the manufacture of a medicament for the treatment of HIV or HCV infection. In still yet another embodiment, the present invention features the use of at least one compound of the present invention selected from Formulae I, II, III, IV, V, VI, VII or VIII (or a salt, solvate or prodrug thereof), and at least one anti-hepatitis A, anti-hepatitis B, anti-hepatitis D, anti-hepatitis E or anti-hepatitis G agent for the manufacture of a medicament for the treatment of viral hepatitis. In a further embodiment, the present invention features the use of at least one compound of the present invention selected from Formulae I, II, III, IV, V, VI, VII or VIII (or a salt, solvate or prodrug thereof), and at least one agent for treating liver inflammation, for the manufacture of a medicament for the treatment of Hepatitis C.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A compound, a tautomer of the compound, or a pharmaceutically acceptable salt of the compound or tautomer, wherein the compound has Formula II:

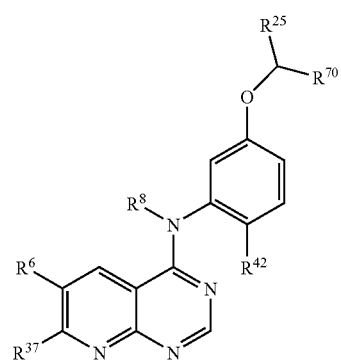

wherein:
$R^6$ is selected from the group consisting of hydrogen and cyano;
$R^8$ is selected from the group consisting of hydrogen and arylalkyl;

$R^{25}$ is selected from the group consisting of hydrogen and alkyl;

$R^{37}$ is selected from the group consisting of hydrogen, alkyl, hydroxyalkyl, and cycloalkyl;

$R^{42}$ is selected from the group consisting of arylsulfanyl, heteroarylsulfanyl, and aryloxy; wherein $R^{42}$ is optionally substituted with one or more substituents independently selected from $R^{46}$;

$R^{46}$ is one or more substituents selected from the group consisting of hydrogen, hydroxy, amino, halogen, dialkylamino, and alkoxycarbonylamino;

$R^{70}$ is selected from the group consisting of aryl, and heterocyclo; wherein $R^{70}$ is optionally substituted with $R^{75}$;

$R^{75}$ is one or more substituents independently selected from the group consisting of hydrogen, halogen, alkoxy, cyano, alkyl, haloalkyl, and aryl.

2. A compound, a tautomer of the compound, or a pharmaceutically acceptable salt of the compound or tautomer, wherein the compound has Formula III:

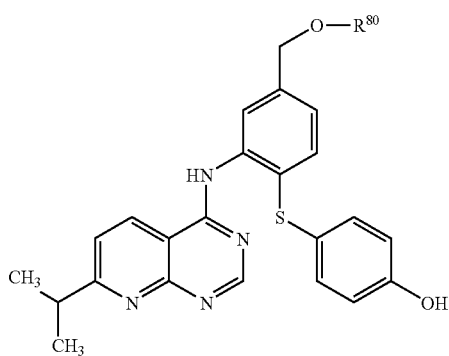

III wherein $R^{80}$ is selected from the group consisting of hydrogen, alkylcarbonyl, and haloaryl.

3. A compound, a tautomer of the compound, or a pharmaceutically acceptable salt of the compound or tautomer, wherein the compound has Formula VII:

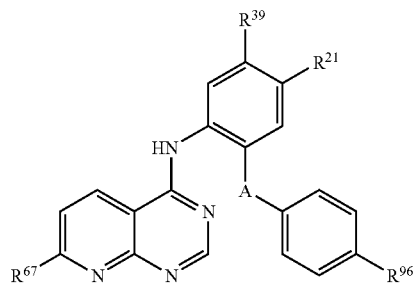

VII wherein:

A is selected from the group consisting of O and S;

$R^{21}$ is selected from the group consisting of hydrogen and hydroxy;

or $R^{21}$ taken together with $R^{39}$ form a 5-12 membered heterocycle containing at least two heteroatoms selected from the group consisting of O, N, and S; or $R^{39}$ is selected from the group consisting of hydrogen, alkyl, arylalkenyl, dialkylamino, heteroaryl, haloheteroaryl, haloarylaminosulfonyl, arylsulfonyloxy, alkylcarbonyloxy, cycloalkylaminocarbonyl, arylalkoxycarbonylamino, alkoxycarbonyl, and NH—$R^{99}$;

$R^{99}$ is selected from the group consisting of hydrogen, arylalkyl, cycloalkylalkyl, aryl, heteroaryl, haloarylalkylamino, arylalkylamino, and alkylheteroaryl;

$R^{67}$ is selected from the group consisting of hydrogen, alkyl, cycloalkyl, and alkylcycloalkyl;

$R^{96}$ is selected from the group consisting of hydrogen, hydroxy, amino, alkoxy, arylsulfonyloxy, alkylcarbonylamino, alkoxy, halogen, alkoxycarbonyloxy, haloalkoxycarbonylamino, and arylalkoxy.

* * * * *